(12) United States Patent
Kirchner et al.

(10) Patent No.: US 8,481,704 B2
(45) Date of Patent: Jul. 9, 2013

(54) NUCLEIC ACID MOLECULE ENCODING HUMAN GM-CSF ANTIGEN BINDING PROTEINS

(75) Inventors: Jacqueline A. Kirchner, Seattle, WA (US); Kenneth A. Brasel, Seattle, WA (US); Kara Olson, White Plains, NY (US); Jose Carlos Escobar, Sammamish, WA (US); Dauphine Barone, Mill Creek, WA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/589,935

(22) Filed: Aug. 20, 2012

(65) Prior Publication Data

US 2013/0071923 A1 Mar. 21, 2013

Related U.S. Application Data

(62) Division of application No. 12/675,013, filed as application No. PCT/US2008/010888 on Sep. 18, 2008, now Pat. No. 8,268,311.

(60) Provisional application No. 61/087,551, filed on Aug. 8, 2008, provisional application No. 60/994,343, filed on Sep. 18, 2007.

(51) Int. Cl.
*C07H 21/04* (2006.01)
*C12P 21/08* (2006.01)
*C12N 15/10* (2006.01)

(52) U.S. Cl.
USPC .............. 536/23.53; 435/69.1; 435/320.1; 435/325

(58) Field of Classification Search
None
See application file for complete search history.

(56) References Cited

U.S. PATENT DOCUMENTS

| | | | |
|---|---|---|---|
| 5,070,013 A | 12/1991 | Abrams et al. | |
| 5,475,087 A | 12/1995 | Seelig et al. | |
| 7,108,852 B2 | 9/2006 | Devalaraja et al. | |
| 7,381,801 B2 | 6/2008 | Renner et al. | |
| 7,455,836 B2 | 11/2008 | Hamilton et al. | |
| 2005/0112119 A1 | 5/2005 | Qin et al. | |
| 2008/0292641 A1 | 11/2008 | Sass et al. | |
| 2008/0317757 A1 | 12/2008 | Nakajima | |
| 2009/0053213 A1 | 2/2009 | Steidl et al. | |
| 2009/0297532 A1 | 12/2009 | Raum et al. | |

FOREIGN PATENT DOCUMENTS

| | | | |
|---|---|---|---|
| EP | 0 265 384 A2 | 4/1988 | |
| EP | 0 344 957 B1 | 12/1989 | |
| EP | 0 499 161 A2 | 8/1992 | |
| EP | 1 593 690 B1 | 11/2005 | |
| EP | 1 947 178 A1 | 7/2008 | |
| WO | WO 97/28190 A1 | 8/1997 | |
| WO | WO 03/068924 A2 | 8/2003 | |
| WO | WO 2005/034733 A2 | 4/2005 | |
| WO | WO 2005/105844 A2 | 11/2005 | |
| WO | WO 2006/111353 A2 | 10/2006 | |
| WO | WO 2006/122797 A2 | 11/2006 | |
| WO | WO 2007/049472 A1 | 5/2007 | |
| WO | WO 2007/067991 A2 | 6/2007 | |
| WO | WO 2007/092939 A2 | 8/2007 | |
| WO | WO 2008/064321 A2 | 5/2008 | |
| WO | WO 2009/134805 A2 | 11/2009 | |

OTHER PUBLICATIONS

Campbell et al., "Granulocyte-macrophage colony stimulating factor exacerbates collagen induced arthritis in mice," *Ann Rheum Dis* 56:364-368, 1997.
Campbell et al., "Protection from Collagen-Induced Arthritis in Granulocyte-Macrophage Colony-Stimulating Factor-Deficient Mice," *J Immunol* 161:3639-3644, 1998.
Chamow and Ashkanazi, "Immunoadhesions: principles and applications," *Tibtech* 14:52-60, 1996.
Dempsey et al., "Monoclonal Antibodies that Recognize Human Granulocyte-Macrophage Colony-Stimulating Factor and Neutralize Its Bioactivity In Vitro," *Hybridoma* 9(6):545-558, 1990.
Hamilton, "GM-CSF in inflammation and autoimmunity," *Trends in Immunology* 23(8):403-408, 2002.
Krinner et al., "A highly stable polyethylene glycol-conjugated human single-chain antibody neutralizing granulocyte-macrophage colony stimulating factor at low nanomolar concentration," *Protein Engineering, Design & Selection* 19(10):461-470, 2006.
Krinner et al., "A human monoclonal IgG1 potently neutralizing the pro-inflammatory cytokine GM-CSF," *Molecular Immunology* 44:916-925, 2007.
McQUALTER et al., "Granulocyte Macrophage Colony-stimulating Factor: A New Putative Therapeutic Target in Multiple Sclerosis," *J Exp Med* 194(7):873-881, 2001.
Ngo et al., The Protein Folding Problem and Tertiary Structure Prediction, pp. 492-495, 1994.
Rudikoff et al., "Single amino acid substitution altering antigen-binding specificity," *Proc Natl Acad Sci* 79:1979-1983, 1982.
Schön et al., "Critical Role of Neutrophils for the Generation of Psoriasiform Skin Lesions in Flaky Skin Mice," *J Invest Dermatol* 114:976-983, 2000.
Steidl et al., "In vitro affinity maturation of human GM-CSF antibodies by targeted CDR-diversification," *Molecular Immunology* 46:135-144, 2008.
Wells, "Additivity of Mutational Effects in Proteins," *Biochemistry* 29(37):8509-8517, 1990.

*Primary Examiner* — Gyan Chandra
(74) *Attorney, Agent, or Firm* — Susan E. Lingenfelter

(57) ABSTRACT

Antigen binding proteins that bind to human GM-CSF protein are provided. Nucleic acids encoding the antigen binding protein, vectors, and cells encoding the same are also provided. The antigen binding proteins can inhibit binding of GM-CSF to GM-CSFR, inhibit GM-CSF-induced proliferation and signaling of myeloid lineage cell lines and inhibit GM-CSF-induced activation of human monocytes.

7 Claims, 29 Drawing Sheets

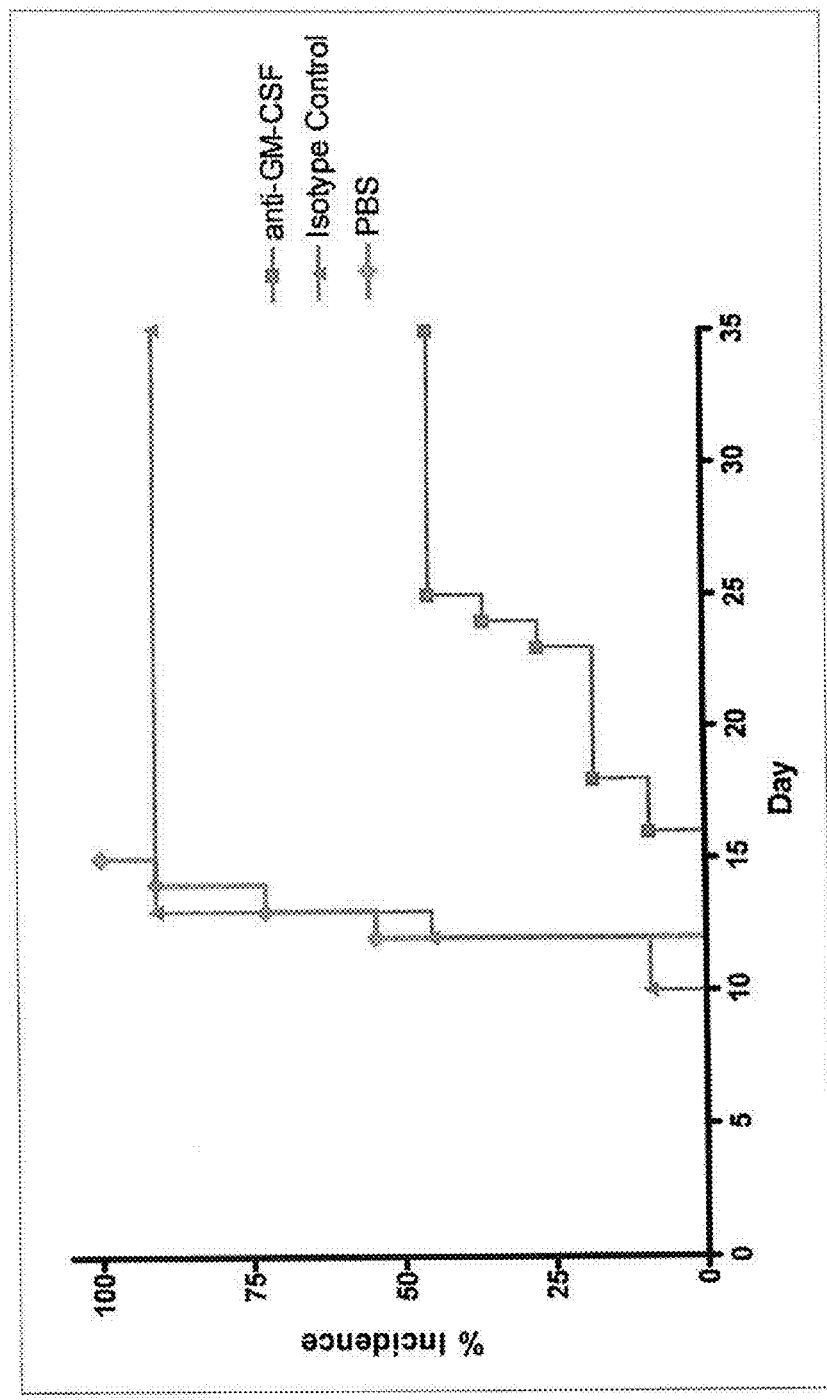

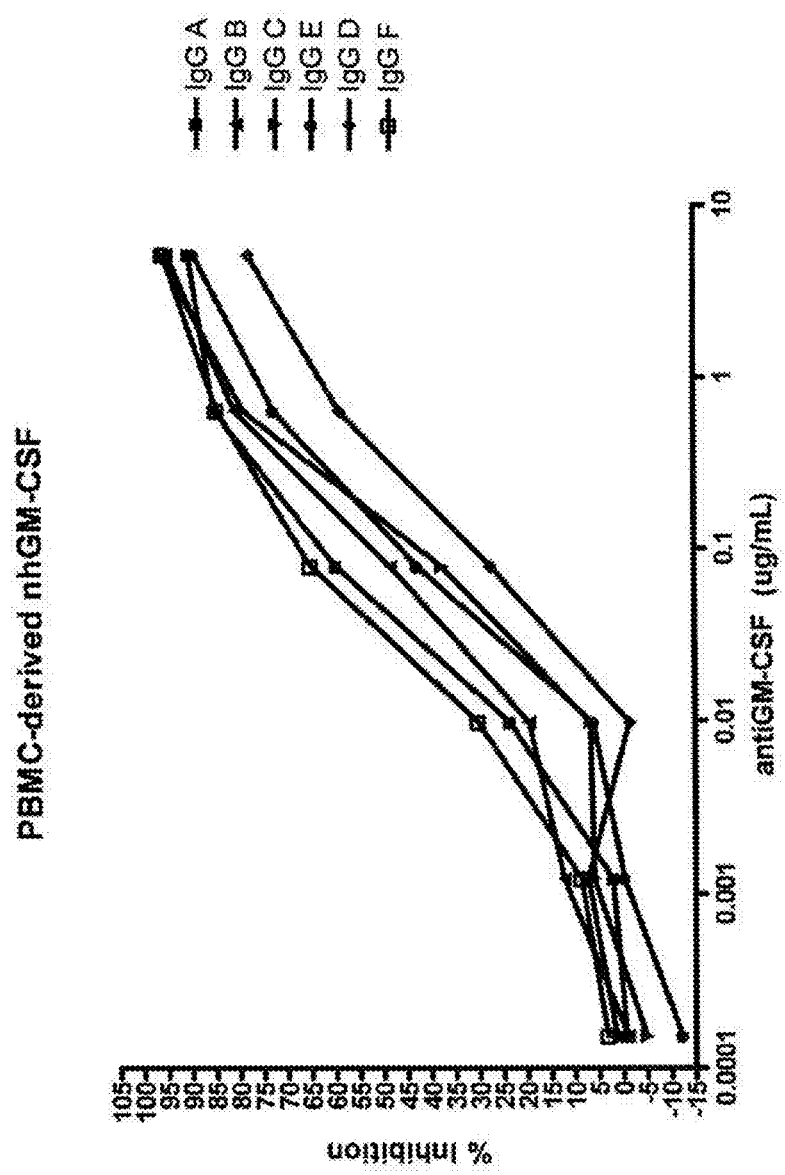

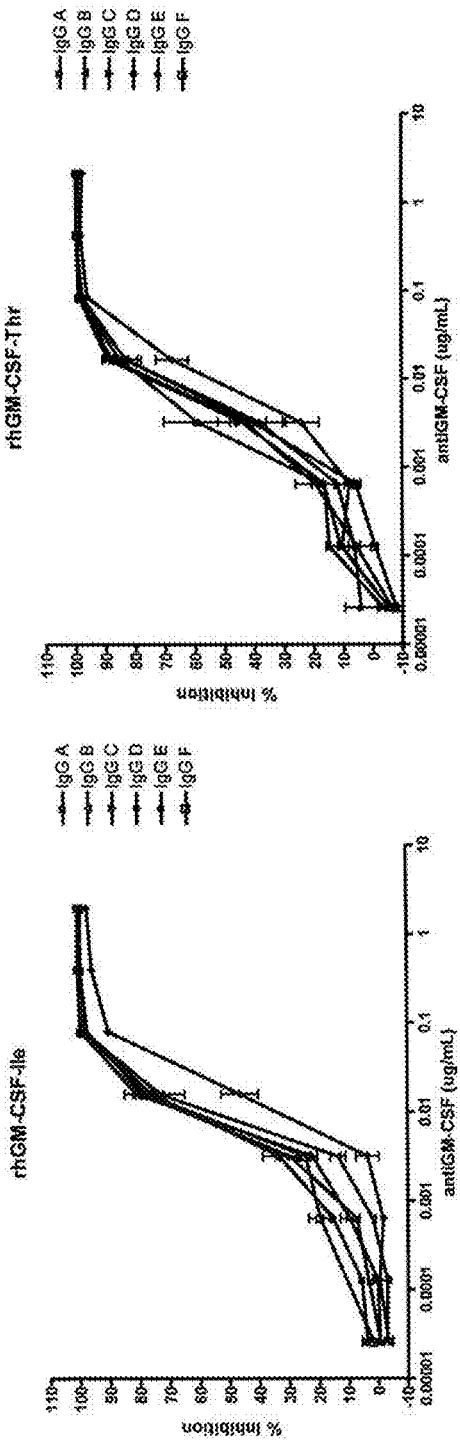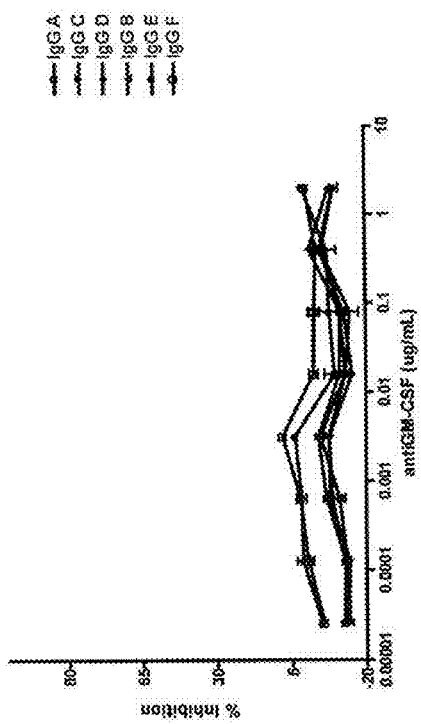
Figure 7b

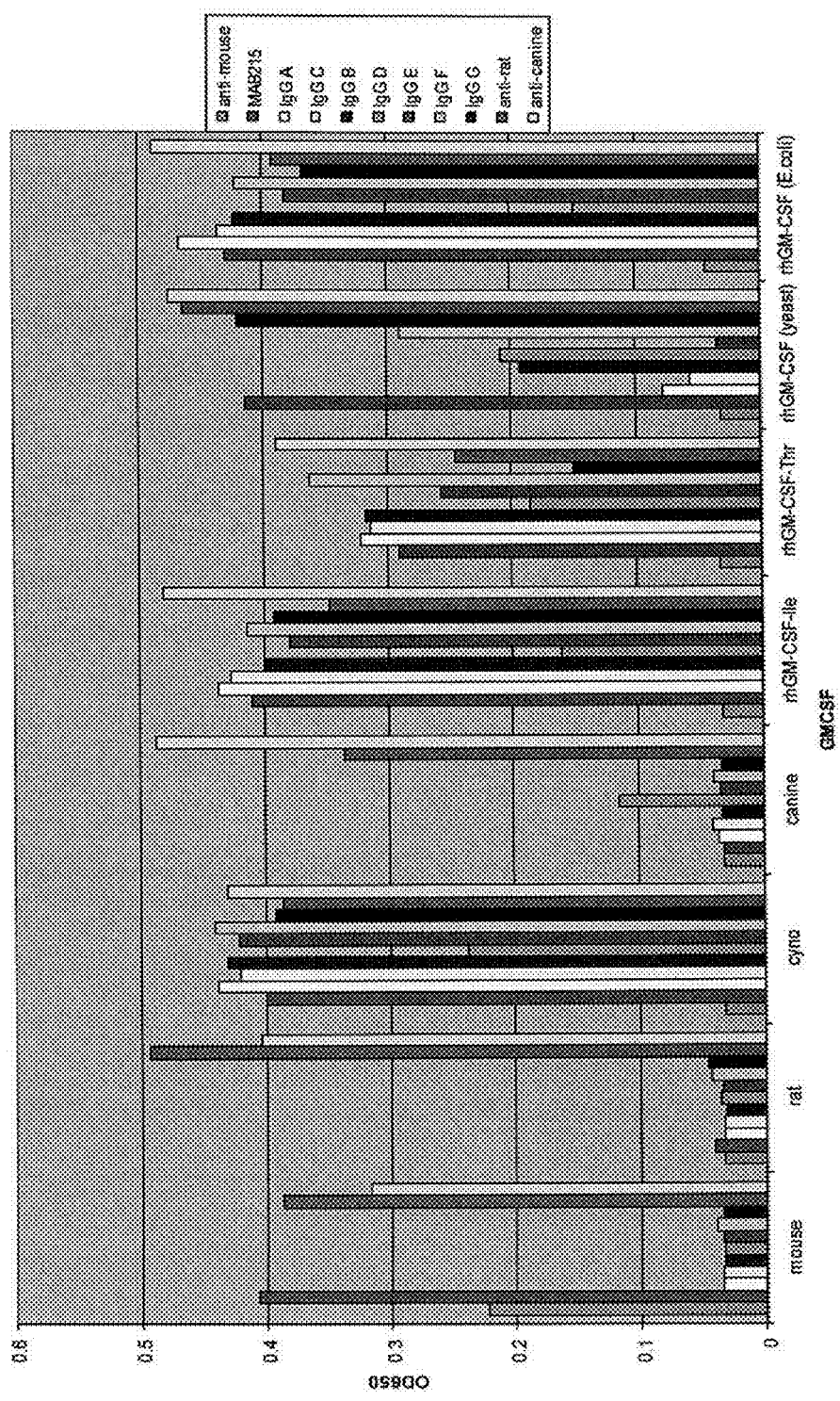

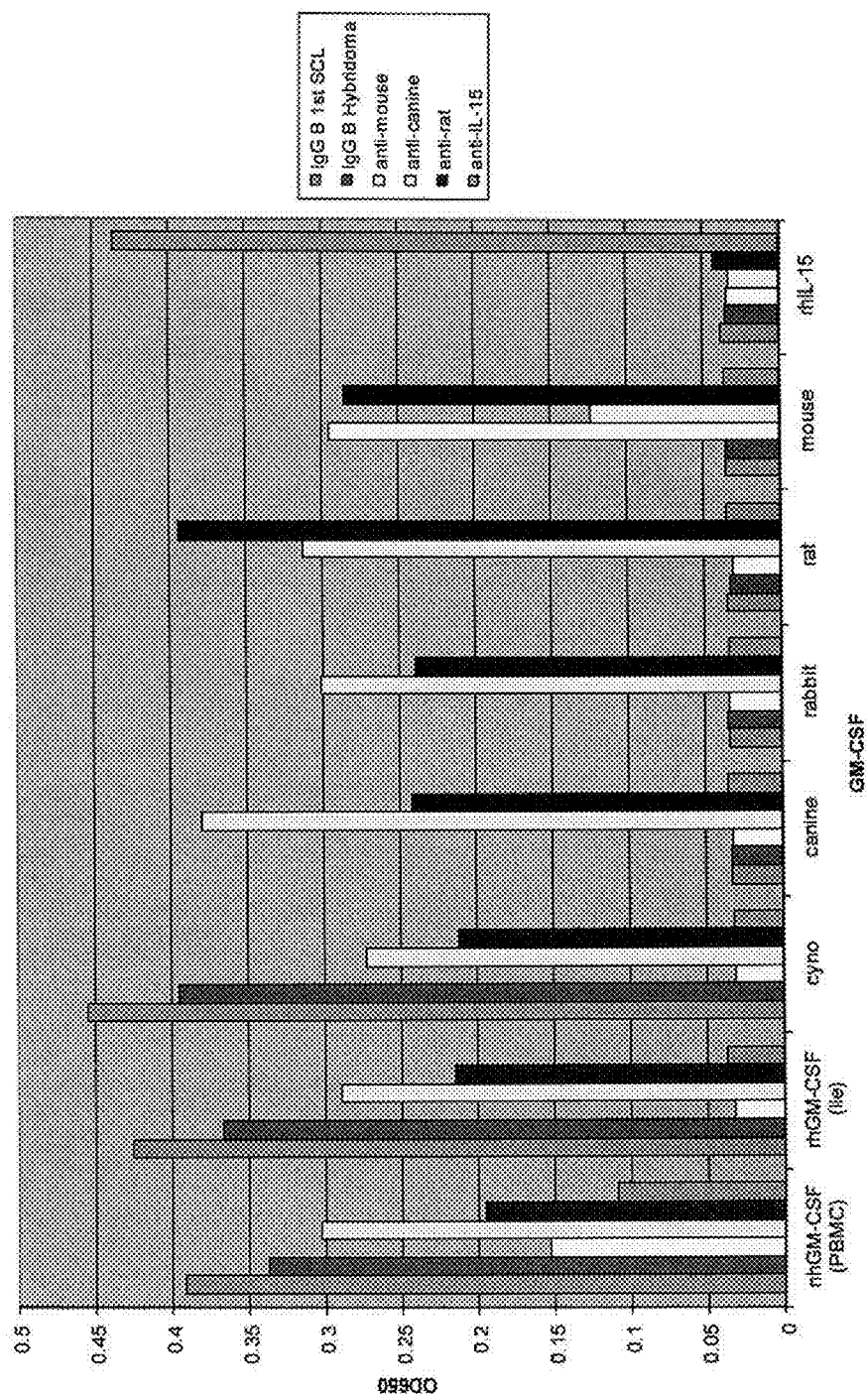

SEQUENCE LISTING

<160> NUMBER OF SEQ ID NOS: 147

<210> SEQ ID NO 1
<211> LENGTH: 240
<212> TYPE: PRT
<213> ORGANISM: Artificial
<220> FEATURE:
<223> OTHER INFORMATION: antibody light chain

<400> SEQUENCE: 1

```
Met Val Leu Gln Thr Gln Val Phe Ile Ser Leu Leu Leu Trp Ile Ser
1               5                   10                  15

Gly Ala Tyr Gly Asp Ile Val Leu Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Ile Leu Tyr Ser Ser Ser Asn Glu Asn Phe Leu Thr Trp Tyr Gln Gln
    50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Pro Glu Asp Val Ala Val Tyr
            100                 105                 110

Tyr Cys Gln Gln Tyr Phe Ser Val Phe Arg Thr Phe Gly Gln Gly Thr
        115                 120                 125

Arg Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 2
<211> LENGTH: 720
<212> TYPE: DNA
<213> ORGANISM: artificial
<220> FEATURE:

<223> OTHER INFORMATION: antibody light chain gene

<400> SEQUENCE: 2

```
atggtgctgc agacccaggt gtttattagc ctgctgctgt ggattagcgg cgcgtatggc      60
gacatcgtgc tgacccagtc tccagactcc ctggctgtgt ctctgggcga gagggccacc     120
atcaactgca gtccagccag agtattttta tacagctcca gcaatgagaa cttcttaact     180
tggtaccagc agaaaccagg acagcctcct aagctgctca tttactgggc atctacccgg     240
gaatccgggg tccctgaccg attcagtggc agcgggtctg gacagatttt cactctcacc     300
atcagcagcc tgcagcctga agatgtggca gtttattact gtcagcaata ttttagtgtt     360
tttcggacgt tcggccaagg gaccagggtg gaaatcaaac gtacggtggc tgcaccatct     420
gtcttcatct tcccgccatc tgatgagcag ttgaaatctg gaactgcctc tgttgtgtgc     480
ctgctgaata acttctatcc cagagaggcc aaagtacagt ggaaggtgga taacgccctc     540
caatcgggta actcccagga gagtgtcaca gagcaggaca gcaaggacag cacctacagc     600
ctcagcagca ccctgacgct gagcaaagca gactacgaga aacacaaagt ctacgcctgc     660
gaagtcaccc atcagggcct gagctcgccc gtcacaaaga gcttcaacag gggagagtgt     720
```

<210> SEQ ID NO 3
<211> LENGTH: 113
<212> TYPE: PRT
<213> ORGANISM: artificial
<220> FEATURE:
<223> OTHER INFORMATION: antibody variable domain

<400> SEQUENCE: 3

```
Asp Ile Val Leu Thr Gln Ser Pro Asp Ser Leu Ala Val Ser Leu Gly
1               5                  10                  15

Glu Arg Ala Thr Ile Asn Cys Lys Ser Ser Gln Ser Ile Leu Tyr Ser
            20                  25                  30

Ser Ser Asn Glu Asn Phe Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Pro Glu Asp Val Ala Val Tyr Tyr Cys Gln Gln
                85                  90                  95

Tyr Phe Ser Val Phe Arg Thr Phe Gly Gln Gly Thr Arg Val Glu Ile
                100                 105                 110

Lys
```

<210> SEQ ID NO 4
<211> LENGTH: 17
<212> TYPE: PRT
<213> ORGANISM: artificial
<220> FEATURE:
<223> OTHER INFORMATION: CDR1 peptide

<400> SEQUENCE: 4

```
Lys Ser Ser Gln Ser Ile Leu Tyr Ser Ser Ser Asn Glu Asn Phe Leu
1               5                  10                  15

Thr
```

<210> SEQ ID NO 5
<211> LENGTH: 7
<212> TYPE: PRT

```
<213> ORGANISM: artificial
<220> FEATURE:
<223> OTHER INFORMATION: CDR2 peptide

<400> SEQUENCE: 5

Trp Ala Ser Thr Arg Glu Ser
1               5

<210> SEQ ID NO 6
<211> LENGTH: 9
<212> TYPE: PRT
<213> ORGANISM: artificial
<220> FEATURE:
<223> OTHER INFORMATION: CDR3 peptide

<400> SEQUENCE: 6

Gln Gln Tyr Phe Ser Val Phe Arg Thr
1               5

<210> SEQ ID NO 7
<211> LENGTH: 465
<212> TYPE: PRT
<213> ORGANISM: artificial
<220> FEATURE:
<223> OTHER INFORMATION: antibody heavy chain

<400> SEQUENCE: 7

Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Gly Tyr Tyr Ile His Trp Val Arg Gln Ala Pro Gly Gln Gly Leu
        50                  55                  60

Glu Trp Met Gly Trp Ile Asn Pro Asn Ser Gly Gly Thr Asn Ser Ala
65                  70                  75                  80

Gln Lys Phe Arg Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Glu Gly Tyr Ser Tyr Gly Tyr Phe Asp Tyr
        115                 120                 125

Trp Gly Gln Gly Thr Leu Val Thr Val Ser Ser Ala Ser Thr Lys Gly
            130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255
```

```
Ser Val Phe Leu Phe Pro Pro Lys Pro Lys Asp Thr Leu Met Ile Ser
            260                 265                 270
Arg Thr Pro Glu Val Thr Cys Val Val Asp Val Ser His Glu Asp
        275                 280                 285
Pro Glu Val Gln Phe Asn Trp Tyr Val Asp Gly Val Glu Val His Asn
        290                 295                 300
Ala Lys Thr Lys Pro Arg Glu Glu Gln Phe Asn Ser Thr Phe Arg Val
305                 310                 315                 320
Val Ser Val Leu Thr Val Val His Gln Asp Trp Leu Asn Gly Lys Glu
                325                 330                 335
Tyr Lys Cys Lys Val Ser Asn Lys Gly Leu Pro Ala Pro Ile Glu Lys
            340                 345                 350
Thr Ile Ser Lys Thr Lys Gly Gln Pro Arg Glu Pro Gln Val Tyr Thr
        355                 360                 365
Leu Pro Pro Ser Arg Glu Glu Met Thr Lys Asn Gln Val Ser Leu Thr
        370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Met Leu
                405                 410                 415
Asp Ser Asp Gly Ser Phe Phe Leu Tyr Ser Lys Leu Thr Val Asp Lys
            420                 425                 430
Ser Arg Trp Gln Gln Gly Asn Val Phe Ser Cys Ser Val Met His Glu
        435                 440                 445
Ala Leu His Asn His Tyr Thr Gln Lys Ser Leu Ser Leu Ser Pro Gly
        450                 455                 460
Lys
465

<210> SEQ ID NO 8
<211> LENGTH: 1395
<212> TYPE: DNA
<213> ORGANISM: artificial
<220> FEATURE:
<223> OTHER INFORMATION: antibody heavy chain gene

<400> SEQUENCE: 8
atggattgga cctggcgtat tctgtttctg gtggcggcgg cgaccggcgc gcatagccag      60
gtgcagctgg tgcagtctgg ggctgaggtg aagaagcctg ggcctcagt gaaggtctcc     120 tgcaaggctt ctggatacac cttcaccggc tactatatac actgggtgcg acaggccct     180 ggacaagggc ttgagtggat gggatggatc aaccctaaca gtggtggcac aaactctgca     240
cagaagtttc gggcagggt caccatgacc agggacacgt ccatcagcac agcctacatg     300
gagctgagca ggctgagatc tgacgacacg gccgtgtatt actgtgcgcg agagggtgga     360
tacagctatg gttactttga ctactggggc caggaaccc tggtcaccgt ctcctcagct     420
agcaccaagg gcccatcggt cttccccctg gcgccctgct ccaggagcac ctccgagagc     480
acagcggccc tgggctgcct ggtcaaggac tacttcccg aaccggtgac ggtgtcgtgg     540
aactcaggcg ctctgaccag cggcgtgcac accttccag ctgtcctaca gtcctcagga     600
ctctactccc tcagcagcgt ggtgaccgtg ccctccagca acttcggcac ccagacctac     660
acctgcaacg tagatcacaa gcccagcaac accaaggtgg acaagacagt tgagcgcaaa     720
tgttgtgtcg agtgcccacc gtgcccagca ccacctgtgg caggaccgtc agtcttcctc     780
ttccccccaa aacccaagga caccctcatg atctcccgga cccctgaggt cacgtgcgtg     840
```

```
gtggtggacg tgagccacga agaccccgag gtccagttca actggtacgt ggacggcgtg    900
gaggtgcata atgccaagac aaagccacgg gaggagcagt tcaacagcac gttccgtgtg    960
gtcagcgtcc tcaccgttgt gcaccaggac tggctgaacg gcaaggagta caagtgcaag   1020
gtctccaaca aggcctccc agcccccatc gagaaaacca tctccaaaac caagggcag    1080
ccccgagaac acaggtgta caccctgccc ccatcccggg aggagatgac caagaaccag   1140
gtcagcctga cctgcctggt caaaggcttc taccccagcg acatcgccgt ggagtgggag   1200
agcaatgggc agccggagaa caactacaag accacacctc ccatgctgga ctccgacggc   1260
tccttcttcc tctacagcaa gctcaccgtg gacaagagca ggtggcagca ggggaacgtc   1320
ttctcatgct ccgtgatgca tgaggctctg cacaaccact acacgcagaa gagcctctcc   1380
ctgtctccgg gtaaa                                                    1395
```

<210> SEQ ID NO 9
<211> LENGTH: 120
<212> TYPE: PRT
<213> ORGANISM: artificial
<220> FEATURE:
<223> OTHER INFORMATION: antibody variable domain

<400> SEQUENCE: 9

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Ile His Trp Val Arg Gln Ala Pro Gly Gln Gly Leu Glu Trp Met
            35                  40                  45

Gly Trp Ile Asn Pro Asn Ser Gly Gly Thr Asn Ser Ala Gln Lys Phe
        50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Gly Tyr Ser Tyr Gly Tyr Phe Asp Tyr Trp Gly Gln
            100                 105                 110

Gly Thr Leu Val Thr Val Ser Ser
        115                 120
```

<210> SEQ ID NO 10
<211> LENGTH: 5
<212> TYPE: PRT
<213> ORGANISM: artificial
<220> FEATURE:
<223> OTHER INFORMATION: CDR1 peptide

<400> SEQUENCE: 10

```
Gly Tyr Tyr Ile His
1               5
```

<210> SEQ ID NO 11
<211> LENGTH: 17
<212> TYPE: PRT
<213> ORGANISM: artificial
<220> FEATURE:
<223> OTHER INFORMATION: CDR2 peptide

<400> SEQUENCE: 11

```
Trp Ile Asn Pro Asn Ser Gly Gly Thr Asn Ser Ala Gln Lys Phe Arg
1               5                   10                  15
```

Gly

```
<210> SEQ ID NO 12
<211> LENGTH: 11
<212> TYPE: PRT
<213> ORGANISM: artificial
<220> FEATURE:
<223> OTHER INFORMATION: CDR3 peptide

<400> SEQUENCE: 12
```

Glu Gly Gly Tyr Ser Tyr Gly Tyr Phe Asp Tyr
1               5                   10

```
<210> SEQ ID NO 13
<211> LENGTH: 235
<212> TYPE: PRT
<213> ORGANISM: artificial
<220> FEATURE:
<223> OTHER INFORMATION: antibody light chain

<400> SEQUENCE: 13
```

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Asp Arg Ala Thr Leu Ser Cys Arg Ala Ser Gln Ser
            35                  40                  45

Val Ser Ser Ser Tyr Phe Ala Trp Tyr Gln Gln Lys Pro Gly Gln Ala
        50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Asp Arg Ser Pro Arg Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

```
<210> SEQ ID NO 14
<211> LENGTH: 705
<212> TYPE: DNA
<213> ORGANISM: artificial
<220> FEATURE:
<223> OTHER INFORMATION: antibody light chain gene

<400> SEQUENCE: 14
```

```
atggaaaccc cggcgcagct gctgtttctg ctgctgctgt ggctgccgga taccaccggc    60
gaaattgtgt tgacgcagtc tccaggcacc ctgtctttgt ctccagggga cagagccacc   120
ctctcctgca gggccagtca gagtgttagt agcagctact ttgcctggta ccagcagaaa   180
cctggccagg ctcccaggct cctcatttat ggtgcatcca gtagggccac tggcatccca   240
gacaggttca gtggcagtgg gtctgggaca gacttcactc tcaccatcag cagactggag   300
cctgaagatt ttgcagtgta ttactgtcag cagtatgata ggtcacctcg acgttcggc    360 caagggacca aggtggaaat caaacgtacg gtggctgcac catctgtctt catcttcccg   420
ccatctgatg agcagttgaa atctggaact gcctctgttg tgtgcctgct gaataacttc   480
tatcccagag aggccaaagt acagtggaag gtggataacg ccctccaatc gggtaactcc   540
caggagagtg tcacagagca ggacagcaag gacagcacct acagcctcag cagcaccctg   600
acgctgagca aagcagacta cgagaaacac aaagtctacg cctgcgaagt cacccatcag   660
ggcctgagct cgcccgtcac aaagagcttc aacaggggag agtgt               705
```

<210> SEQ ID NO 15
<211> LENGTH: 108
<212> TYPE: PRT
<213> ORGANISM: artificial
<220> FEATURE:
<223> OTHER INFORMATION: antibody variable domain

<400> SEQUENCE: 15

```
Glu Ile Val Leu Thr Gln Ser Pro Gly Thr Leu Ser Leu Ser Pro Gly
1               5                   10                  15

Asp Arg Ala Thr Leu Ser Cys Arg Ala Ser Gln Ser Val Ser Ser
            20                  25                  30

Tyr Phe Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Arg Ser Pro
                85                  90                  95

Arg Thr Phe Gly Gln Gly Thr Lys Val Glu Ile Lys
            100                 105
```

<210> SEQ ID NO 16
<211> LENGTH: 12
<212> TYPE: PRT
<213> ORGANISM: artificial
<220> FEATURE:
<223> OTHER INFORMATION: CDR1 peptide

<400> SEQUENCE: 16

```
Arg Ala Ser Gln Ser Val Ser Ser Ser Tyr Phe Ala
1               5                   10
```

<210> SEQ ID NO 17
<211> LENGTH: 7
<212> TYPE: PRT
<213> ORGANISM: artificial
<220> FEATURE:
<223> OTHER INFORMATION: CDR2 peptide

<400> SEQUENCE: 17

```
Gly Ala Ser Ser Arg Ala Thr
1               5
```

```
<210> SEQ ID NO 18
<211> LENGTH: 9
<212> TYPE: PRT
<213> ORGANISM: artificial
<220> FEATURE:
<223> OTHER INFORMATION: CDR3 peptide

<400> SEQUENCE: 18

Gln Gln Tyr Asp Arg Ser Pro Arg Thr
1               5

<210> SEQ ID NO 19
<211> LENGTH: 463
<212> TYPE: PRT
<213> ORGANISM: artificial
<220> FEATURE:
<223> OTHER INFORMATION: antibody heavy chain

<400> SEQUENCE: 19

Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ser Ser Gly Tyr Thr Phe
            35                  40                  45

Thr Gly Tyr Tyr Met His Trp Val Arg Gln Ala Pro Gly Gln Gly Leu
        50                  55                  60

Glu Trp Met Gly Trp Ile Asn Pro Asn Ser Gly Gly Thr Asn Tyr Ala
65                  70                  75                  80

Gln Lys Phe Lys Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Asp Lys Trp Leu Asp Gly Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
    290                 295                 300
```

```
Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
            325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460

<210> SEQ ID NO 20
<211> LENGTH: 1389
<212> TYPE: DNA
<213> ORGANISM: artificial
<220> FEATURE:
<223> OTHER INFORMATION: antibody heavy chain gene

<400> SEQUENCE: 20
atggattgga cctggcgtat tctgtttctg gtggcggcgg cgaccggcgc gcatagccag      60
gtgcagctgg tgcagtctgg ggctgaggtg aagaagcctg ggcctcagt gaaggtctcc     120 tgtaagtctt ctggatacac cttcaccggc tactatatgc actgggtgcg acaggcccct    180
ggacaagggc ttgagtggat gggatggatc aaccctaaca gtggtggcac aaactatgca    240
cagaagttta agggcagggt caccatgacc agggacacgt ccatcagcac agcctacatg    300
gagctgagca ggctgagatc tgacgacacg gccgtgtatt actgtgcgag ataagtgg     360 ctggacggct ttgactactg gggccaggga accctggtca ccgtctcctc agctagcacc    420
aagggcccat cggtcttccc cctggcgccc tgctccagga gcacctccga gagcacagcg    480
gccctgggct gcctggtcaa ggactacttc cccgaaccgg tgacggtgtc gtggaactca    540
ggcgctctga ccagcggcgt gcacaccttc ccagctgtcc tacagtcctc aggactctac    600
tccctcagca gcgtggtgac cgtgccctcc agcaacttcg gcacccagac ctacacctgc    660
aacgtagatc acaagcccag caacaccaag gtggacaaga cagttgagcg caaatgttgt    720
gtcgagtgcc caccgtgccc agcaccacct gtggcaggac cgtcagtctt cctcttcccc    780
ccaaaaccca aggacaccct catgatctcc cggacccctg aggtcacgtg cgtggtggtg    840
gacgtgagcc acgaagaccc cgaggtccag ttcaactggt acgtggacgg cgtggaggtg    900
cataatgcca agacaaagcc acgggaggag cagttcaaca gcacgttccg tgtggtcagc    960
gtcctcaccg ttgtgcacca ggactggctg aacggcaagg agtacaagtg caaggtctcc   1020
aacaaaggcc tcccagcccc catcgagaaa accatctcca aaaccaaagg gcagccccga   1080
gaaccacagg tgtacaccct gcccccatcc cgggaggaga tgaccaagaa ccaggtcagc   1140
ctgacctgcc tggtcaaagg cttctacccc agcgacatcg ccgtggagtg ggagagcaat   1200
```

```
gggcagccgg agaacaacta caagaccaca cctcccatgc tggactccga cggctccttc   1260
ttcctctaca gcaagctcac cgtggacaag agcaggtggc agcaggggaa cgtcttctca   1320
tgctccgtga tgcatgaggc tctgcacaac cactacacgc agaagagcct ctccctgtct   1380
ccgggtaaa                                                           1389
```

```
<210> SEQ ID NO 21
<211> LENGTH: 118
<212> TYPE: PRT
<213> ORGANISM: artificial
<220> FEATURE:
<223> OTHER INFORMATION: antibody variable domain

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ser Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Lys Trp Leu Asp Gly Phe Asp Tyr Trp Gly Gln Gly Thr
            100                 105                 110

Leu Val Thr Val Ser Ser
        115

<210> SEQ ID NO 22
<211> LENGTH: 5
<212> TYPE: PRT
<213> ORGANISM: artificial
<220> FEATURE:
<223> OTHER INFORMATION: CDR1 peptide

<400> SEQUENCE: 22

Gly Tyr Tyr Met His
1               5

<210> SEQ ID NO 23
<211> LENGTH: 17
<212> TYPE: PRT
<213> ORGANISM: artificial
<220> FEATURE:
<223> OTHER INFORMATION: CDR2 peptide

<400> SEQUENCE: 23

Trp Ile Asn Pro Asn Ser Gly Gly Thr Asn Tyr Ala Gln Lys Phe Lys
1               5                   10                  15

Gly

<210> SEQ ID NO 24
<211> LENGTH: 9
<212> TYPE: PRT
<213> ORGANISM: artificial
<220> FEATURE:
<223> OTHER INFORMATION: CDR3 peptide

<400> SEQUENCE: 24
```

Asp Lys Trp Leu Asp Gly Phe Asp Tyr
1               5

<210> SEQ ID NO 25
<211> LENGTH: 235
<212> TYPE: PRT
<213> ORGANISM: artificial
<220> FEATURE:
<223> OTHER INFORMATION: antibody light chain

<400> SEQUENCE: 25

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Ser
            35                  40                  45

Val Ser Ser Tyr Phe Ala Trp Tyr Gln Gln Lys Pro Gly Gln Ala
    50                  55                  60

Pro Arg Leu Leu Ile Tyr Gly Thr Ser Arg Ala Thr Gly Ile Pro
65                  70                  75                  80

Asp Arg Phe Ser Gly Ser Gly Ser Gly Thr Asp Phe Thr Leu Thr Val
                85                  90                  95

Ser Arg Leu Glu Pro Glu Asp Phe Ala Val Tyr Tyr Cys Gln Gln Tyr
                100                 105                 110

Asp Arg Ser Pro Arg Thr Phe Gly Gln Gly Thr Lys Val Glu Ile Lys
            115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 26
<211> LENGTH: 705
<212> TYPE: DNA
<213> ORGANISM: artificial
<220> FEATURE:
<223> OTHER INFORMATION: antibody light chain gene

<400> SEQUENCE: 26
atggaaaccc cggcgcagct gctgtttctg ctgctgctgt ggctgccgga taccaccggc      60
gaaattgtgt tgacgcagtc tccaggcacc ctgtctttgt ctccagggga aagagccacc     120
ctctcctgca gggccagtca gagtgttagc agcagctact tcgcctggta ccaacagaaa     180
cctggccagg ctcccaggct cctcatctat ggtacatcca gcagggccac tggcatccca     240
gacaggttca gtggcagtgg gtctgggaca gacttcactc tcaccgtcag cagactggag     300
cctgaggatt ttgcagtgta ttactgtcag cagtatgata ggtcacctcg gacgttcggc     360

```
caagggacca aggtggaaat caaacgtacg gtggctgcac catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca agcagactac gagaaacac aaagtctacg cctgcgaagt cacccatcag    660
ggcctgagct cgcccgtcac aaagagcttc aacagggag agtgt                     705
```

<210> SEQ ID NO 27
<211> LENGTH: 108
<212> TYPE: PRT
<213> ORGANISM: artificial
<220> FEATURE:
<223> OTHER INFORMATION: antibody variable domain

<400> SEQUENCE: 27

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Phe Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
    50                  55                  60

Gly Ser Gly Ser Gly Thr Asp Phe Thr Leu Thr Val Ser Arg Leu Glu
65                  70                  75                  80

Pro Glu Asp Phe Ala Val Tyr Tyr Cys Gln Gln Tyr Asp Arg Ser Pro
                85                  90                  95

Arg Thr Phe Gly Gln Gly Thr Lys Val Glu Ile Lys
            100                 105

<210> SEQ ID NO 28
<211> LENGTH: 17
<212> TYPE: PRT
<213> ORGANISM: artificial
<220> FEATURE:
<223> OTHER INFORMATION: consensus sequence
<220> FEATURE:
<221> NAME/KEY: MISC_FEATURE
<222> LOCATION: (11)..(11)
<223> OTHER INFORMATION: Xaa is Tyr or Ser
<220> FEATURE:
<221> NAME/KEY: MISC_FEATURE
<222> LOCATION: (13)..(13)
<223> OTHER INFORMATION: Xaa is Gln or Arg
<220> FEATURE:
<221> NAME/KEY: MISC_FEATURE
<222> LOCATION: (14)..(14)
<223> OTHER INFORMATION: Xaa is Lys or Arg
<220> FEATURE:
<221> NAME/KEY: MISC_FEATURE
<222> LOCATION: (16)..(16)
<223> OTHER INFORMATION: Xaa is Lys, Arg or Gln

<400> SEQUENCE: 28

Trp Ile Asn Pro Asn Ser Gly Gly Thr Asn Xaa Ala Xaa Xaa Phe Xaa
1               5                   10                  15

Gly

<210> SEQ ID NO 29
<211> LENGTH: 7
<212> TYPE: PRT
<213> ORGANISM: artificial

-continued

```
<220> FEATURE:
<223> OTHER INFORMATION: CDR2 peptide

<400> SEQUENCE: 29

Gly Thr Ser Ser Arg Ala Thr
1               5

<210> SEQ ID NO 30
<211> LENGTH: 12
<212> TYPE: PRT
<213> ORGANISM: artificial
<220> FEATURE:
<223> OTHER INFORMATION: consensus sequence
<220> FEATURE:
<221> NAME/KEY: MISC_FEATURE
<222> LOCATION: (5)..(5)
<223> OTHER INFORMATION: Xaa is Ser or Tyr
<220> FEATURE:
<221> NAME/KEY: MISC_FEATURE
<222> LOCATION: (6)..(6)
<223> OTHER INFORMATION: Xaa is Val, Ile or Leu
<220> FEATURE:
<221> NAME/KEY: MISC_FEATURE
<222> LOCATION: (7)..(7)
<223> OTHER INFORMATION: Xaa is Ser or Asn
<220> FEATURE:
<221> NAME/KEY: MISC_FEATURE
<222> LOCATION: (8)..(8)
<223> OTHER INFORMATION: Xaa is Ser or Cys
<220> FEATURE:
<221> NAME/KEY: MISC_FEATURE
<222> LOCATION: (9)..(9)
<223> OTHER INFORMATION: Xaa is Ser, Thr or Ile
<220> FEATURE:
<221> NAME/KEY: MISC_FEATURE
<222> LOCATION: (11)..(11)
<223> OTHER INFORMATION: Xaa is Phe or Leu

<400> SEQUENCE: 30

Arg Ala Ser Gln Xaa Xaa Xaa Xaa Xaa Tyr Xaa Ala
1               5                   10

<210> SEQ ID NO 31
<211> LENGTH: 463
<212> TYPE: PRT
<213> ORGANISM: artificial sequence
<220> FEATURE:
<223> OTHER INFORMATION: antibody heavy chain

<400> SEQUENCE: 31

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Ala Val Lys Lys
                20                  25                  30

Pro Gly Ala Ser Val Lys Val Ser Cys Lys Ala Ser Gly Tyr Thr Phe
            35                  40                  45

Thr Gly Tyr Tyr Ile His Trp Val Arg Gln Ala Pro Gly Gln Gly Leu
        50                  55                  60

Glu Trp Met Gly Trp Ile Asn Pro Asn Ser Gly Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Ser Met Glu Leu Ser Arg Leu Arg Ser Asp Asp Thr Ala Val
                100                 105                 110

Tyr Phe Cys Ala Arg Asp Arg Trp Leu Asp Ala Phe Asp Ile Trp Gly
            115                 120                 125

Gln Gly Thr Met Val Thr Val Ser Ser Ala Ser Thr Lys Gly Pro Ser
```

```
            130                 135                 140
Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460

<210> SEQ ID NO 32
<211> LENGTH: 1389
<212> TYPE: DNA
<213> ORGANISM: artificial
<220> FEATURE:
<223> OTHER INFORMATION: antibody heavy chain gene

<400> SEQUENCE: 32
atggattgga cctggcgtat tctgtttctg gtggcggcgg cgaccggcgc gcatagccag      60
gtgcagttgg tgcagtctgg ggctgcggtg aagaagcctg ggcctcagt gaaggtctcc     120 tgcaaggctt ctggatacac cttcaccggc tactatatac actgggtgcg acaggcccct    180
ggacaagggc ttgagtggat gggatggatc aaccctaaca gtggtggcac aaactatgca    240
```

```
caaaagtttc agggcagggt caccatgacc aggacacgt ccatcagcac agcctccatg    300
gaactgagca ggctgagatc tgacgacacg gccgtttatt tctgtgcgag agatcggtgg    360
ctggatgctt ttgatatctg gggccaaggg acaatggtca ccgtctcttc tgctagcacc    420
aagggcccat cggtcttccc cctggcgccc tgctccagga gcacctccga gagcacagcg    480
gccctgggct gcctggtcaa ggactacttc cccgaaccgg tgacggtgtc gtggaactca    540
ggcgctctga ccagcggcgt gcacaccttc ccagctgtcc tacagtcctc aggactctac    600
tccctcagca gcgtggtgac cgtgccctcc agcaacttcg gcacccagac ctacacctgc    660
aacgtagatc acaagcccag caacaccaag gtggacaaga cagttgagcg caaatgttgt    720
gtcgagtgcc caccgtgccc agcaccacct gtggcaggac cgtcagtctt cctcttcccc    780
ccaaaaccca aggacaccct catgatctcc cggacccctg aggtcacgtg cgtggtggtg    840
gacgtgagcc acgaagaccc cgaggtccag ttcaactggt acgtggacgg cgtggaggtg    900
cataatgcca agacaaagcc acgggaggag cagttcaaca gcacgttccg tgtggtcagc    960
gtcctcaccg ttgtgcacca ggactggctg aacggcaagg agtacaagtg caaggtctcc   1020
aacaaaggcc tcccagcccc catcgagaaa accatctcca aaaccaaagg cagccccga   1080 gaaccacagg tgtacaccct gcccccatcc cgggaggaga tgaccaagaa ccaggtcagc   1140
ctgacctgcc tggtcaaagg cttctacccc agcgacatcg ccgtggagtg ggagagcaat   1200
gggcagccgg agaacaacta caagaccaca cctcccatgc tggactccga cggctccttc   1260
ttcctctaca gcaagctcac cgtggacaag agcaggtggc agcaggggaa cgtcttctca   1320
tgctccgtga tgcatgaggc tctgcacaac cactacacgc agaagagcct ctccctgtct   1380
ccgggtaaa                                                           1389
```

<210> SEQ ID NO 33
<211> LENGTH: 118
<212> TYPE: PRT
<213> ORGANISM: artificial
<220> FEATURE:
<223> OTHER INFORMATION: antibody variable domain

<400> SEQUENCE: 33

```
Gln Val Gln Leu Val Gln Ser Gly Ala Ala Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Ile His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Ser
65                  70                  75                  80

Met Glu Leu Ser Arg Leu Arg Ser Asp Asp Thr Ala Val Tyr Phe Cys
                85                  90                  95

Ala Arg Asp Arg Trp Leu Asp Ala Phe Asp Ile Trp Gly Gln Gly Thr
            100                 105                 110

Met Val Thr Val Ser Ser
        115
```

<210> SEQ ID NO 34
<211> LENGTH: 7
<212> TYPE: PRT
<213> ORGANISM: artificial
<220> FEATURE:

```
<223> OTHER INFORMATION: consensus sequence
<220> FEATURE:
<221> NAME/KEY: MISC_FEATURE
<222> LOCATION: (2)..(2)
<223> OTHER INFORMATION: Xaa is Ala or Thr

<400> SEQUENCE: 34

Gly Xaa Ser Ser Arg Ala Thr
1               5

<210> SEQ ID NO 35
<211> LENGTH: 17
<212> TYPE: PRT
<213> ORGANISM: artificial
<220> FEATURE:
<223> OTHER INFORMATION: CDR2 peptide

<400> SEQUENCE: 35

Trp Ile Asn Pro Asn Ser Gly Gly Thr Asn Tyr Ala Gln Lys Phe Gln
1               5                   10                  15

Gly

<210> SEQ ID NO 36
<211> LENGTH: 9
<212> TYPE: PRT
<213> ORGANISM: artificial
<220> FEATURE:
<223> OTHER INFORMATION: CDR3 peptide

<400> SEQUENCE: 36

Asp Arg Trp Leu Asp Ala Phe Asp Ile
1               5

<210> SEQ ID NO 37
<211> LENGTH: 235
<212> TYPE: PRT
<213> ORGANISM: artificial
<220> FEATURE:
<223> OTHER INFORMATION: antibody light chain

<400> SEQUENCE: 37

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Tyr
        35                  40                  45

Ile Ser Asn Thr Tyr Leu Ala Trp Phe Gln Gln Lys Pro Gly Gln Ala
    50                  55                  60

Pro Arg Leu Leu Ile Tyr Gly Ala Ala Thr Arg Ala Thr Gly Ile Pro
65                  70                  75                  80

Asp Arg Phe Ser Gly Ser Gly Ser Gly Thr Asp Phe Thr Phe Thr Ile
                85                  90                  95

Ser Arg Leu Glu Pro Glu Asp Phe Ala Val Tyr Tyr Cys Gln Gln Tyr
            100                 105                 110

Gly Ser Ser Pro Trp Thr Phe Gly Gln Gly Thr Thr Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
```

165                 170                 175
Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 38
<211> LENGTH: 705
<212> TYPE: DNA
<213> ORGANISM: artificial
<220> FEATURE:
<223> OTHER INFORMATION: antibody light chain gene

<400> SEQUENCE: 38
atggaaaccc cggcgcagct gctgtttctg ctgctgctgt ggctgccgga taccaccggc    60
gaaattgtgt tgacgcagtc tccaggcacc ctgtctttgt ctccagggga agagccacc    120 ctctcctgca gggccagtca gtatattagc aacacctatt tagcctggtt ccagcagaaa   180
cctggccagg ctcccaggct cctcatctat ggtgcagcca ccagggccac tggcatccca   240
gacaggttca gtggcagtgg gtctgggaca gacttcactt tcaccatcag cagactggag   300
cctgaagatt ttgcagtgta ttactgtcag cagtatggta gctcaccgtg gacgttcggc   360
caagggacca cggtggaaat caaacgtacg gtggctgcac catctgtctt catcttcccg   420
ccatctgatg agcagttgaa atctggaact gcctctgttg tgtgcctgct gaataacttc   480
tatcccagag aggccaaagt acagtggaag gtggataacg ccctccaatc gggtaactcc   540
caggagagtg tcacagagca ggacagcaag gacagcacct acagcctcag cagcaccctg   600
acgctgagca agcagactac gagaaacac aaagtctacg cctgcgaagt cacccatcag   660
ggcctgagct cgcccgtcac aaagagcttc aacaggggag agtgt               705

<210> SEQ ID NO 39
<211> LENGTH: 108
<212> TYPE: PRT
<213> ORGANISM: artificial
<220> FEATURE:
<223> OTHER INFORMATION: antibody variable domain

<400> SEQUENCE: 39

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Tyr Ile Ser Asn Thr
            20                  25                  30

Tyr Leu Ala Trp Phe Gln Gln Lys Pro Gly Gln Ala Pro Arg Leu Leu
        35                  40                  45

Ile Tyr Gly Ala Ala Thr Arg Ala Thr Gly Ile Pro Asp Arg Phe Ser
    50                  55                  60

Gly Ser Gly Ser Gly Thr Asp Phe Thr Phe Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Thr Val Glu Ile Lys
            100                 105

```
<210> SEQ ID NO 40
<211> LENGTH: 12
<212> TYPE: PRT
<213> ORGANISM: artificial
<220> FEATURE:
<223> OTHER INFORMATION: CDR1 peptide

<400> SEQUENCE: 40

Arg Ala Ser Gln Tyr Ile Ser Asn Thr Tyr Leu Ala
1               5                   10

<210> SEQ ID NO 41
<211> LENGTH: 7
<212> TYPE: PRT
<213> ORGANISM: artificial
<220> FEATURE:
<223> OTHER INFORMATION: CDR2 peptide

<400> SEQUENCE: 41

Gly Ala Ala Thr Arg Ala Thr
1               5

<210> SEQ ID NO 42
<211> LENGTH: 9
<212> TYPE: PRT
<213> ORGANISM: artificial
<220> FEATURE:
<223> OTHER INFORMATION: CDR3 peptide

<400> SEQUENCE: 42

Gln Gln Tyr Gly Ser Ser Pro Trp Thr
1               5

<210> SEQ ID NO 43
<211> LENGTH: 463
<212> TYPE: PRT
<213> ORGANISM: artificial
<220> FEATURE:
<223> OTHER INFORMATION: antibody heavy chain

<400> SEQUENCE: 43

Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Gly Tyr Tyr Met His Trp Val Arg Gln Ala Pro Gly Gln Gly Leu
        50                  55                  60

Glu Trp Met Gly Trp Ile Asn Pro Asn Ser Gly Gly Thr Asn Tyr Ala
65                  70                  75                  80

Gln Arg Phe Arg Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Ala Pro Tyr Asp Trp Thr Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175
```

```
Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
450                 455                 460

<210> SEQ ID NO 44
<211> LENGTH: 1389
<212> TYPE: DNA
<213> ORGANISM: artificial
<220> FEATURE:
<223> OTHER INFORMATION: antibody heavy chain gene

<400> SEQUENCE: 44
atggattgga cctggcgtat tctgtttctg gtggcggcgg cgaccggcgc gcatagccag     60
gtgcagttgg tgcagtctgg ggctgaggtg aagaagcctg ggcctcagt gaaggtctcc    120 tgcaaggctt ctggatacac cttcaccggc tactatatgc actgggtgcg acaggcccct    180
ggacaagggc ttgagtggat gggatggatc aaccctaaca gtggtggcac aaactatgca    240
cagaggtttc ggggcagggt caccatgacc agggacacgt ccatcagcac agcctacatg    300
gaactgagca ggctgagatc tgacgacacg gccgtgtatt actgtgcgag agccccgtat    360
gactggacct ttgactactg gggccaggga ccctggtca ccgtctcctc agctagcacc    420
aagggcccat cggtcttccc cctggcgccc tgctccagga gcacctccga gagcacagcg    480
```

```
gccctgggct gcctggtcaa ggactacttc cccgaaccgg tgacggtgtc gtggaactca    540
ggcgctctga ccagcggcgt gcacaccttc ccagctgtcc tacagtcctc aggactctac    600
tccctcagca gcgtggtgac cgtgccctcc agcaacttcg gcacccagac ctacacctgc    660
aacgtagatc acaagcccag caacaccaag gtggacaaga cagttgagcg caaatgttgt    720
gtcgagtgcc caccgtgccc agcaccacct gtggcaggac cgtcagtctt cctcttcccc    780
ccaaaaccca aggacaccct catgatctcc cggacccctg aggtcacgtg cgtggtggtg    840
gacgtgagcc acgaagaccc cgaggtccag ttcaactggt acgtggacgg cgtggaggtg    900
cataatgcca agacaaagcc acgggaggag cagttcaaca gcacgttccg tgtggtcagc    960
gtcctcaccg ttgtgcacca ggactggctg aacggcaagg agtacaagtg caaggtctcc    1020
aacaaaggcc tcccagcccc catcgagaaa accatctcca aaaccaaagg cagccccga    1080 gaaccacagg tgtacaccct gcccccatcc cgggaggaga tgaccaagaa ccaggtcagc    1140
ctgacctgcc tggtcaaagg cttctacccc agcgacatcg ccgtggagtg ggagagcaat    1200
gggcagccgg agaacaacta caagaccaca cctcccatgc tggactccga cggctccttc    1260
ttcctctaca gcaagctcac cgtggacaag agcaggtggc agcaggggaa cgtcttctca    1320
tgctccgtga tgcatgaggc tctgcacaac cactacacgc agaagagcct ctccctgtct    1380
ccgggtaaa                                                            1389

<210> SEQ ID NO 45
<211> LENGTH: 118
<212> TYPE: PRT
<213> ORGANISM: artificial
<220> FEATURE:
<223> OTHER INFORMATION: antibody variable domain

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Arg Phe
        50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ala Pro Tyr Asp Trp Thr Phe Asp Tyr Trp Gly Gln Gly Thr
            100                 105                 110

Leu Val Thr Val Ser Ser
        115

<210> SEQ ID NO 46
<211> LENGTH: 9
<212> TYPE: PRT
<213> ORGANISM: artificial
<220> FEATURE:
<223> OTHER INFORMATION: consensus sequence
<220> FEATURE:
<221> NAME/KEY: MISC_FEATURE
<222> LOCATION: (3)..(3)
<223> OTHER INFORMATION: Xaa is Tyr or Ser
<220> FEATURE:
<221> NAME/KEY: MISC_FEATURE
```

```
<222> LOCATION: (4)..(4)
<223> OTHER INFORMATION: Xaa is Phe, Gly or Ala
<220> FEATURE:
<221> NAME/KEY: MISC_FEATURE
<222> LOCATION: (5)..(5)
<223> OTHER INFORMATION: Xaa is Ser, Thr or Trp
<220> FEATURE:
<221> NAME/KEY: MISC_FEATURE
<222> LOCATION: (6)..(6)
<223> OTHER INFORMATION: Xaa is Val, Ser or Phe
<220> FEATURE:
<221> NAME/KEY: MISC_FEATURE
<222> LOCATION: (7)..(7)
<223> OTHER INFORMATION: Xaa is Phe or Pro
<220> FEATURE:
<221> NAME/KEY: MISC_FEATURE
<222> LOCATION: (8)..(8)
<223> OTHER INFORMATION: Xaa is Arg, Trp, or Ile

<400> SEQUENCE: 46

Gln Gln Xaa Xaa Xaa Xaa Xaa Xaa Thr
1               5

<210> SEQ ID NO 47
<211> LENGTH: 17
<212> TYPE: PRT
<213> ORGANISM: artificial
<220> FEATURE:
<223> OTHER INFORMATION: CDR2 peptide

<400> SEQUENCE: 47

Trp Ile Asn Pro Asn Ser Gly Gly Thr Asn Tyr Ala Gln Arg Phe Arg
1               5                   10                  15

Gly

<210> SEQ ID NO 48
<211> LENGTH: 9
<212> TYPE: PRT
<213> ORGANISM: artificial
<220> FEATURE:
<223> OTHER INFORMATION: CDR3 peptide

<400> SEQUENCE: 48

Ala Pro Tyr Asp Trp Thr Phe Asp Tyr
1               5

<210> SEQ ID NO 49
<211> LENGTH: 235
<212> TYPE: PRT
<213> ORGANISM: artificial
<220> FEATURE:
<223> OTHER INFORMATION: antibody light chain

<400> SEQUENCE: 49

Met Glu Thr Pro Ala Gln Leu Leu Phe Leu Leu Leu Leu Trp Leu Pro
1               5                   10                  15

Asp Thr Thr Gly Glu Val Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Cys Ser Ser Tyr Leu Ala Trp Tyr Gln Gln Lys Pro Asp Gln Ala
    50                  55                  60

Pro Arg Leu Leu Ile Ser Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95
```

```
Ser Ser Leu Glu Pro Glu Asp Phe Ala Val Tyr Tyr Cys Gln Gln Tyr
            100                 105                 110

Asp Arg Ser Pro Arg Thr Phe Gly Gln Gly Thr Lys Val Glu Ile Lys
            115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 50
<211> LENGTH: 705
<212> TYPE: DNA
<213> ORGANISM: artificial
<220> FEATURE:
<223> OTHER INFORMATION: antibody light chain gene

<400> SEQUENCE: 50
atggaaaccc cggcgcagct gctgtttctg ctgctgctgt ggctgccgga taccaccggc     60
gaagttgtgt tgacgcagtc tccaggcacc ctgtctttgt ctccagggga aagagccacc    120
ctctcctgca gggccagtca gagcgtttgc agcagctact tagcctggta ccagcagaaa    180
cctgaccagg ctcccaggct cctcatctct ggtgcgtcca gcagggccac tggcatccca    240
gacaggttca gtggcagtgg gtctgggaca gacttcactc tcaccatcag cagcctggag    300
cctgaagatt ttgcagtgta ttactgtcag cagtatgata ggtcacctcg acgttcggc     360 caagggacca aggtggagat caaacgtacg gtggctgcac catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca aagcagacta cgagaaacac aaagtctacg cctgcgaagt cacccatcag    660
ggcctgagct cgcccgtcac aaagagcttc aacaggggag agtgt                    705

<210> SEQ ID NO 51
<211> LENGTH: 108
<212> TYPE: PRT
<213> ORGANISM: artificial
<220> FEATURE:
<223> OTHER INFORMATION: antibody variable domain

<400> SEQUENCE: 51

Glu Val Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Cys Ser Ser
            20                  25                  30

Tyr Leu Ala Trp Tyr Gln Gln Lys Pro Asp Gln Ala Pro Arg Leu Leu
        35                  40                  45
```

```
Ile Ser Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Tyr Asp Arg Ser Pro
                 85                  90                  95

Arg Thr Phe Gly Gln Gly Thr Lys Val Glu Ile Lys
                100                 105

<210> SEQ ID NO 52
<211> LENGTH: 12
<212> TYPE: PRT
<213> ORGANISM: artificial
<220> FEATURE:
<223> OTHER INFORMATION: CDR1 peptide

<400> SEQUENCE: 52

Arg Ala Ser Gln Ser Val Cys Ser Ser Tyr Leu Ala
1               5                   10

<210> SEQ ID NO 53
<211> LENGTH: 144
<212> TYPE: PRT
<213> ORGANISM: Macaca fascicularis

<400> SEQUENCE: 53

Met Trp Leu Gln Gly Leu Leu Leu Gly Thr Val Ala Cys Ser Ile
1               5                   10                  15

Ser Ala Pro Ala Arg Ser Pro Ser Pro Gly Thr Gln Pro Trp Glu His
                 20                  25                  30

Val Asn Ala Ile Gln Glu Ala Arg Arg Leu Leu Asn Leu Ser Arg Asp
             35                  40                  45

Thr Ala Ala Glu Met Asn Lys Thr Val Glu Val Val Ser Glu Met Phe
 50                  55                  60

Asp Leu Gln Glu Pro Ser Cys Leu Gln Thr Arg Leu Glu Leu Tyr Lys
 65                  70                  75                  80

Gln Gly Leu Gln Gly Ser Leu Thr Lys Leu Lys Gly Pro Leu Thr Met
                 85                  90                  95

Met Ala Ser His Tyr Lys Gln His Cys Pro Pro Thr Pro Glu Thr Ser
                100                 105                 110

Cys Ala Thr Gln Ile Ile Thr Phe Gln Ser Phe Lys Glu Asn Leu Lys
            115                 120                 125

Asp Phe Leu Leu Val Ile Pro Phe Asp Cys Trp Glu Pro Val Gln Glu
        130                 135                 140

<210> SEQ ID NO 54
<211> LENGTH: 144
<212> TYPE: PRT
<213> ORGANISM: Canis familiaris

<400> SEQUENCE: 54

Met Trp Leu Gln Asn Leu Leu Phe Leu Gly Thr Val Val Cys Ser Ile
1               5                   10                  15

Ser Ala Pro Thr Arg Ser Pro Thr Leu Val Thr Arg Pro Ser Gln His
                 20                  25                  30

Val Asp Ala Ile Gln Glu Ala Leu Ser Leu Leu Asn Asn Ser Asn Asp
             35                  40                  45

Val Thr Ala Val Met Asn Lys Ala Val Lys Val Val Ser Glu Val Phe
 50                  55                  60
```

```
Asp Pro Glu Gly Pro Thr Cys Leu Glu Thr Arg Leu Gln Leu Tyr Lys
 65                  70                  75                  80

Glu Gly Leu Gln Gly Ser Leu Thr Ser Leu Lys Asn Pro Leu Thr Met
                 85                  90                  95

Met Ala Asn His Tyr Lys Gln His Cys Pro Pro Thr Pro Glu Ser Pro
            100                 105                 110

Cys Ala Thr Gln Asn Ile Asn Phe Lys Ser Phe Lys Glu Asn Leu Lys
            115                 120                 125

Asp Phe Leu Phe Asn Ile Pro Phe Asp Cys Trp Lys Pro Val Lys Lys
            130                 135                 140
```

<210> SEQ ID NO 55
<211> LENGTH: 463
<212> TYPE: PRT
<213> ORGANISM: artificial
<220> FEATURE:
<223> OTHER INFORMATION: antibody heavy chain

<400> SEQUENCE: 55

```
Met Asp Trp Thr Trp Arg Ile Leu Phe Leu Val Ala Ala Ala Thr Gly
 1                5                  10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Gly Tyr Tyr Ile His Trp Val Arg Gln Ala Pro Gly Gln Gly Leu
        50                  55                  60

Glu Trp Met Gly Trp Ile Asn Pro Asn Ser Gly Gly Arg Asn Tyr Ala
 65                 70                  75                  80

Gln Lys Phe Gln Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Asp Arg Trp Leu Asp Ala Phe Glu Ile Trp Gly
        115                 120                 125

Gln Gly Thr Met Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
```

|                                     |                                  | 290                                |                                      |                                  | 295                                  |                                     |                                  | 300                                  |                                  |                                      |                                  |
| ----------------------------------- | -------------------------------- | ---------------------------------- | ------------------------------------ | -------------------------------- | ------------------------------------ | ----------------------------------- | -------------------------------- | ------------------------------------ | -------------------------------- | ------------------------------------ | -------------------------------- |

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
            325                 330                 335

Cys Lys Val Ser Asn Lys Gly Leu Pro Ala Pro Ile Glu Lys Thr Ile
                340                 345                 350

Ser Lys Thr Lys Gly Gln Pro Arg Glu Pro Gln Val Tyr Thr Leu Pro
            355                 360                 365

Pro Ser Arg Glu Glu Met Thr Lys Asn Gln Val Ser Leu Thr Cys Leu
        370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460

```
<210> SEQ ID NO 56
<211> LENGTH: 1389
<212> TYPE: DNA
<213> ORGANISM: artificial
<220> FEATURE:
<223> OTHER INFORMATION: antibody heavy chain gene

<400> SEQUENCE: 56
atggattgga cctggcgtat tctgtttctg gtggcggcgg cgaccggcgc gcatagccag      60
gtgcagctgg tgcagtctgg ggctgaggtg aagaagcctg ggcctcagt gaaggtctcc     120 tgcaaggctt ctggatacac cttcaccggc tactatatac actgggtgcg acaggcccct    180
ggacaagggc ttgagtggat gggatggatc aaccctaaca gtggtggcag aaactatgca    240
cagaagtttc agggcagggt caccatgacc aggacacgt ccatcagcac agcctacatg     300
gagctgagca ggctgagatc tgacgacacg gccgtgtatt actgtgcgag agaccggtgg    360
ctggatgctt ttgagatctg ggccaaggg acaatggtca ccgtctcttc agctagcacc     420
aagggcccat cggtcttccc cctggcgccc tgctccagga gcacctccga gagcacagcg    480
gccctgggct gcctggtcaa ggactacttc cccgaaccgg tgacggtgtc gtggaactca    540
ggcgctctga ccagcggcgt gcacaccttc ccagctgtcc tacagtcctc aggactctac    600
tccctcagca gcgtggtgac cgtgccctcc agcaacttcg gcacccagac ctacacctgc    660
aacgtagatc acaagcccag caacaccaag gtggacaaga cagttgagcg caaatgttgt    720
gtcgagtgcc caccgtgccc agcaccacct gtggcaggac cgtcagtctt cctcttcccc    780
ccaaaaccca aggacaccct catgatctcc cggacccctg aggtcacgtg cgtggtggtg    840
gacgtgagcc acgaagaccc cgaggtccag ttcaactggt acgtggacgg cgtggaggtg    900
cataatgcca agacaaagcc acgggaggag cagttcaaca gcacgttccg tgtggtcagc    960
gtcctcaccg ttgtgcacca ggactggctg aacggcaagg agtacaagtg caaggtctcc   1020
aacaaaggcc tcccagcccc catcgagaaa accatctcca aaaccaaagg gcagccccga   1080
gaaccacagg tgtacaccct gcccccatcc cgggaggaga tgaccaagaa ccaggtcagc   1140
```

-continued

```
ctgacctgcc tggtcaaagg cttctacccc agcgacatcg ccgtggagtg ggagagcaat    1200
gggcagccgg agaacaacta caagaccaca cctcccatgc tggactccga cggctccttc    1260
ttcctctaca gcaagctcac cgtggacaag agcaggtggc agcagggaa cgtcttctca    1320 tgctccgtga tgcatgaggc tctgcacaac cactacacgc agaagagcct ctccctgtct    1380
ccgggtaaa                                                             1389
```

<210> SEQ ID NO 57
<211> LENGTH: 118
<212> TYPE: PRT
<213> ORGANISM: artificial
<220> FEATURE:
<223> OTHER INFORMATION: antibody variable domain

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45

Gly Trp Ile Asn Pro Asn Ser Gly Gly Arg Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Arg Trp Leu Asp Ala Phe Glu Ile Trp Gly Gln Gly Thr
            100                 105                 110

Met Val Thr Val Ser Ser
        115

<210> SEQ ID NO 58
<211> LENGTH: 81
<212> TYPE: PRT
<213> ORGANISM: Mus musculus

<400> SEQUENCE: 58

Met Trp Leu Gln Asn Leu Leu Phe Leu Gly Ile Val Val Tyr Ser Leu
1               5                   10                  15

Ser Ala Pro Thr Arg Ser Pro Ile Thr Val Thr Arg Pro Trp Lys His
            20                  25                  30

Val Glu Ala Ile Lys Glu Ala Leu Asn Leu Leu Asp Asp Met Pro Val
        35                  40                  45

Thr Leu Asn Glu Glu Val Glu Val Val Ser Asn Glu Ile Asp Ser Leu
    50                  55                  60

Lys Thr Phe Leu Thr Asp Ile Pro Phe Glu Cys Lys Lys Pro Val Gln
65                  70                  75                  80

Lys

<210> SEQ ID NO 59
<211> LENGTH: 17
<212> TYPE: PRT
<213> ORGANISM: artificial
<220> FEATURE:
<223> OTHER INFORMATION: CDR2 peptide

<400> SEQUENCE: 59

Trp Ile Asn Pro Asn Ser Gly Gly Arg Asn Tyr Ala Gln Lys Phe Gln

```
1               5                   10                  15
Gly

<210> SEQ ID NO 60
<211> LENGTH: 9
<212> TYPE: PRT
<213> ORGANISM: artificial
<220> FEATURE:
<223> OTHER INFORMATION: CDR3 peptide

<400> SEQUENCE: 60

Asp Arg Trp Leu Asp Ala Phe Glu Ile
1               5

<210> SEQ ID NO 61
<211> LENGTH: 235
<212> TYPE: PRT
<213> ORGANISM: artificial
<220> FEATURE:
<223> OTHER INFORMATION: antibody light chain

<400> SEQUENCE: 61

Met Ala Trp Ala Pro Leu Leu Leu Thr Leu Leu Ala His Cys Thr Gly
1               5                   10                  15

Ser Trp Ala Asn Phe Met Leu Ala Gln Pro His Ser Val Ser Glu Ser
            20                  25                  30

Pro Gly Lys Thr Val Thr Ile Ser Cys Ile Arg Thr Ser Gly Ser Ile
        35                  40                  45

Ala Ser Asn Tyr Val Gln Trp Tyr Gln Gln Arg Pro Gly Ser Ser Pro
    50                  55                  60

Thr Thr Val Ile Tyr Glu Asp Asp Gln Arg Pro Ser Gly Val Pro Asp
65                  70                  75                  80

Arg Phe Ser Gly Ser Ile Asp Ser Ser Ser Asn Ser Ala Ser Leu Thr
                85                  90                  95

Ile Ser Gly Leu Lys Thr Glu Asp Glu Ala Asp Tyr Tyr Cys Gln Ser
            100                 105                 110

Cys Asp Ile Ser Asn Val Val Phe Gly Gly Gly Thr Lys Leu Thr Val
        115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
    210                 215                 220

Val Glu Lys Thr Val Ala Pro Thr Glu Cys Ser
225                 230                 235

<210> SEQ ID NO 62
<211> LENGTH: 705
<212> TYPE: DNA
<213> ORGANISM: artificial
<220> FEATURE:
<223> OTHER INFORMATION: antibody light chain gene
```

-continued

```
<400> SEQUENCE: 62
atggcgtggg cgccgctgct gctgaccctg ctggcgcatt gcaccggcag ctgggcgaat    60
tttatgctgg ctcagcccca ctctgtgtcg gagtctccgg ggaagacggt aaccatctcc   120
tgtattcgca ccagtggcag cattgccagc aactatgtac agtggtatca gcagcgcccg   180
ggcagttccc ccaccactgt gatctatgag gatgaccaaa gaccctctgg ggtccctgat   240
cgattctctg ctccatcga cagctcctcc aattctgcct ccctcaccat ctctggactg   300
aagactgagg acgaggctga ctactactgt cagtcttgtg atatcagcaa tgtggtattc   360
ggcggaggga ccaagctgac cgtcctaggc caaccgaaag cggcgccctc ggtcactctg   420
ttcccgccct cctctgagga gcttcaagcc aacaaggcca cactggtgtg tctcataagt   480
gacttctacc cgggagccgt gacagtggcc tggaaggcag atagcagccc cgtcaaggcg   540
ggagtggaga ccaccacacc ctccaaacaa agcaacaaca gtacgcggc cagcagctat    600 ctgagcctga cgcctgagca gtggaagtcc cacagaagct acagctgcca ggtcacgcat   660
gaagggagca ccgtggagaa gacagtggcc cctacagaat gttca                  705
```

```
<210> SEQ ID NO 63
<211> LENGTH: 110
<212> TYPE: PRT
<213> ORGANISM: artificial
<220> FEATURE:
<223> OTHER INFORMATION: antibody variable domain

<400> SEQUENCE: 63

Asn Phe Met Leu Ala Gln Pro His Ser Val Ser Glu Ser Pro Gly Lys
 1               5                  10                  15

Thr Val Thr Ile Ser Cys Ile Arg Thr Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Cys Asp Ile
                85                  90                  95

Ser Asn Val Val Phe Gly Gly Gly Thr Lys Leu Thr Val Leu
            100                 105                 110
```

```
<210> SEQ ID NO 64
<211> LENGTH: 13
<212> TYPE: PRT
<213> ORGANISM: artificial
<220> FEATURE:
<223> OTHER INFORMATION: CDR1 peptide

<400> SEQUENCE: 64

Ile Arg Thr Ser Gly Ser Ile Ala Ser Asn Tyr Val Gln
 1               5                  10
```

```
<210> SEQ ID NO 65
<211> LENGTH: 7
<212> TYPE: PRT
<213> ORGANISM: artificial
<220> FEATURE:
<223> OTHER INFORMATION: CDR2 peptide

<400> SEQUENCE: 65
```

```
Glu Asp Asp Gln Arg Pro Ser
1               5

<210> SEQ ID NO 66
<211> LENGTH: 9
<212> TYPE: PRT
<213> ORGANISM: artificial
<220> FEATURE:
<223> OTHER INFORMATION: CDR3 peptide

<400> SEQUENCE: 66

Gln Ser Cys Asp Ile Ser Asn Val Val
1               5

<210> SEQ ID NO 67
<211> LENGTH: 463
<212> TYPE: PRT
<213> ORGANISM: artificial
<220> FEATURE:
<223> OTHER INFORMATION: antibody heavy chain

<400> SEQUENCE: 67

Met Asp Trp Thr Trp Ser Ile Leu Phe Leu Val Ala Ala Pro Thr Gly
1               5                  10                  15

Ala His Ser Gln Val Gln Leu Val Gln Ser Gly Ala Glu Val Lys Gln
                20                  25                  30

Pro Gly Ala Ser Val Lys Val Ser Cys Glu Ala Ser Gly Tyr Thr Phe
            35                  40                  45

Thr Ser Tyr Gly Ile Ser Trp Val Arg Gln Ala Pro Gly Gln Gly Leu
        50                  55                  60

Glu Trp Met Gly Trp Ile Ser Ala Tyr Asn Gly Asn Thr Asp Tyr Ala
65                  70                  75                  80

Gln Lys Leu Gln Gly Arg Val Thr Met Thr Thr Asp Thr Ser Thr Ser
                85                  90                  95

Ala Ala Tyr Met Glu Leu Arg Ser Leu Arg Ser Asp Asp Thr Ala Val
            100                 105                 110

Tyr Tyr Cys Ala Arg Gln Arg Tyr Tyr Tyr Ser Met Asp Val Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285
```

```
Val Gln Phe Asn Trp Tyr Val Asp Gly Val Glu Val His Asn Ala Lys
        290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                    325                 330                 335

Cys Lys Val Ser Asn Lys Gly Leu Pro Ala Pro Ile Glu Lys Thr Ile
                340                 345                 350

Ser Lys Thr Lys Gly Gln Pro Arg Glu Pro Gln Val Tyr Thr Leu Pro
            355                 360                 365

Pro Ser Arg Glu Glu Met Thr Lys Asn Gln Val Ser Leu Thr Cys Leu
        370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                    405                 410                 415

Asp Gly Ser Phe Phe Leu Tyr Ser Lys Leu Thr Val Asp Lys Ser Arg
                420                 425                 430

Trp Gln Gln Gly Asn Val Phe Ser Cys Ser Val Met His Glu Ala Leu
            435                 440                 445

His Asn His Tyr Thr Gln Lys Ser Leu Ser Leu Ser Pro Gly Lys
        450                 455                 460

<210> SEQ ID NO 68
<211> LENGTH: 1389
<212> TYPE: DNA
<213> ORGANISM: artificial
<220> FEATURE:
<223> OTHER INFORMATION: antibody heavy chain gene

<400> SEQUENCE: 68
atggattgga cctggagcat tctgtttctg gtggcggcgc cgaccggcgc gcatagccag        60
gttcagctgg tgcagtctgg agctgaggtg aagcagcctg ggcctcagt gaaggtctcc       120 tgcgaggctt ctggttacac cttcaccagc tatggtatca gctgggtgcg acaggccct       180 ggacaagggc ttgagtggat gggatggatc agcgcttaca atggtaacac agactatgca      240
cagaagctcc agggcagagt caccatgacc acagacacat ccacgagcgc agcctacatg      300
gagctgagga gcctgagatc tgacgacacg gccgtgtatt actgtgcgag acaacggtat      360
tactacagta tggacgtctg gggccaaggg accacggtca ccgtctcctc agctagcacc      420
aagggcccat cggtcttccc cctggcgccc tgctccagga gcacctccga gagcacagcg      480
gccctgggct gcctggtcaa ggactacttc cccgaaccgg tgacggtgtc gtggaactca      540
ggcgctctga ccagcggcgt gcacaccttc ccagctgtcc tacagtcctc aggactctac      600
tccctcagca gcgtggtgac cgtgccctcc agcaacttcg gcacccagac ctacacctgc      660
aacgtagatc acaagcccag caacaccaag gtggacaaga cagttgagcg caaatgttgt      720
gtcgagtgcc caccgtgccc agcaccacct gtggcaggac cgtcagtctt cctcttcccc      780
ccaaaaccca aggacaccct catgatctcc cggacccctg aggtcacgtg cgtggtggtg      840
gacgtgagcc acgaagaccc cgaggtccag ttcaactggt acgtggacgg cgtggaggtg      900
cataatgcca agacaaagcc acgggaggag cagttcaaca gcacgttccg tgtggtcagc      960
gtcctcaccg ttgtgcacca ggactggctg aacggcaagg agtacaagtg caaggtctcc     1020
aacaaaggcc tcccagcccc catcgagaaa accatctcca aaaccaaagg cagcccccga     1080
gaaccacagg tgtacaccct gcccccatcc cgggaggaga tgaccaagaa ccaggtcagc     1140
```

```
ctgacctgcc tggtcaaagg cttctacccc agcgacatcg ccgtggagtg ggagagcaat    1200
gggcagccgg agaacaacta caagaccaca cctcccatgc tggactccga cggctccttc    1260
ttcctctaca gcaagctcac cgtggacaag agcaggtggc agcagggaa cgtcttctca     1320 tgctccgtga tgcatgaggc tctgcacaac cactacacgc agaagagcct ctccctgtct    1380
ccgggtaaa                                                            1389
```

```
<210> SEQ ID NO 69
<211> LENGTH: 118
<212> TYPE: PRT
<213> ORGANISM: artificial
<220> FEATURE:
<223> OTHER INFORMATION: antibody variable domain

<400> SEQUENCE: 69

Gln Val Gln Leu Val Gln Ser Gly Ala Glu Val Lys Gln Pro Gly Ala
1               5                   10                  15

Ser Val Lys Val Ser Cys Glu Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asp Tyr Ala Gln Lys Leu
    50                  55                  60

Gln Gly Arg Val Thr Met Thr Thr Asp Thr Ser Thr Ser Ala Ala Tyr
65                  70                  75                  80

Met Glu Leu Arg Ser Leu Arg Ser Asp Asp Thr Ala Val Tyr Tyr Cys
                85                  90                  95

Ala Arg Gln Arg Tyr Tyr Tyr Ser Met Asp Val Trp Gly Gln Gly Thr
            100                 105                 110

Thr Val Thr Val Ser Ser
        115
```

```
<210> SEQ ID NO 70
<211> LENGTH: 5
<212> TYPE: PRT
<213> ORGANISM: artificial
<220> FEATURE:
<223> OTHER INFORMATION: CDR1 peptide

<400> SEQUENCE: 70

Ser Tyr Gly Ile Ser
1               5
```

```
<210> SEQ ID NO 71
<211> LENGTH: 17
<212> TYPE: PRT
<213> ORGANISM: artificial
<220> FEATURE:
<223> OTHER INFORMATION: CDR2 peptide

<400> SEQUENCE: 71

Trp Ile Ser Ala Tyr Asn Gly Asn Thr Asp Tyr Ala Gln Lys Leu Gln
1               5                   10                  15

Gly
```

```
<210> SEQ ID NO 72
<211> LENGTH: 9
<212> TYPE: PRT
<213> ORGANISM: artificial
<220> FEATURE:
<223> OTHER INFORMATION: CDR3 peptide
```

<400> SEQUENCE: 72

Gln Arg Tyr Tyr Tyr Ser Met Asp Val
1               5

<210> SEQ ID NO 73
<211> LENGTH: 235
<212> TYPE: PRT
<213> ORGANISM: artificial
<220> FEATURE:
<223> OTHER INFORMATION: antibody light chain

<400> SEQUENCE: 73

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Val
    50                  55                  60

Pro Arg Leu Leu Ile Tyr Gly Thr Ser Ser Arg Ala Thr Gly Ile Pro
65                  70                  75                  80

Asp Arg Phe Ser Gly Ser Gly Ser Gly Thr Asp Phe Thr Leu Thr Val
                85                  90                  95

Ser Arg Leu Glu Pro Glu Asp Phe Ala Val Tyr Tyr Cys Leu Gln Tyr
            100                 105                 110

Asp Arg Ser Pro Arg Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 74
<211> LENGTH: 705
<212> TYPE: DNA
<213> ORGANISM: artificial
<220> FEATURE:
<223> OTHER INFORMATION: antibody light chain gene

<400> SEQUENCE: 74
atggaaaccc cggcgcagct gctgtttctg ctgctgctgt ggctgccgga taccaccggc      60
gaaattgtgt tgacgcagtc tccaggcacc ctgtctttgt ctccagggga aagagccacc     120
ctctcctgca gggccagtca gagtgttagc agcagctact tagcctggta ccagcagaaa     180
cctggccagg ttcccaggct cctcatctat ggtacatcca gcagggccac tggcatccca     240
gacaggttca gtggcagtgg gtctgggaca gacttcactc tcaccgtcag cagactggag     300

```
cctgaagatt tgcagtgta ttactgtctc cagtatgata ggtcacctcg gacgttcggc    360
caagggacca aggtggaaat caaacgtacg gtggctgcac atctgtctt catcttcccg    420 ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca agcagactac gagaaacac aaagtctacg cctgcgaagt cacccatcag    660
ggcctgagct cgcccgtcac aaagagcttc aacaggggag agtgt    705
```

```
<210> SEQ ID NO 75
<211> LENGTH: 108
<212> TYPE: PRT
<213> ORGANISM: artificial
<220> FEATURE:
<223> OTHER INFORMATION: antibody variable domain

<400> SEQUENCE: 75
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Val Pro Arg Leu Leu
        35                  40                  45

Ile Tyr Gly Thr Ser Ser Arg Ala Thr Gly Ile Pro Asp Arg Phe Ser
    50                  55                  60

Gly Ser Gly Ser Gly Thr Asp Phe Thr Leu Thr Val Ser Arg Leu Glu
65                  70                  75                  80

Pro Glu Asp Phe Ala Val Tyr Tyr Cys Leu Gln Tyr Asp Arg Ser Pro
                85                  90                  95

Arg Thr Phe Gly Gln Gly Thr Lys Val Glu Ile Lys
            100                 105

```
<210> SEQ ID NO 76
<211> LENGTH: 127
<212> TYPE: PRT
<213> ORGANISM: Rattus rattus

<400> SEQUENCE: 76
```

Ala Pro Thr Arg Ser Pro Asn Pro Val Thr Arg Pro Trp Lys His Val
1               5                   10                  15

Asp Ala Ile Lys Glu Ala Leu Ser Leu Leu Asn Asp Met Arg Ala Leu
            20                  25                  30

Glu Asn Glu Lys Asn Glu Asp Val Asp Ile Ile Ser Asn Glu Phe Ser
        35                  40                  45

Ile Gln Arg Pro Thr Cys Val Gln Thr Arg Leu Lys Leu Tyr Lys Gln
    50                  55                  60

Gly Leu Arg Gly Asn Leu Thr Lys Leu Asn Gly Ala Leu Thr Met Ile
65                  70                  75                  80

Ala Ser His Tyr Gln Thr Asn Cys Pro Pro Thr Pro Glu Thr Asp Cys
                85                  90                  95

Glu Ile Glu Val Thr Thr Phe Glu Asp Phe Ile Lys Asn Leu Lys Gly
            100                 105                 110

Phe Leu Phe Asp Ile Pro Phe Asp Cys Trp Lys Pro Val Gln Lys
        115                 120                 125

<210> SEQ ID NO 77

```
<211> LENGTH: 7
<212> TYPE: PRT
<213> ORGANISM: artificial
<220> FEATURE:
<223> OTHER INFORMATION: CDR2 peptide

<400> SEQUENCE: 77

Gly Thr Ser Ser Arg Ala Thr
1               5

<210> SEQ ID NO 78
<211> LENGTH: 9
<212> TYPE: PRT
<213> ORGANISM: artificial
<220> FEATURE:
<223> OTHER INFORMATION: CDR3 peptide

<400> SEQUENCE: 78

Leu Gln Tyr Asp Arg Ser Pro Arg Thr
1               5

<210> SEQ ID NO 79
<211> LENGTH: 462
<212> TYPE: PRT
<213> ORGANISM: artificial
<220> FEATURE:
<223> OTHER INFORMATION: antibody heavy chain

<400> SEQUENCE: 79

Met Asp Trp Thr Trp Ser Ile Leu Phe Leu Val Ala Ala Pro Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Gly Tyr Tyr Met His Trp Val Arg Gln Ala Pro Gly Gln Gly Leu
        50                  55                  60

Glu Trp Met Gly Trp Ile Asn Pro Asn Ser Gly Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Tyr Met Glu Leu Ser Trp Leu Arg Ser Asp Asp Thr Ala Val
            100                 105                 110

Tyr Tyr Cys Ala Arg Asp Arg Trp Leu Asp Ala Phe Asp Ile Trp Gly
        115                 120                 125

Gln Gly Thr Met Val Thr Val Ser Ala Ser Thr Lys Gly Pro Ser Val
130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Asn Phe Gly Thr Gln Thr Tyr Thr Cys Asn Val Asp His Lys
    210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
```

```
            245                 250                 255
Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Phe Arg Val Val Ser Val
305                 310                 315                 320

Leu Thr Val Val His Gln Asp Trp Leu Asn Gly Lys Glu Tyr Lys Cys
                325                 330                 335

Lys Val Ser Asn Lys Gly Leu Pro Ala Pro Ile Glu Lys Thr Ile Ser
            340                 345                 350

Lys Thr Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Met Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 80
<211> LENGTH: 1386
<212> TYPE: DNA
<213> ORGANISM: artificial
<220> FEATURE:
<223> OTHER INFORMATION: antibody heavy chain gene

<400> SEQUENCE: 80
atggattgga cctggagcat tctgtttctg gtggcggcgc cgaccggcgc gcatagccag      60
gtgcagctgg tgcagtctgg ggctgaggtg aagaagcctg ggcctcagt gaaggtctcc     120 tgcaaggctt ctggatacac cttcaccggc tactatatgc actgggtgcg acaggcccct    180
ggacaagggc ttgagtggat gggatggatc aaccctaaca gtggtggcac aaactatgca    240
cagaagtttc agggcagggt caccatgacc aggacacgt ccatcagcac agcctacatg     300
gagctgagct ggctgagatc tgacgacacg gccgtatatt actgtgcgag accggtgg     360 ctggatgctt ttgatatctg gggccaaggg acaatggtca ccgtctctgc tagcaccaag    420
ggcccatcgg tcttccccct ggcgccctgc tccaggagca cctccgagag cacagcggcc    480
ctgggctgcc tggtcaagga ctacttcccc gaaccggtga cggtgtcgtg gaactcaggc    540
gctctgacca gcggcgtgca caccttccca gctgtcctac agtcctcagg actctactcc    600
ctcagcagcg tggtgaccgt gccctccagc aacttcggca cccagaccta cacctgcaac    660
gtagatcaca agcccagcaa caccaaggtg gacaagacag ttgagcgcaa atgttgtgtc    720
gagtgcccac cgtgcccagc accacctgtg gcaggaccgt cagtcttcct cttccccca    780 aaacccaagg acaccctcat gatctcccgg acccctgagg tcacgtgcgt ggtggtggac    840
gtgagccacg aagaccccga ggtccagttc aactggtacg tggacggcgt ggaggtgcat    900
```

```
aatgccaaga caaagccacg ggaggagcag ttcaacagca cgttccgtgt ggtcagcgtc    960
ctcaccgttg tgcaccagga ctggctgaac ggcaaggagt acaagtgcaa ggtctccaac   1020
aaaggcctcc cagcccccat cgagaaaacc atctccaaaa ccaaagggca gccccgagaa   1080
ccacaggtgt acaccctgcc cccatcccgg gaggagatga ccaagaacca ggtcagcctg   1140
acctgcctgg tcaaaggctt ctaccccagc gacatcgccg tggagtggga gagcaatggg   1200
cagccggaga caactacaa gaccacacct cccatgctgg actccgacgg ctccttcttc    1260
ctctacagca agctcaccgt ggacaagagc aggtggcagc aggggaacgt cttctcatgc   1320
tccgtgatgc atgaggctct gcacaaccac tacacgcaga agagcctctc cctgtctccg   1380
ggtaaa                                                              1386
```

```
<210> SEQ ID NO 81
<211> LENGTH: 117
<212> TYPE: PRT
<213> ORGANISM: artificial
<220> FEATURE:
<223> OTHER INFORMATION: antibody variable domain

<400> SEQUENCE: 81
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Trp Leu Arg Ser Asp Asp Thr Ala Val Tyr Tyr Cys
                85                  90                  95

Ala Arg Asp Arg Trp Leu Asp Ala Phe Asp Ile Trp Gly Gln Gly Thr
            100                 105                 110

Met Val Thr Val Ser
        115

```
<210> SEQ ID NO 82
<211> LENGTH: 144
<212> TYPE: PRT
<213> ORGANISM: Oryctolagus cuniculus

<400> SEQUENCE: 82
```

Met Trp Leu Gln Asn Leu Phe Leu Leu Gly Ser Val Val Cys Thr Ile
1               5                   10                  15

Ser Ala Pro Thr His Gln Pro Asn Thr Val Ser Gln Pro Leu Lys His
            20                  25                  30

Val Asp Ala Ile Lys Glu Ala Arg Ile Ile Leu Ser Arg Ser Asn Asp
        35                  40                  45

Ser Ala Ala Val Pro Gly Glu Met Val Glu Val Ser Glu Met Phe
    50                  55                  60

Asp Pro Gln Lys Pro Thr Cys Leu Gln Thr Arg Leu Glu Leu Tyr Lys
65                  70                  75                  80

Gln Gly Leu Arg Gly Ser Leu Glu Arg Leu Ser Ser Thr Leu Thr Leu
                85                  90                  95

Met Ala Ser His Tyr Lys Gln Asn Cys Pro Pro Thr Pro Glu Thr Ser

```
                  100                 105                 110
Cys Glu Thr Glu Phe Ile Thr Phe Lys Ser Phe Lys Glu Asn Leu Lys
        115                 120                 125

Cys Phe Leu Phe Val Ile Pro Phe Asn Cys Trp Glu Pro Val Gln Lys
        130                 135                 140

<210> SEQ ID NO 83
<211> LENGTH: 11
<212> TYPE: PRT
<213> ORGANISM: artificial
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: Xaa is Glu or no amino acid residue
<220> FEATURE:
<221> NAME/KEY: MISC_FEATURE
<222> LOCATION: (2)..(2)
<223> OTHER INFORMATION: Xaa is Gly or no amino acid residue
<220> FEATURE:
<221> NAME/KEY: MISC_FEATURE
<222> LOCATION: (3)..(3)
<223> OTHER INFORMATION: Xaa is Pro, Asp or Gly
<220> FEATURE:
<221> NAME/KEY: MISC_FEATURE
<222> LOCATION: (4)..(4)
<223> OTHER INFORMATION: Xaa is Tyr, Trp, Arg or Lys
<220> FEATURE:
<221> NAME/KEY: MISC_FEATURE
<222> LOCATION: (5)..(5)
<223> OTHER INFORMATION: Xaa is Ser, Trp, Phe or Thr
<220> FEATURE:
<221> NAME/KEY: MISC_FEATURE
<222> LOCATION: (6)..(6)
<223> OTHER INFORMATION: Xaa is Thr or Leu
<220> FEATURE:
<221> NAME/KEY: MISC_FEATURE
<222> LOCATION: (7)..(7)
<223> OTHER INFORMATION: Xaa is Asp or Gly
<220> FEATURE:
<221> NAME/KEY: MISC_FEATURE
<222> LOCATION: (8)..(8)
<223> OTHER INFORMATION: Xaa is Tyr or no amino acid residue
<220> FEATURE:
<221> NAME/KEY: MISC_FEATURE
<222> LOCATION: (11)..(11)
<223> OTHER INFORMATION: Xaa is Met, Thr or Val

<400> SEQUENCE: 83

Xaa Xaa Xaa Xaa Xaa Xaa Xaa Xaa Phe Asp Xaa
1               5                   10

<210> SEQ ID NO 84
<211> LENGTH: 9
<212> TYPE: PRT
<213> ORGANISM: artificial
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: Xaa is Gln or Leu
<220> FEATURE:
<221> NAME/KEY: MISC_FEATURE
<222> LOCATION: (3)..(3)
<223> OTHER INFORMATION: Xaa is Gln or Leu
<220> FEATURE:
<221> NAME/KEY: MISC_FEATURE
<222> LOCATION: (3)..(3)
<223> OTHER INFORMATION: Xaa is Thr or Ser
<220> FEATURE:
<221> NAME/KEY: MISC_FEATURE
<222> LOCATION: (4)..(4)
<223> OTHER INFORMATION: Xaa is Asp, Gly or Phe
```

```
<220> FEATURE:
<221> NAME/KEY: MISC_FEATURE
<222> LOCATION: (5)..(5)
<223> OTHER INFORMATION: Xaa is Arg, Thr or Ser
<220> FEATURE:
<221> NAME/KEY: MISC_FEATURE
<222> LOCATION: (6)..(6)
<223> OTHER INFORMATION: Xaa is Ser or Val
<220> FEATURE:
<221> NAME/KEY: MISC_FEATURE
<222> LOCATION: (7)..(7)
<223> OTHER INFORMATION: Xaa is Phe or Pro
<220> FEATURE:
<221> NAME/KEY: MISC_FEATURE
<222> LOCATION: (8)..(8)
<223> OTHER INFORMATION: Xaa is Arg or Trp

<400> SEQUENCE: 84

Xaa Gln Xaa Xaa Xaa Xaa Xaa Xaa Thr
1               5

<210> SEQ ID NO 85
<211> LENGTH: 235
<212> TYPE: PRT
<213> ORGANISM: artificial
<220> FEATURE:
<223> OTHER INFORMATION: antibody light chain

<400> SEQUENCE: 85

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Leu Gly Glu Arg Ala Ile Leu Ser Cys Arg Ala Ser Gln Ser
        35                  40                  45

Leu Ser Ser Ile Tyr Leu Ala Trp Tyr Gln Gln Lys Pro Gly Gln Ala
    50                  55                  60

Pro Gly Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Ser Leu Glu Pro Glu Asp Phe Ala Val Tyr Tyr Cys Gln Gln Tyr
            100                 105                 110

Ala Thr Ser Pro Trp Thr Phe Gly Gln Gly Thr Lys Val Glu Val Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 86
<211> LENGTH: 704
```

```
<212> TYPE: DNA
<213> ORGANISM: artificial
<220> FEATURE:
<223> OTHER INFORMATION: antibody light chain gene

<400> SEQUENCE: 86
atggaaaccc cggcgcagct gctgtttctg ctgctgctgt ggctgccgga taccaccggc    60
gaaattgtgt tgacgcagtc tccaggcacc ctgtctttgt ctctagggga aagagccatc   120
ctctcctgca gggccagtca gagtcttagc agcatctact tagcctggta ccagcagaaa   180
cctggccagg ctcccggtct cctcatctat ggtgcttcca gcagggccac tggcatccca   240
gacaggttca gtggcagtgg gtctgggaca gacttcactc tcaccatcag tagtctggag   300
cctgaagatt ttgcagtgta ttactgtcag cagtatgcta cctcaccgtg gacgttcggc   360
caagggacca aggtggaagt caaacgtacg gtggctgcac catctgtctt catcttcccg   420
ccatctgatg agcagttgaa atctggaact gcctctgttg tgtgcctgct gaataacttc   480
tatcccagag aggccaaagt acagtggaag gtggataacg ccctccaatc gggtaactcc   540
caggagagtg tcacagagca ggacagcaag gacagcacct acagcctcag cagcaccctg   600
acgctgagca agcagactac gagaaacac aaagtctacg cctgcgaagt cacccatcag   660
ggcctgagct cgcccgtcac aaagagcttc aacaggggag agtg                    704

<210> SEQ ID NO 87
<211> LENGTH: 108
<212> TYPE: PRT
<213> ORGANISM: artificial
<220> FEATURE:
<223> OTHER INFORMATION: antibody variable domain

<400> SEQUENCE: 87

Glu Ile Val Leu Thr Gln Ser Pro Gly Thr Leu Ser Leu Ser Leu Gly
1               5                   10                  15

Glu Arg Ala Ile Leu Ser Cys Arg Ala Ser Gln Ser Leu Ser Ser Ile
            20                  25                  30

Tyr Leu Ala Trp Tyr Gln Gln Lys Pro Gly Gln Ala Pro Gly Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Ala Thr Ser Pro
                85                  90                  95

Trp Thr Phe Gly Gln Gly Thr Lys Val Glu Val Lys
            100                 105

<210> SEQ ID NO 88
<211> LENGTH: 12
<212> TYPE: PRT
<213> ORGANISM: artificial
<220> FEATURE:
<223> OTHER INFORMATION: CDR1 peptide

<400> SEQUENCE: 88

Arg Ala Ser Gln Ser Leu Ser Ser Ile Tyr Leu Ala
1               5                   10

<210> SEQ ID NO 89
<211> LENGTH: 11
<212> TYPE: PRT
<213> ORGANISM: artificial
```

-continued

```
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: Xaa is Ser or Ala
<220> FEATURE:
<221> NAME/KEY: MISC_FEATURE
<222> LOCATION: (2)..(2)
<223> OTHER INFORMATION: Xaa is Ser or Ala
<220> FEATURE:
<221> NAME/KEY: MISC_FEATURE
<222> LOCATION: (3)..(3)
<223> OTHER INFORMATION: Xaa is Trp or Phe
<220> FEATURE:
<221> NAME/KEY: MISC_FEATURE
<222> LOCATION: (4)..(4)
<223> OTHER INFORMATION: Xaa is Asp or Thr
<220> FEATURE:
<221> NAME/KEY: MISC_FEATURE
<222> LOCATION: (9)..(9)
<223> OTHER INFORMATION: Xaa is Gly, Trp or no amino acid residue
<220> FEATURE:
<221> NAME/KEY: MISC_FEATURE
<222> LOCATION: (10)..(10)
<223> OTHER INFORMATION: Xaa is Val, Leu or Pro
<220> FEATURE:
<221> NAME/KEY: MISC_FEATURE
<222> LOCATION: (11)..(11)
<223> OTHER INFORMATION: Xaa is Val or no amino acid residue

<400> SEQUENCE: 89

Xaa Xaa Xaa Xaa Asp Ser Ser Asn Xaa Xaa Xaa
1               5                   10

<210> SEQ ID NO 90
<211> LENGTH: 9
<212> TYPE: PRT
<213> ORGANISM: artificial
<220> FEATURE:
<223> OTHER INFORMATION: CDR3 peptide

<400> SEQUENCE: 90

Gln Gln Tyr Ala Thr Ser Pro Trp Thr
1               5

<210> SEQ ID NO 91
<211> LENGTH: 463
<212> TYPE: PRT
<213> ORGANISM: artificial
<220> FEATURE:
<223> OTHER INFORMATION: antibody heavy chain

<400> SEQUENCE: 91

Met Asp Trp Thr Trp Ser Ile Leu Phe Leu Val Ala Ala Pro Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Phe Thr Phe
            35                  40                  45

Ser Gly Tyr Tyr Met Tyr Trp Val Arg Gln Ala Pro Gly Gln Gly Leu
        50                  55                  60

Glu Trp Met Gly Trp Ile Asn Pro Asn Ser Gly Gly Thr Asn Tyr Ala
65                  70                  75                  80

Arg Lys Phe Gln Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110
```

```
Tyr Tyr Cys Ala Arg Arg Pro Trp Glu Leu Pro Phe Asp Tyr Trp Gly
            115                 120                 125

Gln Gly Thr Leu Val Thr Val Ser Ser Ala Ser Thr Lys Gly Pro Ser
130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460

<210> SEQ ID NO 92
<211> LENGTH: 1389
<212> TYPE: DNA
<213> ORGANISM: artificial
<220> FEATURE:
<223> OTHER INFORMATION: antibody heavy chain gene

<400> SEQUENCE: 92
atggattgga cctggagcat tctgtttctg gtggcggcgc cgaccggcgc gcatagccag      60
gtgcagctgg tgcagtctgg ggctgaggtg aagaagcctg ggccctcagt gaaggtctcc     120
```

```
tgcaaggctt ctggattcac cttcagcggc tactatatgt actgggtgcg acaggcccct    180
ggacaagggc ttgagtggat gggatggatc aaccctaaca gtggtggcac aaactatgca    240
cggaagtttc agggcagggt caccatgacc aggacacgt ccatcagcac agcctacatg     300
gagctgagca ggctgagatc tgacgacacg gccgtatatt actgtgcgag agaccgtgg    360 gagcttccct ttgactactg gggccaggga accctggtca ccgtctcctc agctagcacc    420
aagggcccat cggtcttccc cctggcgccc tgctccagga gcacctccga gagcacagcg    480
gccctgggct gcctggtcaa ggactacttc cccgaaccgg tgacggtgtc gtggaactca    540
ggcgctctga ccagcggcgt gcacaccttc cagctgtcc acagtcctc aggactctac      600 tccctcagca gcgtggtgac cgtgccctcc agcaacttcg gcacccagac ctacacctgc    660
aacgtagatc acaagcccag caacaccaag gtggacaaga cagttgagcg caaatgttgt    720
gtcgagtgcc caccgtgccc agcaccacct gtggcaggac cgtcagtctt cctcttcccc    780
ccaaaaccca aggacaccct catgatctcc cggaccctg aggtcacgtg cgtggtggtg      840
gacgtgagcc acgaagaccc cgaggtccag ttcaactggt acgtggacgg cgtggaggtg    900
cataatgcca agacaaagcc acgggaggag cagttcaaca gcacgttccg tgtggtcagc    960
gtcctcaccg ttgtgcacca ggactggctg aacggcaagg agtacaagtg caaggtctcc    1020
aacaaaggcc tcccagcccc catcgagaaa accatctcca aaaccaaagg cagccccga    1080 gaaccacagg tgtacaccct gcccccatcc cgggaggaga tgaccaagaa ccaggtcagc    1140
ctgacctgcc tggtcaaagg cttctacccc agcgacatcg ccgtggagtg ggagagcaat    1200
gggcagccgg agaacaacta caagaccaca cctcccatgc tggactccga cggctccttc    1260
ttcctctaca gcaagctcac cgtggacaag agcaggtggc agcaggggaa cgtcttctca    1320
tgctccgtga tgcatgaggc tctgcacaac cactacacgc agaagagcct ctccctgtct    1380
ccgggtaaa                                                            1389
```

<210> SEQ ID NO 93
<211> LENGTH: 118
<212> TYPE: PRT
<213> ORGANISM: artificial
<220> FEATURE:
<223> OTHER INFORMATION: antibody variable domain

<400> SEQUENCE: 93

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Gly Tyr
            20                  25                  30

Tyr Met Tyr Trp Val Arg Gln Ala Pro Gly Gln Gly Leu Glu Trp Met
        35                  40                  45

Gly Trp Ile Asn Pro Asn Ser Gly Gly Thr Asn Tyr Ala Arg Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Arg Pro Trp Glu Leu Pro Phe Asp Tyr Trp Gly Gln Gly Thr
            100                 105                 110

Leu Val Thr Val Ser Ser
        115
```

<210> SEQ ID NO 94

-continued

```
<211> LENGTH: 5
<212> TYPE: PRT
<213> ORGANISM: artificial
<220> FEATURE:
<223> OTHER INFORMATION: CDR1 peptide

<400> SEQUENCE: 94

Gly Tyr Tyr Met Tyr
1               5

<210> SEQ ID NO 95
<211> LENGTH: 17
<212> TYPE: PRT
<213> ORGANISM: artificial
<220> FEATURE:
<223> OTHER INFORMATION: CDR2 peptide

<400> SEQUENCE: 95

Trp Ile Asn Pro Asn Ser Gly Gly Thr Asn Tyr Ala Arg Lys Phe Gln
1               5                   10                  15

Gly

<210> SEQ ID NO 96
<211> LENGTH: 9
<212> TYPE: PRT
<213> ORGANISM: artificial
<220> FEATURE:
<223> OTHER INFORMATION: CDR3 peptide

<400> SEQUENCE: 96

Arg Pro Trp Glu Leu Pro Phe Asp Tyr
1               5

<210> SEQ ID NO 97
<211> LENGTH: 234
<212> TYPE: PRT
<213> ORGANISM: artificial
<220> FEATURE:
<223> OTHER INFORMATION: antibody light chain

<400> SEQUENCE: 97

Met Glu Thr Pro Ala Gln Leu Leu Phe Leu Leu Leu Leu Trp Leu Pro
1               5                   10                  15

Asp Thr Thr Gly Asp Ile Gln Met Thr Gln Ser Pro Ser Ser Leu Ser
                20                  25                  30

Ala Ser Val Gly Asp Arg Val Thr Ile Thr Cys Arg Ala Ser Gln Ser
            35                  40                  45

Ile Ser Asn Tyr Leu Asn Trp Tyr Gln Gln Lys Pro Gly Lys Ala Pro
        50                  55                  60

Lys Leu Leu Ile Tyr Thr Ala Ser Ser Leu Gln Ser Gly Val Pro Ser
65                  70                  75                  80

Arg Phe Ser Gly Arg Gly Ser Gly Thr Asp Phe Thr Leu Thr Ile Ser
                85                  90                  95

Ser Leu Gln Pro Glu Asp Phe Ala Thr Tyr Tyr Cys Gln Gln Ser Phe
            100                 105                 110

Ser Phe Pro Ile Thr Phe Gly Pro Gly Thr Lys Val Asp Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
```

```
                    165                 170                 175
Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 98
<211> LENGTH: 701
<212> TYPE: DNA
<213> ORGANISM: artificial
<220> FEATURE:
<223> OTHER INFORMATION: antibody light chain gene

<400> SEQUENCE: 98
atggaaaccc cggcgcagct gctgtttctg ctgctgctgt ggctgccgga taccaccggc      60
gacatccaga tgacccagtc tccatcctcc ctgtctgcat ctgtaggaga cagagtcacc     120
atcacttgcc gggcaagtca gagcattagc aactatttaa attggtatca gcagaaacca     180
gggaaagccc ctaagctcct gatctatact gcatccagtt tgcaaagtgg ggtcccatca     240
aggttcagtg gcagaggatc tgggacagat ttcactctca ccatcagcag tctgcaacct     300
gaagattttg caacttacta ctgtcaacag agtttcagtt ccccaatcac tttcggccct     360
gggaccaaag tggatatcaa acgtacggtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag cacectgacg     600 ctgagcaaag cagactacga aaacacaaa gtctacgcct gcgaagtcac ccatcagggc     660
ctgagctcgc ccgtcacaaa gagcttcaac aggggagagt g                        701

<210> SEQ ID NO 99
<211> LENGTH: 107
<212> TYPE: PRT
<213> ORGANISM: artificial
<220> FEATURE:
<223> OTHER INFORMATION: antibody variable domain

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Thr Ala Ser Ser Leu Gln Ser Gly Val Pro Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Phe Pro Ile
                85                  90                  95

Thr Phe Gly Pro Gly Thr Lys Val Asp Ile Lys
            100                 105
```

```
<210> SEQ ID NO 100
<211> LENGTH: 11
<212> TYPE: PRT
<213> ORGANISM: artificial
<220> FEATURE:
<223> OTHER INFORMATION: CDR1 peptide

<400> SEQUENCE: 100

Arg Ala Ser Gln Ser Ile Ser Asn Tyr Leu Asn
1               5                   10

<210> SEQ ID NO 101
<211> LENGTH: 7
<212> TYPE: PRT
<213> ORGANISM: artificial
<220> FEATURE:
<223> OTHER INFORMATION: CDR2 peptide

<400> SEQUENCE: 101

Thr Ala Ser Ser Leu Gln Ser
1               5

<210> SEQ ID NO 102
<211> LENGTH: 9
<212> TYPE: PRT
<213> ORGANISM: artificial
<220> FEATURE:
<223> OTHER INFORMATION: CDR3 peptide

<400> SEQUENCE: 102

Gln Gln Ser Phe Ser Phe Pro Ile Thr
1               5

<210> SEQ ID NO 103
<211> LENGTH: 465
<212> TYPE: PRT
<213> ORGANISM: artificial
<220> FEATURE:
<223> OTHER INFORMATION: antibody heavy chain

<400> SEQUENCE: 103

Met Asp Trp Thr Trp Ser Ile Leu Phe Leu Val Ala Ala Pro Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Tyr Met His Trp Val Arg Gln Ala Pro Gly Gln Gly Leu
    50                  55                  60

Glu Trp Met Gly Trp Ile Asn Pro Asn Ser Gly Gly Thr Asn Tyr Ala
65                  70                  75                  80

Gln Lys Phe Lys Gly Arg Val Thr Met Thr Arg Asp Thr Ser Ile Ser
                85                  90                  95

Thr Ala His Met Glu Leu Ser Arg Leu Arg Ser Asp Asp Thr Ala Val
            100                 105                 110

Tyr Tyr Cys Val Arg Asn Gly Asp Tyr Val Phe Thr Tyr Phe Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175
```

Thr Val Ser Trp Asn Ser Gly Ala Leu Thr Ser Gly Val His Thr Phe
            180                 185                 190
Pro Ala Val Leu Gln Ser Ser Gly Leu Tyr Ser Leu Ser Ser Val Val
            195                 200                 205
Thr Val Pro Ser Ser Asn Phe Gly Thr Gln Thr Tyr Thr Cys Asn Val
            210                 215                 220
Asp His Lys Pro Ser Asn Thr Lys Val Asp Lys Thr Val Glu Arg Lys
225                 230                 235                 240
Cys Cys Val Glu Cys Pro Pro Cys Pro Ala Pro Pro Val Ala Gly Pro
                245                 250                 255
Ser Val Phe Leu Phe Pro Pro Lys Pro Lys Asp Thr Leu Met Ile Ser
            260                 265                 270
Arg Thr Pro Glu Val Thr Cys Val Val Val Asp Val Ser His Glu Asp
            275                 280                 285
Pro Glu Val Gln Phe Asn Trp Tyr Val Asp Gly Val Glu Val His Asn
            290                 295                 300
Ala Lys Thr Lys Pro Arg Glu Glu Gln Phe Asn Ser Thr Phe Arg Val
305                 310                 315                 320
Val Ser Val Leu Thr Val Val His Gln Asp Trp Leu Asn Gly Lys Glu
                325                 330                 335
Tyr Lys Cys Lys Val Ser Asn Lys Gly Leu Pro Ala Pro Ile Glu Lys
            340                 345                 350
Thr Ile Ser Lys Thr Lys Gly Gln Pro Arg Glu Pro Gln Val Tyr Thr
            355                 360                 365
Leu Pro Pro Ser Arg Glu Glu Met Thr Lys Asn Gln Val Ser Leu Thr
            370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Met Leu
                405                 410                 415
Asp Ser Asp Gly Ser Phe Phe Leu Tyr Ser Lys Leu Thr Val Asp Lys
            420                 425                 430
Ser Arg Trp Gln Gln Gly Asn Val Phe Ser Cys Ser Val Met His Glu
            435                 440                 445
Ala Leu His Asn His Tyr Thr Gln Lys Ser Leu Ser Leu Ser Pro Gly
450                 455                 460
Lys
465

<210> SEQ ID NO 104
<211> LENGTH: 1395
<212> TYPE: DNA
<213> ORGANISM: artificial
<220> FEATURE:
<223> OTHER INFORMATION: antibody heavy chain gene

<400> SEQUENCE: 104
atggattgga cctggagcat tctgtttctg gtggcggcgc cgaccggcgc gcatagccag    60
gtgcagctgg tgcagtctgg ggctgaggtg aagaagcctg ggcctcagt gaaggtctcc    120 tgcaaggctt ctggatacac cttcaccggc tactatatgc actgggtgcg acaggccct    180 ggacaaggc ttgagtggat gggatggatc aaccctaaca gtggtggcac aaactatgca    240
cagaagttta agggcagggt caccatgacc agggacacgt ccatcagcac agcccacatg    300
gagctgagca ggctgagatc tgacgacacg gccgtgtatt actgtgtgag aaacggtgac    360

```
tatgttttta cctactttga ctactggggc cagggaaccc tggtcaccgt ctcctcagct    420
agcaccaagg gcccatcggt cttcccctg gcgccctgct ccaggagcac ctccgagagc    480
acagcggccc tgggctgcct ggtcaaggac tacttccccg aaccggtgac ggtgtcgtgg    540
aactcaggcg ctctgaccag cggcgtgcac accttcccag ctgtcctaca gtcctcagga    600
ctctactccc tcagcagcgt ggtgaccgtg ccctccagca acttcggcac ccagacctac    660
acctgcaacg tagatcacaa gcccagcaac accaaggtgg acaagacagt tgagcgcaaa    720
tgttgtgtcg agtgcccacc gtgcccagca ccacctgtgg caggaccgtc agtcttcctc    780
ttccccccaa aacccaagga caccctcatg atctcccgga cccctgaggt cacgtgcgtg    840
gtggtggacg tgagccacga agaccccgag gtccagttca actggtacgt ggacggcgtg    900
gaggtgcata atgccaagac aaagccacgg gaggagcagt tcaacagcac gttccgtgtg    960
gtcagcgtcc tcaccgttgt gcaccaggac tggctgaacg gcaaggagta caagtgcaag    1020
gtctccaaca aaggcctccc agcccccatc gagaaaacca tctccaaaac caaagggcag    1080
ccccgagaac cacaggtgta caccctgccc ccatcccggg aggagatgac caagaaccag    1140
gtcagcctga cctgcctggt caaaggcttc taccccagcg acatcgccgt ggagtgggag    1200
agcaatgggc agccggagaa caactacaag accacacctc ccatgctgga ctccgacggc    1260
tccttcttcc tctacagcaa gctcaccgtg gacaagagca ggtggcagca ggggaacgtc    1320
ttctcatgct ccgtgatgca tgaggctctg cacaaccact acacgcagaa gagcctctcc    1380
ctgtctccgg gtaaa    1395

<210> SEQ ID NO 105
<211> LENGTH: 120
<212> TYPE: PRT
<213> ORGANISM: artificial
<220> FEATURE:
<223> OTHER INFORMATION: antibody variable domain

<400> SEQUENCE: 105

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Lys Gly Arg Val Thr Met Thr Arg Asp Thr Ser Ile Ser Thr Ala His
65                  70                  75                  80

Met Glu Leu Ser Arg Leu Arg Ser Asp Asp Thr Ala Val Tyr Tyr Cys
                85                  90                  95

Val Arg Asn Gly Asp Tyr Val Phe Thr Tyr Phe Asp Tyr Trp Gly Gln
            100                 105                 110

Gly Thr Leu Val Thr Val Ser Ser
        115                 120

<210> SEQ ID NO 106
<211> LENGTH: 17
<212> TYPE: PRT
<213> ORGANISM: artificial
<220> FEATURE:
<223> OTHER INFORMATION: consensus sequence
<220> FEATURE:
<221> NAME/KEY: MISC_FEATURE
<222> LOCATION: (1)..(1)
```

```
<223> OTHER INFORMATION: Xaa is Trp or no amino acid residue
<220> FEATURE:
<221> NAME/KEY: MISC_FEATURE
<222> LOCATION: (2)..(2)
<223> OTHER INFORMATION: Xaa is Ile or Tyr
<220> FEATURE:
<221> NAME/KEY: MISC_FEATURE
<222> LOCATION: (3)..(3)
<223> OTHER INFORMATION: Xaa is Asn, Ser or Ile
<220> FEATURE:
<221> NAME/KEY: MISC_FEATURE
<222> LOCATION: (4)..(4)
<223> OTHER INFORMATION: Xaa is Pro, Ala, Tyr
<220> FEATURE:
<221> NAME/KEY: MISC_FEATURE
<222> LOCATION: (5)..(5)
<223> OTHER INFORMATION: Xaa is Asn or Tyr
<220> FEATURE:
<221> NAME/KEY: MISC_FEATURE
<222> LOCATION: (6)..(6)
<223> OTHER INFORMATION: Xaa is Ser or Asn
<220> FEATURE:
<221> NAME/KEY: MISC_FEATURE
<222> LOCATION: (8)..(8)
<223> OTHER INFORMATION: Xaa is Gly or Asn
<220> FEATURE:
<221> NAME/KEY: MISC_FEATURE
<222> LOCATION: (9)..(9)
<223> OTHER INFORMATION: Xaa is Thr or Arg
<220> FEATURE:
<221> NAME/KEY: MISC_FEATURE
<222> LOCATION: (10)..(10)
<223> OTHER INFORMATION: Xaa is Asn or Asp
<220> FEATURE:
<221> NAME/KEY: MISC_FEATURE
<222> LOCATION: (11)..(11)
<223> OTHER INFORMATION: Xaa is Tyr or Ser
<220> FEATURE:
<221> NAME/KEY: MISC_FEATURE
<222> LOCATION: (12)..(12)
<223> OTHER INFORMATION: Xaa is Ala or Asn
<220> FEATURE:
<221> NAME/KEY: MISC_FEATURE
<222> LOCATION: (13)..(13)
<223> OTHER INFORMATION: Xaa is Gln or Arg
<220> FEATURE:
<221> NAME/KEY: MISC_FEATURE
<222> LOCATION: (14)..(14)
<223> OTHER INFORMATION: Xaa is Lys or Arg
<220> FEATURE:
<221> NAME/KEY: MISC_FEATURE
<222> LOCATION: (15)..(15)
<223> OTHER INFORMATION: Xaa is Phe or Lys
<220> FEATURE:
<221> NAME/KEY: MISC_FEATURE
<222> LOCATION: (16)..(16)
<223> OTHER INFORMATION: Xaa is Gln, Lys or Arg

<400> SEQUENCE: 106

Xaa Xaa Xaa Xaa Xaa Xaa Gly Xaa Xaa Xaa Xaa Xaa Xaa Xaa Xaa
1               5                   10                  15

Gly

<210> SEQ ID NO 107
<211> LENGTH: 17
<212> TYPE: PRT
<213> ORGANISM: artificial
<220> FEATURE:
<223> OTHER INFORMATION: consensus sequence
<220> FEATURE:
<221> NAME/KEY: MISC_FEATURE
<222> LOCATION: (6)..(6)
<223> OTHER INFORMATION: Xaa is Val or Ile
<220> FEATURE:
<221> NAME/KEY: MISC_FEATURE
<222> LOCATION: (11)..(11)
<223> OTHER INFORMATION: Xaa is Ser or Asn
```

```
<220> FEATURE:
<221> NAME/KEY: MISC_FEATURE
<222> LOCATION: (13)..(13)
<223> OTHER INFORMATION: Xaa is Glu or Lys
<220> FEATURE:
<221> NAME/KEY: MISC_FEATURE
<222> LOCATION: (15)..(15)
<223> OTHER INFORMATION: Xaa is Tyr or Phe
<220> FEATURE:
<221> NAME/KEY: MISC_FEATURE
<222> LOCATION: (17)..(17)
<223> OTHER INFORMATION: Xaa is Thr or Ala

<400> SEQUENCE: 107

Lys Ser Ser Gln Ser Xaa Leu Tyr Ser Ser Xaa Asn Xaa Asn Xaa Leu
1               5                   10                  15

Xaa

<210> SEQ ID NO 108
<211> LENGTH: 11
<212> TYPE: PRT
<213> ORGANISM: artificial
<220> FEATURE:
<223> OTHER INFORMATION: CDR3 peptide

<400> SEQUENCE: 108

Asn Gly Asp Tyr Val Phe Thr Tyr Phe Asp Tyr
1               5                   10

<210> SEQ ID NO 109
<211> LENGTH: 235
<212> TYPE: PRT
<213> ORGANISM: artificial
<220> FEATURE:
<223> OTHER INFORMATION: antibody light chain

<400> SEQUENCE: 109

Met Ala Trp Ala Pro Leu Leu Thr Leu Leu Ala His Cys Thr Gly
1               5                   10                  15

Ser Trp Ala Gln Ser Ala Leu Thr Gln Pro Ala Ser Val Ser Gly Ser
                20                  25                  30

Pro Gly Gln Ser Ile Thr Ile Ser Cys Thr Gly Thr Ser Ser Asp Val
            35                  40                  45

Gly Gly Tyr Asn Tyr Val Ser Trp Tyr Gln Gln His Pro Gly Lys Ala
        50                  55                  60

Pro Lys Leu Met Ile Tyr Glu Val Ser Gly Arg Pro Ser Gly Val Ser
65                  70                  75                  80

Asn Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Ser Ser Phe
            100                 105                 110

Thr Gly Ser Ser Thr Trp Leu Phe Gly Gly Gly Thr Lys Leu Thr Val
        115                 120                 125

Leu Gly Gln Pro Lys Ala Ala Pro Ser Val Thr Leu Phe Pro Pro Ser
130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
```

```
                195                 200                 205
Lys Ser His Arg Ser Tyr Ser Cys Gln Val Thr His Glu Gly Ser Thr
    210                 215                 220

Val Glu Lys Thr Val Ala Pro Thr Glu Cys Ser
225                 230                 235

<210> SEQ ID NO 110
<211> LENGTH: 705
<212> TYPE: DNA
<213> ORGANISM: artificial
<220> FEATURE:
<223> OTHER INFORMATION: antibody light chain gene

<400> SEQUENCE: 110
atggcgtggg cgccgctgct gctgaccctg ctggcgcatt gcaccggcag ctgggcgcag      60
tctgccctga ctcagcctgc ctccgtgtct gggtctcctg gacagtcgat caccatctcc     120
tgcactggaa ccagcagtga cgttggtggt tataactatg tctcctggta ccagcagcac     180
ccaggcaaag cccccaaact catgatttat gaggtcagtg gtcggccctc aggggtttct     240
aatcgcttct ctggctccaa gtctggcaac acggcctccc tgaccatctc tggactccag     300
gctgaggacg aggctgatta ttactgcagc tcttttacag gcagcagcac ttggttattc     360
ggcggaggga ccaaactgac cgtcctaggc caaccgaaag cggcgccctc ggtcactctg     420
ttcccgccct cctctgagga gcttcaagcc aacaaggcca cactggtgtg tctcataagt     480
gacttctacc cgggagccgt gacagtggcc tggaaggcag atagcagccc cgtcaaggcg     540
ggagtggaga ccaccacacc ctccaaacaa agcaacaaca gtacgcggc cagcagctat     600 ctgagcctga cgcctgagca gtggaagtcc cacagaagct acagctgcca ggtcacgcat     660
gaagggagca ccgtggagaa gacagtggcc cctacagaat gttca                     705

<210> SEQ ID NO 111
<211> LENGTH: 110
<212> TYPE: PRT
<213> ORGANISM: artificial
<220> FEATURE:
<223> OTHER INFORMATION: antibody variable domain

<400> SEQUENCE: 111

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Gly Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Phe Thr Gly Ser
                85                  90                  95

Ser Thr Trp Leu Phe Gly Gly Gly Thr Lys Leu Thr Val Leu
            100                 105                 110

<210> SEQ ID NO 112
<211> LENGTH: 14
<212> TYPE: PRT
<213> ORGANISM: artificial
<220> FEATURE:
<223> OTHER INFORMATION: CDR1 peptide
```

```
<400> SEQUENCE: 112

Thr Gly Thr Ser Ser Asp Val Gly Gly Tyr Asn Tyr Val Ser
 1               5                  10

<210> SEQ ID NO 113
<211> LENGTH: 7
<212> TYPE: PRT
<213> ORGANISM: artificial
<220> FEATURE:
<223> OTHER INFORMATION: CDR2 peptide

<400> SEQUENCE: 113

Glu Val Ser Gly Arg Pro Ser
 1               5

<210> SEQ ID NO 114
<211> LENGTH: 10
<212> TYPE: PRT
<213> ORGANISM: artificial
<220> FEATURE:
<223> OTHER INFORMATION: CDR3 peptide

<400> SEQUENCE: 114

Ser Ser Phe Thr Gly Ser Ser Thr Trp Leu
 1               5                  10

<210> SEQ ID NO 115
<211> LENGTH: 464
<212> TYPE: PRT
<213> ORGANISM: artificial
<220> FEATURE:
<223> OTHER INFORMATION: antibody heavy chain

<400> SEQUENCE: 115

Met Asp Trp Thr Trp Ser Ile Leu Phe Leu Val Ala Ala Pro Thr Gly
 1               5                  10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
             35                  40                  45

Thr Gly Tyr Tyr Met His Trp Val Arg Gln Ala Pro Gly Gln Gly Leu
         50                  55                  60

Glu Trp Met Gly Trp Ile Asn Pro Asn Ser Gly Gly Thr Asn Tyr Ala
 65                  70                  75                  80

Gln Lys Phe Arg Gly Arg Val Thr Met Thr Arg Asp Thr Ser Ile Ser
                 85                  90                  95

Thr Ala Tyr Met Glu Leu Ser Arg Leu Arg Ser Asp Asp Thr Ala Val
                100                 105                 110

Tyr Tyr Cys Ala Arg Phe Gly Tyr Phe Gly Tyr Tyr Phe Asp Tyr Trp
            115                 120                 125

Gly Gln Gly Thr Leu Val Thr Val Ser Ser Ala Ser Thr Lys Gly Pro
        130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205
```

```
Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Lys Pro Lys Asp Thr Leu Met Ile Ser Arg
    260                 265                 270

Thr Pro Glu Val Thr Cys Val Val Asp Val Ser His Glu Asp Pro
    275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Phe Arg Val Val
305                 310                 315                 320

Ser Val Leu Thr Val Val His Gln Asp Trp Leu Asn Gly Lys Glu Tyr
                325                 330                 335

Lys Cys Lys Val Ser Asn Lys Gly Leu Pro Ala Pro Ile Glu Lys Thr
                340                 345                 350

Ile Ser Lys Thr Lys Gly Gln Pro Arg Glu Pro Gln Val Tyr Thr Leu
    355                 360                 365

Pro Pro Ser Arg Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Met Leu Asp
                405                 410                 415

Ser Asp Gly Ser Phe Phe Leu Tyr Ser Lys Leu Thr Val Asp Lys Ser
                420                 425                 430

Arg Trp Gln Gln Gly Asn Val Phe Ser Cys Ser Val Met His Glu Ala
                435                 440                 445

Leu His Asn His Tyr Thr Gln Lys Ser Leu Ser Leu Ser Pro Gly Lys
    450                 455                 460

<210> SEQ ID NO 116
<211> LENGTH: 1392
<212> TYPE: DNA
<213> ORGANISM: artificial
<220> FEATURE:
<223> OTHER INFORMATION: antibody heavy chain gene

<400> SEQUENCE: 116
atggattgga cctggagcat tctgtttctg gtggcggcgc cgaccggcgc gcatagccag    60
gtgcaactgg tgcagtctgg ggctgaggtg aagaagcctg ggcctcagt gaaggtctcc   120 tgcaaggctt ctggatacac cttcaccggc tactatatgc actgggtgcg acaggcccct   180
ggacaagggc ttgagtggat gggatggatc aatcctaaca gtggtggcac aaactatgca   240
cagaagtttc ggggcagggt caccatgacc aggacacgt ccatcagcac agcctacatg   300
gagctgagca ggctgagatc tgacgacacg gccgtgtatt actgtgcgag atttggatat   360
tttggctact actttgacta ctggggccag ggaaccctgg tcaccgtctc ctcagctagc   420
accaagggcc catcggtctt ccccctggcg ccctgctcca ggagcacctc cgagagcaca   480
gcggccctgg gctgcctggt caaggactac ttccccgaac cggtgacggt gtcgtggaac   540
tcaggcgctc tgaccagcgg cgtgcacacc ttcccagctg tcctacagtc ctcaggactc   600
tactccctca gcagcgtggt gaccgtgccc tccagcaact tcggcaccca gacctacacc   660
```

```
tgcaacgtag atcacaagcc cagcaacacc aaggtggaca agacagttga gcgcaaatgt    720
tgtgtcgagt gcccaccgtg cccagcacca cctgtggcag gaccgtcagt cttcctcttc    780
cccccaaaac ccaaggacac cctcatgatc tcccggaccc ctgaggtcac gtgcgtggtg    840
gtggacgtga gccacgaaga ccccgaggtc cagttcaact ggtacgtgga cggcgtggag    900
gtgcataatg ccaagacaaa gccacgggag gagcagttca acagcacgtt ccgtgtggtc    960
agcgtcctca ccgttgtgca ccaggactgg ctgaacggca aggagtacaa gtgcaaggtc   1020
tccaacaaag gcctcccagc ccccatcgag aaaaccatct ccaaaaccaa agggcagccc   1080
cgagaaccac aggtgtacac cctgccccca tcccgggagg agatgaccaa gaaccaggtc   1140
agcctgacct gcctggtcaa aggcttctac cccagcgaca tcgccgtgga gtgggagagc   1200
aatgggcagc cggagaacaa ctacaagacc acacctccca tgctggactc cgacggctcc   1260
ttcttcctct acagcaagct caccgtggac aagagcaggt ggcagcaggg gaacgtcttc   1320
tcatgctccg tgatgcatga ggctctgcac aaccactaca cgcagaagag cctctccctg   1380
tctccgggta aa                                                       1392
```

<210> SEQ ID NO 117
<211> LENGTH: 119
<212> TYPE: PRT
<213> ORGANISM: artificial
<220> FEATURE:
<223> OTHER INFORMATION: antibody variable domain

<400> SEQUENCE: 117

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Phe Gly Tyr Phe Gly Tyr Tyr Phe Asp Tyr Trp Gly Gln Gly
            100                 105                 110

Thr Leu Val Thr Val Ser Ser
        115
```

<210> SEQ ID NO 118
<211> LENGTH: 12
<212> TYPE: PRT
<213> ORGANISM: artificial
<220> FEATURE:
<223> OTHER INFORMATION: consensus sequence
<220> FEATURE:
<221> NAME/KEY: MISC_FEATURE
<222> LOCATION: (4)..(4)
<223> OTHER INFORMATION: Xaa is Gln or Pro
<220> FEATURE:
<221> NAME/KEY: MISC_FEATURE
<222> LOCATION: (5)..(5)
<223> OTHER INFORMATION: Xaa is Ser or Tyr
<220> FEATURE:
<221> NAME/KEY: MISC_FEATURE
<222> LOCATION: (6)..(6)
<223> OTHER INFORMATION: Xaa is Val, Leu or Ile

```
-continued

<220> FEATURE:
<221> NAME/KEY: MISC_FEATURE
<222> LOCATION: (7)..(7)
<223> OTHER INFORMATION: Xaa is Ser or Cys
<220> FEATURE:
<221> NAME/KEY: MISC_FEATURE
<222> LOCATION: (8)..(8)
<223> OTHER INFORMATION: Xaa is Ser or Asn
<220> FEATURE:
<221> NAME/KEY: MISC_FEATURE
<222> LOCATION: (9)..(9)
<223> OTHER INFORMATION: Xaa is Ser, Ile, Thr or no amino acid residue
<220> FEATURE:
<221> NAME/KEY: MISC_FEATURE
<222> LOCATION: (11)..(11)
<223> OTHER INFORMATION: Xaa is Phe or Leu
<220> FEATURE:
<221> NAME/KEY: MISC_FEATURE
<222> LOCATION: (12)..(12)
<223> OTHER INFORMATION: Xaa is Ala or Asn

<400> SEQUENCE: 118

Arg Ala Ser Xaa Xaa Xaa Xaa Xaa Tyr Xaa Xaa
1               5                   10

<210> SEQ ID NO 119
<211> LENGTH: 17
<212> TYPE: PRT
<213> ORGANISM: artificial
<220> FEATURE:
<223> OTHER INFORMATION: CDR2 peptide

<400> SEQUENCE: 119

Trp Ile Asn Pro Asn Ser Gly Gly Thr Asn Tyr Ala Gln Lys Phe Arg
1               5                   10                  15

Gly

<210> SEQ ID NO 120
<211> LENGTH: 10
<212> TYPE: PRT
<213> ORGANISM: artificial
<220> FEATURE:
<223> OTHER INFORMATION: CDR3 peptide

<400> SEQUENCE: 120

Phe Gly Tyr Phe Gly Tyr Tyr Phe Asp Tyr
1               5                   10

<210> SEQ ID NO 121
<211> LENGTH: 235
<212> TYPE: PRT
<213> ORGANISM: artificial
<220> FEATURE:
<223> OTHER INFORMATION: antibody light chain

<400> SEQUENCE: 121

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Pro Ser
            35                  40                  45

Val Ser Ser Ser Tyr Phe Ala Trp Tyr Gln Gln Lys Pro Gly Gln Ala
        50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
```

```
                    85                  90                  95
Ser Arg Leu Glu Pro Glu Asp Phe Ala Val Tyr Tyr Cys Gln Gln Tyr
                100                 105                 110

Gly Trp Ser Pro Arg Thr Phe Gly Gln Gly Thr Lys Val Glu Ile Lys
            115                 120                 125

Arg Thr Val Ala Ala Pro Ser Val Phe Ile Phe Pro Pro Ser Asp Glu
        130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 122
<211> LENGTH: 704
<212> TYPE: DNA
<213> ORGANISM: artificial
<220> FEATURE:
<223> OTHER INFORMATION: antibody light chain gene

<400> SEQUENCE: 122
atggaaaccc cggcgcagct gctgtttctg ctgctgctgt ggctgccgga taccaccggc      60
gaaattgtgt tgacgcagtc tccaggcacc ctgtctttgt ctccagggga agagccacc     120 ctctcctgca gggccagtcc gagtgttagc agcagctact tgcctggta ccagcaaaaa     180 cctggccagg ctcccaggct cctcatctat ggtgcatcca gcagggccac tggcatccca     240
gacaggttca gtggcagtgg gtctgggaca gacttcactc tcaccatcag cagactggag     300
cctgaagatt ttgcagtgta ttactgtcag cagtatggtt ggtcacctcg acgttcggc     360 caagggacca aggtggaaat caaacgtacg gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcaccctg     600
acgctgagca aagcagacta cgagaaacac aaagtctacg cctgcgaagt cacccatcag     660
ggcctgagct cgcccgtcac aaagagcttc aacaggggag agtg                     704

<210> SEQ ID NO 123
<211> LENGTH: 108
<212> TYPE: PRT
<213> ORGANISM: artificial
<220> FEATURE:
<223> OTHER INFORMATION: antibody variable domain

<400> SEQUENCE: 123

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Pro Ser Val Ser Ser
            20                  25                  30

Tyr Phe Ala Trp Tyr Gln Gln Lys Pro Gly Gln Ala Pro Arg Leu Leu
```

-continued

```
                35                  40                  45
Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Trp Ser Pro
                 85                  90                  95

Arg Thr Phe Gly Gln Gly Thr Lys Val Glu Ile Lys
            100                 105

<210> SEQ ID NO 124
<211> LENGTH: 12
<212> TYPE: PRT
<213> ORGANISM: artificial
<220> FEATURE:
<223> OTHER INFORMATION: CDR1 peptide

<400> SEQUENCE: 124

Arg Ala Ser Pro Ser Val Ser Ser Ser Tyr Phe Ala
 1               5                  10

<210> SEQ ID NO 125
<211> LENGTH: 15
<212> TYPE: PRT
<213> ORGANISM: artificial
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: Xaa is Ile, Ser or Thr
<220> FEATURE:
<221> NAME/KEY: MISC_FEATURE
<222> LOCATION: (2)..(2)
<223> OTHER INFORMATION: Xaa is Arg or Gly
<220> FEATURE:
<221> NAME/KEY: MISC_FEATURE
<222> LOCATION: (3)..(3)
<223> OTHER INFORMATION: Xaa is Thr or Ser
<220> FEATURE:
<221> NAME/KEY: MISC_FEATURE
<222> LOCATION: (4)..(4)
<223> OTHER INFORMATION: Xaa is Arg or Ser
<220> FEATURE:
<221> NAME/KEY: MISC_FEATURE
<222> LOCATION: (5)..(5)
<223> OTHER INFORMATION: Xaa is Gly or Ser
<220> FEATURE:
<221> NAME/KEY: MISC_FEATURE
<222> LOCATION: (6)..(6)
<223> OTHER INFORMATION: Xaa is Ser, His or Asp
<220> FEATURE:
<221> NAME/KEY: MISC_FEATURE
<222> LOCATION: (8)..(8)
<223> OTHER INFORMATION: Xaa is Ile or Val
<220> FEATURE:
<221> NAME/KEY: MISC_FEATURE
<222> LOCATION: (9)..(9)
<223> OTHER INFORMATION: Xaa is Ala or Gly
<220> FEATURE:
<221> NAME/KEY: MISC_FEATURE
<222> LOCATION: (10)..(10)
<223> OTHER INFORMATION: Xaa is Gly or no amino acid residue
<220> FEATURE:
<221> NAME/KEY: MISC_FEATURE
<222> LOCATION: (11)..(11)
<223> OTHER INFORMATION: Xaa is Ser or Tyr
<220> FEATURE:
<221> NAME/KEY: MISC_FEATURE
<222> LOCATION: (13)..(13)
<223> OTHER INFORMATION: Xaa is Tyr or Thr
<220> FEATURE:
<221> NAME/KEY: MISC_FEATURE
```

```
<222> LOCATION: (15)..(15)
<223> OTHER INFORMATION: Xaa is Gln, Asn or Ser

<400> SEQUENCE: 125

Xaa Xaa Xaa Xaa Xaa Xaa Tyr Xaa Xaa Xaa Xaa Asn Xaa Val Xaa
1               5                   10                  15

<210> SEQ ID NO 126
<211> LENGTH: 9
<212> TYPE: PRT
<213> ORGANISM: artificial
<220> FEATURE:
<223> OTHER INFORMATION: CDR3 peptide

<400> SEQUENCE: 126

Gln Gln Tyr Gly Trp Ser Pro Arg Thr
1               5

<210> SEQ ID NO 127
<211> LENGTH: 463
<212> TYPE: PRT
<213> ORGANISM: artificial
<220> FEATURE:
<223> OTHER INFORMATION: antibody heavy chain

<400> SEQUENCE: 127

Met Asp Trp Thr Trp Ser Ile Leu Phe Leu Val Ala Ala Pro Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Gly Tyr Tyr Met His Trp Val Arg Gln Ala Pro Gly Gln Gly Leu
        50                  55                  60

Glu Trp Met Gly Trp Ile Asn Pro Asn Ser Gly Gly Thr Asn Tyr Ala
65                  70                  75                  80

Gln Lys Phe Arg Gly Arg Val Thr Met Thr Arg Asp Thr Ser Ile Ser
                85                  90                  95

Thr Ala Tyr Val Glu Leu Ser Arg Leu Arg Ser Asp Asp Thr Ala Val
            100                 105                 110

Tyr Tyr Cys Ala Arg Asp Pro Tyr Thr Ser Gly Phe Asp Tyr Trp Gly
        115                 120                 125

Gln Gly Thr Leu Val Thr Val Ser Ser Ala Ser Thr Lys Gly Pro Ser
130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
```

```
                260             265             270
Pro Glu Val Thr Cys Val Val Asp Val Ser His Glu Asp Pro Glu
        275             280             285
Val Gln Phe Asn Trp Tyr Val Asp Gly Val Glu Val His Asn Ala Lys
        290             295             300
Thr Lys Pro Arg Glu Glu Gln Phe Asn Ser Thr Phe Arg Val Val Ser
305             310             315             320
Val Leu Thr Val Val His Gln Asp Trp Leu Asn Gly Lys Glu Tyr Lys
                325             330             335
Cys Lys Val Ser Asn Lys Gly Leu Pro Ala Pro Ile Glu Lys Thr Ile
                340             345             350
Ser Lys Thr Lys Gly Gln Pro Arg Glu Pro Gln Val Tyr Thr Leu Pro
                355             360             365
Pro Ser Arg Glu Glu Met Thr Lys Asn Gln Val Ser Leu Thr Cys Leu
        370             375             380
Val Lys Gly Phe Tyr Pro Ser Asp Ile Ala Val Glu Trp Glu Ser Asn
385             390             395             400
Gly Gln Pro Glu Asn Asn Tyr Lys Thr Thr Pro Pro Met Leu Asp Ser
                405             410             415
Asp Gly Ser Phe Phe Leu Tyr Ser Lys Leu Thr Val Asp Lys Ser Arg
                420             425             430
Trp Gln Gln Gly Asn Val Phe Ser Cys Ser Val Met His Glu Ala Leu
                435             440             445
His Asn His Tyr Thr Gln Lys Ser Leu Ser Leu Ser Pro Gly Lys
        450             455             460

<210> SEQ ID NO 128
<211> LENGTH: 1389
<212> TYPE: DNA
<213> ORGANISM: artificial
<220> FEATURE:
<223> OTHER INFORMATION: antibody heavy chain gene

<400> SEQUENCE: 128
atggattgga cctggagcat tctgtttctg gtggcggcgc cgaccggcgc gcatagccag     60
gtacaactgg tgcagtctgg ggctgaggtg aagaagcctg ggcctcagt gaaggtctcc    120 tgcaaggctt ctggatacac cttcaccggc tactatatgc actgggtgcg acaggcccct    180
ggacaagggc ttgagtggat gggatggatc aaccctaaca gtggtggcac aaattatgca    240
cagaagtttc agggcagggt caccatgacc agggacacgt ccatcagcac agcctacgtg    300
gagctgagca ggctgagatc tgacgacacg gccgtatatt actgtgcgag acccgtat     360 accagtggct ttgactactg gggccaggga ccctggtca cgtctcctc agctagcacc      420 aagggcccat cggtcttccc cctggcgccc tgctccagga gcacctccga gagcacagcg    480
gccctgggct gcctggtcaa ggactacttc cccgaaccgg tgacggtgtc gtggaactca    540
ggcgctctga ccagcggcgt gcacaccttc ccagctgtcc tacagtcctc aggactctac    600
tccctcagca gcgtggtgac cgtgccctcc agcaacttcg gcacccagac ctacacctgc    660
aacgtagatc acaagcccag caacaccaag gtggacaaga cagttgagcg caaatgttgt    720
gtcgagtgcc caccgtgccc agcaccacct gtggcaggac cgtcagtctt cctcttcccc    780
ccaaaaccca aggacaccct catgatctcc cggacccctg aggtcacgtg cgtggtggtg    840
gacgtgagcc acgaagaccc cgaggtccag ttcaactggt acgtggacgg cgtggaggtg    900
cataatgcca agacaaagcc acgggaggag cagttcaaca gcacgttccg tgtggtcagc    960
```

```
gtcctcaccg ttgtgcacca ggactggctg aacggcaagg agtacaagtg caaggtctcc   1020
aacaaaggcc tcccagcccc catcgagaaa accatctcca aaaccaaagg gcagccccga   1080
gaaccacagg tgtacaccct gccccatcc cgggaggaga tgaccaagaa ccaggtcagc    1140
ctgacctgcc tggtcaaagg cttctacccc agcgacatcg ccgtggagtg ggagagcaat   1200
gggcagccgg agaacaacta caagaccaca cctcccatgc tggactccga cggctccttc   1260
ttcctctaca gcaagctcac cgtggacaag agcaggtggc agcaggggaa cgtcttctca   1320
tgctccgtga tgcatgaggc tctgcacaac cactacacgc agaagagcct ctccctgtct   1380
ccgggtaaa                                                            1389
```

<210> SEQ ID NO 129
<211> LENGTH: 118
<212> TYPE: PRT
<213> ORGANISM: artificial
<220> FEATURE:
<223> OTHER INFORMATION: antibody variable domain

<400> SEQUENCE: 129

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Arg Gly Arg Val Thr Met Thr Arg Asp Thr Ser Ile Ser Thr Ala Tyr
65                  70                  75                  80

Val Glu Leu Ser Arg Leu Arg Ser Asp Asp Thr Ala Val Tyr Tyr Cys
                85                  90                  95

Ala Arg Asp Pro Tyr Thr Ser Gly Phe Asp Tyr Trp Gly Gln Gly Thr
            100                 105                 110

Leu Val Thr Val Ser Ser
        115
```

<210> SEQ ID NO 130
<211> LENGTH: 7
<212> TYPE: PRT
<213> ORGANISM: artificial
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: Xaa is Gly, Thr or Trp
<220> FEATURE:
<221> NAME/KEY: MISC_FEATURE
<222> LOCATION: (2)..(2)
<223> OTHER INFORMATION: Xaa is Thr or Ala
<220> FEATURE:
<221> NAME/KEY: MISC_FEATURE
<222> LOCATION: (3)..(3)
<223> OTHER INFORMATION: Xaa is Ser or Ala
<220> FEATURE:
<221> NAME/KEY: MISC_FEATURE
<222> LOCATION: (4)..(4)
<223> OTHER INFORMATION: Xaa is Ser or Thr
<220> FEATURE:
<221> NAME/KEY: MISC_FEATURE
<222> LOCATION: (5)..(5)
<223> OTHER INFORMATION: Xaa is Arg or Leu
<220> FEATURE:
<221> NAME/KEY: MISC_FEATURE
<222> LOCATION: (6)..(6)

```
<223> OTHER INFORMATION: Xaa is Ala, Glu or Gln
<220> FEATURE:
<221> NAME/KEY: MISC_FEATURE
<222> LOCATION: (7)..(7)
<223> OTHER INFORMATION: Xaa is Thr or Ser

<400> SEQUENCE: 130

Xaa Xaa Xaa Xaa Xaa Xaa Xaa
1               5

<210> SEQ ID NO 131
<211> LENGTH: 7
<212> TYPE: PRT
<213> ORGANISM: artificial
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: Xaa is Glu or Ser
<220> FEATURE:
<221> NAME/KEY: MISC_FEATURE
<222> LOCATION: (2)..(2)
<223> OTHER INFORMATION: Xaa is Asp, Val or Asn
<220> FEATURE:
<221> NAME/KEY: MISC_FEATURE
<222> LOCATION: (3)..(3)
<223> OTHER INFORMATION: Xaa is Asp, Ser or Asn
<220> FEATURE:
<221> NAME/KEY: MISC_FEATURE
<222> LOCATION: (4)..(4)
<223> OTHER INFORMATION: Xaa is Gln, Gly or His

<400> SEQUENCE: 131

Xaa Xaa Xaa Xaa Arg Pro Ser
1               5

<210> SEQ ID NO 132
<211> LENGTH: 9
<212> TYPE: PRT
<213> ORGANISM: artificial
<220> FEATURE:
<223> OTHER INFORMATION: CDR3 peptide

<400> SEQUENCE: 132

Asp Pro Tyr Thr Ser Gly Phe Asp Tyr
1               5

<210> SEQ ID NO 133
<211> LENGTH: 235
<212> TYPE: PRT
<213> ORGANISM: artificial
<220> FEATURE:
<223> OTHER INFORMATION: antibody light chain

<400> SEQUENCE: 133

Met Ala Trp Ala Pro Leu Leu Thr Leu Leu Ala His Cys Thr Gly
1               5                   10                  15

Ser Trp Ala Gln Ser Val Leu Thr Gln Pro Pro Ser Ala Ser Gly Thr
                20                  25                  30

Pro Gly Gln Arg Val Thr Ile Ser Cys Ser Gly Ser Arg Ser His Ile
            35                  40                  45

Gly Ser Asn Thr Val Asn Trp Tyr Gln His Leu Pro Gly Thr Ala Pro
        50                  55                  60

Lys Leu Leu Ile Tyr Ser Asn Asn His Arg Pro Ser Gly Val Pro Asp
65                  70                  75                  80

Arg Phe Ser Gly Ser Lys Ser Gly Thr Ser Ala Ser Leu Ala Ile Ser
                85                  90                  95
```

Gly Leu Gln Ser Glu Asp Glu Ala Asp Tyr Tyr Cys Ala Ala Trp Asp
                100                 105                 110

Asp Ser Leu Asn Gly Pro Val Phe Gly Gly Thr Lys Leu Thr Val
            115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
    210                 215                 220

Val Glu Lys Thr Val Ala Pro Thr Glu Cys Ser
225                 230                 235

<210> SEQ ID NO 134
<211> LENGTH: 705
<212> TYPE: DNA
<213> ORGANISM: artificial
<220> FEATURE:
<223> OTHER INFORMATION: antibody light chain

<400> SEQUENCE: 134
atggcgtggg cgccgctgct gctgaccctg ctggcgcatt gcaccggcag ctgggcgcag      60
tctgtgctga ctcagccacc ctcagcgtct gggaccccccg ggcagagggt caccatctct     120
tgttctggaa gccgctccca catcggaagt aatactgtaa actggtacca gcacctccca     180
ggaacggccc ccaaactcct catctatagt aataatcatc ggccctcagg ggtccctgac     240
cgattctctg gctccaagtc tggcacctca gcctccctgg ccatcagtgg gctccagtct     300
gaggatgagg ctgattatta ctgtgcagca tgggatgaca gcctgaatgg tccggtattc     360
ggcggaggga ccaagctgac cgtcctaggc caaccgaaag cggcgccctc ggtcactctg     420
ttcccgccct cctctgagga gcttcaagcc aacaaggcca cactggtgtg tctcataagt     480
gacttctacc cgggagccgt gacagtggcc tggaaggcag atagcagccc cgtcaaggcg     540
ggagtggaga ccaccacacc ctccaaacaa agcaacaaca gtacgcggc cagcagctat      600 ctgagcctga cgcctgagca gtggaagtcc cacagaagct acagctgcca ggtcacgcat     660
gaagggagca ccgtggagaa gacagtggcc cctacagaat gttca                     705

<210> SEQ ID NO 135
<211> LENGTH: 110
<212> TYPE: PRT
<213> ORGANISM: artificial
<220> FEATURE:
<223> OTHER INFORMATION: consensus sequence

<400> SEQUENCE: 135

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser His Ile Gly Ser Asn
            20                  25                  30

Thr Val Asn Trp Tyr Gln His Leu Pro Gly Thr Ala Pro Lys Leu Leu
        35                  40                  45

```
Ile Tyr Ser Asn Asn His Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110

<210> SEQ ID NO 136
<211> LENGTH: 13
<212> TYPE: PRT
<213> ORGANISM: artificial
<220> FEATURE:
<223> OTHER INFORMATION: CDR1 peptide

<400> SEQUENCE: 136

Ser Gly Ser Arg Ser His Ile Gly Ser Asn Thr Val Asn
1               5                   10

<210> SEQ ID NO 137
<211> LENGTH: 7
<212> TYPE: PRT
<213> ORGANISM: artificial
<220> FEATURE:
<223> OTHER INFORMATION: CDR2 peptide

<400> SEQUENCE: 137

Ser Asn Asn His Arg Pro Ser
1               5

<210> SEQ ID NO 138
<211> LENGTH: 11
<212> TYPE: PRT
<213> ORGANISM: artificial
<220> FEATURE:
<223> OTHER INFORMATION: CDR3 peptide

<400> SEQUENCE: 138

Ala Ala Trp Asp Asp Ser Leu Asn Gly Pro Val
1               5                   10

<210> SEQ ID NO 139
<211> LENGTH: 465
<212> TYPE: PRT
<213> ORGANISM: artificial
<220> FEATURE:
<223> OTHER INFORMATION: antibody heavy chain

<400> SEQUENCE: 139

Met Asp Trp Thr Trp Ser Ile Leu Phe Leu Val Ala Ala Pro Thr Gly
1               5                   10                  15

Ala His Ser Gln Val Gln Leu Gln Glu Ser Gly Pro Gly Leu Val Lys
                20                  25                  30

Pro Ser Gln Thr Leu Ser Leu Thr Cys Thr Val Ser Gly Gly Ser Ile
            35                  40                  45

Arg Ser Gly Gly Tyr Tyr Trp Ser Trp Ile Arg Gln His Pro Gly Lys
    50                  55                  60

Gly Leu Glu Trp Ile Gly Tyr Ile Tyr Tyr Ser Gly Ser Thr Tyr Tyr
65                  70                  75                  80

Asn Pro Ser Leu Lys Ser Arg Val Thr Ile Ser Val Asp Thr Ser Lys
                85                  90                  95
```

```
Asn Gln Phe Ser Leu Lys Leu Asn Ser Val Thr Ala Ala Asp Thr Ala
                100                 105                 110
Val Tyr Tyr Cys Ala Arg Glu Asp Thr Ala Met Asp Tyr Phe Asp Tyr
            115                 120                 125
Trp Gly Gln Gly Thr Leu Val Thr Val Ser Ser Ala Ser Thr Lys Gly
        130                 135                 140
Pro Ser Val Phe Pro Leu Ala Pro Cys Ser Arg Ser Thr Ser Glu Ser
145                 150                 155                 160
Thr Ala Ala Leu Gly Cys Leu Val Lys Asp Tyr Phe Pro Glu Pro Val
                165                 170                 175
Thr Val Ser Trp Asn Ser Gly Ala Leu Thr Ser Gly Val His Thr Phe
            180                 185                 190
Pro Ala Val Leu Gln Ser Ser Gly Leu Tyr Ser Leu Ser Ser Val Val
        195                 200                 205
Thr Val Pro Ser Ser Asn Phe Gly Thr Gln Thr Tyr Thr Cys Asn Val
210                 215                 220
Asp His Lys Pro Ser Asn Thr Lys Val Asp Lys Thr Val Glu Arg Lys
225                 230                 235                 240
Cys Cys Val Glu Cys Pro Pro Cys Pro Ala Pro Pro Val Ala Gly Pro
                245                 250                 255
Ser Val Phe Leu Phe Pro Pro Lys Pro Lys Asp Thr Leu Met Ile Ser
            260                 265                 270
Arg Thr Pro Glu Val Thr Cys Val Val Val Asp Val Ser His Glu Asp
        275                 280                 285
Pro Glu Val Gln Phe Asn Trp Tyr Val Asp Gly Val Glu Val His Asn
290                 295                 300
Ala Lys Thr Lys Pro Arg Glu Glu Gln Phe Asn Ser Thr Phe Arg Val
305                 310                 315                 320
Val Ser Val Leu Thr Val Val His Gln Asp Trp Leu Asn Gly Lys Glu
                325                 330                 335
Tyr Lys Cys Lys Val Ser Asn Lys Gly Leu Pro Ala Pro Ile Glu Lys
            340                 345                 350
Thr Ile Ser Lys Thr Lys Gly Gln Pro Arg Glu Pro Gln Val Tyr Thr
        355                 360                 365
Leu Pro Pro Ser Arg Glu Glu Met Thr Lys Asn Gln Val Ser Leu Thr
370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Met Leu
                405                 410                 415
Asp Ser Asp Gly Ser Phe Phe Leu Tyr Ser Lys Leu Thr Val Asp Lys
            420                 425                 430
Ser Arg Trp Gln Gln Gly Asn Val Phe Ser Cys Ser Val Met His Glu
        435                 440                 445
Ala Leu His Asn His Tyr Thr Gln Lys Ser Leu Ser Leu Ser Pro Gly
    450                 455                 460
Lys
465

<210> SEQ ID NO 140
<211> LENGTH: 1395
<212> TYPE: DNA
<213> ORGANISM: artificial
<220> FEATURE:
<223> OTHER INFORMATION: antibody heavy chain gene
```

<400> SEQUENCE: 140

```
atggattgga cctggagcat tctgtttctg gtggcggcgc cgaccggcgc gcatagccag    60
gtgcagctgc aggagtcggg cccaggactg gtgaagcctt cacagaccct gtccctcacc   120
tgcactgtct ctggtggctc catcagaagt ggtggttact actggagctg gatccgccag   180
cacccaggga agggcctgga gtggattggg tatatctatt acagtgggag cacctactac   240
aacccgtccc tcaagagtcg agttaccata tcagtagaca cgtctaagaa ccagttctcc   300
ctgaagctga actctgtgac tgccgcggac acggccgtgt attactgtgc gagagaggat   360
acagctatgg actactttga ctactggggc cagggaaccc tggtcaccgt ctcctcagct   420
agcaccaagg gcccatcggt cttccccctg gcgccctgct ccaggagcac ctccgagagc   480
acagcggccc tgggctgcct ggtcaaggac tacttccccg aaccggtgac ggtgtcgtgg   540
aactcaggcg ctctgaccag cggcgtgcac accttcccag ctgtcctaca gtcctcagga   600
ctctactccc tcagcagcgt ggtgaccgtg ccctccagca acttcggcac ccagacctac   660
acctgcaacg tagatcacaa gcccagcaac accaaggtgg acaagacagt tgagcgcaaa   720
tgttgtgtcg agtgcccacc gtgcccagca ccacctgtgg caggaccgtc agtcttcctc   780
ttccccccaa aacccaagga caccctcatg atctcccgga cccctgaggt cacgtgcgtg   840
gtggtggacg tgagccacga agaccccgag gtccagttca actggtacgt ggacggcgtg   900
gaggtgcata atgccaagac aaagccacgg gaggagcagt tcaacagcac gttccgtgtg   960
gtcagcgtcc tcaccgttgt gcaccaggac tggctgaacg gcaaggagta caagtgcaag  1020
gtctccaaca aaggcctccc agcccccatc gagaaaacca tctccaaaac caaagggcag  1080
ccccgagaac acaggtgta cccctgcccc catcccggg aggagatgac caagaaccag  1140
gtcagcctga cctgcctggt caaaggcttc taccccagcg acatcgccgt ggagtgggag  1200
agcaatgggc agccggagaa caactacaag accacacctc ccatgctgga ctccgacggc  1260
tccttcttcc tctacagcaa gctcaccgtg gacaagagca ggtggcagca ggggaacgtc  1320
ttctcatgct ccgtgatgca tgaggctctg cacaaccact acacgcagaa gagcctctcc  1380
ctgtctccgg gtaaa                                                   1395
```

<210> SEQ ID NO 141
<211> LENGTH: 120
<212> TYPE: PRT
<213> ORGANISM: artificial
<220> FEATURE:
<223> OTHER INFORMATION: consensus sequence

<400> SEQUENCE: 141

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Arg Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Asn Ser Val Thr Ala Ala Asp Thr Ala Val Tyr Tyr
                85                  90                  95

Cys Ala Arg Glu Asp Thr Ala Met Asp Tyr Phe Asp Tyr Trp Gly Gln
            100                 105                 110
```

```
Gly Thr Leu Val Thr Val Ser Ser
        115                 120

<210> SEQ ID NO 142
<211> LENGTH: 7
<212> TYPE: PRT
<213> ORGANISM: artificial
<220> FEATURE:
<223> OTHER INFORMATION: CDR1 peptide

<400> SEQUENCE: 142

Ser Gly Gly Tyr Tyr Trp Ser
1               5

<210> SEQ ID NO 143
<211> LENGTH: 16
<212> TYPE: PRT
<213> ORGANISM: artificial
<220> FEATURE:
<223> OTHER INFORMATION: CDR2 peptide

<400> SEQUENCE: 143

Tyr Ile Tyr Tyr Ser Gly Ser Thr Tyr Tyr Asn Pro Ser Leu Lys Ser
1               5                   10                  15

<210> SEQ ID NO 144
<211> LENGTH: 10
<212> TYPE: PRT
<213> ORGANISM: artificial
<220> FEATURE:
<223> OTHER INFORMATION: CDR3 peptide

<400> SEQUENCE: 144

Glu Asp Thr Ala Met Asp Tyr Phe Asp Tyr
1               5                   10

<210> SEQ ID NO 145
<211> LENGTH: 127
<212> TYPE: PRT
<213> ORGANISM: artificial
<220> FEATURE:
<223> OTHER INFORMATION: GM-CSF-Ile

<400> SEQUENCE: 145

Ala Pro Ala Arg Ser Pro Ser Pro Ser Thr Gln Pro Trp Glu His Val
1               5                   10                  15

Asn Ala Ile Gln Glu Ala Leu Arg Leu Leu Asp Leu Ser Arg Asp Thr
            20                  25                  30

Ala Ala Glu Met Asn Glu Glu Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Lys Pro Val Gln Glu
        115                 120                 125

<210> SEQ ID NO 146
<211> LENGTH: 127
```

```
<212> TYPE: PRT
<213> ORGANISM: Homo sapiens

<400> SEQUENCE: 146

Ala Pro Ser Arg Ser Pro Ser Arg Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Ile Asn Glu Thr Val Glu Val Val Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Thr Pro Phe Asp Cys Trp Glu Pro Val Gln Gly
        115                 120                 125

<210> SEQ ID NO 147
<211> LENGTH: 12
<212> TYPE: PRT
<213> ORGANISM: artificial
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: Xaa is Gly or no amino acid residue
<220> FEATURE:
<221> NAME/KEY: MISC_FEATURE
<222> LOCATION: (2)..(2)
<223> OTHER INFORMATION: Xaa is Gly or no amino acid residue
<220> FEATURE:
<221> NAME/KEY: MISC_FEATURE
<222> LOCATION: (4)..(4)
<223> OTHER INFORMATION: Xaa is Tyr or Phe
<220> FEATURE:
<221> NAME/KEY: MISC_FEATURE
<222> LOCATION: (5)..(5)
<223> OTHER INFORMATION: Xaa is Thr or Ser
<220> FEATURE:
<221> NAME/KEY: MISC_FEATURE
<222> LOCATION: (7)..(7)
<223> OTHER INFORMATION: Xaa is Thr, Ser or Gly
<220> FEATURE:
<221> NAME/KEY: MISC_FEATURE
<222> LOCATION: (8)..(8)
<223> OTHER INFORMATION: Xaa is Gly or Ser
<220> FEATURE:
<221> NAME/KEY: MISC_FEATURE
<222> LOCATION: (10)..(10)
<223> OTHER INFORMATION: Xaa is Tyr or Gly
<220> FEATURE:
<221> NAME/KEY: MISC_FEATURE
<222> LOCATION: (11)..(11)
<223> OTHER INFORMATION: Xaa is Ile or Met
<220> FEATURE:
<221> NAME/KEY: MISC_FEATURE
<222> LOCATION: (12)..(12)
<223> OTHER INFORMATION: Xaa is His or Ser

<400> SEQUENCE: 147

Xaa Xaa Gly Xaa Xaa Phe Xaa Xaa Tyr Xaa Xaa Xaa
1               5                   10
```

NUCLEIC ACID MOLECULE ENCODING HUMAN GM-CSF ANTIGEN BINDING PROTEINS

CROSS-REFERENCE TO RELATED APPLICATIONS

This application is a divisional of U.S. patent application Ser. No. 12/675,013, filed Jan. 18, 2011, which is a national stage application under 35 U.S.C. §371 of International Application No. PCT/US2008/010888, having an international filing date of Sep. 18, 2008; which claims the benefit of U.S. provisional application Ser. No. 61/087,551, filed Aug. 8, 2008, and U.S. provisional application Ser. No. 60/994,343, filed Sep. 18, 2007, the disclosures of which are relied upon and incorporated by reference herein.

REFERENCE TO THE SEQUENCE LISTING

The present application is being filed along with a Sequence Listing in electronic format. The Sequence Listing is provided as a file entitled A-1292-US-DIV_Sequence_Listing.txt., created Aug. 15, 2012, which is 162 KB in size. The information in the electronic format of the Sequence Listing is incorporate herein by reference in its entirety.

BACKGROUND

Granulocyte macrophage colony stimulating factor (GM-CSF; CSF2) is a well-studied protein which has long been appreciated for its hematopoietic properties (i.e. stimulation of proliferation and differentiation of progenitor cells and proliferation of mature cells of the myeloid lineage) (reviewed in Blood 77:1131, 1991; Rev Infect Dis 12: 41, 1990; Med. Oncol. 13:141, 1996). GM-CSF is constitutively produced by lung epithelial cells and the Paneth cells of the intestine (BBRC 312:897, 2003), but a wide variety of cells express GM-CSF upon activation with predominant expression from T cells, macrophages/monocytes, fibroblasts and endothelial cells (J Infect Dis 172:1573, 1995; J Infect Dis 185:1490, 2002; J Allergy Cin Immunol 112:653, 2003). The GM-CSF receptor (GM-CSFR; CSFR2) consists of a heterologous complex of two proteins; a high affinity alpha polypeptide which is specific for GM-CSF, and a low affinity common beta polypeptide which is shared by GM-CSF, IL-3 and IL-5 (reviewed in J Allergy Cin Immunol 112:653, 2003; Cytokine and Growth Factor Reviews 12:19, 2001). GM-CSFR is expressed on all cells of the myeloid lineage.

GM-CSF augments the activity of the innate immune system by mediating signals that cause or effect differentiation, survival, proliferation and activation of myeloid lineage cells including macrophages/monocytes, dendritic cells (DCs), neutrophils and eosinophils (reviewed in: J Immun 143:1198, 1989; Rev Infect Dis 12:41, 1990; Blood 77:1131, 1991; Trends in Immun. 23:403, 2002; Growth Factors 22:225, 2004). GM-CSF is an important factor for in vitro generation of monocyte-derived DCs and type 1 macrophages (PNAS 101:4560, 2004), and has been shown to induce differentiation and activation of DCs in vivo (Blood 95:2337, 2000). Human monocyte-derived macrophages generated in the presence of GM-CSF (Type 1 macrophages) produce high levels of proinflammatory cytokines such as IL-23, but not IL-12, whereas Type 2 macrophages generated in the presence of M-CSF (CSF1) produce anti-inflammatory cytokines such as IL-10, but not IL-23 (PNAS 101: 4560, 2004).

Human monocytes or macrophages stimulated with GM-CSF have increased function including cytotoxicity, production of other proinflammatory cytokines TNFα and IL-6) and phagocytosis. Based on these effects, much effort has recently been applied to developing GM-CSF as a potent adjuvant for use in infectious disease or with administration of vaccines (reviewed in Eur J Clin Microbiol Infect Dis. 13::S47, 1994; Curr Opin Hematol. 7:168, 2000). Indeed, administration of rhGM-CSF in some clinical settings dramatically improves outcome and clearance of fungal infection (Eur J Clin Microbiol Infect Dis 13: S18, 1994; J Med Microbiol 47: 1998).

Microglia are the resident macrophages of the CNS and data from in vitro studies indicates that GM-CSF is a key cytokine which enhances survival, activation, proliferation and even differentiation of both fetal and adult microglial cells (Glia 12:309, 1994; J Immunol Methods 300:32, 2005). In addition, there are several reports from mouse MS model studies which provide evidence for a critical role of APCs (microglia or DCs) in the perivascular space of the CNS for disease initiation and persistence (Nat. Med. 11:146-2005; Nat. Med. 11:328, 2005; Nat. Med. 11:335, 2005). GM-CSF stimulation of microglia upregulates MHCII and enhances antigen presentation It is only recently that GM-CSF's role as a proinflammatory cytokine in disease, and dispensability as a hematopoietic growth factor, has been established (reviewed in Trends in Immun. 23: 403, 2002; Growth Factors 22: 225, 2004) and its role in causing or enhancing inflammatory/autoimmune disease.

Elevated levels of GM-CSF have been observed at local sites of inflammation in multiple sclerosis (MS), rheumatoid arthritis (RA), asthma, psoriasis, atopic dermatitis and sarcoidosis. Elevation of GM-CSF is not typically observed in the serum, thus determining disease association requires analysis of the target tissues. In MS, two clinical studies were performed in which levels of GM-CSF protein were measured by ELISA in cerebrospinal fluid (CSF) and serum from Relapsing-Remitting (RR)MS patients with active disease (new symptoms or worsening of existing symptoms within 2 weeks of tissue collection) and compared with either RRMS patients with stable disease (no episodes for prior 6 months) or other neurological disease (OND) controls (Eur Neurol 33:152, 1993; Immunopharmacol. Immunotoxicol. 20:373, 1998). Importantly, the OND controls did not include Alzheimer's Disease or vascular dementia patients, as highly increased levels of GM-CSF were reported in the CSF and sera of such patients (Acta Neurol Scand 103:166, 2001).

GM-CSF levels were in the low pg range, but were significantly higher in RRMS active disease CSF compared to stable disease CSF, and in MS active disease CSF compared to OND CSF. In addition, there were higher levels of TNF-alpha in CSF of active versus stable disease, and higher levels of both TGF-beta and IL-10 in CSF of stable versus active disease. The studies included very careful inclusion criteria with respect to ongoing treatment of patients and clinical definition of active versus stable disease, as well as synchronicity of sample collection. Interestingly, there were no significant differences in GM-CSF levels in serum between any of the groups. In addition, one study observed selective immunohistochemical detection of GM-CSF in astrocytes of MS lesions and not in control CNS white matter (n=3 MS donors, Glia 12:309, 1994). Finally, activated T cells and monocytes/macrophages are capable of producing large amounts of GM-CSF upon activation during an inflammatory response. There is ample evidence for the presence of both of these cell types in MS lesions (Ann Neurol. 47:707, 2000), and for T cells in CSF (reviewed in Curr. Neurol. Neurosci. Rep. 1: 257, 2001).

In addition to association of GM-CSF expression with MS, there is an abundance of disease association data for other inflammatory/autoimmune diseases and even some evidence for disease exacerbation with administration of exogenous GM-CSF. In RA, elevated levels of GM-CSF have been detected in synovial fluid (SF) of patients with RA or Psoriatic arthritis (PsA) compared to OA (bioassay, Clin. Exp. Immunol. 72:67, 1988) and compared to non-RA controls (bioassay, Rheumatol Int. 14:177, 1995). In addition, there is a strong correlation between the presence of CD68+ macrophages in joints with disease severity in RA patients (Ann Rheum Dis 64:834, 2005). Finally, it has been reported that GM-CSF treatment of RA patients with Felty's syndrome (neutropenia) can exacerbate disease (Blood 74:2769, 1989).

In asthma, GM-CSF has been found to be elevated in bronchial biopsies from asthmatic patients by immunohistochemistry and a correlation was observed between decrease in GM-CSF levels and increase in FEV1 following steroid treatment (Chest 105:687, 1994; Am Rev Respir Dis 147: 1557, 1993). GM-CSF was also reported to be elevated in the sputum of intermittent, mild asthma patients (Ann Allergy Asthma Immunol 86:304, 2001). Data to support antagonism of GM-CSF includes a study in which the eosinophil promoting activity from BALF of symptomatic patients was attenuated by anti-GM-CSF mAb (in vitro, Eur. Respir. J. 12:872, 1998).

In psoriasis, GM-CSF expression was detected in psoriatic skin but not control skin samples (Arch Dermatol Res. 287: 158, 1995; Clin Exp Dermatol. 19:383, 1994; Dermatologica. 181:16, 1990). It has also been reported that GM-CSF treatment of psoriasis can exacerbate disease (Br J. Dermatol. 128:468, 1993).

In atopic dermatitis (AD), a significantly greater number of GM-CSF mRNA expressing cells were detected by in situ hybridization in biopsies of lesions of chronic AD than in acute AD or nonlesion skin (p<0.05; J Clin Invest. 95:211, 1995). In a second study, higher levels of GM-CSF were detected by immunohistochemistry of lesional AD skin (both epidermal and dermal compartments) and keratinocyte cultures established from uninvolved skin of AD patients exhibited increased spontaneous and PMA-stimulated production of GM-CSF compared with keratinocytes from nonatopic controls (J Clin Invest. 99:3009, 1997).

Mice deficient in GM-CSF (Science 264:713, 1994; PNAS 91:5592, 1994) and GM-CSFRc (Immunity 2:211, 1995; PNAS 92:9565, 1995) were generated by multiple groups. The mice had no overt differences in steady state levels of hematopoiesis, but did have histological evidence of alveolar proteinosis, were more susceptible to infections, and exhibited a modest delay in IgG production and diminished antigen-specific T cell responses after KLH immunization (PNAS 94:12557, 1997). GM-CSF−/− mice are resistant to MOG35-55-induced EAE (J Exp Med. 194:873, 2001), collagen-induced arthritis (CIA; JI 161:3639, 1998) and mBSA/IL-1-induced arthritis (Arthritis Rheum 44:111, 2001). In contrast, GM-CSF transgenic (Tg) mice have been generated in a number of labs and are associated with the development of inflammatory/autoimmune disease (Cell 51:675, 1987; JI 166:2090, 2001; J Clin Invest 97:1102, 1996; J Allergy Clin Immunol 111:1076, 2003; Lab Invest 77:615, 1997).

Thus there is a need in the art for GM-CSF inhibitors.

SUMMARY

Antigen-binding proteins that bind GM-CSF, in particular human GM-CSF, are provided. The human GM-CSF antigen-binding proteins can inhibit, interfere with, or modulate at least one of the biological responses related to GM-CSF, and, as such, are useful for ameliorating the effects of GM-CSF-related diseases or disorders. Binding of certain antigen-binding proteins to GM-CSF can, therefore, inhibit, interfere with, or block GM-CSF signaling, reduce monocyte migration into tumors, and reduce the accumulation of tumor-associated macrophages (TAMs).

Also provided are expression systems, including cell lines, for the production of GM-CSF antigen binding proteins and methods for diagnosing and treating diseases related to human GM-CSF.

Some of the isolated antigen-binding proteins that are provided that comprise (A) one or more heavy chain complementary determining regions (CDRHs) selected from the group consisting of: (i) a CDRH1 selected from the group consisting of SEQ ID NO: 10, 22, 70 94 and 142; (ii) a CDRH2 selected from the group consisting of SEQ ID NO: 11, 23, 28, 35, 47, 59, 71, 95, 106, 119 and 143; (iii) a CDRH3 selected from the group consisting of SEQ ID NO: 12, 24, 36, 48, 60, 72, 83, 96, 108, 120, 132, and 144; and (iv) a CDRH of (i), (ii) and (iii) that contains one or more amino acid substitutions, deletions or insertions of no more than four amino acids; (B) one or more light chain complementary determining regions (CDRLs) selected from the group consisting of: (i) a CDRL1 selected from the group consisting of SEQ ID NO: 4, 16, 30, 40, 52, 64, 88, 100, 107, 112, 118, 124, 125 and 136; (ii) a CDRL2 selected from the group consisting of SEQ ID NO: 5, 17, 29, 34, 41, 65, 77, 101, 113, 130, 131 and 137; (iii) a CDRL3 selected from the group consisting of SEQ ID NO: 6, 18, 42, 46, 66, 78, 84, 89, 90, 102, 114, 126, and 138; and (iv) a CDRL of (i), (ii) and (iii) that contains one or more amino acid substitutions, deletions or insertions of no more than four amino acids; or (C) one or more heavy chain CDRHs of (A) and one or more light chain CDRLs of (B).

In one embodiment, the isolated antigen-binding protein may comprise at least one or two CDRH of the above-mentioned (A) and at least one or two CDRL of the above-mentioned (B). In yet another aspect, the isolated antigen-binding protein includes CDRH1, CDRH2, CDRH3, CDRL1, CDRL2 and CDRL3.

In addition, the CDRH of the above-mentioned (A) is further selected from the group consisting of: (i) a CDRH1 selected from the group consisting of SEQ ID NO: 10, 22, 70 94 and 142; (ii) a CDRH2 selected from the group consisting of SEQ ID NO: 11, 23, 28, 35, 47, 59, 71, 95, 106, 119 and 143; (iii) a CDRH3 selected from the group consisting of SEQ ID NO: 12, 24, 36, 48, 60, 72, 83, 96, 108, 120, 132, and 144; and (iv) a CDRH of (i), (ii) and (iii) that contains one or more amino acid substitutions, deletions or insertions of no more than two amino acids; the CDRH of the above-mentioned (B) is selected from the group consisting of: (i) a CDRL1 selected from the group consisting of SEQ ID NO: 4, 16, 30, 40, 52, 64, 88, 100, 107, 112, 118, 124, 125 and 136; (ii) a CDRL2 selected from the group consisting of SEQ ID NO: 5, 17, 29, 34, 41, 65, 77, 101, 113, 130, 131 and 137; (iii) a CDRL3 selected from the group consisting of SEQ ID NO: 6, 18, 42, 46, 66, 78, 84, 89, 90, 102, 114, 126, and 138; and (iv) a CDRL of (i), (ii) and (iii) that contains one or more amino acid substitutions, deletions or insertions of no more than 2 amino acids; or (C) one or more heavy chain CDRHs of (A) and one or more light chain CDRLs of (B).

In yet another embodiment, the isolated antigen-binding protein may comprise (A) a CDRH selected from the group consisting of (i) a CDRH1 selected from the group consisting of SEQ ID NO: 10, 22, 70 94 and 142; (ii) a CDRH2 selected from the group consisting of SEQ ID NO: 11, 23, 28, 35, 47, 59, 71, 95, 106, 119 and 143; (iii) a CDRH3 selected from the group consisting of SEQ ID NO: 12, 24, 36, 48, 60, 72, 83, 96, 108, 120, 132, and 144; (B) a CDRL selected from the group consisting of (i) a CDRL1 selected from the group consisting of SEQ ID NO: 4, 16, 30, 40, 52, 64, 88, 100, 107, 112, 118, 124, 125 and 136; (ii) a CDRL2 selected from the group consisting of SEQ ID NO: 5, 17, 29, 34, 41, 65, 77, 101, 113, 130, 131 and 137; (iii) a CDRL3 selected from the group consisting of SEQ ID NO: 6, 18, 42, 46, 66, 78, 84, 89, 90, 102, 114, 126, and 138; or (C) one or more heavy chain CDRHs of (A) and one or more light chain CDRLs of (B). In one embodiment, the isolated antigen-binding protein may include (A) a CDRH1 selected from the group consisting of SEQ ID NO: 10, 22, 70 94 and 142; a CDRH2 selected from the group consisting of SEQ ID NO: 11, 23, 28, 35, 47, 59, 71, 95, 106, 119 and 143; a CDRH3 selected from the group consisting of SEQ ID NO: 12, 24, 36, 48, 60, 72, 83, 96, 108, 120, 132, and 144; and (B) a CDRL1 selected from the group consisting of SEQ ID NO: 4, 16, 30, 40, 52, 64, 88, 100, 107, 112, 118, 124, 125 and 136; a CDRL2 selected from the group consisting of SEQ ID NO: 5, 17, 29, 34, 41, 65, 77, 101, 113, 130, 131 and 137; and CDRL3 selected from the group consisting of SEQ ID NO: 6, 18, 42, 46, 66, 78, 84, 89, 90, 102, 114, 126, and 138. In another embodiment, the variable heavy chain (VH) has at least 90% sequence identity with an amino acid sequence selected from the group consisting of SEQ ID NO: 9, 21, 33, 45, 57, 69, 81, 93, 105, 117, 129, and 141, and/or the variable light chain (VL) has at least 90% sequence identity with an amino acid sequence selected from the group consisting of SEQ ID NO: 3, 15, 27, 39, 51, 63, 75, 87, 99, 111, 123, and 135. In a further embodiment, the VH is selected from the group consisting of SEQ ID NO: 9, 21, 33, 45, 57, 69, 81, 93, 105, 117, 129, and 141, and/or the VL is selected from the group consisting of SEQ ID NO: 3, 15, 27, 39, 51, 63, 75, 87, 99, 111, 123, and 135.

In another aspect, an isolated antigen binding protein is provided that specifically binds to an epitope containing GM-CSF sequences wherein the antibody binding to GM-CSF antagonizes activation of GM-CSF mediated signaling in a cell containing a GM-CSFR.

In yet another aspect, an isolated antigen binding protein is provided that binds GM-CSF that comprises: (A) one or more heavy chain CDRs (CDRHs) selected from the group consisting of (i) a CDRH1 with at least 80% identify to a CDRH1 selected from the group consisting of SEQ ID NO: 10, 22, 70 94 and 142; (ii) a CDRH2 with at least 80% identity to a CDRH2 selected from the group consisting of SEQ ID NO: 11, 23, 28, 35, 47, 59, 71, 95, 106, 119 and 143; (iii) a CDRH3 with at least 80% identity to a CDRH3 selected from the group consisting of SEQ ID NO: 12, 24, 36, 48, 60, 72, 83, 96, 108, 120, 132, and 144; (B) one or more light chain CDRs (CDRLs) selected from the group consisting of: (i) a CDRL1 that is 80% identical to a CDRL1 selected from the group consisting of SEQ ID NO: 4, 16, 30, 40, 52, 64, 88, 100, 107, 112, 118, 124, 125 and 136; (ii) a CDRL2 that is 80% identical to a CDRL2 selected from the group consisting of SEQ ID NO: 5, 17, 29, 34, 41, 65, 77, 101, 113, 130, 131 and 137; (iii) a CDRL3 that is 80% identical to a CDRL3 selected from the group consisting of SEQ ID NO: 6, 18, 42, 46, 66, 78, 84, 89, 90, 102, 114, 126, and 138; or (C) one or more heavy chain CDRHs of (A) and one or more light chain CDRLs of (B). In one embodiment, the isolated antigen-binding protein includes (A) one or more CDRHs selected from the group consisting of: (i) a CDRH1 with at least 90% identity to a CDRH1 selected from the group consisting of SEQ ID NO: 10, 22, 70 94 and 142; (ii) a CDRH2 with at least 90% identity to a CDRH2 selected from the group consisting of SEQ ID NO: 11, 23, 28, 35, 47, 59, 71, 95, 106, 119 and 143; (iii) a CDRH3 with at least 90% identity to a CDRH3 selected from the group consisting of SEQ ID NO: 12, 24, 36, 48, 60, 72, 83, 96, 108, 120, 132, and 144; (B) one or more CDRLs selected from the group consisting of: (i) a CDRL1 that is at least 90% identical to a CDRL1 selected from the group consisting of SEQ ID NO: 4, 16, 30, 40, 52, 64, 88, 100, 107, 112, 118, 124, 125 and 136; (ii) a CDRL2 that is at least 90% identical to a CDRL2 selected from the group consisting of SEQ ID NO: 5, 17, 29, 34, 41, 65, 77, 101, 113, 130, 131 and 137; (iii) a CDRL3 that is at least 90% identical to a CDRL3 selected from the group consisting of SEQ ID NO: 6, 18, 42, 46, 66, 78, 84, 89, 90, 102, 114, 126, and 138; or (C) one or more heavy chain CDRHs of (A) and one or more light chain CDRLs of (B).

In a further aspect, there is a provision of an isolated antigen-binding protein that binds GM-CSF, the antigen-binding protein including A) a heavy chain complementary determining region (CDRH) selected from the group consisting of (i) a CDRH3 selected from the group consisting of SEQ ID NOs: 12, 24, 36, 48, 60, 72, 83, 96, 108, 120, 132, and 144; (ii) a CDRH3 that differs in amino acid sequence from the CDRH3 of (i) by an amino acid addition, deletion or substitution of not more than two amino acids; (iii) a CDRH3 amino acid sequence selected from the group consisting of $X_1X_2X_3X_4X_5X_6X_7X_8FDX_9$ (SEQ ID NO: 83) wherein $X_1$ is selected from the group consisting of E and no amino acid, $X_2$ is selected from the group consisting of G and no amino acid, $X_3$ is selected from the group consisting of P, D and G, $X_4$ is selected from the group consisting of Y, W, R and K, $X_5$ is selected from the group consisting of S, W, F, and T, $X_6$ is selected from the group consisting of Y and L, $X_7$ is selected from the group consisting of D and G, $X_8$ is selected from the group consisting of Y, no amino acid, and A, and $X_9$ is selected from the group consisting of M, T, and V; and/or B) a light chain complementary determining region (CDRL) selected from the group consisting of (i) a CDRL3 selected from the group consisting of SEQ ID NOs: 6, 18, 42, 46, 66, 78, 84, 89, 90, 102, 114, 126, and 138 (ii) a CDRL3 that differs in amino acid sequence from the CDRL3 of (i) by an amino acid addition, deletion or substitution of not more than two amino acids; and iii) a CDRL3 amino acid sequence selected from the group consisting of $X_1QX_2X_3X_4X_5X_6X_7T$ (SEQ ID NO: 84) wherein X1 is selected from the group consisting of Q and L, $X_2$ is selected from the group consisting of Y and S, $X_3$ is selected from the group consisting of D, G and F, $X_4$ is selected from the group consisting of R, T, and S, $X_5$ is selected from the group consisting of S and V, $X_6$ is selected from the group consisting of F and P, and $X_7$ is selected from the group consisting of R and W; and $X_1X_2X_3X_4DSSNX_5X_6X_7$ (SEQ ID NO: 89) wherein $X_1$ is selected from the group consisting of S and A, $X_2$ is selected from the group consisting of S and A, $X_3$ is selected from the group consisting of W and F, $X_4$ is selected from the group consisting of D and T, $X_5$ is selected from the group consisting of G, W, and no amino acid, X6 is selected from the group consisting of V, L, and P, and $X_6$ is selected from the group consisting of V and no amino acid.

Within another embodiment, the antigen binding protein further comprising: A) a CDRH selected from the group consisting of: (i) a CDRH1 selected from the group consisting of SEQ ID NOs: 10, 22, 70 94 and 142; (ii) a CDRH1 that differs in amino acid sequence from the CDRH1 of (i) by an amino acid addition, deletion or substitution of not more than two amino acids; (iii) a CDRH1 amino acid sequence selected from the group consisting of $X_1X_2GX_3X_4XFX_5X_6YX_7X_8X_9$ (SEQ ID NO: 94) wherein $X_1$ is selected from the group consisting of G and no amino acid, $X_2$ is selected from the group consisting of G and no amino acid, $X_3$ is selected from the group consisting of Y and F, $X_4$ is selected from the group consisting of T and S, $X_5$ is selected from the group consisting of T, S and G, $X_6$ is selected from the group consisting of G and S, $X_7$ is selected from the group consisting of Y and G, $X_8$ is selected from the group consisting of I and M, and $X_9$ is selected from the group consisting of H and S, or (iv) a CDRH2 selected from the group consisting of SEQ ID NOs: 5, 17, 29, 34, 41, 65, 77, 101, 113, 130, 131 and 137; (v) a CDRH2 that differs in amino acid sequence from the CDRH2 of (iv) by an amino acid addition, deletion or substitution of not more than two amino acids; or (vi) a CDRH2 amino acid sequence consisting of $X_1X_2X_3X_4X_5X_6GX_7X_8X_9X_{10}X_{11}X_{12}X_{13}X_{14}X_{15}G$ (SEQ ID NO: 106) wherein $X_1$ is selected from the group consisting of W and no amino acid, $X_2$ is selected from the group consisting of I and Y, $X_3$ is selected from the group consisting of N, S and I, $X_4$ is selected from the group consisting of P, A and Y, $X_5$ is selected from the group consisting of N and Y, $X_6$ is selected from the group consisting of S and N, $X_7$ is selected from the group consisting of G and N, $X_8$ is selected from the group consisting of T and R, $X_9$ is selected from the group consisting of N and D, $X_{10}$ is selected from the group consisting of Y and S, $X_{11}$ is selected from the group consisting of A and N, $X_{12}$ is selected from the group consisting of Q and R, $X_{13}$ is selected from the group consisting of K and R, $X_{14}$ is selected from the group consisting of F and L, and $X_{15}$ is selected from the group consisting of Q, K and R; or B) a CDRL selected from the group consisting of: (i) a CDRL1 selected from the group consisting of SEQ ID NOs: 4, 16, 30, 40, 52, 64, 88, 100, 107, 112, 118, 124, 125 and 136; (ii) a CDRL1 that differs in amino acid sequence from the CDRL1 of (i) by an amino acid addition, deletion or substitution of not more than two amino acids; (iii) a CDRL1 amino acid sequence selected from the group consisting of KSSQSX$_1$XLYSSX$_2$NX$_3$NX$_4$LX$_5$ (SEQ ID NO: 107) wherein $X_1$ is selected from the group consisting of V and I, $X_2$ is selected from the group consisting of S and N, $X_3$ is selected from the group consisting of E and K, $X_4$ is selected from the group consisting of Y and F, and $X_5$ is selected from the group consisting of T and A; RASX$_1$X$_2$X$_3$X$_4$X$_5$X$_6$YX$_7$X$_8$ (SEQ ID NO: 118) wherein $X_1$ is selected from the group consisting of Q and P, $X_2$ is selected from the group consisting of S and Y, $X_3$ is selected from the group consisting of V, L and I, $X_4$ is selected from the group consisting of S and C, $X_5$ is selected from the group consisting of S and N, $X_6$ is selected from the group consisting of S, I, T and no amino acid, $X_7$ is selected from the group consisting of F and L, and $X_8$ is selected from the group consisting of A and N; or $X_1X_2X_3X_4X_5X_6YX_7X_8X_9X_{10}NX_{11}VX_{12}$ (SEQ ID NO: 125) wherein $X_1$ is selected from the group consisting of I, S and T, $X_2$ is selected from the group consisting of R and G, $X_3$ is selected from the group consisting of T and S, $X_4$ is selected from the group consisting of R and S, $X_5$ is selected from the group consisting of G and S, $X_6$ is selected from the group consisting of S, H and D, $X_7$ is selected from the group consisting of I and V, $X_8$ is selected from the group consisting of A and G, $X_9$ is selected from the group consisting of no amino acid and G, $X_{10}$ is selected from the group consisting of S and Y, $X_{11}$ is selected from the group consisting of Y and T, and $X_{12}$ is selected from the group consisting of Q, N and S; or (iv) a CDRL2 selected from the group consisting of SEQ ID NOs: 5, 17, 29, 34, 41, 65, 77, 101, 113, 130, 131 and 137; (v) a CDRL2 that differs in amino acid sequence from the CDRL2 of (iv) by an amino acid addition, deletion or substitution of not more than two amino acids; or (vi) a CDRL2 amino acid sequence selected from the group consisting of $X_1X_2X_3X_4X_5X_6X_7$ (SEQ ID NO: 130) wherein $X_1$ is selected from the group consisting of G, T and W, X2 is selected from the group consisting of T and A, X3 is selected from the group consisting of S and A, X4 is selected from the group consisting of S and T, X5 is selected from the group consisting of R and L, X6 is selected from the group consisting of A, E and Q, and X7 is selected from the group consisting of T and S; or $X_1X_2X_3X_4RPS$ (SEQ ID NO: 131) wherein X1 is selected from the group consisting of E and S, X2 is selected from the group consisting of D, V and N, X3 is selected from the group consisting of D, S and N, and X4 is selected from the group consisting of Q, G and H.

In one aspect, the isolated antigen-binding proteins provided herein can be a monoclonal antibody, a polyclonal antibody, a recombinant antibody, a human antibody, a humanized antibody, a chimeric antibody, a multispecific antibody, or an antibody fragment thereof. In another embodiment, the antibody fragment of the isolated antigen-binding proteins can be an Fab fragment, an Fab' fragment, an F(ab')$_2$ fragment, an Fv fragment, a diabody, or a single chain antibody molecule. In a further embodiment, the isolated antigen binding protein is a human antibody and can be an IgG1, IgG2, IgG3, or IgG4.

In yet another aspect, the isolated antigen-binding protein can be coupled to a labeling group and can compete for binding to the extracellular portion of human GM-CSF with an antigen binding protein of one of the isolated antigen-binding proteins provided.

In yet another aspect, the isolated antigen binding protein that competes for binding to the receptor interacting portion of human GM-CSF with an antigen binding protein as provided herein. In one embodiment, the antigen binding protein is a monoclonal antibody, a polyclonal antibody, a recombinant antibody, a human antibody, a humanized antibody, a chimeric antibody, a multispecific antibody, or an antibody fragment thereof. In related embodiments are provided human and monoclonal antibodies and antigen fragments including a Fab fragment, a Fab' fragment, a $F(ab')_2$ fragment, a Fv fragment, a diabody, or a single chain antibody molecule. In other embodiments the antigen binding protein is of the IgG1-, IgG2- IgG3- or IgG4-type. Further provided is the isolated antigen binding protein coupled to a labeling group.

In yet another aspect, the invention further contemplates inhibiting GM-CSF activity to limit signals that cause or effect differentiation, survival, proliferation and activation of myeloid lineage cells including macrophages/monocytes, dendritic cells (DCs), neutrophils and eosinophils, and/or differentiation and/or activation of DCs. In addition, the invention contemplates inhibiting GM-CSF activity to limit monocyte-derived macrophages (Type 1 macrophages) from producing high levels of proinflammatory cytokines such as IL-23.

In a further aspect, also provided are isolated polynucleotides that encode the antigen-binding proteins that bind to GM-CSF, wherein the isolated polynucleotides are operably-linked to a control sequence.

In another aspect, also provided are expression vectors and host cells transformed or transfected with the expression vectors that comprising the aforementioned isolated polynucleotides that encode antigen-binding proteins that can bind to GM-CSF.

In another aspect, also provided are methods of preparing the antigen-binding proteins that includes the step of preparing the antigen binding protein from a host cell that secretes the antigen-binding protein.

In yet another aspect, a pharmaceutical composition is provided comprising at least one of the aforementioned antigen-binding proteins provided and a pharmaceutically acceptable excipient. In one embodiment, the pharmaceutical composition may comprise an additional active agent that is selected from the group consisting of a radioisotope, radionuclide, a toxin, or a therapeutic and a chemotherapeutic group.

In yet another aspect, a method is provided for treating or preventing a condition associated with GM-CSF in a patient, comprising administering to a patient an effective amount of at least one isolated antigen-binding protein. In one embodiment the condition is selected from the group consisting of rheumatic disorders, autoimmune disorders, hematological disorders, oncological disorders, inflammatory disorders, degenerative conditions of the nervous system, gastrointestinal, gastrourinary disorders, endocrine disorders and the like. In one embodiment, the condition is a disorder or disease that is selected from the group consisting of multiple sclerosis (MS), rheumatoid arthritis (RA), asthma, psoriasis, atopic dermatitis and sarcoidosis. In another embodiment is included treatment with an isolated antigen-binding protein alone or as a combination therapy. In yet another embodiment the condition is selected from breast cancer, prostate cancer, colorectal cancer, endometrial adenocarcinoma, leukemia, lymphoma, melanoma, gastric cancer, astrocytic cancer, endometrial cancer, cervical cancer, bladder cancer, renal cancer, and ovarian cancer.

In another aspect, the invention provides a method of inhibiting binding of GM-CSF to the extracellular portion of GM-CSFR in a patient comprising administering an effective amount of at least one antigen-binding protein provided herein.

In yet another aspect, the invention provides a method of inhibiting phosphorylation of human GM-CSFR in a patient comprising administering an effective amount of at least one antigen binding protein as described herein.

In yet another aspect, the isolated antigen binding protein reduces monocyte chemotaxis when administered to a patient. In one embodiment, the antigen binding protein inhibits monocyte migration. In yet another embodiment monocyte migration into tumors is inhibited when the isolated antigen binding protein is administered to a patient.

Further provided, as yet another aspect is a method of treating multiple sclerosis comprising administering an isolated antigen-binding protein as described herein.

Also contemplated are conditions were multiple sclerosis is relapsing-remitting multiple sclerosis, progressive-relapsing multiple sclerosis, primary-progressive multiple sclerosis or secondary progressive multiple sclerosis.

In one aspect also provided is a method of treating rheumatoid arthritis comprising administering an isolated antigen-binding protein as described herein.

In additional aspects are provided isolated antigen binding proteins that are cross-reactive with cynomologous GM-CSF within 1 log of human GM-CSF and that bind GM-CSF with an $IC_{50}$ of <1 nM as measured in a GM-CSF dependent assay.

These and other aspects will be described in greater detail herein. Each of the aspects provided can encompass various embodiments provided herein. It is therefore anticipated that each of the embodiments involving one element or combinations of elements can be included in each aspect described. Other features, objects, and advantages of the disclosed are apparent in the detailed description that follows.

BRIEF DESCRIPTION OF THE DRAWINGS

FIGS. 1a-d: A) Prophylactic administration of anti-murine GM-CSF MAb in active EAE delayed onset and reduced incidence of disease. To induce active SJL/$PLP_{139-151}$ EAE, 11 mice were given 250 µg $PLP_{139-151}$+CFA subcutaneous and subjected to a three week assessment. Eleven mice per group were given 500 µg anti-murine GM-CSF mAb, isotype control mAb or PBS on day of immunization. Daily weights and scoring were taken. Clinical scoring 0: no disease; 1: limp tail; 2: slight impairment of righting reflex or abnormal gait; 3: severe hind limb weakness, partial hind limb paralysis; 4: complete hind limb paralysis, mobile using forelimbs. Anti-GM-CSF mAb shows delay of onset compared to controls, with incidence at 45% compared to 91-100% in controls.

B and C) Prophylactic administration of anti-GM-CSF mAb prevented weight loss (B) and reduced mean clinical score (C).

D) Results from single dose of 500 µg anti-mGM-CSF mAb, isotype control mAb or PBS on day of disease onset, n=14 mice. Therapeutic administration of anti-GM-CSF mAb in active EAE reduced mean clinical score. P<0.05 vs isotype control or PBS.

Figure 2A:
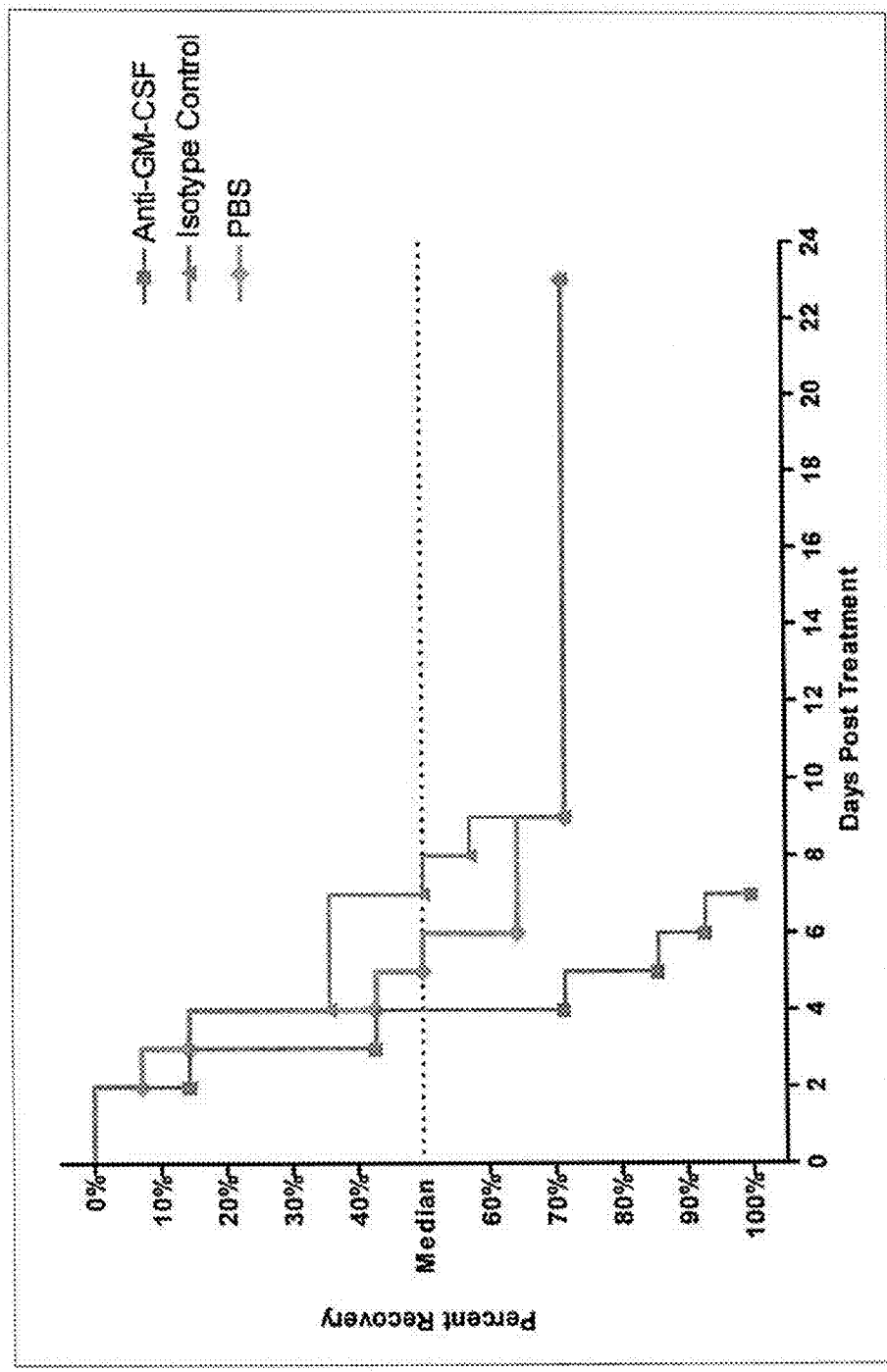
Figure 2B:
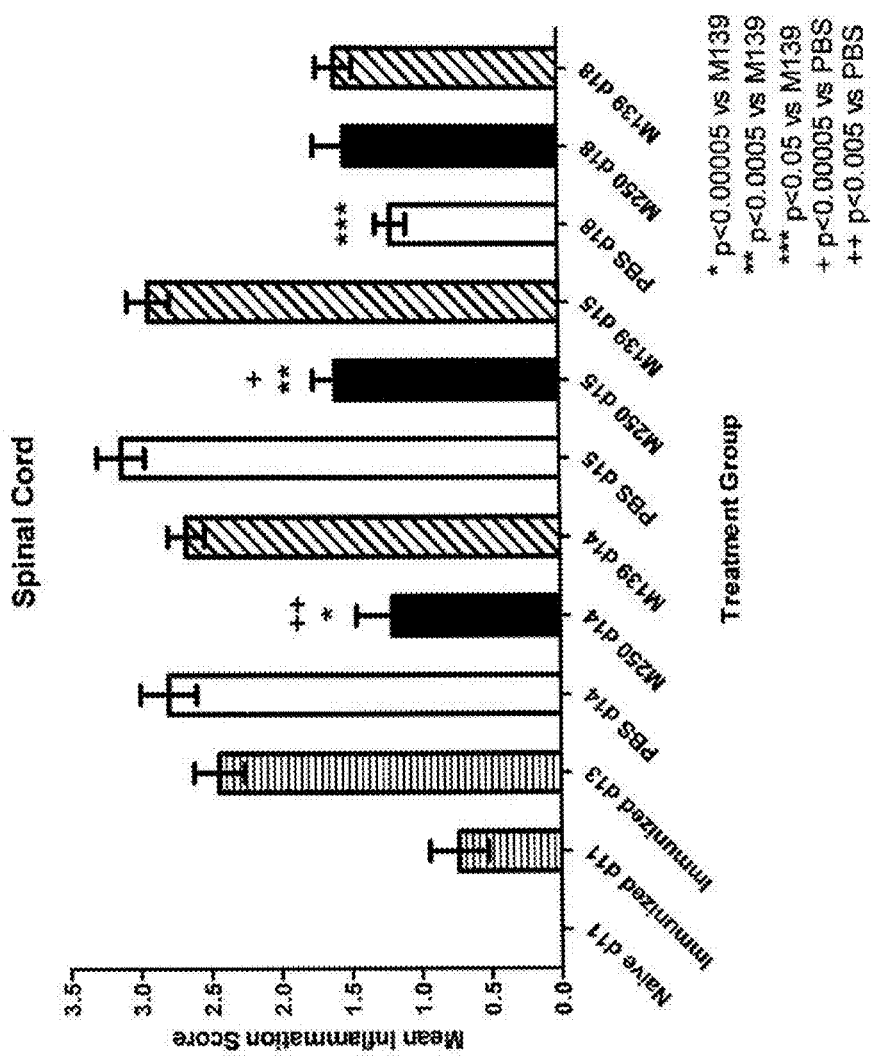
Figure 2C:
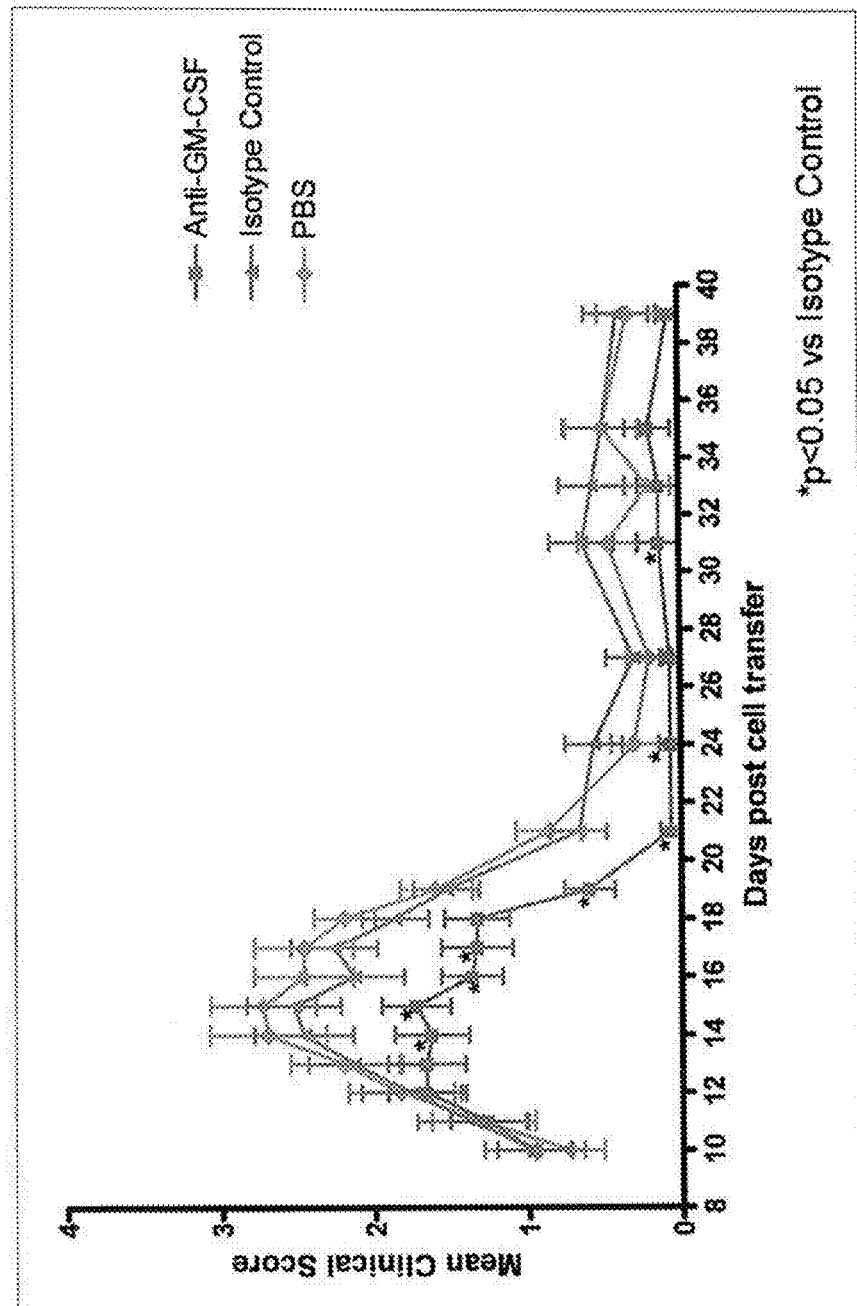

FIGS. 2a-c: A) Therapeutic administration of anti-mGM-CSF mAb in active EAE accelerated recovery. Recovery=decrease of ≧1 full score≧2d consecutively to score of ≦1.

B) Therapeutic anti-mGM-CSF mAb treatment on day of disease onset (day 13 post-immunization) reduced CNS inflammation compared to mice treated with anti-mGM-CSF mAb, isotype control mAb or PBS control.

C and D) Prophylactic or therapeutic administration of anti-mGM-CSF mAb in adoptive transfer EAE ameliorated disease. In the adoptive transfer EAE model, 15 mice were given 100 µg $PLP_{139-151}$+CFA and, lymph node were harvested on day 10 post-immunization stimulated with PLP peptide 4 days in vitro and injected into recipient mice. Mice were subjected to three week assessment of weight and clinical score. FIG. C shows treatment on day of cell transfer, FIG. D shows treatment on day of EAE onset.

Figure 3:
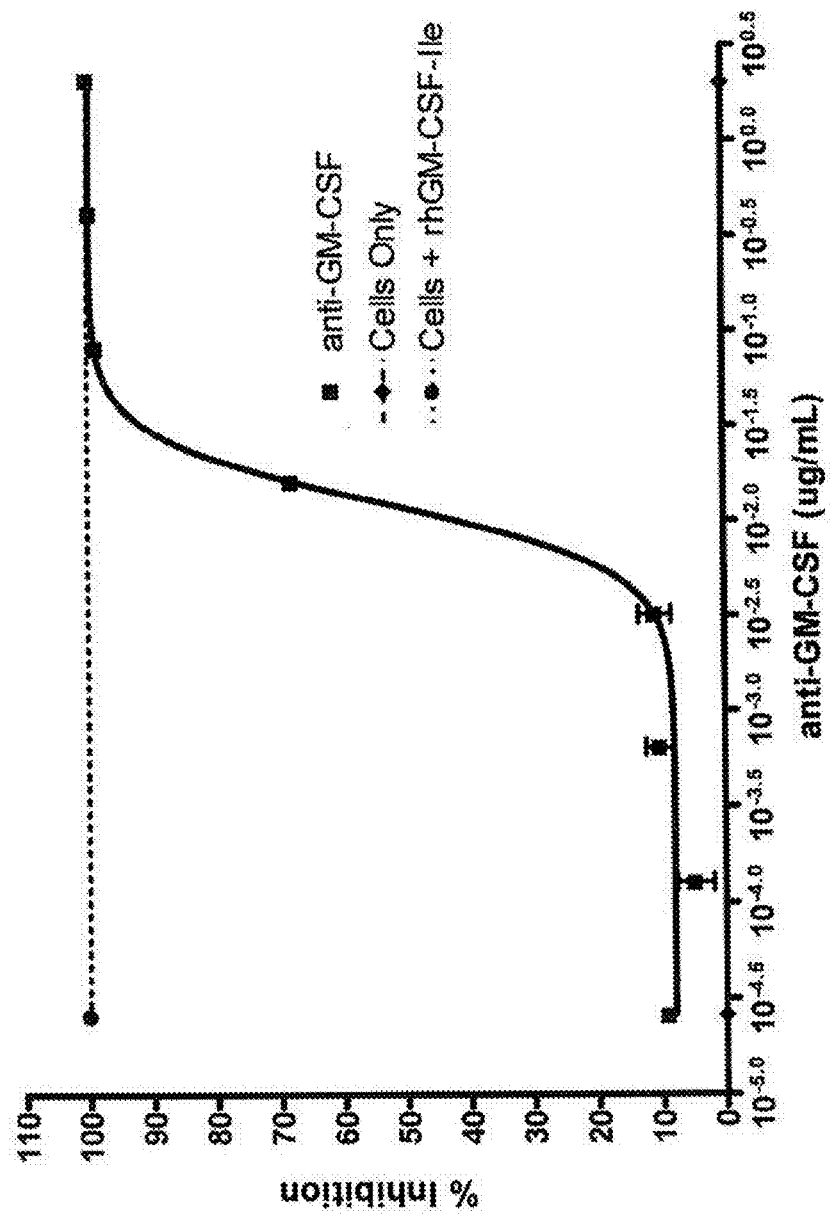

FIG. 3: Representative TF-1 Stat5 phosphorylation assay showing anti-GM-CSF mAb inhibition or 0.4 ng/ml rhGM-CSF-Ile.

Figure 4:
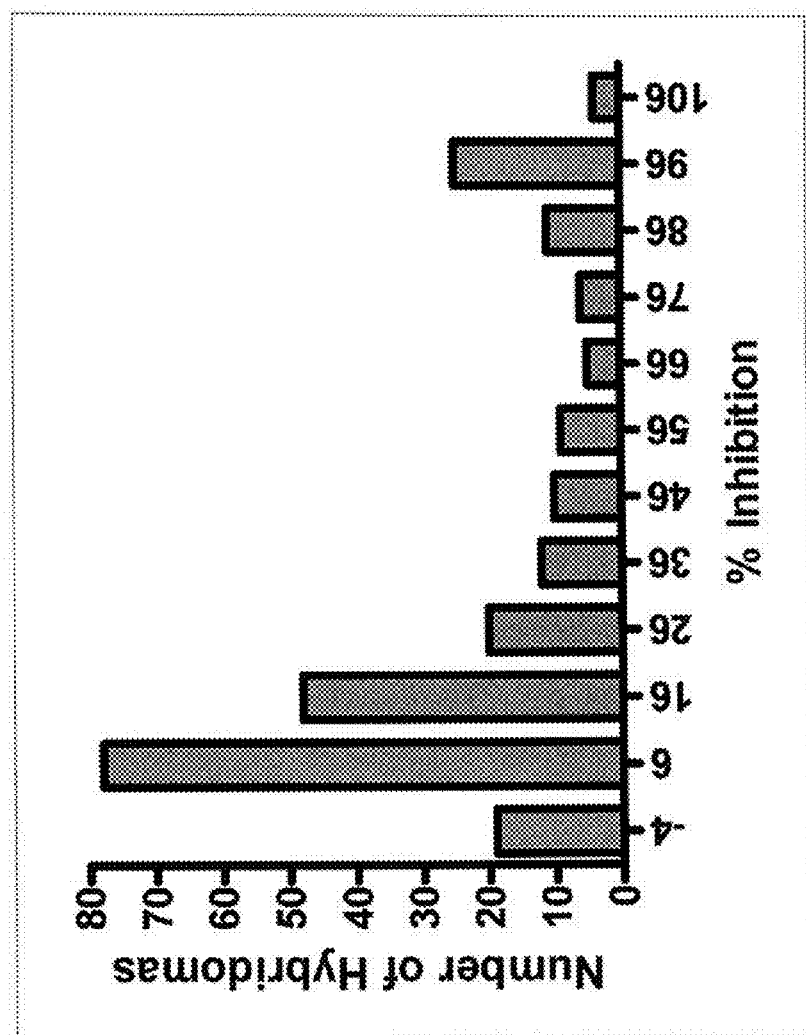

FIG. 4: Histogram showing distribution of inhibition of rhGM-CSF-Ile in the TF-1 STAT5 phosphorylation assay my hybridoma supernatant from E. coli rhGM-CSF immunized mice.

Figure 5:
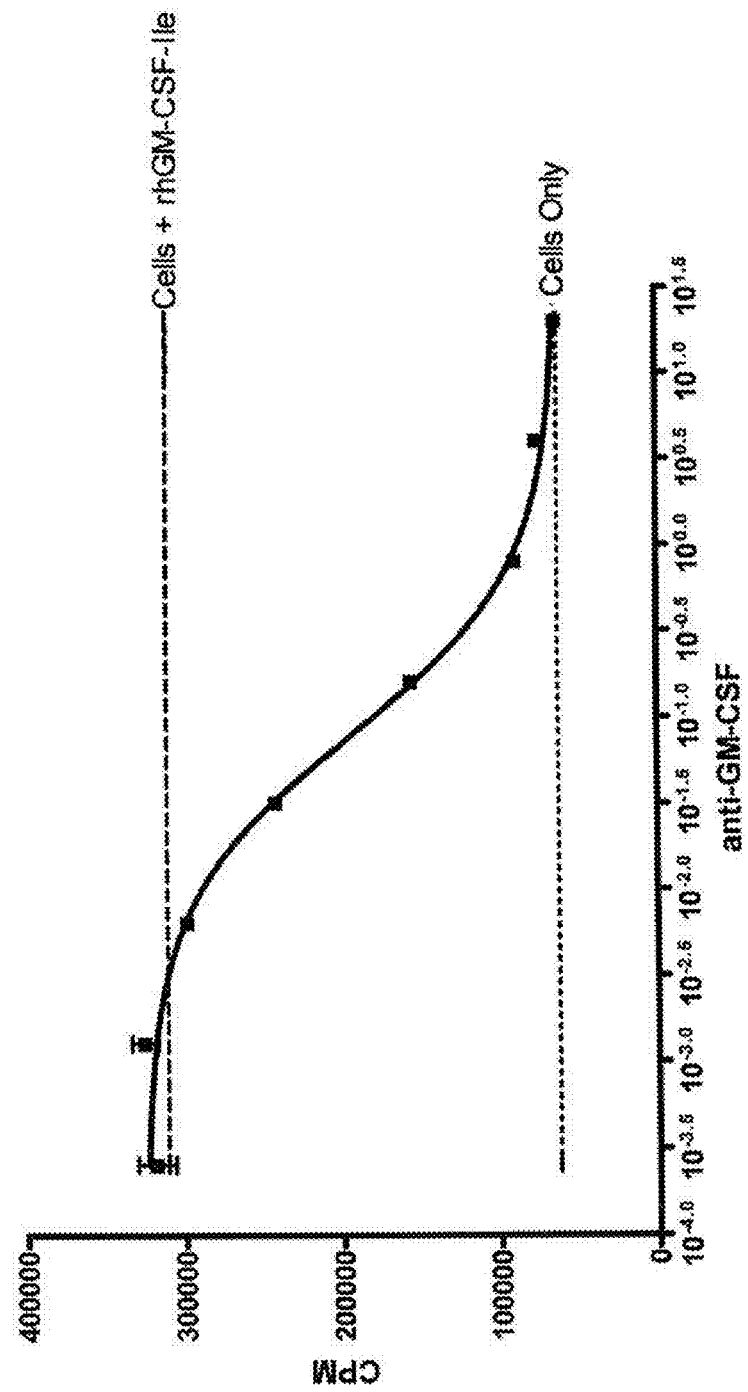
Figure 6A:
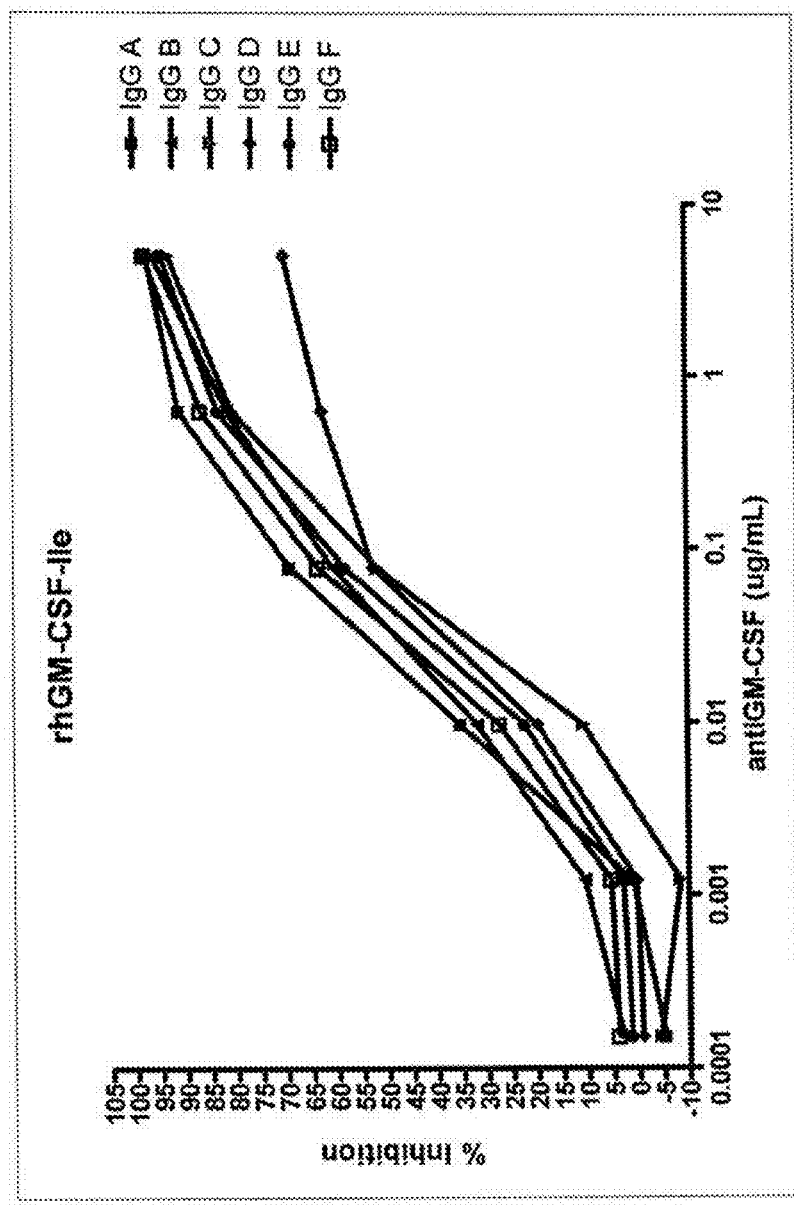
Figure 6B:
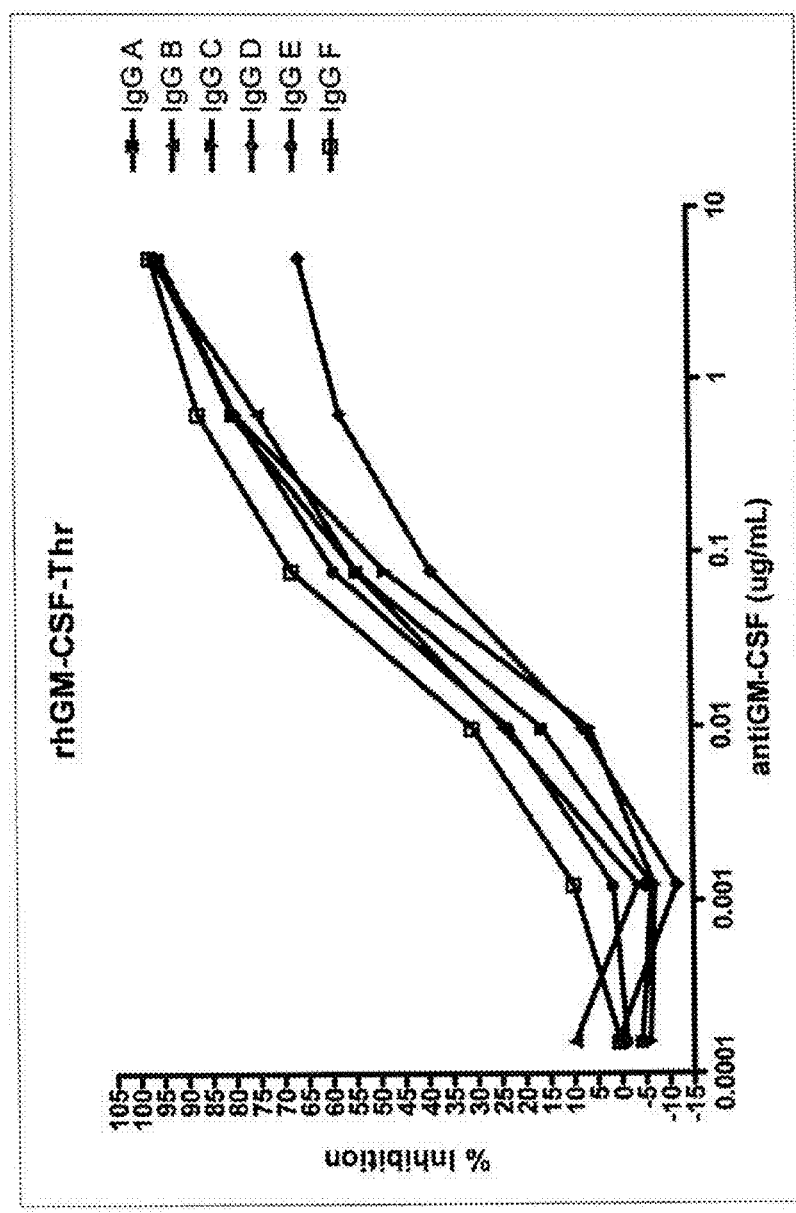
Figure 6C:
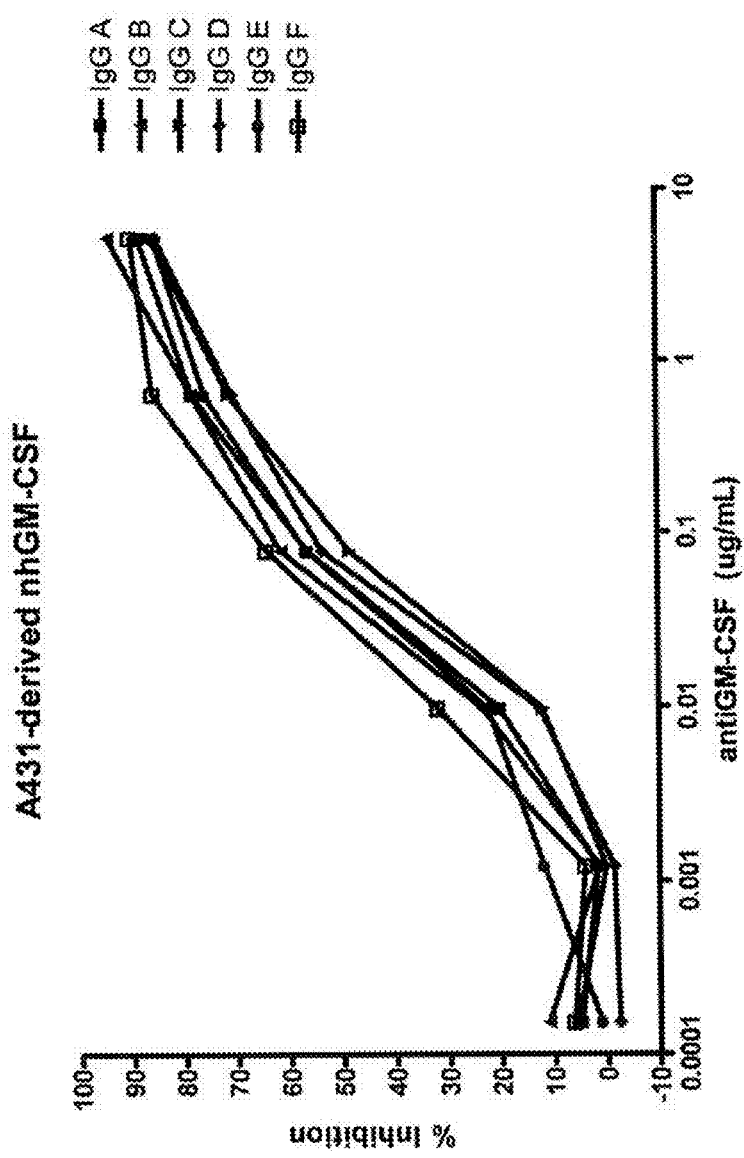
Figure 6D:
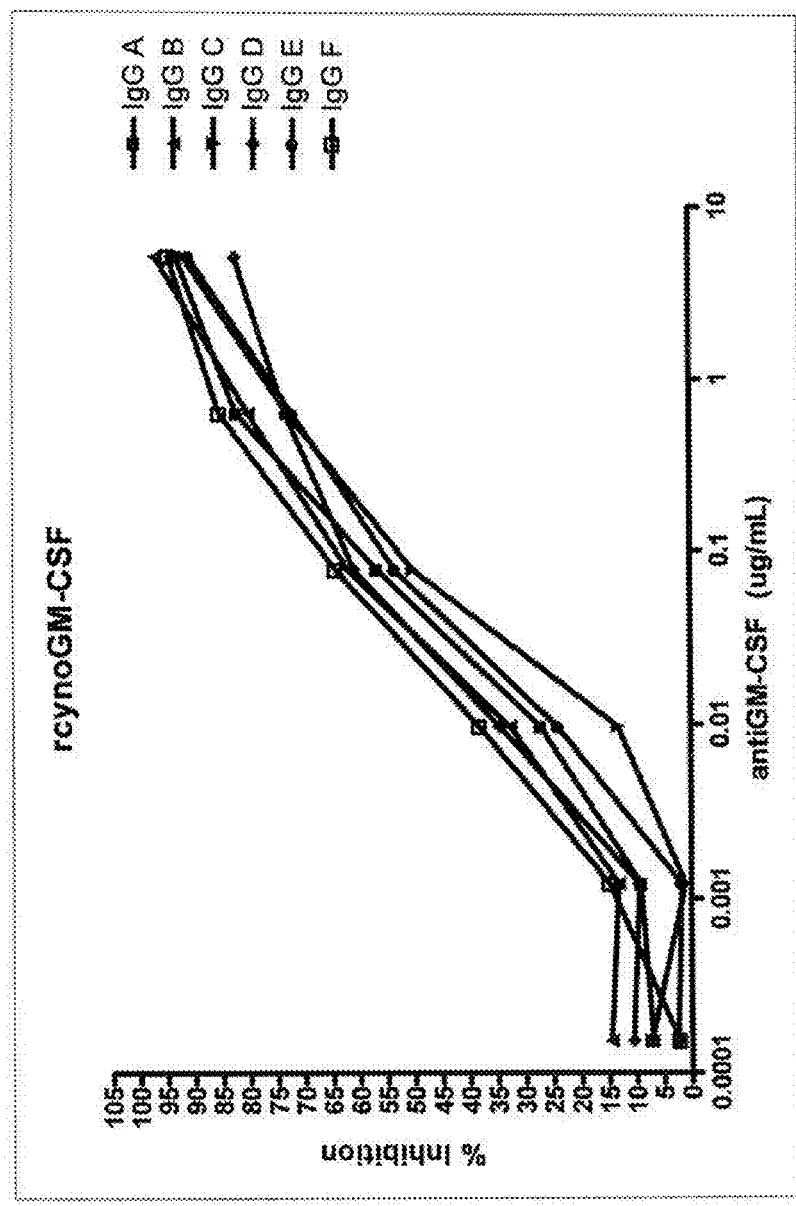
Figure 6F:
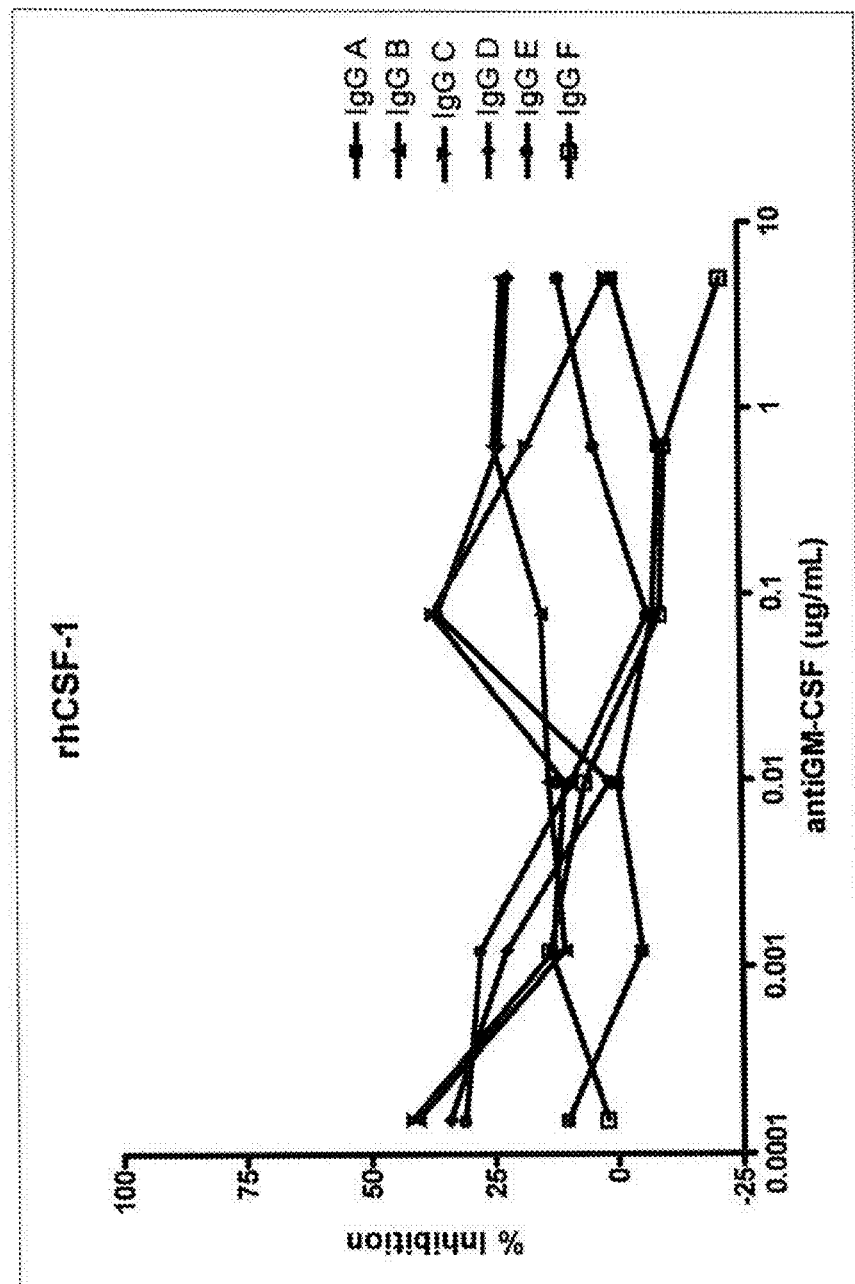

FIG. 5: Representative AML-5 proliferation assay showing anti-GM-CSF mAb inhibition of 0.15 ng/ml rhGM-CSF-Ile.

FIGS. 6a-f: Inhibition of GM-CSF and CSF-1 by mAb purified from hybridoma supernatants in the AML-5 proliferation assay.

Figure 7A:
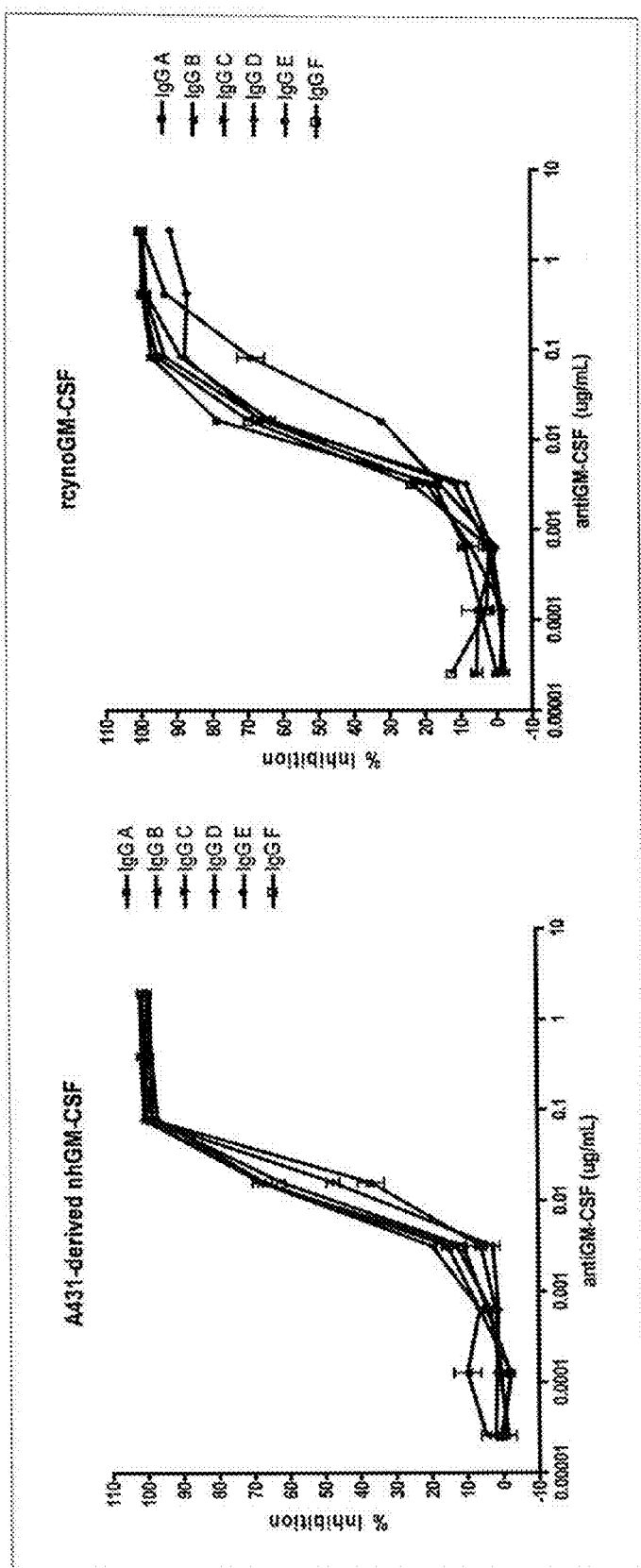

FIGS. 7a-b: Inhibition of GM-CSF and IL-3 by mAb purified from hybridoma supernatants in the TF-1 Stat5 phosphorylation assay.

FIGS. 8a-b: Results from ELISA measuring binding of hybridoma supernatant anti-GM-CSF mAb or recombinant anti-GM-CSF mAb to GM-CSF from various species.

Figure 9:
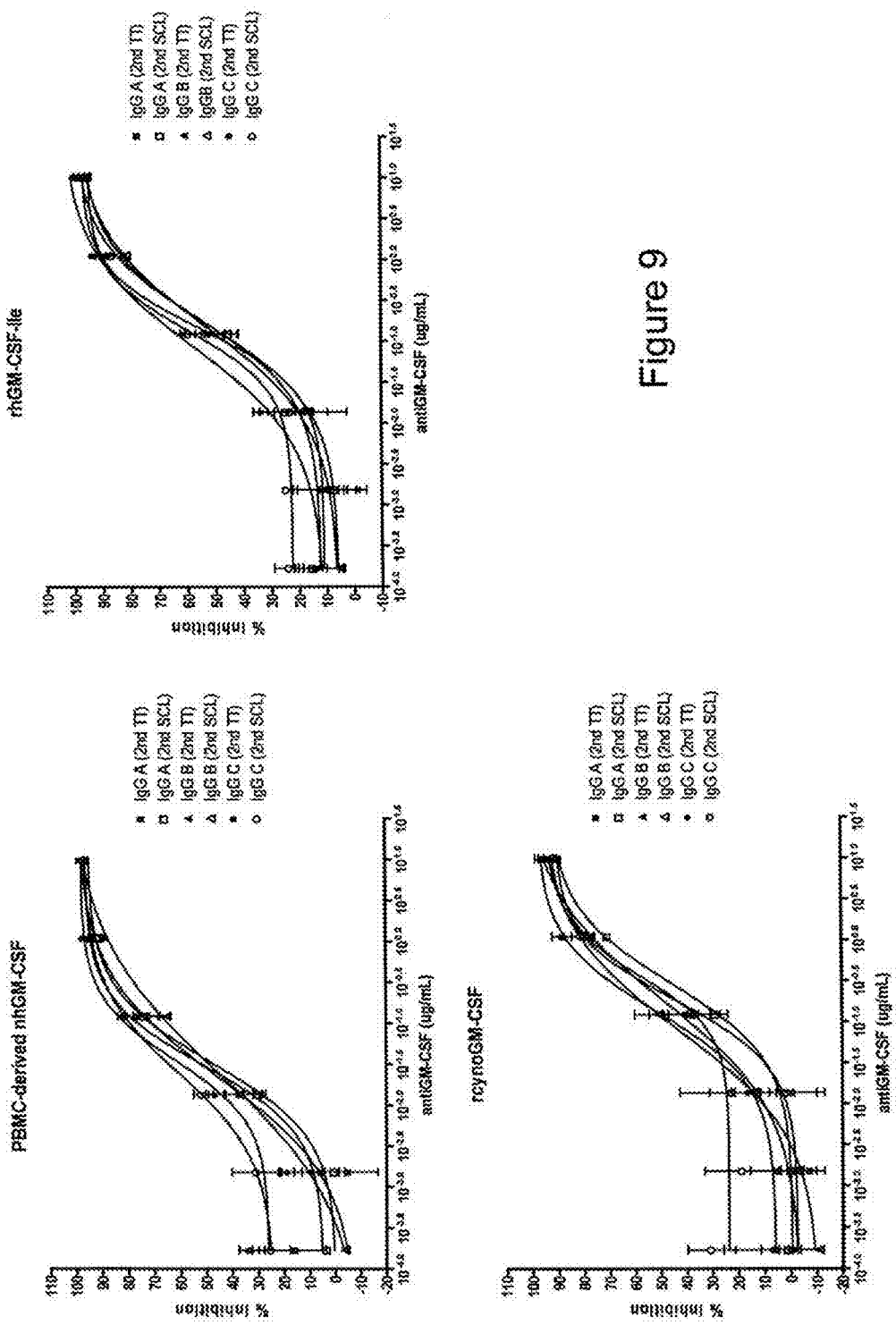

FIG. 9: Inhibition of human and cyno GM-CSF by recombinant mAb ($2^{nd}$ TT and $2^{nd}$ SCL) in the AML-5 proliferation assay.

Figure 10:
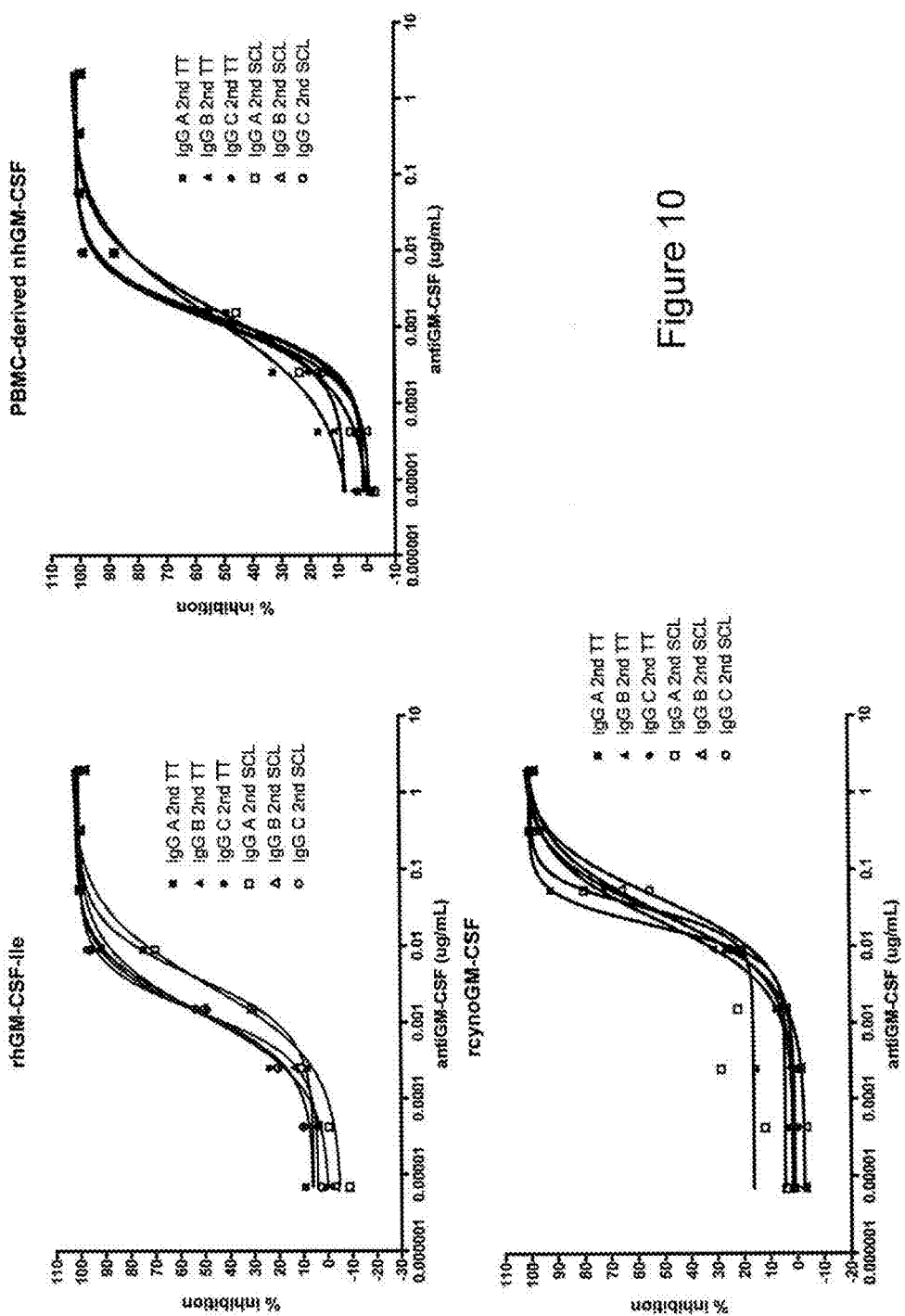

FIG. 10: Inhibition of human and cyno GM-CSF by recombinant mAb ($2^{nd}$ TT and $2^{nd}$ SCL) in the TF-1 Stat-5 phosphorylation assay.

Figure 11:
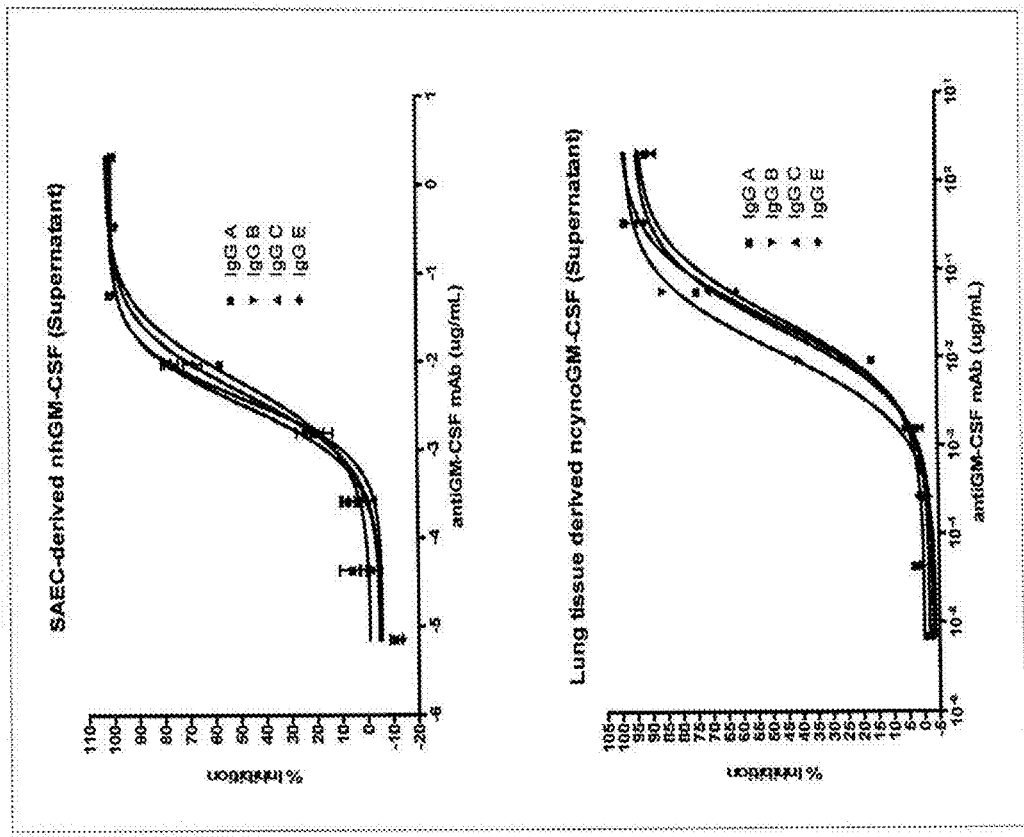

FIG. 11: Inhibition of native human and cyno lung-derived GM-CSF by recombinant mAb ($1^{st}$ TT) in the TF-1 Stat5 phosphorylation assay.

Figure 12:
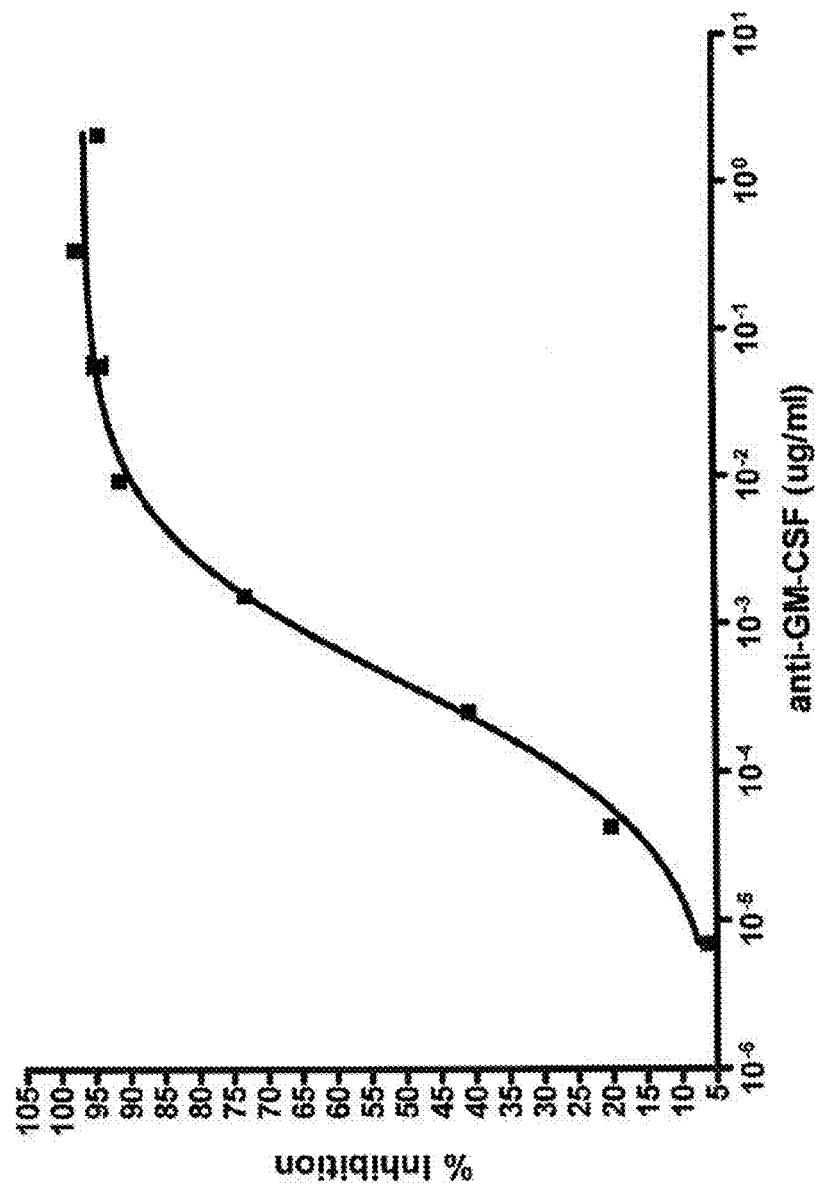

FIG. 12: Inhibition of native cyno PBMC-derived GM-CSF by recombinant mAb ($2^{nd}$ SCL) IgG B in the TF-1 Stat5 phosphorylation assay.

Figure 13:
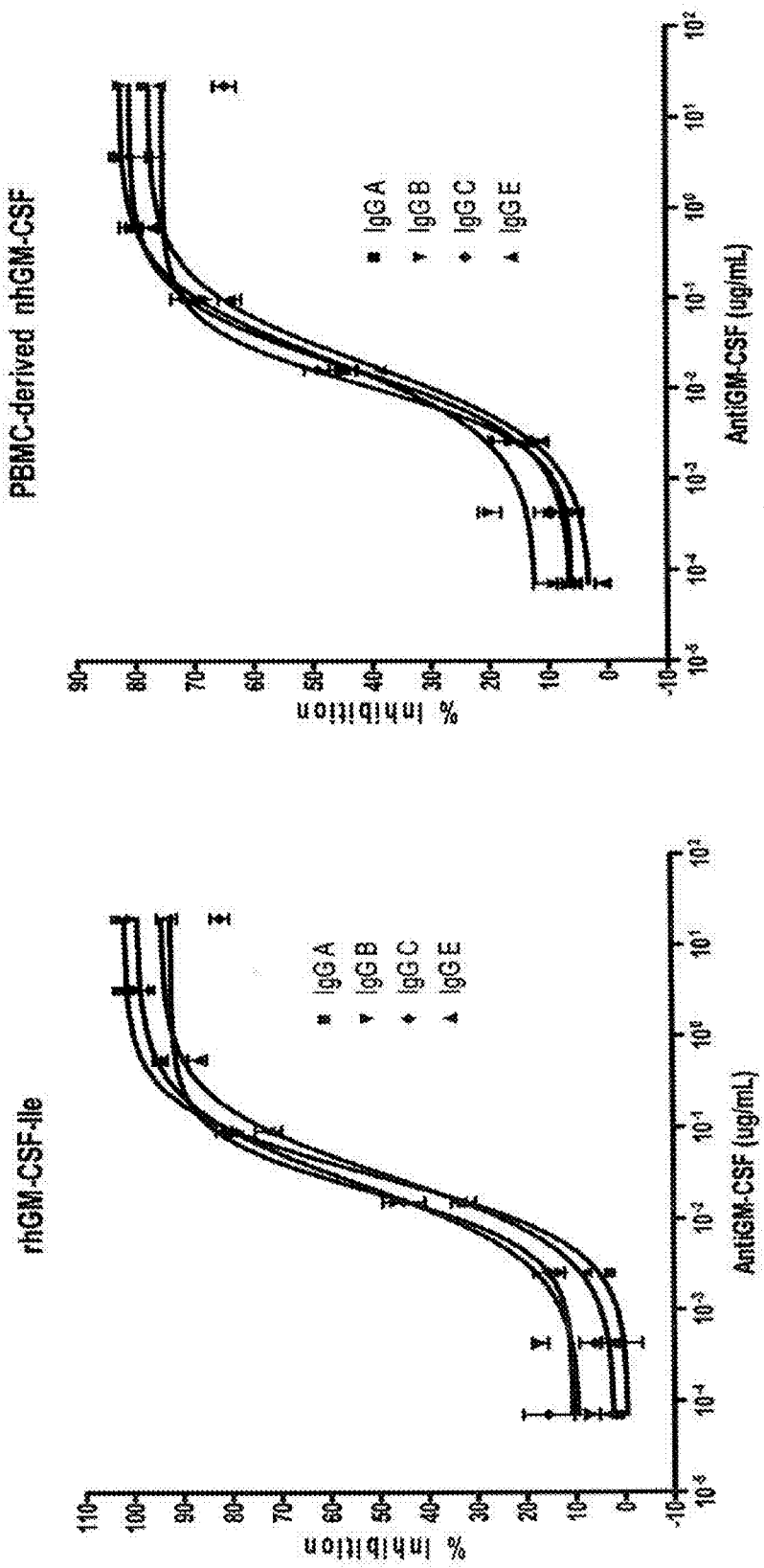

FIG. 13: Inhibition of human GM-CSF by recombinant mAb ($2^{nd}$ TT) in the human monocyte assay.

Figure 14:
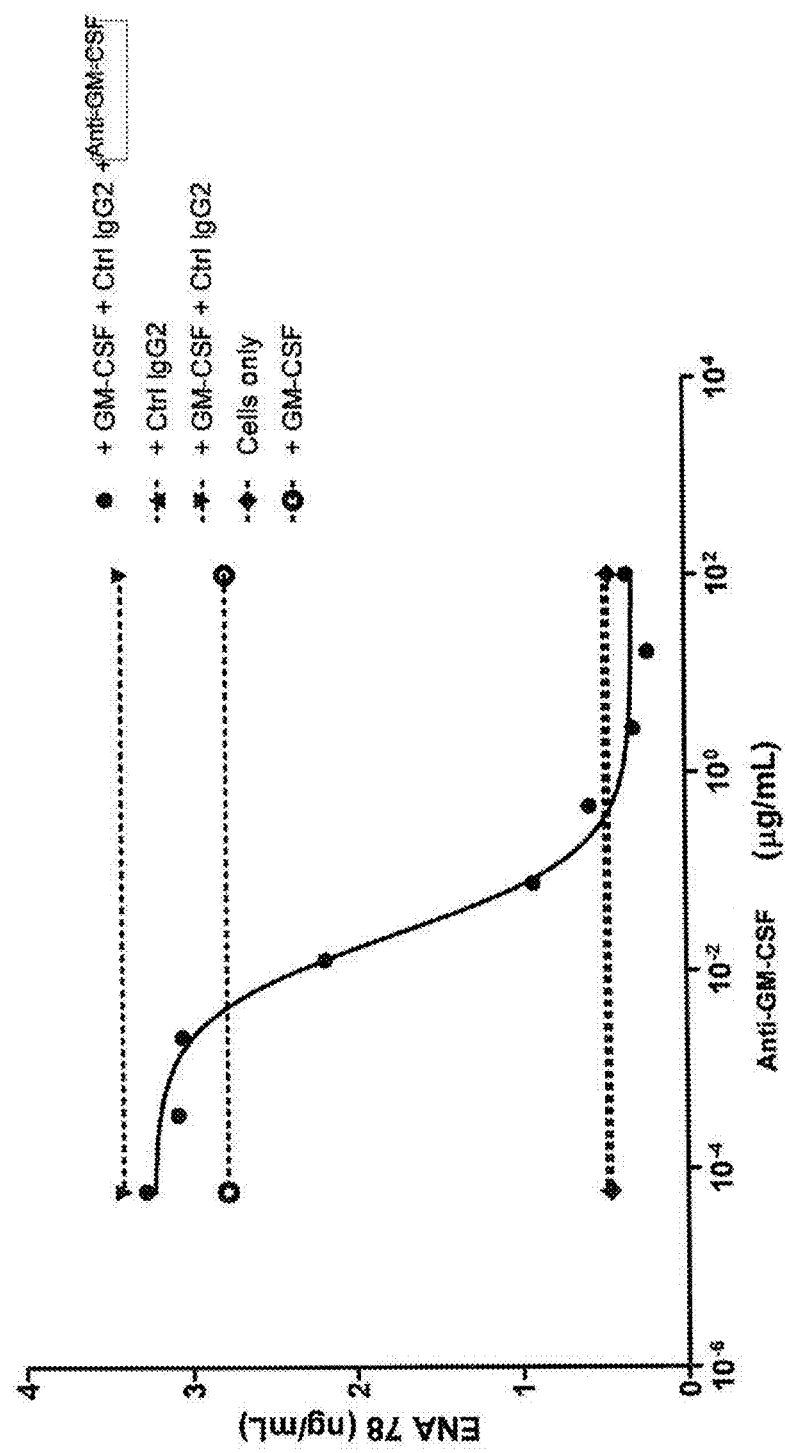

FIG. 14: Inhibition of GM-CSF-induced production of MIP-1b and ENA78 in whole blood by recombinant mAb ($2^{nd}$ SCL) IgG B.

Figure 15A:
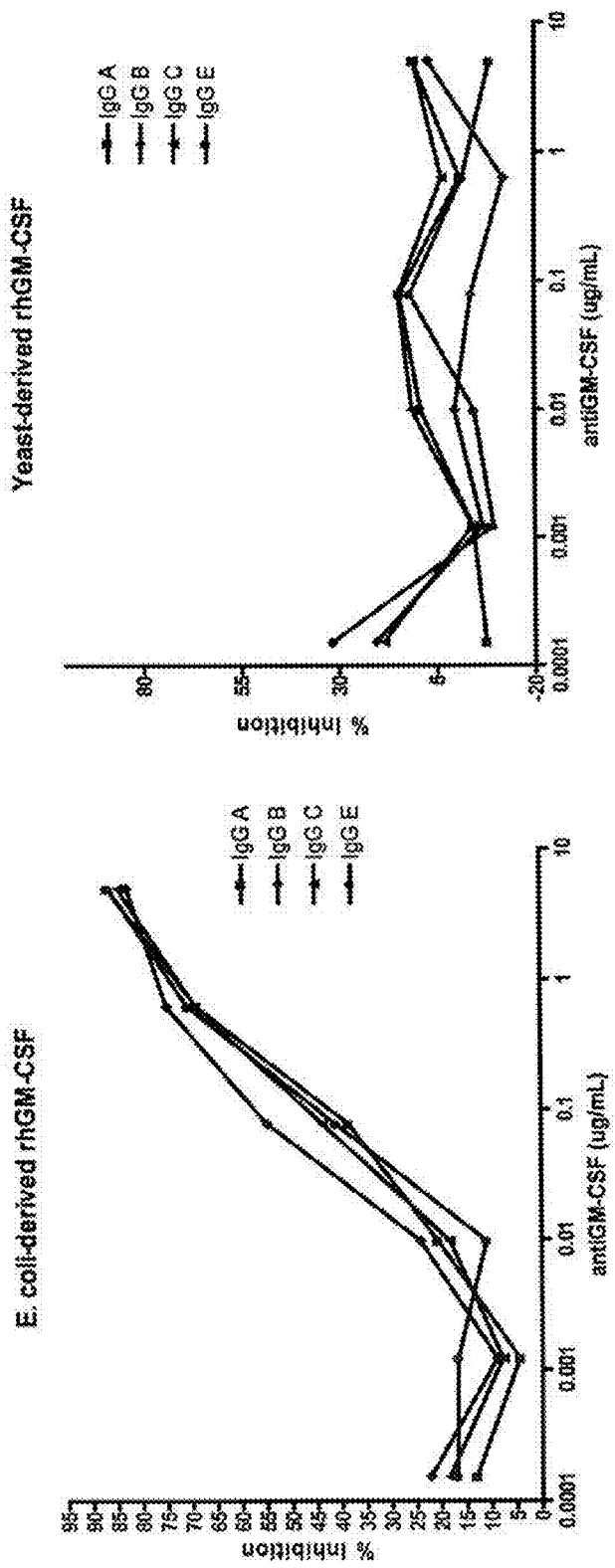
Figure 15B:
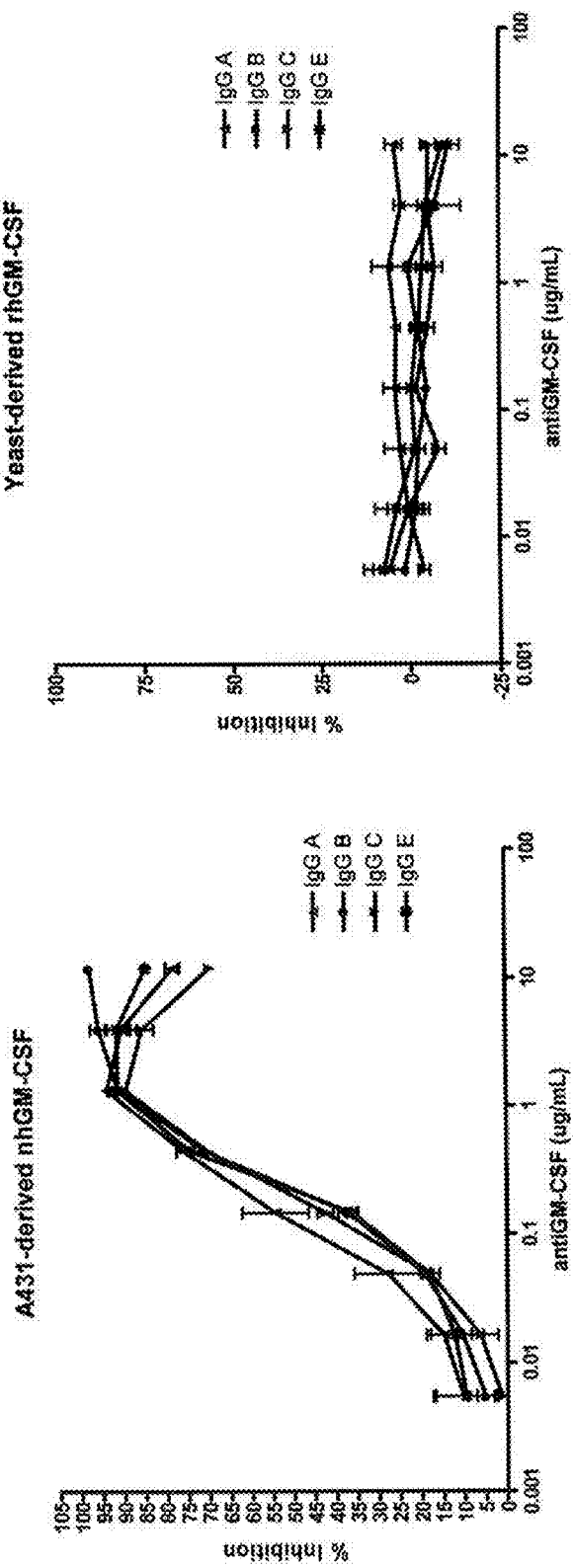

FIGS. 15a-b: mAb purified from hybridoma supernatants does not inhibit yeast-derived rhGM-CSF (Leukine®) in the AML-5 proliferation assay (a) or the monocyte assay (b).

Figure 16:
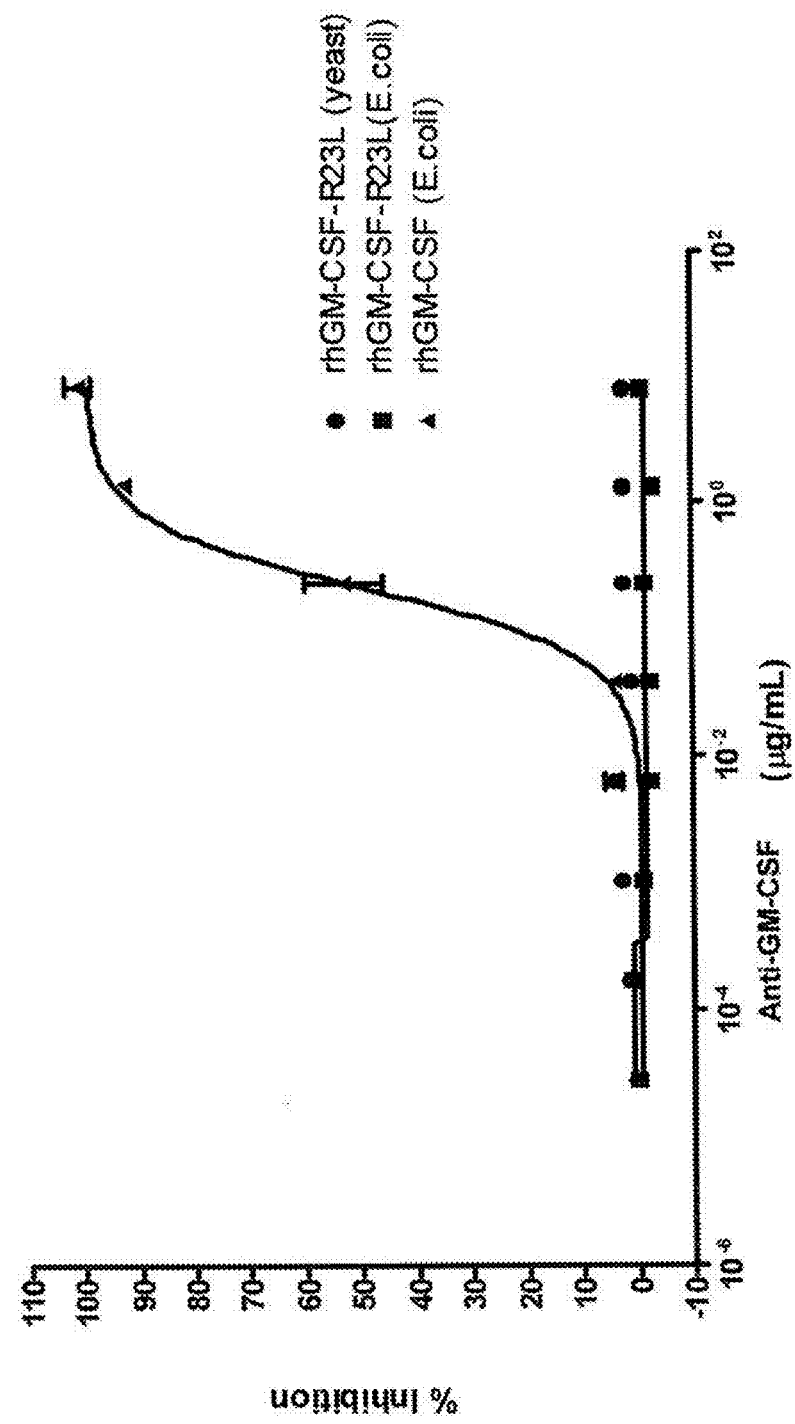

FIG. 16: mAb neutralized *E. coli*-derived rhGM-CSF but not yeast-derived rhGM-CSF (Leukine®) or unglycosylated *E. coli*-derived rhGM-CSF-R23L.

DETAILED DESCRIPTION

It should be understood that this invention is not limited to the particular methodology, protocols, and reagents, etc., described herein and as such may vary. The terminology used herein is for the purpose of describing particular embodiments only, and is not intended to limit the scope of the disclosed, which is defined solely by the claims.

The methods and techniques of the present application are generally performed according to conventional methods well known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990).

The term "polynucleotide" includes both single-stranded and double-stranded nucleic acids and includes genomic DNA, RNA, mRNA, cDNA, or synthetic origin or some combination thereof which is not associated with sequences normally found in nature. Isolated polynucleotides comprising specified sequences may include, in addition to the specified sequences, coding sequences for up to ten or even up to twenty other proteins or portions thereof, or may include operably linked regulatory sequences that control expression of the coding region of the recited nucleic acid sequences, and/or may include vector sequences. The nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The term "oligonucleotide" means a polynucleotide comprising 100 or fewer nucleotides. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides may be single stranded or double stranded, e.g., for use in the construction of a mutant gene. Oligonucleotides may be sense or antisense oligonucleotides. An oligonucleotide can include a detectable label, such as a radiolabel, a fluorescent label, a hapten or an antigenic label, for detection assays. Oligonucleotides may be used, for example, as PCR primers, cloning primers or hybridization probes.

The term "control sequence" refers to a polynucleotide sequence that can affect the expression and processing of coding sequences to which it is ligated. The nature of such control sequences may depend upon the host organism. In particular embodiments, control sequences for prokaryotes may include a promoter, a ribosomal binding site, and a transcription termination sequence. For example, control sequences for eukaryotes may include promoters comprising one or a plurality of recognition sites for transcription factors, transcription enhancer sequences, and transcription termination sequence. "Control sequences" can include leader sequences and/or fusion partner sequences.

The term "vector" means any molecule or entity (e.g., nucleic acid, plasmid, bacteriophage or virus) used to transfer protein coding information into a host cell. The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct may include, but is not limited to, sequences that affect or control transcription, translation, and, if introns are present, affect RNA splicing of a coding region operably linked thereto.

As used herein, "operably linked" means that the components to which the term is applied are in a relationship that allows them to carry out their inherent functions. For example, a control sequence, e.g., a promoter, in a vector that is "operably linked" to a protein coding sequence are arranged such that normal activity of the control sequence leads to transcription of the protein coding sequence resulting in recombinant expression of the encoded protein.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., 2001, Molecular Cloning: A Laboratory Manual, supra; Davis et al., 1986, *Basic Methods in Molecular Biology*, Elsevier; Chu et al., 1981, *Gene* 13:197. Such techniques can be used to introduce one or more exogenous DNA moieties into suitable host cells.

The terms "polypeptide" or "protein" means a macromolecule having the amino acid sequence of a native protein, that is, a protein produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The term also includes amino acid polymers in which one or more amino acids are chemical analogs of a corresponding naturally-occurring amino acid and polymers. The terms "polypeptide" and "protein" encompass GM-CSF antigen-binding proteins, antibodies, or sequences that have deletions from, additions to, and/or substitutions of one or more amino acid of antigen-binding protein. The term "polypeptide fragment" refers to a polypeptide that has an amino-terminal deletion, a carboxyl-terminal deletion, and/or an internal deletion as compared with the full-length native protein. Such fragments may also contain modified amino acids as compared with the native protein. In certain embodiments, fragments are about five to 500 amino acids long. For example, fragments may be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains. In the case of a GM-CSF-binding antibody, useful fragments include but are not limited to a CDR region, a variable domain of a heavy or light chain, a portion of an antibody chain or just its variable region including two CDRs, and the like.

The term "isolated protein" refers to a protein that is purified from proteins or polypeptides or other contaminants that would interfere with its therapeutic, diagnostic, prophylactic, research or other use.

A "variant" of a polypeptide (e.g., an antigen binding protein, or an antibody) comprises an amino acid sequence wherein one or more amino acid residues are inserted into, deleted from and/or substituted into the amino acid sequence relative to another polypeptide sequence. Variants include fusion proteins. A "derivative" of a polypeptide is a polypeptide (e.g., an antigen binding protein, or an antibody) that has been chemically modified in some manner distinct from insertion, deletion, or substitution variants, e.g., via conjugation to another chemical moiety.

The term "naturally occurring" as used throughout the specification in connection with biological materials such as polypeptides, nucleic acids, host cells, and the like, refers to materials which are found in nature.

An "antigen binding protein" as used herein means a protein that specifically binds a specified target antigen; the antigen of the provided is GM-CSF, or human GM-CSF.

An antigen binding protein is said to "specifically bind" its target antigen when the dissociation constant ($K_d$) is $\leq 10^{-8}$ M. The antibody specifically binds antigen with "high affinity" when the $K_d$ is $\leq 5 \times 10^{-9}$ M, and with "very high affinity" when the $K_d$ is $\leq 5 \times 10^{-10}$ M. In one embodiment, the antibody has a $K_d$ of $\leq 10^{-9}$ M and an off-rate of about $1 \times 10^{-4}$/sec. In one embodiment, the off-rate is $<1 \times 10^{-8}$. In other embodiments, the antibodies will bind to GM-CSF, or human GM-CSF with a $K_d$ of between about $10^{-8}$ M and $10^{-10}$ M, and in yet another embodiment it will bind with a $K_d \leq 2 \times 10^{-10}$.

"Antigen binding region" means a protein, or a portion of a protein, that specifically binds a specified antigen. For example, that portion of an antigen binding protein that contains the amino acid residues that interact with an antigen and confer on the antigen binding protein its specificity and affinity for the antigen is referred to as "antigen binding region." An antigen binding region typically includes one or more "complementary binding regions" ("CDRs"). Certain antigen binding regions also include one or more "framework" regions. A "CDR" is an amino acid sequence that contributes to antigen binding specificity and affinity. "Framework" regions are can aid in maintaining the proper conformation of the CDRs to promote binding between the antigen binding region and an antigen.

In certain aspects, recombinant antigen binding proteins that bind GM-CSF protein, or human GM-CSF, are provided. In this context, a "recombinant protein" is a protein made using recombinant techniques, i.e., through the expression of a recombinant nucleic acid as described herein. Methods and techniques for the production of recombinant proteins are well known in the art.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" as such is a species of an antigen binding protein. An intact antibody generally will comprise at least two full-length heavy chains and two full-length light chains, but in some instances may include fewer chains such as antibodies naturally occurring in camelids which may comprise only heavy chains. Antibodies may be derived solely from a single source, or may be "chimeric," that is, different portions of the antibody may be derived from two different antibodies as described further below. The antigen binding proteins, antibodies, or binding fragments may be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below.

The term "light chain" includes a full-length light chain and fragments thereof having sufficient sequence to confer binding specificity. In a typical mammalian antibody, one will find a full-length light chain that includes a variable region domain, $V_L$, and a constant region domain, $C_L$, where the variable region domain of the light chain is toward the amino-terminus of the polypeptide. Typical human antibody light chains include kappa chains or lambda chains.

The term "heavy chain" includes a full-length heavy chain and fragments thereof having sufficient variable region sequence to confer binding specificity. A mammalian full-length heavy chain antibody typically includes a variable region domain, $V_H$, and three constant region domains, $C_H1$, $C_H2$, and $C_H3$. The $V_H$ domain is toward the amino-terminus of the polypeptide, and the $C_H$ domains are toward the carboxyl-terminus, with the $C_H3$ being closest to the carboxy-terminus of the polypeptide. Human heavy chains typically may be of isotypes that include IgG (including IgG1, IgG2, IgG3 and IgG4 subtypes), IgA (including IgA1 and IgA2 subtypes), IgM and IgE.

The term "functional fragment" (or simply "fragment") of an antibody or immunoglobulin chain (heavy or light chain), as used herein, is an antigen binding protein comprising a portion (regardless of how that portion is obtained or synthesized) of an antibody that lacks at least some of the amino acids present in a full-length chain but which is capable of specifically binding to an antigen. Such fragments are biologically active in that they bind specifically to the target antigen and can compete with other antigen binding proteins, including intact antibodies, for specific binding to a given epitope. In one aspect, such a fragment will retain at least one CDR present in the full-length light or heavy chain, and in some embodiments will comprise a single heavy chain and/or light chain or portion thereof. These biologically active fragments may be produced by recombinant DNA techniques, or may be produced by enzymatic or chemical cleavage of antigen binding proteins, including intact antibodies. Immunologically functional immunoglobulin fragments include, but are not limited to, Fab, Fab', F(ab')$_2$, Fv, domain antibodies and single-chain antibodies, and may be derived from any mammalian source, including but not limited to human, mouse, rat, camelid or rabbit. It is contemplated further that a functional portion of the antigen binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life.

An "Fab fragment" is comprised of one light chain and the $C_H1$ and variable regions of one heavy chain. The heavy chain of an Fab molecule cannot form a disulfide bond with another heavy chain molecule.

An "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

An "Fab' fragment" contains one light chain and a portion of one heavy chain that contains the VH domain and the $C_H1$ domain and also the region between the $C_H1$ and $C_H2$ domains, such that an interchain disulfide bond can be formed between the two heavy chains of two Fab' fragments to form an F(ab')$_2$ molecule.

An "F(ab')$_2$ fragment" contains two light chains and two heavy chains containing a portion of the constant region between the C$_H$1 and C$_H$2 domains, such that an interchain disulfide bond is formed between the two heavy chains. An F(ab')$_2$ fragment thus is composed of two Fab' fragments that are held together by a disulfide bond between the two heavy chains.

The "Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen-binding region. Single chain antibodies are discussed in detail in PCT Publication No. WO 88/01649 and U.S. Pat. Nos. 4,946,778 and 5,260,203.

A "domain antibody" is an immunologically functional immunoglobulin fragment containing only the variable region of a heavy chain or the variable region of a light chain. In some instances, two or more V$_H$ regions are covalently joined with a peptide linker to create a bivalent domain antibody. The two V$_H$ regions of a bivalent domain antibody may target the same or different antigens.

A "bivalent antigen binding protein" or "bivalent antibody" comprises two antigen binding sites. In some instances, the two binding sites have the same antigen specificities. Bivalent antigen binding proteins and bivalent antibodies may be bispecific, see, infra.

A multispecific antigen binding protein" or "multispecific antibody" is one that targets more than one antigen or epitope.

A "bispecific," "dual-specific" or "bifunctional" antigen binding protein or antibody is a hybrid antigen binding protein or antibody, respectively, having two different antigen binding sites. Bispecific antigen binding proteins and antibodies are a species of multispecific antigen binding protein antibody and may be produced by a variety of methods including, but not limited to, fusion of hybridomas or linking of Fab' fragments. See, e.g., Songsivilai and Lachmann, 1990, *Clin. Exp. Immunol.* 79:315-321; Kostelny et al., 1992, *J. Immunol.* 148:1547-1553. The two binding sites of a bispecific antigen binding protein or antibody will bind to two different epitopes, which may reside on the same or different protein targets.

The term "neutralizing antigen binding protein" or "neutralizing antibody" refers to an antigen binding protein or antibody, respectively, that binds to a ligand, prevents binding of the ligand to its binding partner and interrupts the biological response that otherwise would result from the ligand binding to its binding partner. In assessing the binding and specificity of an antigen binding protein, e.g., an antibody or immunologically functional fragment thereof, an antibody or fragment will substantially inhibit binding of a ligand to its binding partner when an excess of antibody reduces the quantity of binding partner bound to the ligand by at least about 20%, 30%, 40%, 50%, 60%, 70%, 80%, 85%, 90%, 95%, 97%, 99% or more (as measured in an in vitro competitive binding assay). In the case of a GM-CSF antigen binding proteins, such a neutralizing molecule will diminish the ability of GM-CSF to bind GM-CSFR.

The term "compete" when used in the context of antigen binding proteins (e.g., neutralizing antigen binding proteins or neutralizing antibodies) that compete for the same epitope means competition between antigen binding proteins is determined by an assay in which the antigen binding protein (e.g., antibody or immunologically functional fragment thereof) under test prevents or inhibits specific binding of a reference antigen binding protein (e.g., a ligand, or a reference antibody) to a common antigen (e.g., a GM-CSF or a fragment thereof). Numerous types of competitive binding assays can be used, for example: solid phase direct or indirect radioimmunoassay (RIA), solid phase direct or indirect enzyme immunoassay (EIA), sandwich competition assay (see, e.g., Stahli et al., 1983, *Methods in Enzymology* 9:242-253); solid phase direct biotin-avidin EIA (see, e.g., Kirkland et al., 1986, *J. Immunol.* 137:3614-3619) solid phase direct labeled assay, solid phase direct labeled sandwich assay (see, e.g., Harlow and Lane, 1988, *Antibodies, A Laboratory Manual*, Cold Spring Harbor Press); solid phase direct label RIA using 1-125 label (see, e.g., Morel et al., 1988, *Molec. Immunol.* 25:7-15); solid phase direct biotin-avidin EIA (see, e.g., Cheung, et al., 1990, *Virology* 176:546-552); and direct labeled RIA (Moldenhauer et al., 1990, *Scand. J. Immunol.* 32:77-82). Typically, such an assay involves the use of purified antigen bound to a solid surface or cells bearing either of these, an unlabelled test antigen binding protein and a labeled reference antigen binding protein.

Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Additional details regarding methods for determining competitive binding are provided in the examples herein. Usually, when a competing antigen binding protein is present in excess, it will inhibit specific binding of a reference antigen binding protein to a common antigen by at least 40%, 45%, 50%, 55%, 60%, 65%, 70% or 75%. In some instance, binding is inhibited by at least 80%, 85%, 90%, 95%, or 97% or more.

The term "antigen" refers to a molecule or a portion of a molecule capable of being bound by a selective binding agent, such as an antigen binding protein (including, e.g., an antibody or immunological functional fragment thereof), and additionally capable of being used in an animal to produce antibodies capable of binding to that antigen. An antigen may possess one or more epitopes that are capable of interacting with different antigen binding proteins, e.g., antibodies.

The term "epitope" includes any determinant capable of specifically binding to an antigen binding protein. An epitope is a region of an antigen that is bound by an antigen binding protein that specifically targets that antigen, and when the antigen is a protein, includes specific amino acids that contact the antigen binding protein. Most often, epitopes reside on proteins which are understood to include non amino acid post-translational modifications, but in some instances may reside on other kinds of molecules, such as nucleic acids. Epitopes may include chemically active surface groupings of molecules such as amino acids, sugar side chains, phosphoryl or sulfonyl groups, and may have specific three dimensional structural characteristics, and/or specific charge characteristics. Generally, antibodies specific for a particular target antigen will preferentially recognize an epitope on the target antigen in a complex mixture of proteins and/or macromolecules.

The term "identity" refers to a relationship between the sequences of two or more polypeptide molecules or two or more polynucleotides, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) must be addressed by a particular mathematical model or computer program (i.e., an "algorithm"). Methods that can be used to calculate the identity of the aligned nucleic acids or polypeptides include those described in *Computational Molecular Biology*, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, *SIAM J. Applied Math.* 48:1073.

In calculating percent identity, the sequences being compared are aligned in a way that gives the largest match between the sequences. The computer program used to determine percent identity is the GCG program package, which includes GAP (Devereux et al., 1984, *Nucl. Acid Res.* 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., 1978, *Atlas of Protein Sequence and Structure* 5:345-352 for the PAM 250 comparison matrix; Henikoff et al., 1992, *Proc. Natl. Acad. Sci. U.S.A.* 89:10915-10919 for the BLOSUM 62 comparison matrix) is also used by the algorithm.

Recommended parameters for determining percent identity for polypeptides or nucleotide sequences using the GAP program are the following:
Algorithm: Needleman et al., 1970, *J. Mol. Biol.* 48:443-453;
Comparison matrix: BLOSUM 62 from Henikoff et al., 1992, supra;
Gap Penalty: 12 (but with no penalty for end gaps)
Gap Length Penalty: 4
Threshold of Similarity: 0

Certain alignment schemes for aligning two amino acid sequences may result in matching of only a short region of the two sequences and this small aligned region may have very high sequence identity even though there is no significant relationship between the two full-length sequences. Accordingly, the selected alignment method (GAP program) can be adjusted if so desired to result in an alignment that spans at least 50 contiguous amino acids of the target polypeptide.

As used herein, "substantially pure" means that the described species of molecule is the predominant species present, that is, on a molar basis it is more abundant than any other individual species in the same mixture. In certain embodiments, a substantially pure molecule is a composition wherein the object species comprises at least 50% (on a molar basis) of all macromolecular species present. In other embodiments, a substantially pure composition will comprise at least 80%, 85%, 90%, 95%, or 99% of all macromolecular species present in the composition.

In certain embodiments, an essentially homogeneous substance has been purified to such a degree that contaminating species cannot be detected in the composition by conventional detection methods and thus the composition consists of a single detectable macromolecular species.

The term "therapeutically effective amount" refers to the amount of a GM-CSF antigen binding protein determined to produce any therapeutic response in a mammal. Such therapeutically effective amounts are readily ascertained by one of ordinary skill in the art.

"Amino acid" includes its normal meaning in the art. The twenty naturally-occurring amino acids and their abbreviations follow conventional usage. See, *Immunology-A Synthesis*, 2nd Edition, (E. S. Golub and D. R. Gren, eds.), Sinauer Associates: Sunderland, Mass. (1991). Stereoisomers (e.g., D-amino acids) of the twenty conventional amino acids, unnatural amino acids such as [alpha]-, [alpha]-disubstituted amino acids, N-alkyl amino acids, and other unconventional amino acids may also be suitable components for polypeptides. Examples of unconventional amino acids include: 4-hydroxyproline, [gamma]-carboxyglutamate, [epsilon]-N, N,N-trimethyllysine, [epsilon]-N-acetyllysine, O-phosphoserine, N-acetylserine, N-formylmethionine, 3-methylhistidine, 5-hydroxylysine, [sigma]-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

A. General Overview

Antigen-binding proteins that bind GM-CSF protein, in particular human GM-CSF (hGM-CSF) protein are provided herein. The antigen binding proteins provided are polypeptides into which one or more complementary determining regions (CDRs), as described herein, are embedded and/or joined. In some antigen binding proteins, the CDRs are embedded into a "framework" region, which orients the CDR(s) such that the proper antigen binding properties of the CDR(s) is achieved. In general, antigen binding proteins that are provided can interfere with, block, reduce or modulate the interaction between GM-CSFR and GM-CSF.

Certain antigen binding proteins described herein are antibodies or are derived from antibodies. In certain embodiments, the polypeptide structure of the antigen binding proteins is based on antibodies, including, but not limited to, monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. The various structures are further described herein.

The antigen binding proteins provided herein have been demonstrated to bind to certain epitopes of GM-CSF, in particular human GM-CSF. As a consequence, the antigen binding proteins provided herein are capable of inhibiting GM-CSF activity. In particular, antigen binding proteins binding to these epitopes inhibit, inter alia, induction of GM-CSFR signaling, GM-CSF induced cell growth or differentiation, and other physiological effects induced by GM-CSF upon binding to GM-CSFR.

The antigen binding proteins that are disclosed herein have a variety of utilities. Some of the antigen binding proteins, for instance, are useful in specific binding assays, affinity purification of GM-CSF, in particular hGM-CSF or its ligands and in screening assays to identify other antagonists of GM-CSF activity. Some of the antigen-binding proteins are useful for inhibiting binding of GM-CSFR to GM-CSF, or inhibiting autophosphorylation of GM-CSF.

The antigen-binding proteins can be used in a variety of treatment applications, as explained herein. For example, certain GM-CSF antigen-binding proteins are useful for treating conditions associated with GM-CSF, such as reducing monocyte chemotaxis in a patient, inhibiting monocyte migration into tumors, or inhibiting accumulation of tumor associated macrophage in a tumor, as is further described herein. Other uses for the antigen binding proteins include, for example, diagnosis of GM-CSF-associated diseases or conditions and screening assays to determine the presence or absence of GM-CSF. Some of the antigen binding proteins described herein are useful in treating consequences, symptoms, and/or the pathology associated with GM-CSF activity. These include, but are not limited to, various types of inflammatory disease.

B. GM-CSF Antigen Binding Proteins

A variety of selective binding agents useful for regulating the activity of GM-CSF are provided. These agents include, for instance, antigen binding proteins that contain an antigen binding domain (e.g., single chain antibodies, domain antibodies, immunoadhesions, and polypeptides with an antigen binding region) and specifically bind to a GM-CSF polypeptide, in particular human GM-CSF. Some of the agents, for example, are useful in inhibiting the binding of GM-CSFR to GM-CSF, and can thus be used to inhibit one or more activities associated with GM-CSF signaling.

In general, the antigen binding proteins that are provided typically comprise one or more CDRs as described herein (e.g., 1, 2, 3, 4, 5 or 6 CDRs). In some instances, the antigen binding protein comprises (a) a polypeptide structure and (b) one or more CDRs that are inserted into and/or joined to the polypeptide structure. The polypeptide structure can take a variety of different forms. For example, it can be, or comprise, the framework of a naturally occurring antibody, or fragment or variant thereof, or may be completely synthetic in nature. Examples of various polypeptide structures are further described below.

In certain embodiments, the polypeptide structure of the antigen binding proteins is an antibody or is derived from an antibody, including, but not limited to, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and portions or fragments of each, respectively. In some instances, the antigen binding protein is an immunological fragment of an antibody (e.g., a Fab, a Fab', a F(ab')$_2$, or a scFv). The various structures are further described and defined herein.

Certain of the antigen binding proteins as provided herein specifically bind to human GM-CSF. "Specifically binds" as used herein means the equilibrium dissociation constant is $<10^{-8}$ to $<10^{-10}$ M, alternatively $<10^{-8}$ to $<10^{-10}$ M.

In embodiments where the antigen binding protein is used for therapeutic applications, an antigen binding protein can inhibit, interfere with or modulate one or more biological activities of a GM-CSF. In this case, an antigen binding protein binds specifically and/or substantially inhibits binding of human GM-CSF to GM-CSFR when an excess of antibody reduces the quantity of human GM-CSF bound to GM-CSFR, or vice versa, by at least about 40%, 60%, 80%, 85%, or more (for example by measuring binding in an in vitro competitive binding assay). GM-CSF has many distinct biological effects, which can be measured in many different assays in different cell types; examples of such assays are provided herein.

Some of the antigen binding proteins that are provided have the structure typically associated with naturally occurring antibodies. The structural units of these antibodies typically comprise one or more tetramers, each composed of two identical couplets of polypeptide chains, though some species of mammals also produce antibodies having only a single heavy chain. In a typical antibody, each pair or couplet includes one full-length "light" chain (in certain embodiments, about 25 kDa) and one full-length "heavy" chain (in certain embodiments, about 50-70 kDa). Each individual immunoglobulin chain is composed of several "immunoglobulin domains", each consisting of roughly 90 to 110 amino acids and expressing a characteristic folding pattern. These domains are the basic units of which antibody polypeptides are composed. The amino-terminal portion of each chain typically includes a variable domain that is responsible for antigen recognition. The carboxy-terminal portion is more conserved evolutionarily than the other end of the chain and is referred to as the "constant region" or "C region". Human light chains generally are classified as kappa and lambda light chains, and each of these contains one variable domain and one constant domain. Heavy chains are typically classified as mu, delta, gamma, alpha, or epsilon chains, and these define the antibody's isotype as IgM, IgD, IgG, IgA, and IgE, respectively. IgG has several subtypes, including, but not limited to, IgG1, IgG2, IgG3, and IgG4. IgM subtypes include IgM, and IgM2. IgA subtypes include IgA1 and IgA2. In humans, the IgA and IgD isotypes contain four heavy chains and four light chains; the IgG and IgE isotypes contain two heavy chains and two light chains; and the IgM isotype contains five heavy chains and five light chains. The heavy chain C region typically comprises one or more domains that may be responsible for effector function. The number of heavy chain constant region domains will depend on the isotype. IgG heavy chains, for example, each contains three C region domains known as $C_H1$, $C_H2$ and $C_H3$. The antibodies that are provided can have any of these isotypes and subtypes. In certain embodiments, the GM-CSF antibody is of the IgG1, IgG2, or IgG4 subtype.

In full-length light and heavy chains, the variable and constant regions are joined by a "J" region of about twelve or more amino acids, with the heavy chain also including a "D" region of about ten more amino acids. See, e.g., Fundamental Immunology, 2nd ed., Ch. 7 (Paul, W., ed.) 1989, New York: Raven Press. The variable regions of each light/heavy chain pair typically form the antigen binding site.

1. Variable Domains of Antibodies

The various heavy chain and light chain variable regions provided herein are depicted in TABLE 1. Each of these variable regions may be attached to the above heavy and light chain constant regions to form a complete antibody heavy and light chain, respectively. Further, each of the so generated heavy and light chain sequences may be combined to form a complete antibody structure.

Provided are antigen binding proteins that contain an antibody heavy chain variable region selected from the group consisting of $V_H1$, $V_H2$, $V_H3$, $V_H4$, $V_H5$, $V_H6$, $V_H7$, $V_H8$, $V_H9$, $V_H10$, $V_H11$, and $V_H12$, and/or an antibody light chain variable region selected from the group consisting of $V_L1$, $V_L2$, $V_L3$, $V_L4$, $V_L5$, $V_L6$, $V_L7$, $V_L8$, $V_L9$, $V_L10$, $V_L11$, and $V_L12$, as shown in TABLE 1 below.

Antigen binding proteins of this type can generally be designated by the formula "$V_Hx/V_Ly$," where "x" corresponds to the number of heavy chain variable regions and "y" corresponds to the number of the light chain variable regions as listed in TABLE 1:

TABLE 1

Exemplary VH and VL Chains

| Designation | Amino Acid Sequence |
|---|---|
| $V_H1$ | QVQLVQSGAEVKKPGASVKVSCKASGYTFTGYYIHVVR QAPGQGLEWMGWINPNSGGTNSAQKFRGRVTMTRDTS ISTAYMELSRLRSDDTAVYYCAREGGYSYGYFDYWGQG TLVTVSS [SEQ. ID. NO: 9] |
| $V_H2$ | QVQLVQSGAEVKKPGASVKVSCKSSGYTFTGYYMHWVR QAPGQGLEWMGWINPNSGGTNYAQKFKGRVTMTRDTSI STAYMELSSRLRSDDTAVYYCARDKWLDGFDYWGQGTLV TVSSS [SEQ. ID. NO: 21] |
| $V_H3$ | QVQLVQSGAAVKKPGASVKVSCKASGYTFTGYYIHWVR QAPGQGLEWMGWINPNSGGTNYAQKFQGRVTMTRDTSI STASMELSRLRSDDTAVYFCARDRWLDAFDIWGQGTMV TVSS [SEQ. ID. NO: 33] |
| $V_H4$ | QVQLVQSGAEVKKPGASVKVSCKASGYTFTGYYMHWVR QAPGQGLEWMGWINPNSGGTNYAQRFRGRVTMTRDTSI STAYMELSRLRSDDTAVYYCARAPYDWTFDYWGQGTLV TVSS [SEQ. ID. NO: 45] |
| $V_H5$ | QVQLVQSGAEVKKPGASVKVSCKASGYTFTGYYIHWVR QAPGQGLEWMGWINPNSGGRNYAQKFQGRVTMTRDTSI STAYMELSRLRSDDTAVYYCARDRWLDAFEIWGQGTMV TVSS [SEQ. ID. NO: 57] |
| $V_H6$ | QVQLVQSGAEVKQPGASVKVSCEASGYTFTSYGISWVR QAPGQGLEWMGWISAYNGNTDYAQKLQGRVTMTTDTST SAAYMELSRLRSDDTAVYYCARQRYYYSMDVWGQGTTV TVSS [SEQ. ID. NO: 69] |
| $V_H7$ | QVQLVQSGAEVKKPGASVKVSCKASGYTFTGYYMHWVR QAPGQGLEWMGWINPNSGGTNYAQKFQGRVTMTRDTSI SSTAYMELWLRSDDTAVYYCARDRWLDAFDIWGQGTMV TVS [SEQ. ID. NO: 81] |
| $V_H8$ | QVQLVQSGAEVKKPGASVKVSCKASGFTFSGYYMYWVR QAPGQGLEWMGWINPNSGGTNYARKFQGRVTMTRDTSI STAYMELSRLRSDDTAVYYCARRPWELPFDYWGQGTLV TVSS [SEQ. ID. NO:93] |
| $V_H9$ | QVQLVQSGAEVKKPGASVKVSCKASGYTFTGYYMHWVR QAPGQGLEWMGWINPNSGGTNYAQKFKGRVTMTRDTSI STAHMELSRLRSDDTAVYYCVRNGDYVFTYFDYWGQGT LVTVSS [SEQ. ID. NO: 105]+ |
| $V_H10$ | QVQLVQSGAEVKKPGASVKVSCKASGYTFTGYYMHWVR QAPGQGLEWMGWINPNSGGTNYAQKFRGRVTMTRDTSI SSTAYMELRLRSDDTAVYYCARFGYFGYYFDYWGQGTL VTVSS [SEQ. ID. NO: 117] |
| $V_H11$ | QVQLVQSGAEVKKPGASVKVSCKASGYTFTGYYMHWVR QAPGQGLEWMGWINPNSGGTNYAQKFRGRVTMTRDTSI STAYVELSRLRSDDTAVYYCARDPYTSGFDYWGQGTLV TYSS [SEQ. ID. NO: 129] |
| $V_H12$ | QVQLQESGPGLVKPSQTLSLTCTVSGGSIRSGGYYWSW IRQHPGKGLEWIGYIYYSGSTYYNPSLKSRVTISVDTS KNQFSLKLNSVTAADTAVYYCAREDTAMDYFDYWGQGT LVTVSS [SEQ. ID. NO: 141] |
| $V_L1$ | DIVLTQSPDSLAVSLGERATINCKSSQSILYSSSNENF LTWYQQKPGQPPKLLIYWASTRESGVPDRFSGSGSGTD FTLTISSLQPEDVAVYYCQQYFSVFRTFGQGTRVEIK [SEQ. ID. NO: 3] |
| $V_L2$ | EIVLTQSPGTLSLSPGDRATLSCRASQSVSSSYFAWYQ QKPGQAPRLLIYGASSRATGIPDRFSGSGSGTDFTLTI SRLEPEDFAVYYCQQYDRSPRTFGQGTKVEIK [SEQ. ID. NO: 15] |

TABLE 1-continued

Exemplary VH and VL Chains

| Designation | Amino Acid Sequence |
|---|---|
| $V_L3$ | EIVLTQSPGTLSLSPGERATLSCRASQSVSSSYFAWYQ QKPGQAPRLLIYGTSSRATGIPDRFSGSGSGTDFTLTV SRLEPEDFAVYYCQQYDRSPRTFGQGTKVEIK [SEQ. ID. NO: 27] |
| $V_L4$ | EIVLTQSPGTLSLSPGERATLSCRASQYISNTYLAWFQ QKPGQAPRLLIYGAATRATGIPDRFSGSGSGTDFTFTI SRLEPEDFAVYYCQQYGSSPWTFGQGTTVEIK [SEQ. ID. NO: 39] |
| $V_L5$ | EVVLTQSPGTLSLSPGERATLSCRASQSVCSSYLAWYQ QKPDQAPRLLISGASSRATGIPDRFSGSGSGTDFTLTI SSLEPEDFAVYYCQQYDRSPRTFGQGTKVEIK [SEQ. ID. NO: 51] |
| $V_L6$ | NFMLAQPHSVSESPGKTVTISCIRTSGSIASNYVQWYQ SQRPGSPTTVIYEDDQRPSGVPDRFSGSIDSSSNSASL DTISGLKTEDEAYYCQSCDISNVVFGGGTKLTVL [SEQ. ID. NO: 63] |
| $V_L7$ | EIVLTQSPGTLSLSPGERATLSCRASQSVSSSYLAWYQ QKPGQVPRLLIYGTSSRATGIPDRFSGSGSGTDFTLTV SRLEPEDFAVYYCLQYDRSPRTFGQGTKVEIK [SEQ. ID. NO: 75] |
| $V_L8$ | EIVLTQSPGTLSLSLGERAILSCRASQSLSSIYLAWYQ QKPGQAPGLLIYGASSRATGIPDRFSGSGSGTDFTLTI SSLEPEDFAVYYCQQYATSPWTFGQGTKVEVK [SEQ. ID. NO: 87] |
| $V_L9$ | DIQMTQSPSSLSASVGDRVTITCRASQSISNYLNWYQQ KPGKAPKLLIYTASSLQSGVPSRFSGRGSGTDFTLTIS SLQPEDFATYYCQQSFSFPITFGPGTKVDIK [SEQ. ID. NO: 99] |
| $V_L10$ | QSALTQPASVSGSPGQSITISCTGTSSDVGGYNYVSWY QQHPGKAPKLMIYEVSGRPSGVSNRFSGSKSGNTASLT ISGLQAEDEADYYCSSFTGSSTWLFGGGTKLTVL [SEQ. ID. NO: 111] |
| $V_L11$ | EIVLTQSPGTLSLSPGERATLSCRASPSVSSSYFAWYQ QKPGQAPRLLIYGASSRATGIPDRFSGSGSGTDFTLTI SRLEPEDFAVYYCQQYGWSPRTFGQGTKVEIK [SEQ. ID. NO: 123] |
| $V_L12$ | QSVLTQPPSASGTPGQRVTISCSGSRSHIGSNTVNWYQ HLPGTAPKLLIYSNNHRPSGVPDRFSGSKSGTSASLAI SGLQSEDEADYYCAAWDDSLNGPVFGGGTKLTVL [SEQ. ID. NO: 135] |

Each of the heavy chain variable regions listed in TABLE 1 may be combined with any of the light chain variable regions shown in TABLE 1 to form an antigen binding protein. Examples of such combinations include $V_H1$ combined with any of $V_L1$, $V_L2$, $V_L3$, $V_L4$, $V_L5$, $V_L6$, $V_L7$, $V_L8$, $V_L9$, $V_L10$, VL11, and VL12, or $V_H2$ combined with any of $V_L1$, $V_L2$, $V_L3$, $V_L4$, $V_L5$, $V_L6$, $V_L7$, $V_L8$, $V_L9$, $V_L10$, VL11, and VL12, etc.

In some instances, the antigen binding protein includes at least one heavy chain variable region and/or one light chain variable region from those listed in TABLE 1. In some instances, the antigen binding protein includes at least two different heavy chain variable regions and/or light chain variable regions from those listed in TABLE 1. An example of such an antigen binding protein comprises (a) one $V_H1$, and (b) one of $V_H2$, $V_H3$, $V_H4$, $V_H5$, $V_H6$, $V_H7$, $V_H8$, $V_H9$, $V_H10$, $V_H11$, or $V_H12$.

Another example comprises (a) one $V_H2$, and (b) one of $V_H1$, $V_H3$, $V_H4$, $V_H5$, $V_H6$, $V_H7$, $V_H8$, $V_H9$, $V_H10$, $V_H11$, or $V_H12$. Again another example comprises (a) one $V_H3$, and (b) one of $V_H1$, $V_H2$, $V_H4$, $V_H5$, $V_H6$, $V_H7$, $V_H8$, $V_H9$, $V_H10$, $V_H11$, or $V_H12$ and the like.

Again another example of such an antigen binding protein comprises (a) one $V_L1$, and (b) one of $V_L2$, $V_L3$, $V_L4$, $V_L5$, $V_L6$, $V_L7$, $V_L8$, $V_L9$, $V_L10$, VL11, or VL12. Again another example of such an antigen binding protein comprises (a) one $V_L2$, and (b) one of $V_L1$, $V_L3$, $V_L4$, $V_L5$, $V_L6$, $V_L7$, $V_L8$, $V_L9$, $V_L10$, VL11, or VL12. Again another example of such an antigen binding protein comprises (a) one $V_L3$, and (b) one of $V_L1$, $V_L2$, $V_L4$, $V_L5$, $V_L6$, $V_L7$, $V_L8$, $V_L9$, $V_L10$, VL11, or VL12 and the like.

The various combinations of heavy chain variable regions may be combined with any of the various combinations of light chain variable regions.

In other instances, the antigen binding protein contains two identical light chain variable regions and/or two identical heavy chain variable regions. As an example, the antigen binding protein may be an antibody or immunologically functional fragment that includes two light chain variable regions and two heavy chain variable regions in combinations of pairs of light chain variable regions and pairs of heavy chain variable regions as listed in TABLE 1.

Some antibodies that are provided comprise a heavy chain variable domain comprising a sequence of amino acids that differs from the sequence of a heavy chain variable domain selected from $V_H1$, $V_H2$, $V_H3$, $V_H4$, $V_H5$, $V_H6$, $V_H7$, $V_H8$, $V_H9$, $V_H10$, $V_H11$, and $V_H12$ at only 1, 2, 3, 4, 5, 6, 7, 8, 9, 10, 11, 12, 13, 14 or 15 amino acid residues, wherein each such sequence difference is independently either a deletion, insertion or substitution of one amino acid. The heavy chain variable region in some antibodies comprises a sequence of amino acids that has at least 70%, 75%, 80%, 85%, 90%, 95%, 97% or 99% sequence identity to the amino acid sequences of the heavy chain variable region of $V_H1$, $V_H2$, $V_H3$, $V_H4$, $V_H5$, $V_H6$, $V_H7$, $V_H8$, $V_H9$, $V_H10$, $V_H11$, and $V_H12$.

Certain antibodies comprise a light chain variable domain comprising a sequence of amino acids that differs from the sequence of a light chain variable domain selected from $V_L1$, $V_L2$, $V_L3$, $V_L4$, $V_L5$, $V_L6$, $V_L7$, $V_L8$, $V_L9$, $V_L10$, VL11, and VL12, at only 1, 2, 3, 4, 5, 6, 7, 8, 9, 10, 11, 12, 13, 14 or 15 amino acid residues, wherein each such sequence difference is independently either a deletion, insertion or substitution of one amino acid. The light chain variable region in some antibodies comprises a sequence of amino acids that has at least 70%, 75%, 80%, 85%, 90%, 95%, 97% or 99% sequence identity to the amino acid sequences of the light chain variable region of $V_L2$, $V_L3$, $V_L4$, $V_L5$, $V_L6$, $V_L7$, $V_L8$, $V_L9$, $V_L10$, VL11, and VL12.

Still other antigen binding proteins, e.g., antibodies or immunologically functional fragments include variant forms of a variant heavy chain and a variant light chain as just described.

2. CDRs

In a traditional antibody, the CDRs are embedded within a framework in the heavy and light chain variable region where they constitute the regions responsible for antigen binding and recognition. Variable domains of immunoglobulin chains of the same species generally exhibit a similar overall structure, comprising relatively conserved framework regions (FR) joined by hypervariable regions, more often called "complementarity determining regions" or CDRs. A variable region comprises at least three heavy or light chain CDRs. The CDRs from the two chains of each heavy chain/light chain pair mentioned above are typically aligned by the framework regions to form a structure that binds specifically with a specific epitope on the target protein (e.g., GM-CSF). From N-terminal to C-terminal, naturally-occurring light and heavy chain variable regions both typically conform to the following order of these elements: FR1, CDR1, FR2, CDR2, FR3, CDR3 and FR4. A numbering system has been devised for assigning numbers to amino acids that occupy positions in each of these domains. Complementarity determining regions (CDRs) and framework regions (FR) of a given antibody may be identified using this system. This numbering system is defined in Kabat et al., Sequences of Proteins of Immunological Interest, 5$^{th}$ Ed., US Dept. of Health and Human Services, PHS, NIH, NIH Publication No. 91-3242, 1991, or Chothia & Lesk, 1987, *J. Mol. Biol.* 196:901-917; Chothia et al., 1989, *Nature* 342:878-883. The CDRs provided herein may not only be used to define the antigen binding domain of a traditional antibody structure, but may be embedded in a variety of other polypeptide structures, as described herein.

The antigen binding proteins disclosed herein are polypeptides into which one or more CDRs are grafted, inserted and/or joined. An antigen binding protein can have 1, 2, 3, 4, 5 or 6 CDRs. However, it is also contemplated that an antigen binding protein can have more than six CDRs. An antigen binding protein thus can have, for example, one heavy chain CDR1 ("CDRH1"), and/or one heavy chain CDR2 ("CDRH2"), and/or one heavy chain CDR3 ("CDRH3"), and/or one light chain CDR1 ("CDRL1"), and/or one light chain CDR2 ("CDRL2"), and/or one light chain CDR3 ("CDRL3"). Some antigen binding proteins include both a CDRH3 and a CDRL3. Certain antigen binding proteins that are disclosed herein comprise one or more amino acid sequences that are identical or have substantial sequence identity to the amino acid sequences of one or more of the CDRs presented in TABLE 2 (CDRHs) and TABLE 3 (CDRLs).

TABLE 2

Exemplary CDRH Sequences

| SEQ ID NO: | Amino Acid Sequence |
|---|---|
| 10 | GYYIH |
| 11 | WINPNSGGTNSAQKFRG |
| 12 | EGGYSYGYFDY |
| 22 | GYYMH |
| 23 | WINPNSGGTNYAQKFKG |
| 24 | DKWLDGFDY |
| 35 | WINPNSGGTNYAQKFQG |
| 36 | DRWLDAFDI |
| 47 | WINPNSGGTNYAQRFRG |
| 48 | APYDWTFDY |
| 59 | WINPNSGGRNYAQKFQG |
| 60 | DRWLDAFEI |
| 70 | SYGIS |
| 71 | WISAYNGNTDYAQKLQG |
| 72 | QRYYYSMDV |
| 94 | GYYMY |

TABLE 2-continued

Exemplary CDRH Sequences

| SEQ ID NO: | Amino Acid Sequence |
| --- | --- |
| 95 | WINPNSGGTNYARKFQG |
| 96 | RPWELPFDY |
| 108 | NGDYVFTYFDY |
| 119 | WINPNSGGTNYAQKFRG |
| 120 | FGYFGYYFDY |
| 132 | DPYTSGFDY |
| 142 | SGGYYWS |
| 143 | YIYYSGSTYYNPSLKS |
| 144 | EDTAMDYFDY |

TABLE 3

Exemplary CDRL Sequences

| SEQ ID NO: | Amino Acid Sequence |
| --- | --- |
| 4 | KSSQSILYSSSNENFLT |
| 5 | WASTRES |
| 6 | QQYFSVFRT |
| 16 | RASQSVSSSYFA |
| 17 | GASSRAT |
| 18 | QQYDRSPRT |
| 40 | RASQYISNTYLA |
| 41 | GAATRAT |
| 42 | QQYGSSPWT |
| 52 | RASQSVCSSYLA |
| 64 | IRTSGSIASNYVQ |
| 65 | EDDQRPS |
| 66 | QSCDISNVV |
| 77 | GTSSRAT |
| 78 | LQYDRSPRT |
| 88 | RASQSLSSIYLA |
| 90 | QQYATSPWT |
| 100 | RASQSISNYLN |
| 101 | TASSLQS |
| 102 | QQSFSFPIT |
| 112 | TGTSSDVGGYNYVS |
| 113 | EVSGRPS |
| 114 | SSFTGSSTWL |
| 124 | RASPSVSSSYFA |

TABLE 3-continued

Exemplary CDRL Sequences

| SEQ ID NO: | Amino Acid Sequence |
| --- | --- |
| 126 | QQYGWSPRT |
| 136 | SGSRSHIGSNTVN |
| 137 | SNNHRPS |
| 138 | AAWDDSLNGPV |

In one aspect, the CDRs disclosed herein include consensus sequences derived from groups of related monoclonal antibodies. As described herein, a "consensus sequence" refers to amino acid sequences having conserved amino acids common among a number of sequences and variable amino acids that vary within a given amino acid sequences. The CDR consensus sequences provided include CDRs corresponding to each of CDRH1, CDRH2, CDRH3, CDRL1, CDRL2 and CDRL3.

Consensus sequences were determined using standard phylogenic analyses of the CDRs corresponding to the $V_H$ and $V_L$ of anti-GM-CSF antibodies. The consensus sequences were determined by keeping the CDRs contiguous within the same sequence corresponding to a $V_H$ or $V_L$.

The CDRH1 consensus sequences include amino acid sequence consisting of $X_1X_2GX_3X_4FX_5X_6YX_7X_8X_9$ (SEQ ID NO: 94) wherein $X_1$ is selected from the group consisting of G and no amino acid, $X_2$ is selected from the group consisting of G and no amino acid, $X_3$ is selected from the group consisting of Y and F, $X_4$ is selected from the group consisting of T and S, $X_5$ is selected from the group consisting of T, S and G, $X_6$ is selected from the group consisting of G and S, $X_7$ is selected from the group consisting of Y and G, $X_8$ is selected from the group consisting of I and M, and $X_9$ is selected from the group consisting of H and S. In one aspect, the CDRH1 consensus is SEQ ID NO: 94, $X_1X_2GX_3X_4XFX_5X_6YX_7X_8X_9$ wherein $X_1$ is selected from the group consisting of G and no amino acid, $X_2$ is selected from the group consisting of G and no amino acid, $X_3$ is selected from the group consisting of Y and F, $X_4$ is selected from the group consisting of T and S, $X_5$ is selected from the group consisting of T, S and G, $X_6$ is selected from the group consisting of G and S, $X_7$ is selected from the group consisting of Y and G, $X_8$ is selected from the group consisting of I and M, and $X_9$ is selected from the group consisting of H and S.

The CDRH2 consensus sequence includes amino acid sequence consisting of $X_1X_2X_3X_4X_5X_6GX_7X_8X_9X_{10}X_{11}X_{12}X_{13}X_{14}X_{15}G$ (SEQ ID NO: 106) wherein $X_1$ is selected from the group consisting of W and no amino acid, $X_2$ is selected from the group consisting of I and Y, $X_3$ is selected from the group consisting of N, S and I, $X_4$ is selected from the group consisting of P, A and Y, $X_5$ is selected from the group consisting of N and Y, $X_6$ is selected from the group consisting of S and N, $X_7$ is selected from the group consisting of G and N, $X_8$ is selected from the group consisting of T and R, $X_9$ is selected from the group consisting of N and D, $X_{10}$ is selected from the group consisting of Y and S, $X_{11}$ is selected from the group consisting of A and N, $X_{12}$ is selected from the group consisting of Q and R, $X_{13}$ is selected from the group consisting of K and R, $X_{14}$ is selected from the group consisting of F and L, and $X_{15}$ is selected from the group consisting of Q, K and R. In one aspect, the CDRH2 consensus sequences is WINPNSGGTNX1AX2X3FX4G, wherein X1 is Y or S, X2 is Q or R, X3 is K or R and X4 is R, K or Q (SEQ ID NO: 28).

The CDRH3 consensus sequence includes amino acid sequences selected from the group consisting of $X_1X_2X_3X_4X_5X_6X_7X_8FDX_8$ (SEQ ID NO: 83) wherein $X_1$ is selected from the group consisting of E and no amino acid, $X_2$ is selected from the group consisting of G and no amino acid, $X_3$ is selected from the group consisting of P, D and G, $X_4$ is selected from the group consisting of Y, W, R and K, $X_5$ is selected from the group consisting of S, W, F, and T, $X_6$ is selected from the group consisting of Y and L, $X_7$ is selected from the group consisting of D and G, $X_8$ is selected from the group consisting of Y, no amino acid, and A, and $X_9$ is selected from the group consisting of M, T, and V.

The CDRL1 consensus sequence includes an amino acid sequences selected from the group consisting of KSSQSX$_1$LYSSX$_2$NX$_3$NX$_4$LX$_5$ (SEQ ID NO: 107) wherein $X_1$ is selected from the group consisting of V and I, $X_2$ is selected from the group consisting of S and N, $X_3$ is selected from the group consisting of E and K, $X_4$ is selected from the group consisting of Y and F, and $X_5$ is selected from the group consisting of T and A; RASX$_1$X$_2$X$_3$X$_4$X$_5$X$_6$YX$_7$X$_8$ (SEQ ID NO: 118) wherein $X_1$ is selected from the group consisting of Q and P, $X_2$ is selected from the group consisting of S and Y, $X_3$ is selected from the group consisting of V, L and I, $X_4$ is selected from the group consisting of S and C, $X_5$ is selected from the group consisting of S and N, $X_6$ is selected from the group consisting of S, I, T and no amino acid, $X_7$ is selected from the group consisting of F and L, and $X_8$ is selected from the group consisting of A and N; and $X_1X_2X_3X_4X_5X_6X_7X_8X_9X_{10}NX_{11}VX_{12}$ (SEQ ID NO: 125) wherein $X_1$ is selected from the group consisting of I, S and T, $X_2$ is selected from the group consisting of R and G, $X_3$ is selected from the group consisting of T and S, $X_4$ is selected from the group consisting of R and S, $X_5$ is selected from the group consisting of G and S, $X_6$ is selected from the group consisting of S, H and D, $X_7$ is selected from the group consisting of I and V, $X_8$ is selected from the group consisting of A and G, $X_9$ is selected from the group consisting of no amino acid and G, $X_{10}$ is selected from the group consisting of S and Y, $X_{11}$ is selected from the group consisting of Y and T, and $X_{12}$ is selected from the group consisting of Q, N and S. In one aspect, the CDRL1 consensus sequence is RASQX1X2X3X4X5YX6A, wherein X1 is s or y, X2 is V, I or L, X3 is S or N, X4 is S or C, X4 is S, T, S or Y. X5 is F or L (SEQ ID NO: 30).

The CDRL2 consensus sequence includes amino acid sequences selected from the group consisting of $X_1X_2X_3X_4X_5X_6X_7$, (SEQ ID NO: 130) wherein $X_1$ is selected from the group consisting of G, T and W, $X_2$ is selected from the group consisting of T and A, $X_3$ is selected from the group consisting of S and A, $X_4$ is selected from the group consisting of S and T, $X_5$ is selected from the group consisting of R and L, $X_6$ is selected from the group consisting of A, E and Q, and $X_7$ is selected from the group consisting of T and S; and $X_1X_2X_3X_4RPS$ (SEQ ID NO: 131) wherein $X_1$ is selected from the group consisting of E and S, $X_2$ is selected from the group consisting of D, V and N, $X_3$ is selected from the group consisting of D, S and N, and $X_4$ is selected from the group consisting of Q, G and H. Within one aspect, the CDRL2 consensus sequence is GX1SSRAT wherein X1 is a or T (SEQ ID NO: 34).

The CDRL3 consensus sequences include amino acid sequence selected from the group consisting of $X_1QX_2X_3X_4X_5X_6X_7T$ (SEQ ID NO: 84) wherein $X_1$ is selected from the group consisting of Q and L, $X_2$ is selected from the group consisting of Y and s, $X_3$ is selected from the group consisting of D, G and F, $X_4$ is selected from the group consisting of R, T, and S, $X_5$ is selected from the group consisting of S and V, $X_6$ is selected from the group consisting of F and P, and $X_7$ is selected from the group consisting of R and W; and $X_1X_2X_3X_4DSSNX_6X_6X_7$ (SEQ ID NO: 89) wherein $X_1$ is selected from the group consisting of S and A, $X_2$ is selected from the group consisting of S and A, $X_3$ is selected from the group consisting of W and F, $X_4$ is selected from the group consisting of D and T, $X_5$ is selected from the group consisting of G, W, and no amino acid, $X_6$ is selected from the group consisting of V, L, and P, and $X_6$ is selected from the group consisting of V and no amino acid. Within one aspect the CDRL3 consensus sequence is QQX1X2X3X4X5X6T, wherein X1 is Y or S, X2 is F, G or A, X3 is S, T or W, X4 is V, S, F, X 5 is F or P, X6 is R, W, or I (SEQ ID NO:46).

In another aspect, the CDRs provided are a (a) a CDRH selected from the group consisting of (i) a CDRH1 selected from the group consisting of SEQ ID NO: 10, 22, 70 94 and 142; (ii) a CDRH2 selected from the group consisting of SEQ ID NO: 11, 23, 28, 35, 47, 59, 71, 95, 106, 119 and 143; (iii) a CDRH3 selected from the group consisting of SEQ ID NO: 12, 24, 36, 48, 60, 72, 83, 96, 108, 120, 132, and 144; and (iv) a CDRH of (i), (ii) and (iii) that contains one or more amino acid substitutions, deletions or insertions of no more than five, four, three, two, or one amino acids; (B) a CDRL selected from the group consisting of (i) a CDRL1 selected from the group consisting of SEQ ID NO: 4, 16, 30, 40, 52, 64, 88, 100, 107, 112, 118, 124, 125 and 136; (ii) a CDRL2 selected from the group consisting of SEQ ID NO: 5, 17, 29, 34, 41, 65, 77, 101, 113, 130, 131 and 137; (iii) a CDRL3 selected from the group consisting of SEQ ID NO: 6, 18, 42, 46, 66, 78, 84, 89, 90, 102, 114, 126, and 138; and (iv) a CDRL of (i), (ii) and (iii) that contains one or more amino acid substitutions, deletions or insertions of no more than five, four, three, two, or one amino acids amino acids.

In yet another aspect, variant forms of the CDRs listed in TABLES 2 and 3 have at least 80%, 85%, 90% or 95% sequence identity to a CDR sequence listed in TABLE 2 and 3.

According to one aspect, provided is an isolated antigen-binding protein that binds GM-CSF comprising (A) one or more heavy chain complementary determining regions (CDRHs) selected from the group consisting of: (i) a CDRH1 selected from the group consisting of SEQ ID NO: 10, 22, 70 94 and 142; (ii) a CDRH2 selected from the group consisting of SEQ ID NO: 11, 23, 28, 35, 47, 59, 71, 95, 106, 119 and 143; (iii) a CDRH3 selected from the group consisting of SEQ ID NO: 12, 24, 36, 48, 60, 72, 83, 96, 108, 120, 132, and 144; and (iv) a CDRH of (i), (ii) and (iii) that contains one or more amino acid substitutions, deletions or insertions of no more than five, four, three, four, two or one amino acids; (B) one or more light chain complementary determining regions (CDRLs) selected from the group consisting of: (i) a CDRL1 selected from the group consisting of SEQ ID NO: 4, 16, 30, 40, 52, 64, 88, 100, 107, 112, 118, 124, 125 and 136; (ii) a CDRL2 selected from the group consisting of SEQ ID NO: 5, 17, 29, 34, 41, 65, 77, 101, 113, 130, 131 and 137; (iii) a CDRL3 selected from the group consisting of SEQ ID NO: 6, 18, 42, 46, 66, 78, 84, 89, 90, 102, 114, 126, and 138; and (iv) a CDRL of (i), (ii) and (iii) that contains one or more amino acid substitutions, deletions or insertions of no more than five, four, three, four, two or one amino acids; or (C) one or more heavy chain CDRHs of (A) and one or more light chain CDRLs of (B).

In yet another embodiment, the isolated antigen-binding protein may comprise (A) a CDRH selected from the group consisting of (i) a CDRH1 selected from the group consisting of SEQ ID NO: 10, 22, 70 94 and 142; (ii) a CDRH2 selected from the group consisting of SEQ ID NO: 11, 23, 28, 35, 47, 59, 71, 95, 106, 119 and 143; and (iii) a CDRH3 selected from the group consisting of SEQ ID NO: 12, 24, 36, 48, 60, 72, 83, 96, 108, 120, 132, and 144; (B) a CDRL selected from the group consisting of (i) a CDRL1 selected from the group consisting of SEQ ID NO: 4, 16, 30, 40, 52, 64, 88, 100, 107, 112, 118, 124, 125 and 136; (ii) a CDRL2 selected from the group consisting of SEQ ID NO: 5, 17, 29, 34, 41, 65, 77, 101, 113, 130, 131 and 137; (iii) a CDRL3 selected from the group consisting of SEQ ID NO: 6, 18, 42, 46, 66, 78, 84, 89, 90, 102, 114, 126, and 138; or (C) one or more heavy chain CDRHs of (A) and one or more light chain CDRLs of (B).

In another embodiment, the variable heavy chain (VH) has at least 80%, 85%, 90% or 95% sequence identity with an amino acid sequence selected from the group consisting of SEQ ID NO: 9, 21, 33, 45, 57, 69, 81, 93, 105, 117, 129, and 141, and/or the variable light chain (VL) has at least 80%, 85%, 90% or 95% sequence identity with an amino acid sequence selected from the group consisting of SEQ ID NO: 3, 15, 27, 39, 51, 63, 75, 87, 99, 111, 123, and 135.

In a further aspect, there is a provision of an isolated antigen-binding protein that binds GM-CSF, the antigen-binding protein including A) a heavy chain complementary determining region (CDRH) selected from the group consisting of (i) a CDRH3 selected from the group consisting of SEQ ID NOs: 12, 24, 36, 48, 60, 72, 83, 96, 108, 120, 132, and 144; (ii) a CDRH3 that differs in amino acid sequence from the CDRH3 of (i) by an amino acid addition, deletion or substitution of not more than two amino acids; (iii) a CDRH3 amino acid sequence selected from the group consisting of $X_1X_2X_3X_4X_5X_6X_7X_8FDX_9$ (SEQ ID NO: 83) wherein $X_1$ is selected from the group consisting of E and no amino acid, $X_2$ is selected from the group consisting of G and no amino acid, $X_3$ is selected from the group consisting of P, D and G, $X_4$ is selected from the group consisting of Y, W, R and K, $X_5$ is selected from the group consisting of S, W, F, and T, $X_6$ is selected from the group consisting of Y and L, $X_7$ is selected from the group consisting of D and G, $X_8$ is selected from the group consisting of Y, no amino acid, and A, and $X_9$ is selected from the group consisting of M, T, and V; and/or B) a light chain complementary determining region (CDRL) selected from the group consisting of (i) a CDRL3 selected from the group consisting of SEQ ID NOs: 6, 18, 42, 46, 66, 78, 84, 89, 90, 102, 114, 126, and 138, (ii) a CDRL3 that differs in amino acid sequence from the CDRL3 of (i) by an amino acid addition, deletion or substitution of not more than two amino acids; and iii) a CDRL3 amino acid sequence selected from the group consisting of $X_1QX_2X_3X_4X_5X_6X_7T$ (SEQ ID NO: 84) wherein X1 is selected from the group consisting of Q and L, $X_2$ is selected from the group consisting of Y and S, $X_3$ is selected from the group consisting of D, G and F, $X_4$ is selected from the group consisting of R, T, and S, $X_5$ is selected from the group consisting of S and V, $X_6$ is selected from the group consisting of F and P, and $X_7$ is selected from the group consisting of R and W; and $X_1X_2X_3X_4DSSNX_5X_6X_7$ (SEQ ID NO: 89) wherein $X_1$ is selected from the group consisting of S and A, $X_2$ is selected from the group consisting of S and A, $X_3$ is selected from the group consisting of W and F, $X_4$ is selected from the group consisting of D and T, $X_5$ is selected from the group consisting of G, W, and no amino acid, X6 is selected from the group consisting of V, L, and P, and $X_6$ is selected from the group consisting of V and no amino acid.

Within another embodiment, the antigen binding protein further comprising: A) a CDRH selected from the group consisting of: (i) a CDRH1 selected from the group consisting of SEQ ID NOs: 10, 22, 70 94 and 142; (ii) a CDRH1 that differs in amino acid sequence from the CDRH1 of (i) by an amino acid addition, deletion or substitution of not more than two amino acids; (iii) a CDRH1 amino acid sequence selected from the group consisting of $X_1X_2GX_3X_4XFX_5X_6YX_7X_8X_9$ (SEQ ID NO: 94) wherein $X_1$ is selected from the group consisting of G and no amino acid, $X_2$ is selected from the group consisting of G and no amino acid, $X_3$ is selected from the group consisting of Y and F, $X_4$ is selected from the group consisting of T and S, $X_5$ is selected from the group consisting of T, S and G, $X_6$ is selected from the group consisting of G and S, $X_7$ is selected from the group consisting of Y and G, $X_8$ is selected from the group consisting of I and M, and $X_9$ is selected from the group consisting of H and S, or (iv) a CDRH2 selected from the group consisting of SEQ ID NOs: 11, 23, 28, 35, 47, 59, 71, 95, 106, 119 and 143; (v) a CDRH2 that differs in amino acid sequence from the CDRH2 of (iv) by an amino acid addition, deletion or substitution of not more than two amino acids; or (vi) a CDRH2 amino acid sequence consisting of $X_1X_2X_3X_4X_5X_6GX_7X_8X_9X_{10}X_{11}X_{12}X_{13}X_{14}X_{15}G$ (SEQ ID NO: 106) wherein $X_1$ is selected from the group consisting of W and no amino acid, $X_2$ is selected from the group consisting of I and Y, $X_3$ is selected from the group consisting of N, S and I, $X_4$ is selected from the group consisting of P, A and Y, $X_5$ is selected from the group consisting of N and Y, $X_6$ is selected from the group consisting of S and N, $X_7$ is selected from the group consisting of G and N, $X_8$ is selected from the group consisting of T and R, $X_9$ is selected from the group consisting of N and D, $X_{10}$ is selected from the group consisting of Y and S, $X_{11}$ is selected from the group consisting of A and N, $X_{12}$ is selected from the group consisting of Q and R, $X_{13}$ is selected from the group consisting of K and R, $X_{14}$ is selected from the group consisting of F and L, and $X_{15}$ is selected from the group consisting of Q, K and R; or B) a CDRL selected from the group consisting of: (i) a CDRL1 selected from the group consisting of SEQ ID NOs: 4, 16, 30, 40, 52, 64, 88, 100, 107, 112, 118, 124, 125 and 136; (ii) a CDRL1 that differs in amino acid sequence from the CDRL1 of (i) by an amino acid addition, deletion or substitution of not more than two amino acids; (iii) a CDRL1 amino acid sequence selected from the group consisting of $KSSQSX_1XLYSSX_2NX_3NX_4LX_5$ (SEQ ID NO: 107) wherein $X_1$ is selected from the group consisting of V and I, $X_2$ is selected from the group consisting of S and N, $X_3$ is selected from the group consisting of E and K, $X_4$ is selected from the group consisting of Y and F, and $X_5$ is selected from the group consisting of T and A; $RASX_1X_2X_3X_4X_5X_6YX_7X_8$ (SEQ ID NO: 118) wherein $X_1$ is selected from the group consisting of Q and P, $X_2$ is selected from the group consisting of S and Y, $X_3$ is selected from the group consisting of V, L and I, $X_4$ is selected from the group consisting of S and C, $X_5$ is selected from the group consisting of S and N, $X_6$ is selected from the group consisting of S, I, T and no amino acid, $X_7$ is selected from the group consisting of F and L, and $X_8$ is selected from the group consisting of A and N; or $X_1X_2X_3X_4X_5X_6YX_7X_8X_9X_{10}NX_{11}VX_{12}$ (SEQ ID NO: 125) wherein $X_1$ is selected from the group consisting of I, S and T, $X_2$ is selected from the group consisting of R and G, $X_3$ is selected from the group consisting of T and S, $X_4$ is selected from the group consisting of R and S, $X_5$ is selected from the group consisting of G and S, $X_6$ is selected from the group consisting of S, H and D, $X_7$ is selected from the group consisting of I and V, $X_8$ is selected from the group consisting of A and G, $X_9$ is selected from the group consisting of no amino acid and G, $X_{10}$ is selected from the group consisting of S and Y, $X_{11}$ is selected from the group consisting of Y and T, and $X_{12}$ is selected from the group consisting of Q, N and S; or (iv) a CDRL2 selected from the group consisting of SEQ ID NOs: 5, 17, 29, 34, 41, 65, 77, 101, 113, 130, 131 and 137; (v) a CDRL2 that differs in amino acid sequence from the CDRL2 of (iv) by an amino acid addition, deletion or substitution of not more than two amino acids; or (vi) a CDRL2 amino acid sequence selected from the group consisting of $X_1X_2X_3X_4X_5X_6X_7$ (SEQ ID NO: 130) wherein X1 is selected from the group consisting of G, T and W, X2 is selected from the group consisting of T and A, X3 is selected from the group consisting of S and A, X4 is selected from the group consisting of S and T, X5 is selected from the group consisting of R and L, X6 is selected from the group consisting of A, E and Q, and X7 is selected from the group consisting of T and S; or X1X2X3X4RPS (SEQ ID NO: 131) wherein X1 is selected from the group consisting of E and S, X2 is selected from the group consisting of D, V and N, X3 is selected from the group consisting of D, S and N, and X4 is selected from the group consisting of Q, G and H.

In one aspect, the isolated antigen-binding proteins provided herein can be a monoclonal antibody, a polyclonal antibody, a recombinant antibody, a human antibody, a humanized antibody, a chimeric antibody, a multispecific antibody, or an antibody fragment thereof.

In another embodiment, the antibody fragment of the isolated antigen-binding proteins provided herein can be a Fab fragment, a Fab' fragment, an F(ab')₂ fragment, an Fv fragment, a diabody, or a single chain antibody molecule.

In a further embodiment, the isolated antigen binding protein provided herein is a human antibody and can be of the IgG1-, IgG2- IgG3- or IgG4-type.

In yet another aspect, the isolated antigen-binding protein provided herein can be coupled to a labeling group and can compete for binding to the extracellular portion of human GM-CSF with an antigen binding protein of one of the isolated antigen-binding proteins provided herein. In one embodiment, the isolated antigen binding protein provided herein can reduce monocyte chemotaxis, inhibit monocyte migration into tumors or inhibit accumulation of tumor associated macrophage in a tumor when administered to a patient.

As will be appreciated by those in the art, for any antigen binding protein with more than one CDR from the depicted sequences, any combination of CDRs independently selected from the depicted sequences is useful. Thus, antigen binding proteins with one, two, three, four, five or six of independently selected CDRs can be generated. However, as will be appreciated by those in the art, specific embodiments generally utilize combinations of CDRs that are non-repetitive, e.g., antigen binding proteins are generally not made with two CDRH2 regions, etc.

Some of the antigen binding proteins provided are discussed in more detail below.

Antigen Binding Proteins and Binding Epitopes

When an antigen binding protein is said to bind an epitope within specified residues, such as GM-CSF, or the extracellular domain of GM-CSF, for example, what is meant is that the antigen binding protein specifically binds to a polypeptide consisting of the specified residues (e.g., a specified segment of GM-CSF). Such an antigen binding protein typically does not contact every residue within GM-CSF, or the extracellular domain of GM-CSF. Nor does every single amino acid substitution or deletion within GM-CSF, or the extracellular domain of GM-CSF, necessarily significantly affect binding affinity. Epitope specificity of an antigen binding protein can be determined in variety of ways. One approach, for example, involves testing a collection of overlapping peptides of about 15 amino acids spanning the sequence of the antigen and differing in increments of a small number of amino acids (e.g., three amino acids). The peptides are immobilized within the wells of a microtiter dish. Immobilization can be effected by biotinylating one terminus of the peptides. Optionally, different samples of the same peptide can be biotinylated at the amino- and the carboxy-terminus and immobilized in separate wells for purposes of comparison. This is useful for identifying end-specific antigen binding proteins. Optionally, additional peptides can be included terminating at a particular amino acid of interest. This approach is useful for identifying end-specific antigen binding proteins to internal fragments of GM-CSF (or the extracellular domain of GM-CSF). An antigen binding protein or immunologically functional fragment is screened for specific binding to each of the various peptides. The epitope is defined as occurring with a segment of amino acids that is common to all peptides to which the antigen binding protein shows specific binding. Details regarding a specific approach for defining an epitope are set forth in Example 13.

Competing Antigen Binding Proteins

In another aspect, antigen binding proteins are provided that compete with one the exemplified antibodies or functional fragments binding to the epitope described above for specific binding to GM-CSF. Such antigen binding proteins may also bind to the same epitope as one of the herein exemplified antigen binding proteins, or an overlapping epitope. Antigen binding proteins and fragments that compete with or bind to the same epitope as the exemplified antigen binding proteins are expected to show similar functional properties. The exemplified antigen binding proteins and fragments include those described above, including those with the heavy and light chains, variable region domains and CDRs included in TABLES 1, 2, and 3.

1. Monoclonal Antibodies

The antigen binding proteins that are provided include monoclonal antibodies that bind to GM-CSF. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XXO Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

In some instances, a hybridoma cell line is produced by immunizing an animal (e.g., a transgenic animal having human immunoglobulin sequences) with a GM-CSF immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds a GM-CSF polypeptide. Such hybridoma cell lines, and anti-GM-CSF monoclonal antibodies produced by them, are aspects of the present application.

Monoclonal antibodies secreted by a hybridoma cell line can be purified using any technique known in the art. Hybridomas or mAbs may be further screened to identify mAbs with particular properties, such as the ability to block a Wnt induced activity. Examples of such screens are provided in the examples below.

2. Chimeric and Humanized Antibodies

Chimeric and humanized antibodies based upon the foregoing sequences are also provided. Monoclonal antibodies for use as therapeutic agents may be modified in various ways prior to use. One example is a chimeric antibody, which is an antibody composed of protein segments from different antibodies that are covalently joined to produce functional immunoglobulin light or heavy chains or immunologically functional portions thereof. Generally, a portion of the heavy chain and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. For methods relating to chimeric antibodies, see, for example, U.S. Pat. No. 4,816,567; and Morrison et al., 1985, *Proc. Natl. Acad. Sci. USA* 81:6851-6855. CDR grafting is described, for example, in U.S. Pat. Nos. 6,180,370, 5,693,762, 5,693,761, 5,585,089, and U.S. Pat. No. 5,530,101.

Generally, the goal of making a chimeric antibody is to create a chimera in which the number of amino acids from the intended patient species is maximized. One example is the "CDR-grafted" antibody, in which the antibody comprises one or more complementarity determining regions (CDRs) from a particular species or belonging to a particular antibody class or subclass, while the remainder of the antibody chain(s) is/are identical with or homologous to a corresponding sequence in antibodies derived from another species or belonging to another antibody class or subclass. For use in humans, the variable region or selected CDRs from a rodent antibody often are grafted into a human antibody, replacing the naturally-occurring variable regions or CDRs of the human antibody.

One useful type of chimeric antibody is a "humanized" antibody. Generally, a humanized antibody is produced from a monoclonal antibody raised initially in a non-human animal. Certain amino acid residues in this monoclonal antibody, typically from non-antigen recognizing portions of the antibody, are modified to be homologous to corresponding residues in a human antibody of corresponding isotype. Humanization can be performed, for example, using various methods by substituting at least a portion of a rodent variable region for the corresponding regions of a human antibody (see, e.g., U.S. Pat. No. 5,585,089, and No. 5,693,762; Jones et al., 1986, *Nature* 321:522-525; Riechmann et al., 1988, *Nature* 332:323-27; Verhoeyen et al., 1988, *Science* 239:1534-1536).

In one aspect, the CDRs of the light and heavy chain variable regions of the antibodies provided herein (see, TABLE 2) are grafted to framework regions (FRs) from antibodies from the same, or a different, phylogenetic species. For example, the CDRs of the heavy and light chain variable regions $V_H1$, $V_H2$, $V_H3$, $V_H4$, $V_H5$, $V_H6$, $V_H7$, $V_H8$, $V_H9$, $V_H10$, $V_H11$, and $V_H12$, and/or $V_L1$, $V_L2$, $V_L3$, $V_L4$, $V_L5$, $V_L6$, $V_L7$, $V_L8$, $V_L9$, $V_L10$, VL11, and VL12, can be grafted to consensus human FRs. To create consensus human FRs, FRs from several human heavy chain or light chain amino acid sequences may be aligned to identify a consensus amino acid sequence. In other embodiments, the FRs of a heavy chain or light chain disclosed herein are replaced with the FRs from a different heavy chain or light chain. In one aspect, rare amino acids in the FRs of the heavy and light chains of anti-GM-CSF antibody are not replaced, while the rest of the FR amino acids are replaced. A "rare amino acid" is a specific amino acid that is in a position in which this particular amino acid is not usually found in an FR. Alternatively, the grafted variable regions from the one heavy or light chain may be used with a constant region that is different from the constant region of that particular heavy or light chain as disclosed herein. In other embodiments, the grafted variable regions are part of a single chain Fv antibody.

In certain embodiments, constant regions from species other than human can be used along with the human variable region(s) to produce hybrid antibodies.

3. Fully Human Antibodies

Fully human antibodies are also provided. Methods are available for making fully human antibodies specific for a given antigen without exposing human beings to the antigen ("fully human antibodies"). One specific means provided for implementing the production of fully human antibodies is the "humanization" of the mouse humoral immune system. Introduction of human immunoglobulin (Ig) loci into mice in which the endogenous Ig genes have been inactivated is one means of producing fully human monoclonal antibodies (mAbs) in mouse, an animal that can be immunized with any desirable antigen. Using fully human antibodies can minimize the immunogenic and allergic responses that can sometimes be caused by administering mouse or mouse-derivatized mAbs to humans as therapeutic agents.

Fully human antibodies can be produced by immunizing transgenic animals (usually mice) that are capable of producing a repertoire of human antibodies in the absence of endogenous immunoglobulin production. Antigens for this purpose typically have six or more contiguous amino acids, and optionally are conjugated to a carrier, such as a hapten. See, e.g., Jakobovits et al., 1993, *Proc. Natl. Acad. Sci. USA* 90:2551-2555; Jakobovits et al., 1993, *Nature* 362:255-258; and Bruggermann et al., 1993, *Year in Immunol.* 7:33. In one example of such a method, transgenic animals are produced by incapacitating the endogenous mouse immunoglobulin loci encoding the mouse heavy and light immunoglobulin chains therein, and inserting into the mouse genome large fragments of human genome DNA containing loci that encode human heavy and light chain proteins. Partially modified animals, which have less than the full complement of human immunoglobulin loci, are then cross-bred to obtain an animal having all of the desired immune system modifications. When administered an immunogen, these transgenic animals produce antibodies that are immunospecific for the immunogen but have human rather than murine amino acid sequences, including the variable regions. For further details of such methods, see, for example, WO96/33735 and WO94/02602. Additional methods relating to transgenic mice for making human antibodies are described in U.S. Pat. No. 5,545,807; U.S. Pat. No. 6,713,610; U.S. Pat. No. 6,673,986; U.S. Pat. No. 6,162,963; U.S. Pat. No. 5,545,807; U.S. Pat. No. 6,300,129; U.S. Pat. No. 6,255,458; U.S. Pat. No. 5,877,397; U.S. Pat. No. 5,874,299 and U.S. Pat. No. 5,545,806; in PCT publications WO91/10741, WO90/04036, and in EP 546073B1 and EP 546073A1.

The transgenic mice described above, referred to herein as "HuMab" mice, contain a human immunoglobulin gene minilocus that encodes unrearranged human heavy ([mu] and [gamma]) and [kappa] light chain immunoglobulin sequences, together with targeted mutations that inactivate the endogenous [mu] and [kappa] chain loci (Lonberg et al., 1994, *Nature* 368:856-859). Accordingly, the mice exhibit reduced expression of mouse IgM or [kappa] and in response to immunization, and the introduced human heavy and light chain transgenes undergo class switching and somatic mutation to generate high affinity human IgG [kappa] monoclonal antibodies (Lonberg et al., supra.; Lonberg and Huszar, 1995, *Intern. Rev. Immunol.* 13: 65-93; Harding and Lonberg, 1995, *Ann. N.Y. Acad. Sci.* 764:536-546). The preparation of HuMab mice is described in detail in Taylor et al., 1992, *Nucleic Acids Research* 20:6287-6295; Chen et al., 1993, *International Immunology* 5:647-656; Tuaillon et al., 1994, *J. Immunol.* 152:2912-2920; Lonberg et al., 1994, *Nature* 368: 856-859; Lonberg, 1994, *Handbook of Exp. Pharmacology* 113:49-101; Taylor et al., 1994, *International Immunology* 6:579-591; Lonberg and Huszar, 1995, *Intern. Rev. Immunol.* 13:65-93; Harding and Lonberg, 1995, *Ann. N.Y. Acad. Sci.* 764:536-546; Fishwild et al., 1996, *Nature Biotechnology* 14:845-85. See, further U.S. Pat. Nos. 5,545,806; 5,569,825; 5,625,126; 5,633,425; 5,789,650; 5,877,397; 5,661,016; 5,814,318; 5,874,299; and U.S. Pat. No. 5,770,429; as well as U.S. Pat. No. 5,545,807; PCT Publication Nos. WO 93/1227; WO 92/22646; and WO 92/03918. Technologies utilized for producing human antibodies in these transgenic mice are disclosed also in PCT Publication No. WO 98/24893, and Mendez et al., 1997, *Nature Genetics* 15:146-156. For example, the HCo7 and HCo12 transgenic mice strains can be used to generate anti-GM-CSF antibodies.

Using hybridoma technology, antigen-specific human mAbs with the desired specificity can be produced and selected from the transgenic mice such as those described above. Such antibodies may be cloned and expressed using a suitable vector and host cell, or the antibodies can be harvested from cultured hybridoma cells.

Fully human antibodies can also be derived from phage-display libraries (as disclosed in Hoogenboom et al., 1991, *J. Mol. Biol.* 227:381; and Marks et al., 1991, *J. Mol. Biol.* 222:581). Phage display techniques mimic immune selection through the display of antibody repertoires on the surface of filamentous bacteriophage, and subsequent selection of phage by their binding to an antigen of choice. One such technique is described in PCT Publication No. WO 99/10494, which describes the isolation of high affinity and functional agonistic antibodies for MPL- and msk-receptors using such an approach.

4. Bispecific or Bifunctional Antigen Binding Proteins

The antigen binding proteins that are provided also include bispecific and bifunctional antibodies that include one or more CDRs or one or more variable regions as described above. A bispecific or bifunctional antibody in some instances is an artificial hybrid antibody having two different heavy/light chain pairs and two different binding sites. Bispecific antibodies may be produced by a variety of methods including, but not limited to, fusion of hybridomas or linking of Fab' fragments. See, e.g., Songsivilai and Lachmann, 1990, *Clin. Exp. Immunol.* 79:315-321; Kostelny et al., 1992, *J. Immunol.* 148:1547-1553.

5. Various Other Forms

Some of the antigen binding proteins that are provided are variant forms of the antigen binding proteins disclosed above (e.g., those having the sequences listed in TABLES 1-4). For instance, some of the antigen binding proteins have one or more conservative amino acid substitutions in one or more of the heavy or light chains, variable regions or CDRs listed in TABLES 1-4.

Naturally-occurring amino acids may be divided into classes based on common side chain properties:
1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of the above classes for a member from another class. Such substituted residues may be introduced into regions of the antibody that are homologous with human antibodies, or into the non-homologous regions of the molecule.

In making such changes, according to certain embodiments, the hydropathic index of amino acids may be considered. The hydropathic profile of a protein is calculated by assigning each amino acid a numerical value ("hydropathy index") and then repetitively averaging these values along the peptide chain. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic profile in conferring interactive biological function on a protein is understood in the art (see, e.g., Kyte et al., 1982, *J. Mol. Biol.* 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In some aspects, those which are within ±1 are included, and in other aspects, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigen-binding or immunogenicity, that is, with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in other embodiments, those which are within ±1 are included, and in still other embodiments, those within ±0.5 are included. In some instances, one may also identify epitopes from primary amino acid sequences on the basis of hydrophilicity. These regions are also referred to as "epitopic core regions."

Exemplary conservative amino acid substitutions are set forth in TABLE 4.

TABLE 4

Conservative Amino Acid Substitutions

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

A skilled artisan will be able to determine suitable variants of polypeptides as set forth herein using well-known techniques. One skilled in the art may identify suitable areas of the molecule that may be changed without destroying activity by targeting regions not believed to be important for activity. The skilled artisan also will be able to identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the 3-dimensional structure and amino acid sequence in relation to that structure in similar polypeptides. In view of such information, one skilled in the art may predict the alignment of amino acid residues of an antibody with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. These variants can then be screened using assays for GM-CSF neutralizing activity, (see examples below) thus yielding information regarding which amino acids can be changed and which must not be changed. In other words, based on information gathered from such routine experiments, one skilled in the art can readily determine the amino acid positions where further substitutions should be avoided either alone or in combination with other mutations.

A number of scientific publications have been devoted to the prediction of secondary structure. See, Moult, 1996, *Curr. Op. in Biotech.* 7:422-427; Chou et al., 1974, *Biochem.* 13:222-245; Chou et al., 1974, *Biochemistry* 113:211-222; Chou et al., 1978, *Adv. Enzymol. Relat. Areas Mol. Biol.* 47:45-148; Chou et al., 1979, *Ann. Rev. Biochem.* 47:251-276; and Chou et al., 1979, *Biophys. J.* 26:367-384. Moreover, computer programs are currently available to assist with predicting secondary structure. One method of predicting secondary structure is based upon homology modeling. For example, two polypeptides or proteins that have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See, Holm et al., 1999, *Nucl. Acid. Res.* 27:244-247. It has been suggested (Brenner et al., 1997, *Curr. Op. Struct. Biol.* 7:369-376) that there are a limited number of folds in a given polypeptide or protein and that once a critical number of structures have been resolved, structural prediction will become dramatically more accurate.

Additional methods of predicting secondary structure include "threading" (Jones, 1997, *Curr. Opin. Struct. Biol.* 7:377-387; Sippl et al., 1996, *Structure* 4:15-19), "profile analysis" (Bowie et al., 1991, *Science* 253:164-170; Gribskov et al., 1990, *Meth. Enzym.* 183:146-159; Gribskov et al., 1987, *Proc. Nat. Acad. Sci.* 84:4355-4358), and "evolutionary linkage" (See, Holm, 1999, supra; and Brenner, 1997, supra).

In some embodiments, amino acid substitutions are made that: (1) reduce susceptibility to proteolysis, (2) reduce susceptibility to oxidation, (3) alter binding affinity for forming protein complexes, (4) alter ligand or antigen binding affinities, and/or (4) confer or modify other physicochemical or functional properties on such polypeptides. For example, single or multiple amino acid substitutions (in certain embodiments, conservative amino acid substitutions) may be made in the naturally-occurring sequence. Substitutions can be made in that portion of the antibody that lies outside the domain(s) forming intermolecular contacts). In such embodiments, conservative amino acid substitutions can be used that do not substantially change the structural characteristics of the parent sequence (e.g., one or more replacement amino acids that do not disrupt the secondary structure that characterizes the parent or native antigen binding protein). Examples of art-recognized polypeptide secondary and tertiary structures are described in Proteins, Structures and Molecular Principles (Creighton, Ed.), 1984, W. H. New York: Freeman and Company; Introduction to Protein Structure (Branden and Tooze, eds.), 1991, New York: Garland Publishing; and Thornton et al., 1991, *Nature* 354:105.

Additional preferred antibody variants include cysteine variants wherein one or more cysteine residues in the parent or native amino acid sequence are deleted from or substituted with another amino acid (e.g., serine). Cysteine variants are useful, inter alia when antibodies must be refolded into a biologically active conformation. Cysteine variants may have fewer cysteine residues than the native antibody, and typically have an even number to minimize interactions resulting from unpaired cysteines.

The heavy and light chains, variable regions domains and CDRs that are disclosed can be used to prepare polypeptides that contain an antigen binding region that can specifically bind to a GM-CSF polypeptide. For example, one or more of the CDRs listed in TABLES 3 and 4 can be incorporated into a molecule (e.g., a polypeptide) covalently or noncovalently to make an immunoadhesion. An immunoadhesion may incorporate the CDR(s) as part of a larger polypeptide chain, may covalently link the CDR(s) to another polypeptide chain, or may incorporate the CDR(s) noncovalently. The CDR(s) enable the immunoadhesion to bind specifically to a particular antigen of interest (e.g., a GM-CSF polypeptide or epitope thereof).

Mimetics (e.g., "peptide mimetics" or "peptidomimetics") based upon the variable region domains and CDRs that are described herein are also provided. These analogs can be peptides, non-peptides or combinations of peptide and non-peptide regions. Fauchere, 1986, *Adv. Drug Res.* 15:29; Veber and Freidinger, 1985, *TINS* p. 392; and Evans et al., 1987, *J. Med. Chem.* 30:1229. Peptide mimetics that are structurally similar to therapeutically useful peptides may be used to produce a similar therapeutic or prophylactic effect. Such compounds are often developed with the aid of computerized molecular modeling. Generally, peptidomimetics are proteins that are structurally similar to an antibody displaying a desired biological activity, such as here the ability to specifically bind GM-CSF, but have one or more peptide linkages optionally replaced by a linkage selected from: —$CH_2NH$—, —$CH_2S$—, —$CH_2$—$CH_2$—, —CH—CH— (cis and trans), —$COCH_2$—, —$CH(OH)CH_2$—, and —$CH_2SO$—, by methods well known in the art. Systematic substitution of one or more amino acids of a consensus sequence with a D-amino acid of the same type (e.g., D-lysine in place of L-lysine) may be used in certain embodiments to generate more stable proteins. In addition, constrained peptides comprising a consensus sequence or a substantially identical consensus sequence variation may be generated by methods known in the art (Rizo and Gierasch, 1992, *Ann. Rev. Biochem.* 61:387), for example, by adding internal cysteine residues capable of forming intramolecular disulfide bridges which cyclize the peptide.

Derivatives of the antigen binding proteins that are described herein are also provided. The derivatized antigen binding proteins can comprise any molecule or substance that imparts a desired property to the antibody or fragment, such as increased half-life in a particular use. The derivatized antigen binding protein can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or Streptavidin)), a therapeutic or diagnostic moiety (e.g., a radioactive, cytotoxic, or pharmaceutically active moiety), or a molecule that increases the suitability of the antigen binding protein for a particular use (e.g., administration to a subject, such as a human subject, or other in vivo or in vitro uses). Examples of molecules that can be used to derivatize an antigen binding protein include albumin (e.g., human serum albumin) and polyethylene glycol (PEG). Albumin-linked and PEGylated derivatives of antigen binding proteins can be prepared using techniques well known in the art. In one embodiment, the antigen binding protein is conjugated or otherwise linked to transthyretin (TTR) or a TTR variant. The TTR or TTR variant can be chemically modified with, for example, a chemical selected from the group consisting of dextran, poly(n-vinyl pyrrolidone), polyethylene glycols, propropylene glycol homopolymers, polypropylene oxide/ethylene oxide co-polymers, polyoxyethylated polyols and polyvinyl alcohols.

Other derivatives include covalent or aggregative conjugates of GM-CSF antigen binding proteins with other proteins or polypeptides, such as by expression of recombinant fusion proteins comprising heterologous polypeptides fused to the N-terminus or C-terminus of a GM-CSF antigen binding protein. For example, the conjugated peptide may be a heterologous signal (or leader) polypeptide, e.g., the yeast alpha-factor leader, or a peptide such as an epitope tag. GM-CSF antigen binding protein-containing fusion proteins can comprise peptides added to facilitate purification or identification of the GM-CSF antigen binding protein (e.g., poly-His). A GM-CSF antigen binding protein also can be linked to the FLAG peptide as described in Hopp et al., 1988, *Bio/Technology* 6:1204; and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.).

Oligomers that contain one or more GM-CSF antigen binding proteins may be employed as GM-CSF antagonists. Oligomers may be in the form of covalently-linked or non-covalently-linked dimers, trimers, or higher oligomers. Oligomers comprising two or more GM-CSF antigen binding proteins are contemplated for use, with one example being a homodimer. Other oligomers include heterodimers, homotrimers, heterotrimers, homotetramers, heterotetramers, etc.

One embodiment is directed to oligomers comprising multiple GM-CSF-binding polypeptides joined via covalent or non-covalent interactions between peptide moieties fused to the GM-CSF antigen binding proteins. Such peptides may be peptide linkers (spacers), or peptides that have the property of promoting oligomerization. Leucine zippers and certain polypeptides derived from antibodies are among the peptides that can promote oligomerization of GM-CSF antigen binding proteins attached thereto, as described in more detail below.

In particular embodiments, the oligomers comprise from two to four GM-CSF antigen binding proteins. The GM-CSF antigen binding protein moieties of the oligomer may be in any of the forms described above, e.g., variants or fragments. Preferably, the oligomers comprise GM-CSF antigen binding proteins that have GM-CSF binding activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, *Proc. Natl. Acad. Sci. USA* 88:10535; Byrn et al., 1990, *Nature* 344:677; and Hollenbaugh et al., 1992 "Construction of Immunoglobulin Fusion Proteins", in Current Protocols in Immunology, Suppl. 4, pages 10.19.1-10.19.11.

One embodiment is directed to a dimer comprising two fusion proteins created by fusing a a GM-CSF antigen binding protein to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT Publication No. WO 93/10151 and U.S. Pat. Nos. 5,426,048 and 5,262,522, is a single chain polypeptide extending from the N-terminal hinge region to the native C-terminus of the Fc region of a human IgG1 antibody. Another useful Fc polypeptide is the Fc mutein described in U.S. Pat. No. 5,457,035, and in Baum et al., 1994, *EMBO J.* 13:3992-4001. The amino acid sequence of this mutein is identical to that of the native Fc sequence presented in PCT Publication No. WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In other embodiments, the variable portion of the heavy and/or light chains of a GM-CSF antigen binding protein such as disclosed herein may be substituted for the variable portion of an antibody heavy and/or light chain.

Alternatively, the oligomer is a fusion protein comprising multiple GM-CSF antigen binding proteins, with or without peptide linkers (spacer peptides). Among the suitable peptide linkers are those described in U.S. Pat. No. 4,751,180 and U.S. Pat. No. 4,935,233.

Another method for preparing oligomeric GM-CSF antigen binding protein derivatives involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT Publication No. WO 94/10308, and the leucine zipper derived from lung surfactant protein D (SPD) described in Hoppe et al., 1994, *FEBS Letters* 344:191. The use of a modified leucine zipper that allows for stable trimerization of a heterologous protein fused thereto is described in Fanslow et al., 1994, *Semin. Immunol.* 6:267-278. In one approach, recombinant fusion proteins comprising a GM-CSF antigen binding protein fragment or derivative fused to a leucine zipper peptide are expressed in suitable host cells, and the soluble oligomeric GM-CSF antigen binding protein fragments or derivatives that form are recovered from the culture supernatant.

Some antigen binding proteins that are provided have a binding affinity ($K_a$) for GM-CSF of at least $10^4$ or $10^5$/M× seconds measured, for instance, as described in the examples below. Other antigen binding proteins have a $K_a$ of at least $10^6$, $10^7$, $10^8$ or $10^9$/M×seconds. Certain antigen binding proteins that are provided have a low disassociation rate. Some antibodies, for instance, have a $K_{off}$ of $1\times10^4$ $s^{-1}$, $1\times10^{-8}$ $s^{-1}$ or lower. In another embodiment, the $K_{off}$ is the same as an antibody having the following combinations of variable region domains of TABLES 2 and 3.

Another aspect provides an antigen-binding protein having a half-life of at least one day in vitro or in vivo (e.g., when administered to a human subject). In one embodiment, the antigen binding protein has a half-life of at least three days. In another embodiment, the antibody or portion thereof has a half-life of four days or longer. In another embodiment, the antibody or portion thereof has a half-life of eight days or longer. In another embodiment, the antibody or antigen-binding portion thereof is derivatized or modified such that it has a longer half-life as compared to the underivatized or unmodified antibody. In another embodiment, the antigen binding protein contains point mutations to increase serum half life, such as described in PCT Publication No. WO 00/09560.

6. Glycosylation

The antigen-binding protein may have a glycosylation pattern that is different or altered from that found in the native species. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antigen binding protein is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antigen binding protein amino acid sequence may be altered through changes at the DNA level, particularly by mutating the DNA encoding the target polypeptide at preselected bases such that codons are generated that will translate into the desired amino acids.

Another means of increasing the number of carbohydrate moieties on the antigen binding protein is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in PCT Publication No. WO 87/05330, and in Aplin and Wriston, 1981, *CRC Crit. Rev, Biochem.*, pp. 259-306.

Removal of carbohydrate moieties present on the starting antigen binding protein may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, *Arch. Biochem. Biophys.* 259:52 and by Edge et al., 1981, *Anal. Biochem.* 118:131. Enzymatic cleavage of carbohydrate moieties on polypeptides can be achieved by the use of a variety of endo- and exo-glycosidases as described by Thotakura et al., 1987, *Meth. Enzymol.* 138:350. Glycosylation at potential glycosylation sites may be prevented by the use of the compound tunicamycin as described by Duskin et al., 1982, *J. Biol. Chem.* 257:3105. Tunicamycin blocks the formation of protein-N-glycoside linkages.

Hence, aspects include glycosylation variants of the antigen binding proteins wherein the number and/or type of glycosylation site(s) has been altered compared to the amino acid sequences of the parent polypeptide. In certain embodiments, antibody protein variants comprise a greater or a lesser number of N-linked glycosylation sites than the native antibody. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate or alter this sequence will prevent addition of an N-linked carbohydrate chain present in the native polypeptide. For example, the glycosylation can be reduced by the deletion of an Asn or by substituting the Asn with a different amino acid. In other embodiments, one or more new N-linked sites are created. Antibodies typically have a N-linked glycosylation site in the Fc region.

7. Labels And Effector Groups

In some embodiments, the antigen-binding comprises one or more labels. The term "labeling group" or "label" means any detectable label. Examples of suitable labeling groups include, but are not limited to, the following: radioisotopes or radionuclides (e.g., $^3H$, $^{14}C$, $^{15}N$, $^{35}S$, $^{90}Y$, $^{99}Tc$, $^{111}In$, $^{125}I$, $^{131}I$), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labeling group is coupled to the antigen binding protein via spacer arms of various lengths to reduce potential steric hindrance. Various methods for labeling proteins are known in the art and may be used as is seen fit.

The term "effector group" means any group coupled to an antigen binding protein that acts as a cytotoxic agent. Examples for suitable effector groups are radioisotopes or radionuclides (e.g., $^3H$, $^{14}C$, $^{15}N$, $^{35}S$, $^{90}Y$, $^{99}Tc$, $^{111}In$, $^{125}I$, $^{131}I$). Other suitable groups include toxins, therapeutic groups, or chemotherapeutic groups. Examples of suitable groups include calicheamicin, auristatins, geldanamycin and maytansine. In some embodiments, the effector group is coupled to the antigen binding protein via spacer arms of various lengths to reduce potential steric hindrance.

In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labeling group is coupled to the antigen binding protein via spacer arms of various lengths to reduce potential steric hindrance. Various methods for labeling proteins are known in the art.

Specific labels include optical dyes, including, but not limited to, chromophores, phosphors and fluorophores, with the latter being specific in many instances. Fluorophores can be either "small molecule" fluores, or proteinaceous fluores.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in *Molecular Probes Handbook of Fluorescent Probes and Research Chemicals*, Richard P. Haugland, Molecular Probes, 1992.

Suitable proteinaceous fluorescent labels also include, but are not limited to, green fluorescent protein, including a *Renilla, Ptilosarcus, or Aequorea* species of GFP (Chalfie et al., 1994, *Science* 263:802-805), EGFP (Clontech, Mountain View, Calif., Genbank Accession Number U55762), blue fluorescent protein (BFP, Quantum Biotechnologies, Inc., Quebec, Canada; Stauber, 1998, *Biotechniques* 24:462-471; Heim et al., 1996, *Curr. Biol.* 6:178-182), enhanced yellow fluorescent protein (EYFP, Clontech), luciferase (Ichiki et al., 1993, *J. Immunol.* 150:5408-5417), β galactosidase (Nolan et al., 1988, *Proc. Natl. Acad. Sci. U.S.A.* 85:2603-2607) and *Renilla* (PCT Patent Application Nos. WO92/15673, WO95/07463, WO98/14605, WO98/26277, WO99/49019, U.S. Pat. No. 5,292,658, U.S. Pat. No. 5,418,155, U.S. Pat. No. 5,683,888, U.S. Pat. No. 5,741,668, U.S. Pat. No. 5,777,079, U.S. Pat. No. 5,804,387, U.S. Pat. No. 5,874,304, U.S. Pat. No. 5,876,995, U.S. Pat. No. 5,925,558).

C. Nucleic Acids Encoding GM-CSF Antigen Binding Proteins

Nucleic acids that encode for the antigen binding proteins described herein, or portions thereof, are also provided, including nucleic acids encoding one or both chains of an antibody, or a fragment, derivative, mutein, or variant thereof, polynucleotides encoding heavy chain variable regions or only CDRs, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, including all values in between, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides and artificial variants thereof (e.g., peptide nucleic acids).

Nucleic acids encoding certain antigen binding proteins, or portions thereof (e.g., full length antibody, heavy or light chain, variable domain, or CDRH1, CDRH2, CDRH3, CDRL1, CDRL2, or CDRL3) may be isolated from B-cells of mice that have been immunized with GM-CSF or an immunogenic fragment thereof. The nucleic acid may be isolated by conventional procedures such as polymerase chain reaction (PCR). Phage display is another example of a known technique whereby derivatives of antibodies and other antigen binding proteins may be prepared. In one approach, polypeptides that are components of an antigen binding protein of interest are expressed in any suitable recombinant expression system, and the expressed polypeptides are allowed to assemble to form antigen binding protein molecules.

Due to the degeneracy of the genetic code, each of the polypeptide sequences listed in TABLES 1-4 or otherwise depicted herein are also encoded by a large number of other nucleic acid sequences besides those provided. One of ordinary skill in the art will appreciate that the present application thus provides adequate written description and enablement for each degenerate nucleotide sequence encoding each antigen binding protein.

An aspect further provides nucleic acids that hybridize to other nucleic acids under particular hybridization conditions. Methods for hybridizing nucleic acids are well-known in the art. See, e.g., Current Protocols in Molecular Biology, John Wiley & Sons, N.Y. (1989), 6.3.1-6.3.6. As defined herein, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65%, 70%, 75%, 80%, 85%, 90%, 95%, 98% or 99% identical to each other, including all values in between, typically remain hybridized to each other.

The basic parameters affecting the choice of hybridization conditions and guidance for devising suitable conditions are set forth by, for example, Sambrook, Fritsch, and Maniatis (2001, Molecular Cloning: A Laboratory Manual, Cold Spring Harbor Laboratory Press, Cold Spring Harbor, N.Y. and Current Protocols in Molecular Biology, 1995, Ausubel et al., eds., John Wiley & Sons, Inc., sections 2.10 and 6.3-6.4), and can be readily determined by those having ordinary skill in the art based on, e.g., the length and/or base composition of the nucleic acid.

Changes can be introduced by mutation into a nucleic acid, thereby leading to changes in the amino acid sequence of a polypeptide (e.g., an antibody or antibody derivative) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. However it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at non-essential amino acid residues. Alternatively, one or more mutations can be introduced into a nucleic acid that selectively change the biological activity of a polypeptide that it encodes. For example, the mutation can quantitatively or qualitatively change the biological activity. Examples of quantitative changes include increasing, reducing or eliminating the activity. Examples of qualitative changes include changing the antigen specificity of an antibody.

Another aspect provides polynucleotides that are suitable for use as primers or hybridization probes for the detection of nucleic acid sequences. A polynucleotide can comprise only a portion of a nucleic acid sequence encoding a full-length polypeptide, for example, a fragment that can be used as a probe or primer or a fragment encoding an active portion (e.g., a GM-CSF binding portion) of a polypeptide.

Probes based on the sequence of a nucleic acid can be used to detect the nucleic acid or similar nucleic acids, for example, transcripts encoding a polypeptide. The probe can comprise a label group, e.g., a radioisotope, a fluorescent compound, an enzyme, or an enzyme co-factor. Such probes can be used to identify a cell that expresses the polypeptide.

Another aspect provides vectors comprising a nucleic acid encoding a polypeptide as described herein or a portion thereof (e.g., a fragment containing one or more CDRs or one or more variable region domains). Examples of vectors include, but are not limited to, plasmids, viral vectors, non-episomal mammalian vectors and expression vectors, for example, recombinant expression vectors. The recombinant expression vectors can comprise a nucleic acid in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see, Voss et al., 1986, *Trends Biochem. Sci.* 11:287, Maniatis et al., 1987, *Science* 236:1237, and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see, id.). It will be appreciated by those skilled in the art that the design of the expression vector can depend on such factors as the choice of the host cell to be transformed, the level of expression of protein desired, etc. The expression vectors can be introduced into host cells to thereby produce proteins or peptides, including fusion proteins or peptides, encoded by nucleic acids as described herein.

Another aspect provides host cells into which a recombinant expression vector has been introduced. A host cell can be any prokaryotic cell (for example, *E. coli*) or eukaryotic cell (for example, yeast, insect, or mammalian cells (e.g., CHO cells)). Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

D. Preparing of Antigen Binding Proteins

Fully human antibodies may be prepared as described above by immunizing transgenic animals containing human immunoglobulin loci or by selecting a phage display library that is expressing a repertoire of human antibodies.

The monoclonal antibodies (mAbs) can be produced by a variety of techniques, including conventional monoclonal antibody methodology, e.g., the standard somatic cell hybridization technique of Kohler and Milstein, 1975, *Nature* 256: 495. Alternatively, other techniques for producing monoclonal antibodies can be employed, for example, the viral or oncogenic transformation of B-lymphocytes. One suitable animal system for preparing hybridomas is the murine system, which is a very well established procedure. Immunization protocols and techniques for isolation of immunized splenocytes for fusion are known in the art. For such procedures, B cells from immunized mice are fused with a suitable immortalized fusion partner, such as a murine myeloma cell line. If desired, rats or other mammals besides can be immunized instead of mice and B cells from such animals can be fused with the murine myeloma cell line to form hybridomas. Alternatively, a myeloma cell line from a source other than mouse may be used. Fusion procedures for making hybridomas also are well known.

The single chain antibodies that are provided may be formed by linking heavy and light chain variable domain (Fv region) fragments via an amino acid bridge (short peptide linker), resulting in a single polypeptide chain. Such single-chain Fvs (scFvs) may be prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108). By combining different $V_L$ and $V_H$-comprising polypeptides, one can form multimeric scFvs that bind to different epitopes (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. U.S.A.* 85:5879; Ward et al., 1989, *Nature* 334:544, de Graaf et al., 2002, *Methods Mol. Biol.* 178:379-387. Single chain antibodies derived from antibodies provided herein include, but are not limited to scFvs comprising the variable domain combinations of the heavy and light chain variable regions depicted in TABLE 1, or combinations of light and heavy chain variable domains having grafted into any of the CDRs depicted in TABLES 2 and 3.

Antibodies provided herein that are of one subclass can be changed to antibodies from a different subclass using subclass switching methods. Thus, IgG antibodies may be derived from an IgM antibody, for example, and vice versa. Such techniques allow the preparation of new antibodies that possess the antigen binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See, e.g., Lantto et al., 2002, *Methods Mol. Biol.* 178:303-316. Accordingly, the antibodies that are provided include those comprising, for example, the variable domain combinations described above having a desired isotype (for example, IgA, IgG1, IgG2, IgG3, IgG4, IgE, and IgD) as well as Fab or F(ab')$_2$ fragments thereof. Moreover, if an IgG4 is desired, it may also be desired to introduce a point mutation (CPSCP->CPPCP) in the hinge region as described in Bloom et al., 1997, *Protein Science* 6:407) to alleviate a tendency to form intra-H chain disulfide bonds that can lead to heterogeneity in the IgG4 antibodies.

Moreover, techniques for deriving antibodies having different properties (i.e., varying affinities for the antigen to which they bind) are also known. One such technique, referred to as chain shuffling, involves displaying immunoglobulin variable domain gene repertoires on the surface of filamentous bacteriophage, often referred to as phage display. Chain shuffling has been used to prepare high affinity antibodies to the hapten 2-phenyloxazol-5-one, as described by Marks et al., 1992, *BioTechnology* 10:779.

Conservative modifications may be made to the heavy and light chain variable regions described in TABLE 1, or the CDRs described in TABLE 2 and 3 (and corresponding modifications to the encoding nucleic acids) to produce a GM-CSF antigen binding protein having functional and biochemical characteristics. Methods for achieving such modifications are described above.

GM-CSF antigen binding proteins may be further modified in various ways. For example, if they are to be used for therapeutic purposes, they may be conjugated with polyethylene glycol (pegylated) to prolong the serum half-life or to enhance protein delivery. Alternatively, the V region of the subject antibodies or fragments thereof may be fused with the Fc region of a different antibody molecule. The Fc region used for this purpose may be modified so that it does not bind complement, thus reducing the likelihood of inducing cell lysis in the patient when the fusion protein is used as a therapeutic agent. In addition, the subject antibodies or functional fragments thereof may be conjugated with human serum albumin to enhance the serum half-life of the antibody or fragment thereof. Another useful fusion partner for the inventive antibodies or fragments thereof is transthyretin (TTR). TTR has the capacity to form a tetramer, thus an antibody-TTR fusion protein can form a multivalent antibody which may increase its binding avidity.

Alternatively, substantial modifications in the functional and/or biochemical characteristics of the antigen binding proteins described herein may be achieved by creating substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulkiness of the side chain. A "conservative amino acid substitution" may involve a substitution of a native amino acid residue with a normative residue that has little or no effect on the polarity or charge of the amino acid residue at that position. See, TABLE 5. Furthermore, any native residue in the polypeptide may also be substituted with alanine, as has been previously described for alanine scanning mutagenesis.

Amino acid substitutions (whether conservative or non-conservative) of the subject antibodies can be implemented by those skilled in the art by applying routine techniques. Amino acid substitutions can be used to identify important residues of the antibodies provided herein, or to increase or decrease the affinity of these antibodies for human GM-CSF or for modifying the binding affinity of other antigen-binding proteins described herein.

E. Methods of Expressing Antigen Binding Proteins

Expression systems and constructs in the form of plasmids, expression vectors, transcription or expression cassettes that comprise at least one polynucleotide as described above are also provided herein, as well host cells comprising such expression systems or constructs.

The antigen binding proteins provided herein may be prepared by any of a number of conventional techniques. For example, GM-CSF antigen binding proteins may be produced by recombinant expression systems, using any technique known in the art. See, e.g., Monoclonal Antibodies, Hybridomas: A New Dimension in Biological Analyses, Kennet et al.(eds.) Plenum Press, New York (1980); and Antibodies: A Laboratory Manual, Harlow and Lane (eds.), Cold Spring Harbor Laboratory Press, Cold Spring Harbor, N.Y. (1988).

Antigen binding proteins can be expressed in hybridoma cell lines (e.g., in particular antibodies may be expressed in hybridomas) or in cell lines other than hybridomas. Expression constructs encoding the antibodies can be used to transform a mammalian, insect or microbial host cell. Transformation can be performed using any known method for introducing polynucleotides into a host cell, including, for example packaging the polynucleotide in a virus or bacteriophage and transducing a host cell with the construct by transfection procedures known in the art, as exemplified by U.S. Pat. No. 4,399,216; U.S. Pat. No. 4,912,040; U.S. Pat. No. 4,740,461; U.S. Pat. No. 4,959,455. The optimal transformation procedure used will depend upon which type of host cell is being transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into nuclei.

Recombinant expression constructs typically comprise a polynucleotide encoding a polypeptide comprising one or more of the following: one or more CDRs provided herein; a light chain constant region; a light chain variable region; a heavy chain constant region (e.g., $C_H1$, $C_H2$ and/or $C_H3$); and/or another scaffold portion of a GM-CSF antigen binding protein. These nucleic acid sequences are inserted into an appropriate expression vector using standard ligation techniques. In one embodiment, the heavy or light chain constant region is appended to the C-terminus of the anti-GM-CSF-specific heavy or light chain variable region and is ligated into an expression vector. The vector is typically selected to be functional in the particular host cell employed (i.e., the vector is compatible with the host cell machinery, permitting amplification and/or expression of the gene can occur). In some embodiments, vectors are used that employ protein-fragment complementation assays using protein reporters, such as dihydrofolate reductase (see, for example, U.S. Pat. No. 6,270,964). Suitable expression vectors can be purchased, for example, from Invitrogen Life Technologies (Carlsbad, Calif.) or BD Biosciences (San Jose, Calif.). Other useful vectors for cloning and expressing the antibodies and fragments include those described in Bianchi and McGrew, 2003, Biotech. Biotechnol. Bioeng. 84:439-44. Additional suitable expression vectors are discussed, for example, in Methods Enzymol., vol. 185 (D. V. Goeddel, ed.), 1990, New York: Academic Press.

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element.

Optionally, the vector may contain a "tag"-encoding sequence, i.e., an oligonucleotide molecule located at the 5' or 3' end of the GM-CSF antigen binding protein coding sequence; the oligonucleotide sequence encodes polyHis (such as hexaHis), or another "tag" such as FLAG®, HA (hemaglutinin influenza virus), or myc, for which commercially available antibodies exist. This tag is typically fused to the polypeptide upon expression of the polypeptide, and can serve as a means for affinity purification or detection of the GM-CSF antigen binding protein from the host cell. Affinity purification can be accomplished, for example, by column chromatography using antibodies against the tag as an affinity matrix. Optionally, the tag can subsequently be removed from the purified GM-CSF antigen binding protein by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Qiagen, Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria, and various viral origins (e.g., SV40, polyoma, adenovirus, vesicular stomatitis virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antigen binding protein that binds to GM-CSF polypeptide. As a result, increased quantities of a polypeptide such as an antigen binding protein are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, such as where glycosylation is desired in a eukaryotic host cell expression system, one may manipulate the various pre- or pro-sequences to improve glycosylation or yield. For example, one may alter the peptidase cleavage site of a particular signal peptide, or add prosequences, which also may affect glycosylation. The final protein product may have, in the −1 position (relative to the first amino acid of the mature protein), one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning will typically contain a promoter that is recognized by the host organism and operably linked to the molecule encoding GM-CSF antigen binding protein. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe a gene to which they are operably linked, that is, with little or no control over gene expression. A large number of promoters, recognized by a variety of potential host cells, are well known. A suitable promoter is operably linked to the DNA encoding heavy chain or light chain comprising a GM-CSF antigen binding protein by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus, and Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, *Nature* 290:304-310); CMV promoter (Thornsen et al., 1984, *Proc. Natl. Acad. U.S.A.* 81:659-663); the promoter contained in the 3' long terminal repeat of Rous sarcoma virus (Yamamoto et al., 1980, Cell 22:787-797); herpes thymidine kinase promoter (Wagner et al., 1981, *Proc. Natl. Acad. Sci. U.S.A.* 78:1444-1445); promoter and regulatory sequences from the metallothionine gene (Prinster et al., 1982, *Nature* 296:39-42); and prokaryotic promoters such as the beta-lactamase promoter (Villa-Kamaroff et al., 1978, *Proc. Natl. Acad. Sci. U.S.A.* 75:3727-3731); or the tac promoter (DeBoer et al., 1983, *Proc. Natl. Acad. Sci. U.S.A.* 80:21-25). Also of interest are the following animal transcriptional control regions, which exhibit tissue specificity and have been utilized in transgenic animals: the elastase I gene control region that is active in pancreatic acinar cells (Swift et al., 1984, *Cell* 38:639-646; Ornitz et al., 1986, *Cold Spring Harbor Symp. Quant. Biol.* 50:399-409; MacDonald, 1987, *Hepatology* 7:425-515); the insulin gene control region that is active in pancreatic beta cells (Hanahan, 1985, *Nature* 315: 115-122); the immunoglobulin gene control region that is active in lymphoid cells (Grosschedl et al., 1984, *Cell* 38:647-658; Adames et al., 1985, *Nature* 318:533-538; Alexander et al., 1987, *Mol. Cell. Biol.* 7:1436-1444); the mouse mammary tumor virus control region that is active in testicular, breast, lymphoid and mast cells (Leder et al., 1986, *Cell* 45:485-495); the albumin gene control region that is active in liver (Pinkert et al., 1987, *Genes and Devel.* 1:268-276); the alpha-feto-protein gene control region that is active in liver (Krumlauf et al., 1985, *Mol. Cell. Biol.* 5:1639-1648; Hammer et al., 1987, *Science* 253:53-58); the alpha 1-antitrypsin gene control region that is active in liver (Kelsey et al., 1987, *Genes and Devel.* 1:161-171); the beta-globin gene control region that is active in myeloid cells (Mogram et al., 1985, *Nature* 315:338-340; Kollias et al., 1986, *Cell* 46:89-94); the myelin basic protein gene control region that is active in oligodendrocyte cells in the brain (Readhead et al., 1987, *Cell* 48:703-712); the myosin light chain-2 gene control region that is active in skeletal muscle (Sani, 1985, *Nature* 314:283-286);

and the gonadotropic releasing hormone gene control region that is active in the hypothalamus (Mason et al., 1986, *Science* 234:1372-1378).

An enhancer sequence may be inserted into the vector to increase transcription of DNA encoding light chain or heavy chain comprising a human GM-CSF antigen binding protein by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antibody. The choice of signal peptide or leader depends on the type of host cells in which the antibody is to be produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al., 1984, *Nature* 312:768; the interleukin-4 receptor signal peptide described in EP Patent No. 0367 566; the type I interleukin-1 receptor signal peptide described in U.S. Pat. No. 4,968,607; the type II interleukin-1 receptor signal peptide described in EP Patent No. 0 460 846.

The expression vectors that are provided may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a polynucleotide encoding light chain, a heavy chain, or a light chain and a heavy chain comprising a GM-CSF antigen binding sequence has been inserted into the proper site of the vector, the completed vector may be inserted into a suitable host cell for amplification and/or polypeptide expression. The transformation of an expression vector for an antigen-binding protein into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., 2001, supra.

A host cell, when cultured under appropriate conditions, synthesizes an antigen binding protein that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines may be selected through determining which cell lines have high expression levels and constitutively produce antigen binding proteins with GM-CSF binding properties. In another embodiment, a cell line from the B cell lineage that does not make its own antibody but has a capacity to make and secrete a heterologous antibody can be selected.

F. Use of Human GM-CSF Antigen Binding Proteins for Diagnostic and Therapeutic Purposes Antigen binding proteins are useful for detecting GM-CSF in biological samples and identification of cells or tissues that produce GM-CSF. Antigen binding proteins that specifically bind to GM-CSF may be used in treatment of diseases related to GM-CSF in a patient in need thereof. For one, the GM-CSF antigen binding proteins can be used in diagnostic assays, e.g., binding assays to detect and/or quantify GM-CSF expressed in a tissue or cell. In addition, GM-CSF antigen binding proteins can be used to inhibit GM-CSF from forming a complex with its receptor, thereby modulating the biological activity of GM-CSF in a cell or tissue. Antigen binding proteins that bind to GM-CSF thus may modulate and/or block interaction with other binding compounds and as such may have therapeutic use in ameliorating diseases related to GM-CSF.

1. Indications

The present invention also relates to the use of GM-CSF inhibitors (as disclosed), such as GM-CSF antibodies, in the manufacture of a medicament for the prevention or therapeutic treatment of each medical disorder disclosed herein. The GM-CSF inhibitors are useful to treat a variety of conditions in which excess GM-CSF plays a role in contributing to the underlying disease or disorder or otherwise contributes to a negative symptom.

Embodiments of the present invention include methods for using the disclosed GM-CSF inhibitors, in particular GM-CSF antibodies, compositions or combination therapies to treat or prevent a variety of rheumatic disorders. These include adult and juvenile rheumatoid arthritis; scleroderma; systemic lupus erythematosus; gout; osteoarthritis; polymyalgia rheumatica; seronegative spondylarthropathies, including ankylosing spondylitis, and Reiter's disease. The subject GM-CSF inhibitors, compositions and combination therapies are used also to treat psoriatic arthritis and chronic Lyme arthritis. Also treatable or preventable with these compounds, compositions and combination therapies are Still's disease and uveitis associated with rheumatoid arthritis. In addition, the compounds, compositions and combination therapies of the invention are used in treating disorders resulting in inflammation of the voluntary muscle and other muscles, including dermatomyositis, inclusion body myositis, polymyositis, and lymphangioleimyomatosis.

The subject invention provides GM-CSF inhibitors, e.g. GM-CSF antibodies, compositions and combination therapies (e.g. GM-CSF inhibitor and a TNF inhibitor such as ENBREL® (etanercept) or other active agents) for the treatment of non-arthritic medical conditions of the bones and joints. This encompasses osteoclast disorders that lead to bone loss, such as but not limited to osteoporosis, including post-menopausal osteoporosis, osteoarthritis, periodontitis resulting in tooth loosening or loss, and prosthesis loosening after joint replacement (generally associated with an inflammatory response to wear debris). This latter condition also is called "orthopedic implant osteolysis." Another condition treatable with the compounds, compositions and combination therapies of the invention is temporal mandibular joint dysfunction (TMJ).

Various other medical disorders treatable with the disclosed GM-CSF inhibitor compositions and combination therapies include; multiple sclerosis; Behcet's syndrome; Sjogren's syndrome; autoimmune hemolytic anemia; beta thalassemia; amyotrophic lateral sclerosis (Lou Gehrig's Disease); Parkinson's disease; and tenosynovitis of unknown cause, as well as various autoimmune disorders or diseases associated with hereditary deficiencies, including x-linked mental retardation.

Also provided are methods for using GM-CSF inhibitors, compositions or combination therapies to treat various disorders of the endocrine system. For example, GM-CSF inhibitor compositions or other GM-CSF inhibitor compositions, with or without TNF inhibitors (e.g., ENBREL) or other active agents described above, are suitable for use to treat juvenile onset diabetes (includes autoimmune diabetes mellitus and insulin-dependent types of diabetes) and also to treat maturity onset diabetes (includes non-insulin dependent and obesity-mediated diabetes). In addition, the subject compounds, compositions and combination therapies are used to treat secondary conditions associated with diabetes, such as diabetic retinopathy, kidney transplant rejection in diabetic patients, obesity-mediated insulin resistance, and renal failure, which itself may be associated with proteinurea and hypertension. Other endocrine disorders also are treatable with these compounds, compositions or combination therapies, including polycystic ovarian disease, X-linked adrenoleukodystrophy, hypothyroidism and thyroiditis, including Hashimoto's thyroiditis (i.e., autoimmune thyroiditis). Further, GM-CSF inhibitors, including GM-CSF inhibitor, alone or in combination with other cytokines, including TNF inhibitors such as ENBREL, are useful in treating or preventing medical conditions associated with thyroid cell dysfunction, including euthyroid sick syndrome.

Conditions of the gastrointestinal system are treatable or preventable with GM-CSF inhibitors, compositions or combination therapies, including coeliac disease. For example, GM-CSF inhibitor compositions, with or without TNF inhibitors (e.g., ENBREL) or other active agents described above are suitable for treating or preventing coeliac disease. In addition, the compounds, compositions and combination therapies of the invention are suitable for treating or preventing Crohn's disease; ulcerative colitis; idiopathic gastroparesis; pancreatitis, including chronic pancreatitis; acute pancreatitis, inflammatory bowel disease and ulcers, including gastric and duodenal ulcers.

Included also are methods for using the subject GM-CSF inhibitors, compositions or combination therapies for treating disorders of the genitourinary system. For example, GM-CSF inhibitor compositions, alone or in combination with IL-1 (e.g., Kineret® (anakinra)) or TNF inhibitors (e.g., ENBREL) or other active agents described above are suitable for treating or preventing glomerulonephritis, including autoimmune glomerulonephritis, glomerulonephritis due to exposure to toxins or glomerulonephritis secondary to infections with haemolytic streptococci or other infectious agents. Also treatable with the compounds, compositions and combination therapies of the invention are uremic syndrome and its clinical complications (for example, renal failure, anemia, and hypertrophic cardiomyopathy), including uremic syndrome associated with exposure to environmental toxins, drugs or other causes. GM-CSF inhibitors, particularly GM-CSF antibodies, alone or in combination with TNF inhibitors, particularly ENBREL, are useful in treating and preventing complications that arise from inflammation of the gallbladder wall that leads to alteration in absorptive function. Included in such complications are cholelithiasis (gallstones) and choliedocholithiasis (bile duct stones) and the recurrence of cholelithiasis and choliedocholithiasis. Further conditions treatable with the compounds, compositions and combination therapies of the invention are complications of hemodialysis; prostate conditions, including benign prostatic hypertrophy, nonbacterial prostatitis and chronic prostatitis; and complications of hemodialysis.

Also provided herein are methods for using GM-CSF inhibitors, compositions or combination therapies to treat various hematologic and oncologic disorders. For example, GM-CSF inhibitor, alone or in combination with an GM-CSF inhibitor, TNF inhibitor (e.g., ENBREL) or other active agents as described above, may be used to treat symptoms associated with various forms of cancer, including acute myelogenous leukemia, chronic myelogenous leukemia, Epstein-Barr virus-positive nasopharyngeal carcinoma, glioma, colon, stomach, prostate, renal cell, cervical and ovarian cancers, lung cancer (SCLC and NSCLC), including cancer-associated cachexia, fatigue, asthenia, paraneoplastic syndrome of cachexia and hypercalcemia. Additional diseases treatable with the subject GM-CSF inhibitors, compositions or combination therapies are solid tumors, including sarcoma, osteosarcoma, and carcinoma, such as adenocarcinoma (for example, breast cancer) and squamous cell carcinoma. In addition, the subject compounds, compositions or combination therapies are useful for treating esophageal cancer, gastric cancer, gall bladder carcinoma, leukemia, including acute myelogenous leukemia, chronic myelogenous leukemia, myeloid leukemia, chronic or acute lymphoblastic leukemia and hairy cell leukemia. Other malignancies with invasive metastatic potential, including multiple myeloma, can be treated with the subject compounds, compositions and combination therapies, and particularly combination therapies that include GM-CSF inhibitor and soluble TNF receptor (e.g., ENBREL). In addition, the disclosed GM-CSF inhibitors, compositions and combination therapies can be used to treat anemias and hematologic disorders, including chronic idiopathic neutropenia, anemia of chronic disease, aplastic anemia, including Fanconi's aplastic anemia; idiopathic thrombocytopenic purpura (ITP); thrombotic thrombocytopenic purpura, myelodysplastic syndromes (including refractory anemia, refractory anemia with ringed sideroblasts, refractory anemia with excess blasts, refractory anemia with excess blasts in transformation); myelofibrosis/myeloid metaplasia; and sickle cell vasocclusive crisis.

Various lymphoproliferative disorders also are treatable with the disclosed GM-CSF inhibitors, compositions or combination therapies. GM-CSF inhibitor, alone or in combination with a TNF inhibitor, such as ENBREL, or other active agents are useful for treating or preventing autoimmune lymphoproliferative syndrome (ALPS), chronic lymphoblastic leukemia, hairy cell leukemia, chronic lymphatic leukemia, peripheral T-cell lymphoma, small lymphocytic lymphoma, mantle cell lymphoma, follicular lymphoma, Burkitt's lymphoma, Epstein-Barr virus-positive T cell lymphoma, histiocytic lymphoma, Hodgkin's disease, diffuse aggressive lymphoma, acute lymphatic leukemias, T gamma lymphoproliferative disease, cutaneous B cell lymphoma, cutaneous T cell lymphoma (i.e., mycosis fungoides) and Sezary syndrome.

In addition, the subject GM-CSF inhibitors, compositions and combination therapies are used to treat hereditary conditions. In particular, GM-CSF inhibitor, alone or in combination with a TNF inhibitor such as ENBREL, is useful to treat diseases such as Gaucher's disease, Huntington's disease, linear IgA disease, and muscular dystrophy.

Other conditions treatable or preventable by the disclosed GM-CSF inhibitors, compositions and combination therapies include those resulting from injuries to the head or spinal cord including subdural hematoma due to trauma to the head. For example, GM-CSF inhibitor, alone or in combination with a TNF inhibitor such as ENBREL are useful in treating head injuries and spinal chord injuries. In connection with this therapy, the compositions and combinations described are suitable for preventing cranial neurologic damage and preventing and treating cervicogenic headache. The compositions and combinations described are further suitable for treating neurological side effects associated with brain irradiation.

The disclosed GM-CSF inhibitors, compositions and combination therapies are further used to treat conditions of the liver. For example GM-CSF inhibitor, alone or in combination with a TNF inhibitor such as ENBREL or other active agents, can be used to treat hepatitis, including acute alcoholic hepatitis, acute drug-induced or viral hepatitis, hepatitis A, B and C, sclerosing cholangitis and inflammation of the liver due to unknown causes. In connection with liver inflammation, GM-CSF inhibitors are further useful in treating hepatic sinusoid epithelium.

In addition, the disclosed GM-CSF inhibitors, compositions and combination therapies are used to treat various disorders that involve hearing loss and that are associated with abnormal IL-1 expression. For example, GM-CSF inhibitor, alone or in combination with TNF inhibitors, can be used to treat or prevent cochlear nerve-associated hearing loss that is thought to result from an autoimmune process, i.e., autoimmune hearing loss. This condition currently is treated with steroids, methotrexate and/or cyclophosphamide. Also treatable or preventable with the disclosed GM-CSF inhibitors, compositions and combination therapies is Meniere's syndrome and cholesteatoma, a middle ear disorder often associated with hearing loss.

Disorders associated with transplantation also are treatable or preventable with the disclosed GM-CSF inhibitors compositions or combination therapies. Such disorders include graft-versus-host disease, and complications resulting from solid organ transplantation, such as heart, liver, skin, kidney, lung (lung transplant airway obliteration) or other transplants, including bone marrow transplants.

Ocular disorders also are treatable or preventable with the disclosed GM-CSF inhibitors, especially GM-CSF antibodies, compositions or combination therapies, including rhegmatogenous retinal detachment, and inflammatory eye disease, including inflammatory eye disease associated with smoking and macular degeneration.

GM-CSF inhibitor compositions and combination therapies also are useful for treating disorders that affect the female reproductive system. Examples include, but are not limited to, multiple implant failure/infertility; fetal loss syndrome or IV embryo loss (spontaneous abortion); preeclamptic pregnancies or eclampsia; endometriosis, chronic cervicitis, and preterm labor.

In addition, the disclosed GM-CSF inhibitor compositions and combination therapies are useful for treating or preventing sciatica, symptoms of aging, severe drug reactions (for example, 11-2 toxicity or bleomycin-induced pneumopathy and fibrosis), or to suppress the inflammatory response prior, during or after the transfusion of allogeneic red blood cells in cardiac or other surgery, or in treating a traumatic injury to a limb or joint, such as traumatic knee injury.

The disclosed GM-CSF inhibitor compositions and combination therapies are useful for treating central nervous system (CNS) injuries, including the effects of neurotoxic neurotransmitters discharged during excitation of inflammation in the central nervous system and to inhibit or prevent the development of glial scars at sites of central nervous system injury. In connection with central nervous system medical conditions, GM-CSF inhibitors are useful in treating temporal lobe epilepsy. In connection with epilepsy and the treatment of seizures, reducing the severity and number of recurring seizures, and reducing the severity of the deleterious effects of seizures. GM-CSF inhibitors alone or in combination with agents described herein are useful for reducing neuronal loss, neuronal degeneration, and gliosis associated with seizures.

Furthermore, the disclosed GM-CSF inhibitor compositions and combination therapies are useful for treating critical illness polyneuropathy and myopathy (CIPNM) acute polyneuropathy; anorexia nervosa; Bell's palsy; chronic fatigue syndrome; transmissible dementia, including Creutzfeld-Jacob disease; demyelinating neuropathy; Guillain-Barre syndrome; vertebral disc disease; Gulf war syndrome; chronic inflammatory demyelinating polyneuropathy, myasthenia gravis; silent cerebral ischemia; sleep disorders, including narcolepsy and sleep apnea; chronic neuronal degeneration; and stroke, including cerebral ischemic diseases.

Other diseases and medical conditions that may be treated or prevented by administering a GM-CSF inhibitor alone or in combination with a herein described active agents include anorexia and/or anorexic conditions, peritonitis, endotoxemia and septic shock, granuloma formation, heat stroke, Churg-Strauss syndrome, chronic inflammation following acute infections such as tuberculosis and leprosy, systemic sclerosis and hypertrophic scarring. In addition to GM-CSF inhibitors in combination with IL-1 inhibitors, TNF inhibitors, IFN-alpha, -beta or -gamma and/or IL-4 inhibitors are suitable for treating hypertrophic scarring.

The GM-CSF inhibitors disclosed herein are useful for reducing the toxicity associated with antibody therapies, chemotherapy, radiation therapy and the effects of other apoptosis inducing agents, e.g. TRAIL and TRADE.

Provided herein are methods of treating or preventing psoriatic lesions that involve administering to a human patient a therapeutically effective amount of a GM-CSF inhibitor. The treatment is effective against psoriatic lesions that occur in patients who have ordinary psoriasis or psoriatic arthritis.

Conditions effectively treated by a GM-CSF inhibitor play a role in the inflammatory response. Lung disorders include asthma, chronic obstructive pulmonary disease, pulmonary alveolar proteinosis, bleomycin-induced pneumopathy and fibrosis, radiation-induced pulmonary fibrosis, cystic fibrosis, collagen accumulation in the lungs, and ARDS. GM-CSF inhibitors are useful for treating patients suffering from various skin disorders, including but not limited to dermatitis herpetiformis (Duhring's disease), atopic dermatitis, contact dermatitis, urticaria (including chronic idiopathic urticaria), and autoimmune blistering diseases, including pemphigus vulgaris and bullous pemphigoid. Other diseases treatable with the combination of a GM-CSF inhibitor include myasthenia gravis, sarcoidosis, including pulmonary sarcoidosis, scleroderma, reactive arthritis, hyper IgE syndrome, multiple sclerosis and idiopathic hypereosinophil syndrome. The therapeutics of the invention are also useful for treating allergic reactions to medication and as an adjuvant to allergy immunotherapy.

Figure 1B:
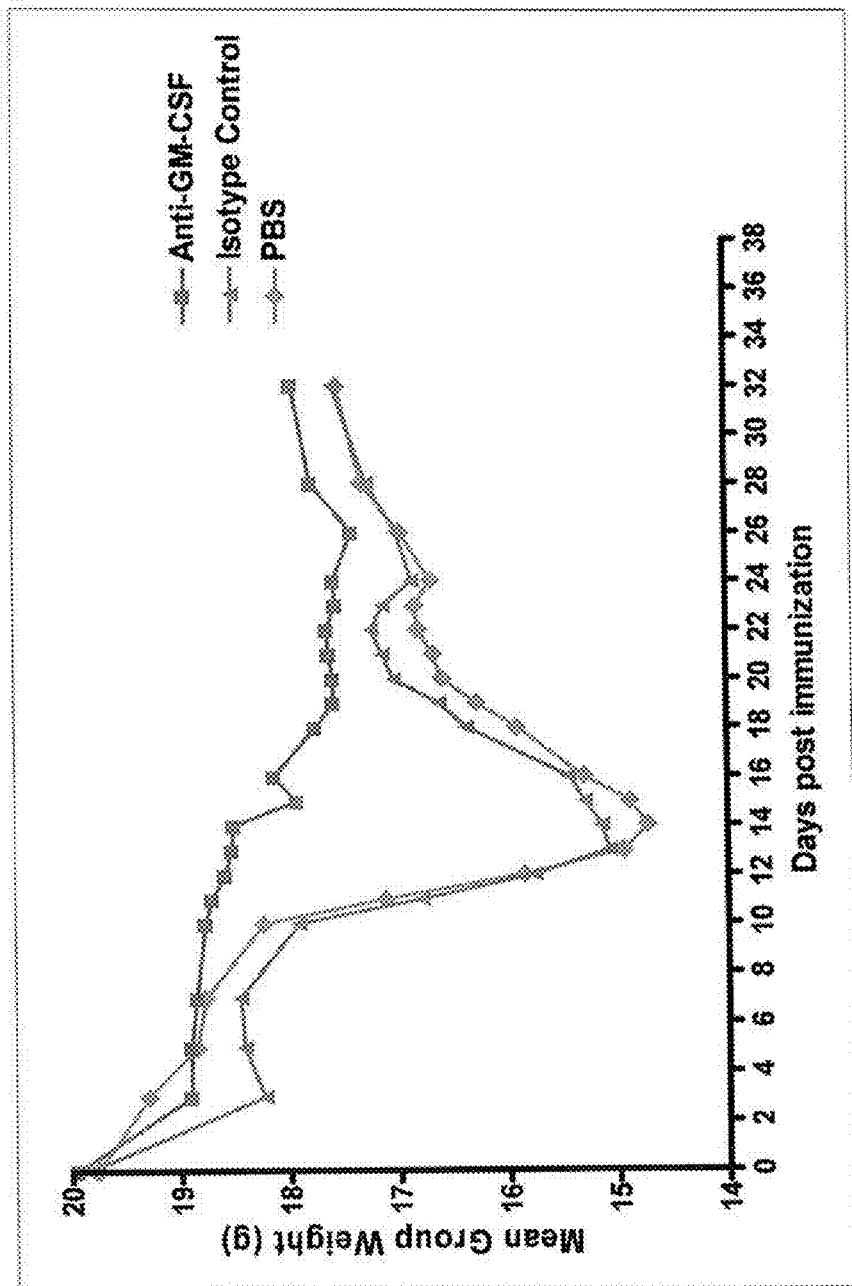
Figure 1C:
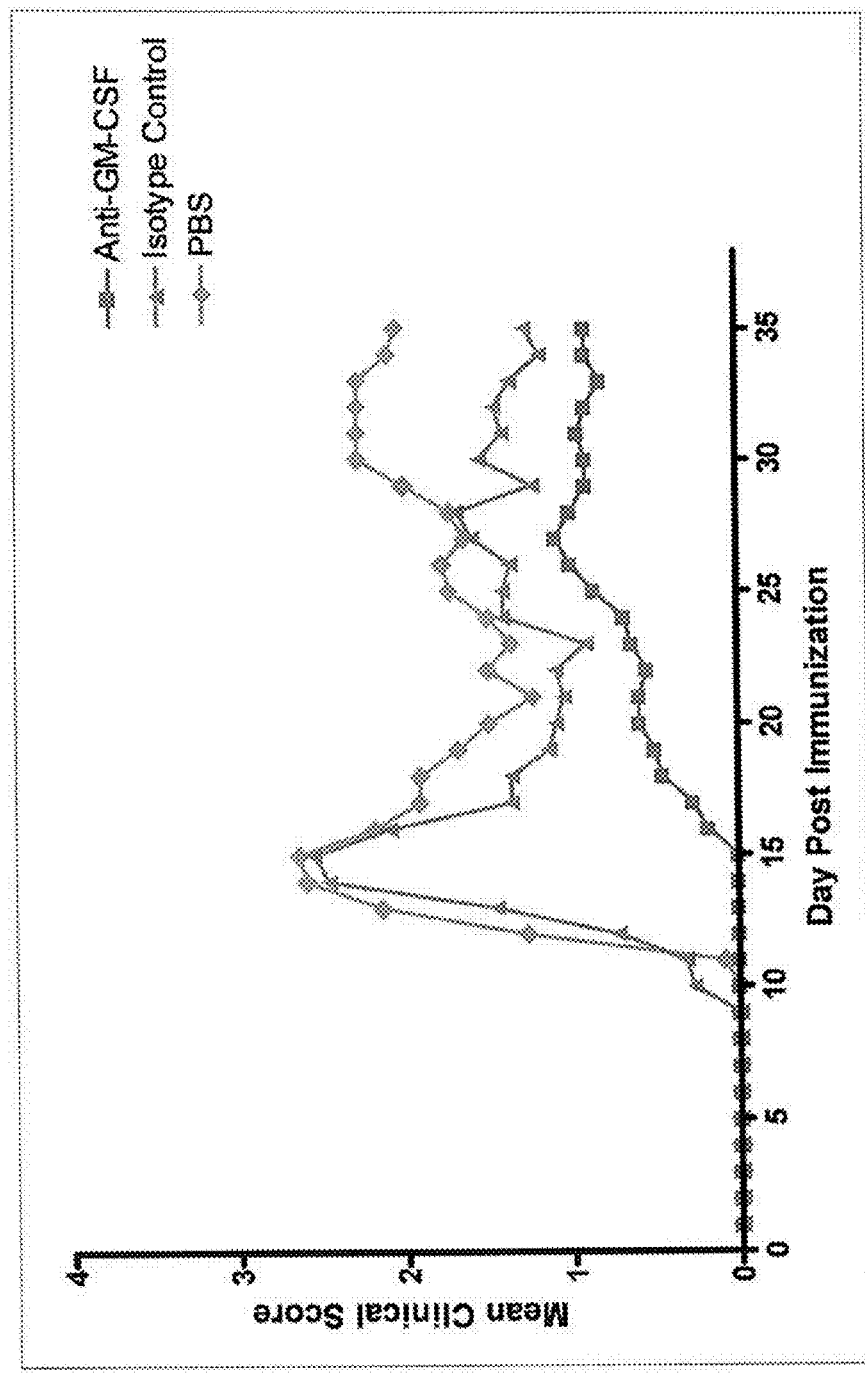
Figure 1D:
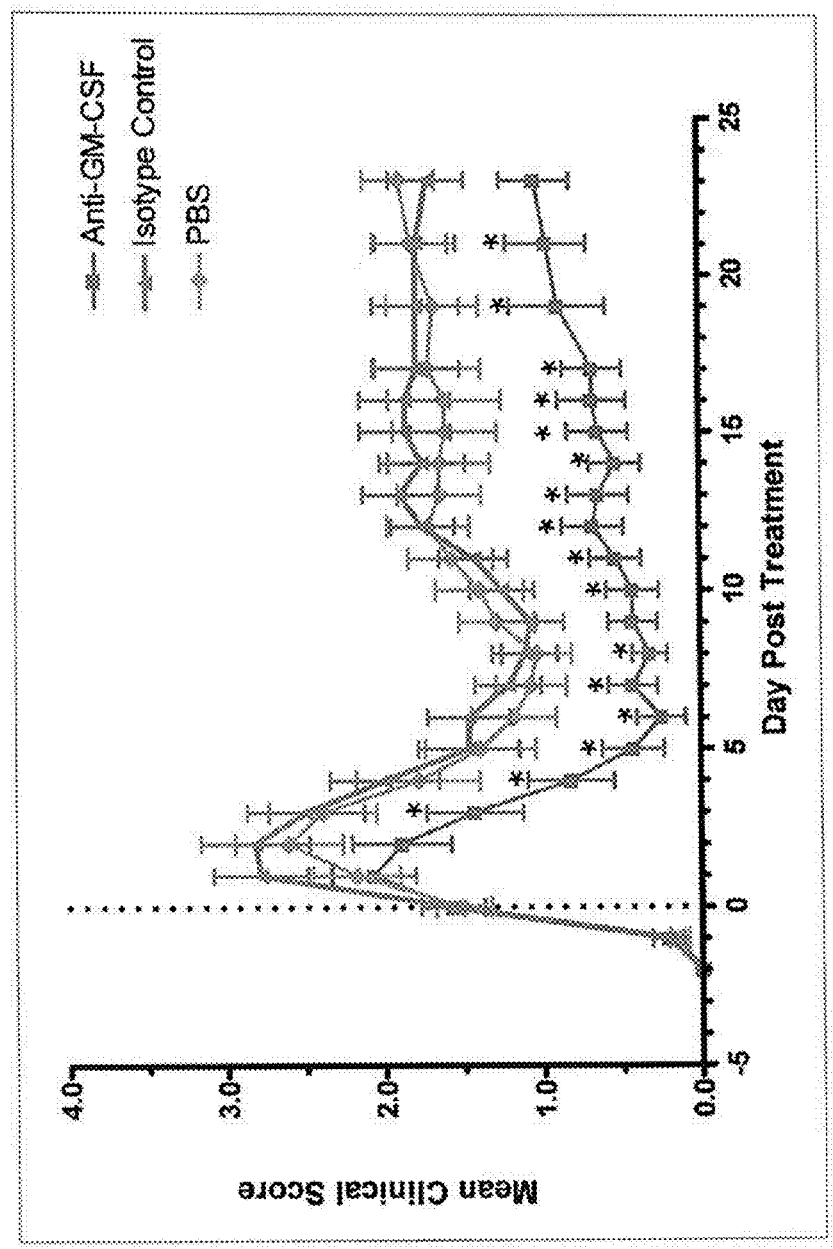

In an embodiment the GM-CSF inhibitor compositions are useful for treating degenerative conditions of the nervous system, such as multiple sclerosis, relapsing remitting multiple sclerosis, progressive-relapsing multiple sclerosis, primary and secondary-progressive multiple sclerosis. Targeting GM-CSF is effective in preclinical models of multiple sclerosis and therapeutic intervention in the GM-CSF pathway in multiple sclerosis may reduce CNS inflammation via direct effects on monocytes, macrophages and dendritic cells, while sparing adaptive immunity. GM-CSF knock out mice are resistant to experimental autoimmune encephalomyelitis (EAE) induction, McQualter, et al., 2001, J. Exp. Med. 194: 873-881. Adoptive transfer of retrovirally-transduced T cells expressing GM-CSF induces exacerbated EAE, Marusic et al., 2002, Neurosci. Lett. 332: 185-9. Adoptive transfer of GM-CSF knock out T cells fails to induce EAE, Ponomarev et al., 2007, J. Immunol., 178:39-48. Applicants have shown that prophylactic treatment with anti-murine GM-CSF antibody in the SJL-PLP$_{139-151}$EAE model of relapsing-remitting multiple sclerosis significantly delayed onset and reduced incidence of disease and reduced both weight loss and mean clinical score, compared to treatment with an isotype control monoclonal antibody, see FIGS. 1 and 2. Therapeutic treatment of SJL/PLP 125-151 EAE with anti-mGM-CSF monoclonal antibody significantly reduced disease severity and CNS inflammation and accelerated recovery. Prophylactic and therapeutic treatment with anti-mGM-CSF monoclonal antibody in SJL-PLP$_{139-151}$ AT-EAE reduced mean clinical score compared to treatment with an isotype control monoclonal antibody, see FIG. 2. GM-CSF inhibitor compositions can be used alone or in combination with other drugs, for example interferon β-1a (AVONEX®; Biogen-Idec and REBIF® EDM Serono, Inc., Pfizer, Inc.), interferon β-1b (BETASERON®; Bayer Health Care.), glatiramer acetate (COPAXONE®; Teva Pharmaceuticals) and/or anti-VLA4 mAb (TYSABRI®, Biogen-Idec, Elan).

In one embodiment of the invention, the various medical disorders disclosed herein as being treatable with GM-CSF inhibitors (e.g., GM-CSF antibodies) are treated in combination with another cytokine or cytokine inhibitor. For example, a GM-CSF inhibitor may be administered in a composition that also contains a compound that inhibits the interaction of other inflammatory cytokines with their receptors. The GM-CSF inhibitor and other cytokine inhibitors may be administered as separate compositions, and these may be administered by the same or different routes. Examples of cytokine inhibitors used in combination with GM-CSF inhibitor include those that antagonize, for example, TGF-beta, IFN-gamma, IL-6 or IL-8 and TNF, particularly TNF-alpha. The combination of a GM-CSF inhibitor and IL-6 can be used to treat and prevent the recurrence of seizures, including seizures induced by GABA-A receptor antagonism, seizures associated with EEG ictal episodes and motor limbic seizures occurring during status epilepticus. Further, the combination of GM-CSF inhibitor and IFN-gamma-1b and/or a c-Kit inhibitor is useful in treating idiopathic pulmonary fibrosis and cystic fibrosis. Other combinations for treating diseases include the use of GM-CSF inhibitor with compounds that interfere with the binding of RANK and RANK-ligand, such as RANK-ligand inhibitors, or soluble forms of RANK, including RANK:Fc. For example, the combination of GM-CSF inhibitor and RANK:Fc are useful for preventing bone destruction in various settings including but not limited to various rheumatic disorders, osteoporosis, multiple myeloma or other malignancies that cause bone degeneration, or anti-tumor therapy aimed at preventing metastasis to bone, or bone destruction associated with prosthesis wear debris or with periodontitis.

The disclosed GM-CSF inhibitors, compositions and combination therapies described herein are useful in medicines for treating side effects and/or complications resulting from bacterial, viral or protozoal infections. According to this embodiment, when an infection triggers an over stimulation of the immune system such that production and/or activity of GM-CSF results in negative effects on the patient, treatment with a GM-CSF inhibitor in patients subject to an infection is useful to ameliorate these side effects and/or complications associated with the infection or therapeutics used to treat the infection. Non limiting examples of such infectious agents and infections are *Mycoplasma pneumonia*, AIDS and conditions associated with AIDS and/or related to AIDS, such as AIDS dementia complex, AIDS associated wasting, lipidistrophy due to antiretroviral therapy; CMV (cytomegalovirus), Kaposi's sarcoma; protozoal diseases, including malaria and schistosomiasis; erythema nodosum leprosum; bacterial or viral meningitis; tuberculosis, including pulmonary tuberculosis; and pneumonitis secondary to a bacterial or viral infection; louse-borne relapsing fevers, such as that caused by *Borrelia recurrentis*; Herpes viruses, such as herpetic stromal keratitis, corneal lesions; and virus-induced corneal disorders; human papillomavirus infections; influenza infection and infectious mononucleosis.

Cardiovascular disorders and injuries are treatable and/or preventable with the disclosed GM-CSF inhibitors, pharmaceutical compositions or combination therapies. In particularly cardiovascular disorders are treatable with GM-CSF inhibitor compositions, alone or in combination with TNF inhibitors (e.g. ENBREL) and or other agents as described above. Cardiovascular disorders thus treatable include aortic aneurysms; including abdominal aortic aneurysms, acute coronary syndrome, arteritis; vascular occlusion, including cerebral artery occlusion; complications of coronary by-pass surgery; ischemia/reperfusion injury; heart disease, including atherosclerotic heart disease, myocarditis, including chronic autoimmune myocarditis and viral myocarditis; heart failure, including chronic heart failure, congestive heart failure, cachexia of heart failure; myocardial infarction; restenosis and/or atherosclerosis after heart surgery or after carotid artery balloon angioplastic procedures; silent myocardial ischemia; left ventricular pump dysfunction, post implantation complications of left ventricular assist devices; Raynaud's phenomena; thrombophlebitis; vasculitis, including Kawasaki's vasculitis; veno-occlusive disease, giant cell arteritis, Wegener's granulomatosis; mental confusion following cardio pulmonary by pass surgery, and Schoenlein-Henoch purpura. Combinations of GM-CSF inhibitors, TNF inhibitors and angiogenesis inhibitors (e.g. anti-VEGF) are useful for treating certain cardiovascular diseases such as aortic aneurysms and tumors.

In addition, the subject GM-CSF inhibitors, compositions and combination therapies are used to treat chronic pain conditions, such as chronic pelvic pain, including chronic prostatitis/pelvic pain syndrome. As a further example, GM-CSF inhibitor and the compositions and combination therapies of the invention are used to treat post-herpetic pain.

In addition to human patients, GM-CSF inhibitors are useful in the treatment of non-human animals, such as pets (dogs, cats, birds, primates, etc.), domestic farm animals (horses cattle, sheep, pigs, birds, etc.), or any animal that suffers from an IL-1-mediated inflammatory or arthritic condition. In such instances, an appropriate dose may be determined according to the animal's body weight. For example, a dose of 0.2-1 mg/kg may be used. Alternatively, the dose is determined according to the animal's surface area, an exemplary dose ranging from 0.1-20 mg/m2, or more preferably, from 5-12 mg/m2. For small animals, such as dogs or cats, a suitable dose is 0.4 mg/kg. GM-CSF inhibitor (preferably constructed from genes derived from the recipient species), or another soluble IL-1 receptor mimic, is administered by injection or other suitable route one or more times per week until the animal's condition is improved, or it may be administered indefinitely.

2. Diagnostic Methods

The antigen binding proteins of the described can be used for diagnostic purposes to detect, diagnose, or monitor diseases and/or conditions associated with GM-CSF. The disclosed provides for the detection of the presence of GM-CSF in a sample using classical immunohistological methods known to those of skill in the art (e.g., Tijssen, 1993, *Practice and Theory of Enzyme Immunoassays, Vol* 15 (Eds R. H. Burdon and P. H. van Knippenberg, Elsevier, Amsterdam); Zola, 1987, *Monoclonal Antibodies: A Manual of Techniques*, pp. 147-158 (CRC Press, Inc.); Jalkanen et al., 1985, *J. Cell. Biol.* 101:976-985; Jalkanen et al., 1987, *J. Cell Biol.* 105: 3087-3096). The detection of GM-CSF can be performed in vivo or in vitro.

Diagnostic applications provided herein include use of the antigen binding proteins to detect expression of GM-CSF and binding of the ligands to GM-CSF. Examples of methods useful in the detection of the presence of GM-CSF include immunoassays, such as the enzyme linked immunosorbent assay (ELISA) and the radioimmunoassay (RIA).

For diagnostic applications, the antigen binding protein typically will be labeled with a detectable labeling group. Suitable labeling groups include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labelling group is coupled to the antigen binding protein via spacer arms of various lengths to reduce potential steric hindrance. Various methods for labelling proteins are known in the art and may be used.

One aspect of the disclosed provides for identifying a cell or cells that express GM-CSF. In a specific embodiment, the antigen binding protein is labeled with a labeling group and the binding of the labeled antigen binding protein to GM-CSF is detected. In a further specific embodiment, the binding of the antigen binding protein to GM-CSF detected in vivo. In a further specific embodiment, the GM-CSF antigen binding protein is isolated and measured using techniques known in the art. See, for example, Harlow and Lane, 1988, *Antibodies: A Laboratory Manual*, New York: Cold Spring Harbor (ed. 1991 and periodic supplements); John E. Coligan, ed., 1993, *Current Protocols In Immunology* New York: John Wiley & Sons.

Another aspect of the disclosed provides for detecting the presence of a test molecule that competes for binding to GM-CSF with the antigen binding proteins provided. An example of one such assay would involve detecting the amount of free antigen binding protein in a solution containing an amount of GM-CSF in the presence or absence of the test molecule. An increase in the amount of free antigen binding protein (i.e., the antigen binding protein not bound to GM-CSF) would indicate that the test molecule is capable of competing for GM-CSF binding with the antigen binding protein. In one embodiment, the antigen binding protein is labeled with a labeling group. Alternatively, the test molecule is labeled and the amount of free test molecule is monitored in the presence and absence of an antigen binding protein.

3. Methods of Treatment: Pharmaceutical Formulations, Routes of Administration

Methods of using the antigen binding proteins are also provided. In some methods, an antigen binding protein is provided to a patient. The antigen binding protein inhibits binding of GM-CSFR to human GM-CSF. The administration of an antigen binding protein in some methods can also inhibit autophosphorylation of human GM-CSF by inhibiting binding of GM-CSFR to human GM-CSF. Further, in certain methods, monocyte chemotaxis is reduced by administering an effective amount of at least one antigen binding protein to a patient. Monocyte migration into tumors in some methods is inhibited by administering an effective amount of an antigen binding protein. In addition, the accumulation of tumor associated macrophage in a tumor can be inhibited by administering an antigen binding protein as provided herein.

Pharmaceutical compositions that comprise a therapeutically effective amount of one or a plurality of the antigen binding proteins and a pharmaceutically acceptable diluent, carrier, solubilizer, emulsifier, preservative, and/or adjuvant are also provided. In addition, methods of treating a patient by administering such pharmaceutical composition are included. The term "patient" includes human patients.

Acceptable formulation materials are nontoxic to recipients at the dosages and concentrations employed. In specific embodiments, pharmaceutical compositions comprising a therapeutically effective amount of human GM-CSF antigen binding proteins are provided.

In certain embodiments, acceptable formulation materials preferably are nontoxic to recipients at the dosages and concentrations employed. In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as Polysorbate 20, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, *Remington's Pharmaceutical Sciences*, 18$^{th}$ Edition, (A. R. Genrmo, ed.), 1995, Mack Publishing Company.

In certain embodiments, the optimal pharmaceutical composition will be determined by one skilled in the art depending upon, for example, the intended route of administration, delivery format and desired dosage. See, for example, *Remington's Pharmaceutical Sciences*, supra. In certain embodiments, such compositions may influence the physical state, stability, rate of in vivo release and rate of in vivo clearance of the antigen binding proteins disclosed. In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In specific embodiments, pharmaceutical compositions comprise Tris buffer of about pH 7.0-8.5, or acetate buffer of about pH 4.0-5.5, and may further include sorbitol or a suitable substitute therefor. In certain embodiments, Human GM-CSF antigen binding protein compositions may be prepared for storage by mixing the selected composition having the desired degree of purity with optional formulation agents (*Remington's Pharmaceutical Sciences*, supra) in the form of a lyophilized cake or an aqueous solution. Further, in certain embodiments, the human GM-CSF antigen binding protein may be formulated as a lyophilizate using appropriate excipients such as sucrose.

The pharmaceutical compositions can be selected for parenteral delivery. Alternatively, the compositions may be selected for inhalation or for delivery through the digestive tract, such as orally. Preparation of such pharmaceutically acceptable compositions is within the skill of the art.

The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions may be provided in the form of a pyrogen-free, parenterally acceptable aqueous solution comprising the desired human GM-CSF antigen binding protein in a pharmaceutically acceptable vehicle. A particularly suitable vehicle for parenteral injection is sterile distilled water in which the human GM-CSF antigen binding protein is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used; having the effect of promoting sustained duration in the circulation. In certain embodiments, implantable drug delivery devices may be used to introduce the desired antigen binding protein.

Certain pharmaceutical compositions are formulated for inhalation. In some embodiments, human GM-CSF antigen binding proteins are formulated as a dry, inhalable powder. In specific embodiments, human GM-CSF antigen binding protein inhalation solutions may also be formulated with a propellant for aerosol delivery. In certain embodiments, solutions may be nebulized. Pulmonary administration and formulation methods therefore are further described in PCT Publication No. WO94/20069 and describes pulmonary delivery of chemically modified proteins. Some formulations can be administered orally. Human GM-CSF antigen binding proteins that are administered in this fashion can be formulated with or without carriers customarily used in the compounding of solid dosage forms such as tablets and capsules. In certain embodiments, a capsule may be designed to release the active portion of the formulation at the point in the gastrointestinal tract when bioavailability is maximized and presystemic degradation is minimized. Additional agents can be included to facilitate absorption of the human GM-CSF antigen binding protein. Diluents, flavorings, low melting point waxes, vegetable oils, lubricants, suspending agents, tablet disintegrating agents, and binders may also be employed.

Some pharmaceutical compositions comprise an effective quantity of one or a plurality of human GM-CSF antigen binding proteins in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving human GM-CSF antigen binding proteins in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, PCT Publication No. WO 93/15722 that describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP 058481), copolymers of L-glutamic acid and gamma ethyl-L-glutamate (Sidman et al., 1983, *Biopolymers* 2:547-556), poly(2-hydroxyethyl-inethacrylate) (Langer et al., 1981, *J. Biomed. Mater. Res.* 15:167-277 and Langer, 1982, *Chem. Tech.* 12:98-105), ethylene vinyl acetate (Langer et al., 1981, supra) or poly-D(−)-3-hydroxybutyric acid (European Patent Application Publication No. EP 133,988). Sustained release compositions may also include liposomes that can be prepared by any of several methods known in the art. See, e.g., Eppstein et al., 1985, *Proc. Natl. Acad. Sci. U.S.A.* 82:3688-3692; European Patent Application Publication Nos. EP 036,676; EP 088,046 and EP 143,949.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for administration can be stored in lyophilized form or in a solution. Parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration. Kits for producing a single-dose administration unit are also provided. Certain kits contain a first container having a dried protein and a second container having an aqueous formulation. In certain embodiments, kits containing single and multi-chambered pre-filled syringes (e.g., liquid syringes and lyosyringes) are provided.

The therapeutically effective amount of a human GM-CSF antigen binding protein-containing pharmaceutical composition to be employed will depend, for example, upon the therapeutic context and objectives. One skilled in the art will appreciate that the appropriate dosage levels for treatment will vary depending, in part, upon the molecule delivered, the indication for which the human GM-CSF antigen binding protein is being used, the route of administration, and the size (body weight, body surface or organ size) and/or condition (the age and general health) of the patient. In certain embodiments, the clinicians may titer the dosage and modify the route of administration to obtain the optimal therapeutic effect.

A typical dosage may range from about 0.1 µg/kg to up to about 30 mg/kg or more, depending on the factors mentioned above. In specific embodiments, the dosage may range from 0.1 µg/kg up to about 30 mg/kg, optionally from 1 µg/kg up to about 30 mg/kg, optionally from 10 µg/kg up to about 10 mg/kg, optionally from about 0.1 mg/kg to 5 mg/kg, or optionally from about 0.3 mg/kg to 3 mg/kg.

Dosing frequency will depend upon the pharmacokinetic parameters of the particular human GM-CSF antigen binding protein in the formulation used. Typically, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter. Appropriate dosages may be ascertained through use of appropriate dose-response data. In certain embodiments, the antigen binding proteins can be administered to patients throughout an extended time period. Chronic administration of an antigen binding protein minimizes the adverse immune or allergic response commonly associated with antigen binding proteins that are not fully human, for example an antibody raised against a human antigen in a non-human animal, for example, a non-fully human antibody or non-human antibody produced in a non-human species.

The route of administration of the pharmaceutical composition is in accord with known methods, e.g., orally, through injection by intravenous, intraperitoneal, intracerebral (intraparenchymal), intracerebroventricular, intramuscular, intraocular, intraarterial, intraportal, or intralesional routes; by sustained release systems or by implantation devices. In certain embodiments, the compositions may be administered by bolus injection or continuously by infusion, or by implantation device.

The composition also may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

It also may be desirable to use human GM-CSF antigen binding protein pharmaceutical compositions according to the disclosed ex vivo. In such instances, cells, tissues or organs that have been removed from the patient are exposed to human GM-CSF antigen binding protein pharmaceutical compositions after which the cells, tissues and/or organs are subsequently implanted back into the patient.

In particular, human GM-CSF antigen binding proteins can be delivered by implanting certain cells that have been genetically engineered, using methods such as those described herein, to express and secrete the polypeptide. In certain embodiments, such cells may be animal or human cells, and may be autologous, heterologous, or xenogeneic. In certain embodiments, the cells may be immortalized. In other embodiments, in order to decrease the chance of an immunological response, the cells may be encapsulated to avoid infiltration of surrounding tissues. In further embodiments, the encapsulation materials are typically biocompatible, semipermeable polymeric enclosures or membranes that allow the release of the protein product(s) but prevent the destruction of the cells by the patient's immune system or by other detrimental factors from the surrounding tissues.

All patents and other publications identified are expressly incorporated herein by reference for the purpose of describing and disclosing, for example, the methodologies described in such publications that might be used in connection with the described. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The following examples, including the experiments conducted and the results achieved, are provided for illustrative purposes only and are not to be construed as limiting the scope of the appended claims.

EXAMPLES

Example 1

Description of GM-CSF and Other Molecules Used for Generation, Selection and Characterization of Anti-GM-CSF Monoclonal Antibodies Several different recombinant and native GM-CSF molecules were used to generate, select and characterize the anti-GM-CSF hybridomas and monoclonal antibodies.
Human GM-CSF There are two naturally occurring allelic variants of human GM-CSF which differ by a single amino acid at position 117. Recombinant human GM-CSF molecules with either threonine (rhGM-CSF-Thr, SEQ ID NO:146) or isoleucine (GM-CSF-Ile, SEQ ID NO:145) at amino acid position 117 were produced from transiently transfected CHO or COS cells and affinity-purified. Native human GM-CSF (nhGM-CSF) was affinity purified from the supernatant of A431 cells after stimulation with PMA (0.01 ug/ml), ionomycin (0.5 ug/ml) and EGF (0.02 ug/ml), from the supernatant of human peripheral blood mononuclear cells (PBMCs) after stimulation with PMA (10 ng/mL) and ionomycin (500 ng/mL), for 48 hours at 37° C., or from the supernatant of human small airway epithelial cells (SAEC) stimulated with TNFα (25 ng/ml) and IL-1 (10 ng/ml). E. coli-derived rhGM-CSF was purchased from R&D Systems (Minneapolis, Minn.). Yeast-derived rhGM-CSF having a substitution of leucine for arginine at amino acid position 23 (Leukine®) was purchased from Berlex, Inc. (Montville, N.J.). E. coli-derived rhGM-CSF-R23L is an E. coli-derived rhGM-CSF having a substitution of leucine for arginine at amino acid position 23. Yeast-derived rhGM-CSF nhGM-CSF (Leukine®), E. coli-derived rhGM-CSF and E. coli-derived rhGM-CSF-R23L demonstrated equivalent GM-CSF activity in the TF-1 STAT5 phosphorylation assay.

Cynomolgus Macaque GM-CSF

Recombinant cynomolgus GM-CSF (rcynoGM-CSF, SEQ ID NO: 53) was produced from transfected E. coli. Native cynomolgus GM-CSF (ncynoGM-CSF) was affinity purified from the supernatant of minced lung tissue after stimulation with TNFα (25 ng/ml) and IL-1 (10 ng/ml), or from the supernatant of cynomolgus PBMCs after stimulation with PMA (10 ng/mL) and ionomycin (500 ng/mL) for 48 hours at 37° C.

Canine GM-CSF

Canine GM-CSF (SEQ ID NO: 54) was produced from transformed E. coli and purified from inclusion bodies using standard column chromatography Rabbit GM-CSF Recombinant rabbit GM-CSF (SEQ ID NO:82) with His tag was produced from 2936E cells, and purified by Talon cobalt IMAC by washing with 5 mM imidazole, 20 mM NaPO4, 300 mM NaCl, pH7.2 and eluting with an imidazole gradient (10 mM to 300 mM).

Mouse GM-CSF

Recombinant mouse GM-CSF (SEQ ID NO:58) was generated from transformed yeast cells and purified with three column chromatography steps: SP-Sepharose (capture), C18 (reverse phase purification) and SP-Sepharose (buffer exchange).

Rat GM-CSF

Recombinant rat GM-CSF was purchased from R&D Systems.

Affinity Purification

Affinity purification of GM-CSF from the supernatant of stimulated cells was performed by cycling supernatant over anti-GMCSF mAb (M8) affinity resin, washing with NaCltrate pH 6.0, and eluting with NaCltrate pH 4.5. The relevant fractions were pooled and buffer exchanged into PBS. The concentration of recombinant GM-CSF was determined by $OD_{280}$, while the concentration of native GM-CSF was determined by ELISA.

Non-GM-CSF Reagents Used for Characterization of Anti-GM-CSF mAb

Recombinant human CSF-1 was purchased from R&D Systems. Recombinant hIL-15 was generated from transfected CHO cells and purified using a two column step purification process. Anion exchange purification was performed with Fractogel TMAE 650M loading at 10 mg/ml resin pH 7.5, then washed with 20 mM Hepes pH 7.5, then 20 mM MES pH 6.5, then 100 mM NaCl, 20 mM MES. Recombinant hIL-15 was eluted with 200 mM NaCl, 20 mM MES pH 6.5. Protein was held at 10 mM NaHPO4 pH 2.0 for 1 hour (viral inactivation step) then subjected to a cation exchange purification step with Fractogel EMD SO3-650(M) loading at 20 mg/ml resin at 10 mM NaHPO4 pH 2.0, washed with 10 mM NaCltrate, 10 mM NaAcetate, 10 mM MES, pH 4.0, and eluted with a gradient elution 10 mM NaCltrate, 10 mM NaAcetate, 10 mM MES, pH 6.0 and buffer exchanged into PBS.

Example 2

Generation and Selection of Neutralizing Human Anti-GM-CSF Antibodies 2.1 Immunization and Selection of GM-CSF-Binding Hybridomas The development of fully human monoclonal antibodies directed against human GM-CSF were obtained using XenoMouse® technology. Two separate cohorts of 10 KL Xenomice each were immunized every 3-4 days for 7 weeks (16 total injections) with either E. coli-derived rhGM-CSF or alternating injections of mammalian cell-derived rhGM-CSF-Ile and rhGM-CSF-Thr. Serum titers were monitored by enzyme-linked immunosorbent assay (ELISA) after the $7^{th}$ and 11th boosts and spleen cells from mice with the best titers were fused to partner cell lines 4 days after the $16^{th}$ boost in order to generate hybridomas. The resulting polyclonal hybridoma supernatants were screened by ELISA for binding to GM-CSF and Alpha screen for the presence of human heavy and kappa and/or lambda light chains. The immunization campaign yielded 499 lines with GM-CSF-binding activity that expressed human heavy and light chains.

2.2 Identification of Hybridomas with GM-CSF Neutralizing Activity Using HGM-CSF-Dependent Cell-Based Bioassays.

499 hybridoma supernatants were further characterized for GM-CSF neutralizing activity using two cell-based bioassays: GM-CSF induced STAT5 phosphorylation in TF-1 cells (2.2.1) and GM-CSF-induced proliferation of AML-5 cells (2.2.2). From these results, 14 hybridomas were selected for cloning.

2.2.1 Inhibition of GM-CSF-Induced STAT-5 Phosphorylation in TF-1 Cells.

TF-1 cells were propagated at 37° C., 10% $CO_2$ in IMDM supplemented with 5% FBS, 10 mM Hepes, 2 mM L-glutamine, 50 U/mL Penicillin, 50 µg/mL Streptomycin, 55 uM beta-mercaptoethanol, and 10 ng/mL E. coli-derived rhGM-CSF. One day prior to the assay, TF-1 cells were harvested by centrifugation at 350×g for 6 minutes and washed 3 times in PBS. The cells were resuspended at $1 \times 10^6$/mL and cultured overnight in IMDM+0.5% FBS without GM-CSF at 37° C., 10% $CO_2$. Assays were performed in 2 mL 96-well round bottom plates in 100 µL total volume. Hybridoma supernatants were plated in duplicate at 1:4 final dilution and incubated with rhGM-CSF-Ile (0.4 ng/mL final concentration) for 30 minutes at 37° C. Serum- and GM-CSF-starved TF-1 cells were harvested, washed in PBS and resuspended in IMDM with 0.5% FBS at $6 \times 10^6$ cells/mL. 50 µL of cell suspension was added ($3 \times 10^5$ cells/well) and the plates were incubated for 15 minutes at 37° C. To fix the cells, 25 µL of 10% paraformaldehyde in PBS was added for a final concentration of 2% paraformaldehyde, and the plates were incubated for 15 minutes at 37° C. 200 µL IMDM+0.5% FBS was added to the wells to halt fixation, and the plates were centrifuged at 350×g for 7 minutes. The cell supernatant was removed and 400 µL of 90% MeOH was slowly added while vigorously mixing the cells. Following overnight incubation −20° C., the plates were spun, washed with 400 µL PBS/2% FCS and incubated with 50 µL of a 1:5 dilution (in PBS with 2% FBS) of anti-PhosphoSTAT5-Alexa488 (Becton Dickinson 612598, Franklin Lakes, N.J.) for 30 minutes at room temperature. The cells were washed, resuspended in PBS with 2% FBS and transferred to round bottom microtiter plates for flow cytometry analysis using a MultiWell FACScalibur (Becton Dickinson). The percentage of STAT5+ cells was determined using FlowJo FACS analysis software. The percent inhibition of STAT5 phosphorylation by the hybridoma supernatants was calculated using the following equation:

$$100-(\{[\% \text{ STAT5+of A}-\% \text{ STAT5+of B}]/[\% \text{ STAT5+of C}-\% \text{ STAT5+of B}]\}*100)$$

Where A=cells+hybridoma supernatant+rhGM-CSF, B=cells only, C=cells+rhGM-CSF

Hybridoma supernatants which inhibited GM-CSF-dependent STAT5 phosphorylation greater than threshold values determined for each assay were further characterized for specificity using IL-3-induced STAT5 phosphorylation, and for potency against nhGM-CSF and rcynoGM-CSF using the TF-1 phosflow bioassay and the AML-5 cell line GM-CSF-induced proliferation bioassay (2.2.2). A representative experiment showing the GM-CSF-dependent phospho-STAT5 response and the ability of an anti-hGM-CSF antibody (MAB215, R&D Systems) to inhibit STAT5 phosphorylation induced by 0.4 ng/mL rhGM-CSF-Ile is shown in FIG. 3. FIG. 4 shows a histogram of percent inhibition of rhGM-CSF-Ile-induced STAT5 phosphorylation by hybridoma supernatants from the cohort immunized with *E. coli*-derived rhGM-CSF.

2.2.2 Inhibition of GM-CSF-Dependent Proliferation of AML-5 Cells by Hybridoma Supernatants.

AML-5 cells were propagated at 37° C., 10% $CO_2$ in IMDM supplemented with 5% FBS, 10 mM Hepes, 2 mM L-glutamine, 50 U/mL Penicillin, 50 μg/mL Streptomycin, 55 μM beta-mercaptoethanol, and 10 ng/mL *E. coli*-derived rhGM-CSF. On the day of experiment, AML-5 cells were centrifuged at 350×g for 5 min and washed 4 times in PBS to remove residual GM-CSF. To test for inhibition of GM-CSF- or CSF-1-induced proliferation of AML-5 cells, polyclonal hybridoma supernatants were plated in duplicate in 96-well flat bottom microtiter plates at 1:10 and/or 1:30 and/or 1:90 final dilutions and cytokine was added at previously determined EC90 values: A431 cell-derived nhGM-CSF and rcynoGM-CSF at 0.05 ng/mL; rhGM-CSF-Ile and rhGM-CSF-Thr at 0.15 ng/mL; and rhCSF-1 at 10 ng/mL. The antibody/cytokine mixture was incubated for 30 minutes at 37° C. prior to the addition of 50 μL AML-5 cells at $5\times10^4$ cells/mL for a total volume of 100 μL ($2.5\times10^3$ cells/well). The plates were incubated at 37° C., 10% $CO_2$ for 72 hours.

To detect AML-5 cell proliferation, the plates were pulsed with one microcurie of tritiated thymidine, harvested 6 hours later, and read on a liquid scintillation counter. The percent inhibition of AML-5 proliferation by hybridoma supernatants was calculated using the following equation:

$$100-(\{\text{CPM of A/CPM of B}\}*100)$$

Where A=cells+hybridoma supernatant+cytokine, and B=cells+cytokine

Hybridoma supernatants which potently inhibited both human and cynomolgus GM-CSF-induced, but not human CSF-1-induced, AML-5 cell proliferation at the 1:30 dilution were selected for cloning to generate monoclonal anti-GM-CSF hybridomas. A representative experiment showing the GM-CSF-dependent proliferative response and the ability of an anti-hGM-CSF antibody (MAB215, R&D Systems) to inhibit AML-5 cell proliferation induced by 0.15 ng/mL rhGM-CSF-Ile is shown in FIG. 5.

2.3 Generation of Monoclonal Hybridoma Cell Lines

Based on the results from the bioassay screens, 14 polyclonal hybridoma lines were selected for cloning to monoclonality by limiting dilution. Cells from the polyclonal hybridoma plates were counted, resuspended at 48 cells/mL and diluted to 24 cells/mL, 4.8 cells/mL and 2.4 cells/mL in 20 mL media. Cells were plated at 200 μl/well, generating plates of four different densities for each line cloned (10 cells/well, 5 cells/well, 1 cell/well, and 0.5 cells/well). Within two weeks following cloning, the plates were visually inspected under a microscope and supernatants were harvested from wells from the 1 cell/well and the 0.5 cell/well cloning plates wherein only a single colony was detected. Supernatants were screened for antigen specificity by ELISA, and antigen positive supernatants were analyzed for heavy and light chain species and isotype composition by ELISA. One to three daughter clones from each line that demonstrated single colony growth in the well, antigen specific immunoreactivity, and human lambda or kappa and IgG combination only were kept and frozen. Monoclonality was confirmed by sequence analysis of each daughter clone.

2.4 Characterization of GM-CSF Neutralizing Activity by Anti-GM-CSF Antibodies Purified from Monoclonal Hybridoma Supernatants 2.4.1 Purification of IgG from Hybridoma Supernatants IgG was affinity purified from monoclonal hybridoma supernatants using Protein A column chromatography and quantified using a NanoDrop ND-1000 UV-Vis Spectrophotometer at A280 (Nanodrop Technologies, Wilmington, Del.).

2.4.2 Inhibition of GM-CSF-Dependent Proliferation of AML-5 Cells by Monoclonal Antibodies.

AML-5 cells were propagated and prepared for the assay as described in Example 2.2.2. To evaluate the ability of monoclonal antibodies purified from hybridoma supernatants to inhibit GM-CSF- or CSF-1-induced proliferation of AML-5 cells, antibodies were each titrated in duplicate in 96-well flat bottom plates (8-fold serial dilutions starting at 5 μg/mL). Cytokine was added at previously determined EC90 values: nhGM-CSF (A431 or human PBMC-derived) at 0.1 ng/mL; rhGM-CSF-Ile at 0.3 ng/mL; rhGM-CSF-Thr at 0.8 ng/mL; rCynoGM-CSF at 0.05 ng/mL; and rhCSF-1 at 3 ng/mL. In each experiment, GM-CSF and CSF-1 were also titrated in 2-fold serial dilutions to calculate the EC90 value in that experiment. Cytokine and antibody were incubated for 30 minutes at 37° C. prior to the addition of AML-5 cells at $2.5\times10^4$ cells/mL in a total volume of 100 μL. The plates were incubated at 37° C., 10% $CO_2$. After three days, the plates were pulsed with one microcurie of tritiated thymidine, harvested 6 hours later, and read on a liquid scintillation counter. The percent inhibition of AML-5 proliferation by mAb purified from hybridoma supernatants was calculated using the following equation:

$$([\text{CPM of A}-\text{CPM of B}]/[\text{CPM of A}-\text{CPM of C}])*100$$

Where A=cells+cytokine, B=cells+mAb+cytokine, and C=cells only

Non-linear regression analysis and 50% inhibition of proliferation (IC50) value calculations were generated using Microsoft Excel (Redmond, Wash.). Experiments in which the amount of cytokine used to stimulate cells was within two-fold of its EC90 value were used to calculate the average IC50 values of the monoclonal hybridoma antibodies (Table 5). Experiments using one or more clones of the same mAb (as confirmed by sequence) were included in the averages.

TABLE 5

Table of IC50 (nM) values for mAb purified from hybridoma supernatants in the AML-5 proliferation and TF-1 Stat5 phosphorylation assays.

| Assay | Cytokine | IgG A | IgG B | IgG C | IgG D | IgG E | IgG F |
|---|---|---|---|---|---|---|---|
| AML-5 Proliferation Assay | rhGM-CSF-Ile | 0.302 | 0.627 | 0.347 | 0.176 | 0.376 | 0.193 |
| | rhGM-CSF-Thr | 0.286 | 0.470 | 0.501 | 0.315 | 0.296 | 0.179 |
| | nhGM-CSF (A431) | 0.414 | 0.299 | 0.442 | 0.299 | 0.323 | 0.179 |
| | nhGM-CSF (PBMC) | 0.235 | 0.947 | 0.659 | 1.373 | 0.575 | 0.214 |
| | rcynoGM-CSF | 0.710 | 0.574 | 0.496 | 0.169 | 0.669 | 0.897 |
| TF-1 Stat5 Phosphorylation Assay | rhGM-CSF-Ile | 0.046 | 0.060 | 0.049 | 0.114 | 0.042 | 0.055 |
| | rhGM-CSF-Thr | 0.016 | 0.023 | 0.027 | 0.061 | 0.035 | 0.027 |
| | nhGM-CSF (A431) | 0.143 | 0.075 | 0.074 | 0.116 | 0.067 | 0.081 |
| | rcynoGM-CSF | 0.057 | 0.075 | 0.066 | 0.066 | 0.274 | 0.063 |

As shown in FIG. 6 and Table 5, several monoclonal antibodies from hybridoma supernatants inhibited GM-CSF-induced, but not CSF-1-induced, AML-5 cell proliferation in a dose-dependent manner. By fitting for the half-maximal inhibition of proliferation, monoclonal antibodies had $IC_{50}$ values of <1 nM against the forms of GM-CSF tested in this assay.

2.4.3 Inhibition of GM-CSF-Dependent STAT-5 Phosphorylation in TF-1 Cells by Anti-GM-CSF Monoclonal Antibodies Purified from Hybridoma Supernatants.

TF-1 cells were propagated and prepared for the assay as described in Example 2.2.1. To evaluate inhibition of GM-CSF- or rhIL-3-induced STAT5 phosphorylation of TF-1 cells, monoclonal antibodies purified from hybridoma supernatants were each titrated in duplicate in 96-well round-bottom deep well plates (5-fold serial dilutions starting at 2 µg/mL). Cytokine was added at previously determined EC90 values: nhGM-CSF (A431) and rcynoGM-CSF at 0.3 ng/mL; rhGM-CSF-Ile and rhGM-CSF-Thr at 0.9 ng/mL; and rhIL-3 at 30 ng/mL. In each assay, GM-CSF and IL-3 were also titrated in 2-fold serial dilutions to calculate the EC90 value in each assay. Cytokine and antibody were incubated for 30 minutes at 37° C. prior to the addition of $3\times10^5$ cells/mL serum and GM-CSF starved TF-1 cells in a total volume of 100 µL. Cells were stimulated for 15 minutes at 37° C. then fixed, permeabilized and analyzed for STAT5 phosphorylation as described in Example 2.2.1. The percent inhibition of Stat5 phosphorylation by mAb purified from clonal hybridoma supernatant was calculated using the following equation:

([% Stat5+ of A–% Stat5+ of B]/[% Stat5+ of A–% Stat5+ of C])*100

Where A=cells+cytokine, B=cells+mAb+cytokine, and C=cells only

Non-linear regression analysis and half-maximal inhibition of proliferation ($IC50_{hm}$ values were calculated using GraphPad Prism 4.01. Experiments in which the amount of cytokine used to stimulate cells was within two-fold of its EC90 value were used to calculate the average IC50 values of the monoclonal antibodies (Table 5).

As shown in FIG. 7 and Table 5, several monoclonal antibodies inhibited GM-CSF-induced, but not rhIL-3-induced, STAT5 phosphorylation in TF-1 cells in a dose-dependent manner. The monoclonal antibodies had $IC50_{hm}$ values of <0.3 nM against the forms of GM-CSF tested in this assay.

Example 3

Cloning and Expression of Recombinant Monoclonal Antibodies (mAb) from Transfected Cell Lines Heavy and light chain variable regions for the antibody clones were subcloned into a human IgG2 framework and transiently or stably transfected and expressed in COS (transient transfection) or CHO (stable transfection) cells. Antibodies expressed by transient transfection in COS cells were purified from supernatant using 2.2×10 cm MabSelectSure rProtein A binding in TBS, pH 7.4, and elution with 50 mM Citrate, pH 3.4+/–0.2. The eluate was adjusted to pH 6.0 using 1M Tris base stock pH 8.0 and buffer exchanged into 10 mM Acetate, 9% Sucrose, pH 5.2 using dialysis. One clone received continued dialysis into a buffer having 10 mM KP, 161 mM L-Arg, pH 7.6 and then concentrated to 20 mg/mL.

Antibodies expressed from stable CHO cell line were purified from supernatant using 1.1×10 cm MabSelectSure rProtein A binding in TBS, pH 7.4 and elution with 100 mM Acetate, pH 3.6. The eluate was buffer exchanged 5 mg into 10 mM Acetate, 9% Sucrose, pH 5.2 using GE desalting column. 20-30 mg of material was then buffer exchanged into Cellgro PBS, pH 7.2 using GE desalting. Pools were 0.2 micron filtered. The material from a second stable cell transfection was purified a second time and maintained in the mM Acetate, 9% Sucrose, pH 5.2 buffer.

Example 4

Kinetic Binding Analysis of Recombinant mAb to rhGM-CSF-Ile by Surface Plasmon Resonance Kinetic binding analysis of anti-GM-CSF recombinant monoclonal antibodies was performed using surface plasmon resonance at 25° C. using a Biacore 3000 instrument (Biacore AB, Uppsala, Sweden) equipped with a CM4 sensor chip. Goat anti-human IgG capture antibody was covalently immobilized to the chip using standard amine-coupling chemistry with HBS-EP as the running buffer. Briefly, each flow cell was activated for 7 minutes with a 1:1 (v/v) mixture of 0.1 M NHS and 0.4 M EDC at a flow rate of 5 µL/min. Goat anti-human IgG at 30 µg/mL in 10 mM sodium acetate, pH 5.5 was immobilized at a density of ~3200 RUs on two flow cells. Residual reactive surfaces were deactivated with a 7-minute injection of 1 M ethanolamine at 5 µL/min. Fifty µL of 10 mM glycine HCl, pH 1.5 at 100 µL/min was injected 3 times over each flow cell to remove any remaining noncovalently bound capture antibody and to condition each surface. The running buffer was switched to HBS-EP with 0.1 mg/mL BSA and 2 mg/mL CM-Dextran for all remaining steps.

Recombinant anti-GM-CSF mAb at 0.5 µg/mL was injected over one goat anti-human IgG surface for 1.5 minutes at 10 µL/min to obtain a surface density of ~111 RUs. The remaining goat anti-human IgG surface was left unmodified as a reference. Five cycles of buffer blanks were initially run to condition the chip surfaces. Recombinant hGM-CSF-Ile samples were prepared at concentrations of 300, 100, 33.3, 11.1, 3.70, and 1.23 nM in triplicate and injected in random order along with 6 buffer blanks at 100 μL/min over both the captured recombinant anti-GM-CSF IgG and reference surfaces. Each complex was allowed to associate for 2.5 minutes, and dissociate for 2.5 minutes. In addition, triplicate samples of 100 nM rhGM-CSF-Ile and buffer blanks were alternately injected over both surfaces at 100 μL/min and allowed to associate for 2.5 minutes and dissociate for 90 minutes in order to collect more dissociation phase data. The surfaces were regenerated after each rhGM-CSF-Ile or buffer injection with a 30-second pulse of 10 mM glycine HCl, pH 1.5 at 100 μL/min, followed by a 30-second injection of buffer.

Data was double referenced by subtracting the reference surface responses to remove bulk refractive index changes, and then subtracting the averaged buffer blank response to remove systematic artifacts from the experimental flow cells. Data collected from the 300 nM curves were deleted from the analysis for lack of kinetic information, as the data lacked curvature and the concentration was ~6000x the $K_D$. The data was processed and globally fit to a 1:1 interaction model with Scrubber (version 2.0a, BioLogic Software, Campbell, Australia) to obtain kinetic rate constants $k_d$ and $k_a$, and the equilibrium binding constant, $K_D$. The results are shown in Table 6.

TABLE 6

Kinetic binding analysis of recombinant mAb to rhGM-CSF-Ile by surface Plasmon resonance.

| mAb | $K_a$ (M$^{-1}$s$^{-1}$) | $K_d$ (s$^{-1}$) | $K_D$ (pM) |
|---|---|---|---|
| IgG A | 3.34 × 10$^5$ | 3.03 × 10$^{-5}$ | 90 |
| IgG B | 6.54 × 10$^5$ | 3.19 × 10$^{-5}$ | 49 |
| IgB C | 8.67 × 10$^5$ | 7.05 × 10$^{-5}$ | 81 |
| IgG E | 9.12 × 10$^5$ | 1.16 × 10$^{-5}$ | 128 |

Example 5

Cross-Reactivity of Anti-GM-CSF Antibody to GM-CSF from Other Species as Measured by ELISA The hybridoma mAb clones and a recombinant mAb from above were evaluated for ability to bind rhGM-CSF-Ile, rhGM-CSF-Thr, yeast-derived rhGM-CSF (Leukine®), E. coli-derived rhGM-CSF, nhGM-CSF and/or recombinant GM-CSF from one or more of the following species: mouse, rat, rabbit, canine and cynomolgus (FIGS. 8A and 8B). Individual wells of a 96-well plate were coated with 50 μL of 1 ug/mL solutions of GM-CSF or control protein and incubated overnight at 4° C. Plates were washed four times with PBS/Tween then the lead anti-GM-CSF mAb (or control antibodies) were added at 2 ug/ml to wells with each of the GM-CSF proteins, incubated for 1 hour at room temperature, and washed 4 times with PBS/Tween. HRP-conjugated anti-human IgG at 1:8000 was added, incubated for 1 hour at room temperature, and plates were washed 4 times with PBS/Tween. TMB developer was added, incubated for 10 minutes and plates were read at 650 nm on a plate reader. The anti-GM-CSF mAb clones and recombinant mAb bound to rhGM-CSF-Ile, rhGM-CSF-Thr, E. coli-derived rhGM-CSF and recombinant cynoGM-CSF, but not to mouse, rat or canine GM-CSF. Some, but not all, of the clones also bound to yeast-derived rhGM-CSF (Leukine®) (FIG. 8A). In a separate assay, one anti-GM-CSF mAb clone from hybridoma supernatant and the second stable cell line (SCL) transfection bound to PBMC-derived nhGM-CSF, rhGM-CSF-Ile, and rcynoGM-CSF, but not to mouse, rat, rabbit or canine GM-CSF (FIG. 8B).

Example 6

Determination of IC50 Values for Recombinant Anti-GM-CSF mAb in Cell-Based Bioassays and Human Whole Blood Using Multiple GM-CSF Molecules As described above, fully human recombinant anti-hGM-CSF antibodies were expressed from both transiently transfected cells and stable transfected cell lines. Material was purified from two independent transient transfections (1$^{st}$ TT and 2$^{nd}$ TT) and two separate harvests of the stable cell lines (1$^{st}$ SCL and 2$^{nd}$ SCL). The following experiments describe the determination of IC50 values for six recombinant antibodies clones against different forms of human and cynomolgus GM-CSF (Tables 7-9).

6.1 Inhibition of GM-CSF-Dependent Proliferation of AML-5 Cells by Recombinant Anti-GM-CSF mAb.

AML-5 proliferation assays were carried out as described in Example 2.4.2 using 9-fold serial dilutions of the mAb starting at 10 μg/mL and cytokine at previously determined EC90 concentrations. For the experiment using the 2$^{nd}$ TT and 1$^{st}$ SCL material (FIG. 9), cytokine was added at the following concentrations: PBMC-derived nhGM-CSF at 0.2 ng/mL; rhGM-CSF-Ile at 0.4 ng/mL; and rCynoGM-CSF at 0.1 ng/mL. For other assays, rhGM-CSF-Thr (0.4 ng/mL) and lung tissue-derived ncynoGM-CSF (3 ng/mL) was tested in addition to the cytokines above. In each experiment, the cytokines used were also titrated using 2-fold serial dilutions to calculate the EC90 value for that experiment. Cytokine and antibody were incubated for 30 minutes at 37° C. prior to the addition of 2.5×10$^4$ AML-5 cells/mL in a total volume of 100 μL. After 72 hours at 37° C., 10% $CO_2$, 1 microCurie of tritiated thymidine was added per well. The cell cultures were harvested 6 hours later and incorporated tritiated thymidine was measured by liquid scintillation counting. The percent inhibition of AML-5 proliferation by recombinant mAb was calculated as in Example 2.4.2. Non-linear regression analysis and 50% inhibition of proliferation (IC50) value calculations were generated using Microsoft Excel. Experiments in which the amount of cytokine used to stimulate cells was within two-fold of its EC90 value were used to calculate average IC50 values for each of the mAb.

All of the transient- and stable cell line-generated recombinant antibodies inhibited GM-CSF-induced AML-5 cell proliferation in a dose-dependent manner. All six lead antibodies from transient transfections inhibited human GM-CSF with IC50 values <0.8 nM and cynomolgus GM-CSF with IC50 values <3.5 nM. All six stable cell line lead antibodies inhibited human GM-CSF with IC50 values <1.5 nM and cynomolgus GM-CSF with IC50 values <3.5 nM. Results for three of the antibodies are shown in FIG. 9. A summary of IC50 values for all antibodies and cytokines tested in the AML-5 proliferation assay are shown in Table 7.

TABLE 7

Table of IC50 (nM) values for recombinant mAb in the AML-5 proliferation assay.

| Cytokine | Antibody | n | IgG A | IgG B | IgG C | IgG E |
|---|---|---|---|---|---|---|
| rhGM-CMS-Ile | 1$^{st}$ TT | 2 | 0.545 | 0.286(n4) | 0.258(n4) | 0.403 |
| | 2$^{nd}$ TT | 3 | 0.579 | 0.581 | 0.380 | 0.380(n2) |
| | 1$^{st}$ SCL | 3 | 0.844 | 1.192 | 0.766 | 0.971(n2) |
| | 2$^{nd}$ SCL | 1 | 0.966 | 0.943 | 0.595 | |
| rhGM-CSF-Thr | 1$^{st}$ TT | 2 | 0.475 | 0.540 | 0.469 | 0.371 |
| | 2$^{nd}$ TT | 1 | 0.181 | 0.200 | 0.165 | 0.249 |
| | 1$^{st}$ SCL | 2 | 0.706 | 0.509 | 0.557 | 0.549 |
| nhGM-CSF (PBMC) | 1$^{st}$ TT | 2 | 0.264 | 0.155 | 0.190 | 0.247 |
| | 2$^{nd}$ TT | 2 | 0.195 | 0.232 | 0.312 | 0.574(n1) |
| | 1$^{st}$ SCL | 2 | 0.308 | 0.270 | 0.160 | 0.360(n1) |
| | 2$^{nd}$ SCL | 1 | 0.251 | 0.213 | 0.081 | |
| rcynoGM-CSF | 1$^{st}$ TT | 1 | 0.395 | 0.072 | 0.253 | 0.215 |
| | 2$^{nd}$ TT | 1 | 1.607 | 1.319 | 0.864 | 0.693 |
| | 1$^{st}$ SCL | 2 | 3.267 | 1.177 | 1.624 | 2.479(n1) |
| | 2$^{nd}$ SCL | 1 | 2.488 | 0.842 | 1.755 | |
| ncynoGM-CSF (lung) | 2$^{nd}$ TT | 1 | 1.530 | 3.242 | 1.222 | 1.331 |
| | 1$^{st}$ SCL | 1 | 1.471 | 2.683 | 1.696 | 1.604 |

6.2 Inhibition of GM-CSF-Dependent STAT5 Phosphorylation in TF-1 Cells by Recombinant Anti-GM-CSF mAb.

TF-1 STAT5 phosphorylation assays were carried out as described in Example 2.4.3 using 6-fold serial dilutions of the mAb starting at 2 µg/mL and cytokine at previously determined EC90 concentrations. For the experiment using the 2$^{nd}$ TT and 2$^{nd}$ SCL material (FIG. 10), cytokine was added at the following concentrations: PBMC-derived nhGM-CSF and rhGM-CSF-Ile at 0.6 ng/mL; rcynoGM-CSF at 0.1 ng/mL. For the experiment using the 1$^{st}$ TT material (FIG. 11), supernatant from stimulated human small airway epithelial cell (SAEC) cultures (final nhGM-CSF concentrations of 0.2 ng/mL) and supernatant from stimulated cynomolgus lung cultures (final ncynoGM-CSF concentrations of 0.1 ng/mL) was used. In FIG. 12, supernatant from stimulated cynomolgus PBMC cultures (final GM-CSF concentration of 1 ng/mL) was added to GM-CSF mAb from a 2$^{nd}$ SCL. For other assays, rhGM-CSF-Thr at 0.75 ng/mL was tested in addition to the cytokines above. In each experiment, the cytokines used were also titrated in 2-fold serial dilutions to calculate the EC90 value for that experiment. After 15 minutes, the cells were fixed and permeabilized and the amount of STAT5 phosphorylation was detected using an anti-phospho-STAT5 antibody as described above in Examples 2.2.1 and 2.4.3. The percent inhibition of Stat5 phosphorylation by recombinant mAb was calculated as in Example 2.4.3. Non-linear regression analysis and half-maximal inhibition of proliferation (IC50$_{hm}$) values were calculated using GraphPad Prism 4.01. Experiments in which the amount of cytokine used to stimulate cells was within two-fold of its EC90 value were used to calculate average IC50 values of the monoclonal antibodies.

6.3 Inhibition of GM-CSF-Dependent Activation of Primary Human Monocytes by Recombinant Anti-GM-CSF mAb.

To evaluate the mAb for their ability to neutralize GM-CSF-induced metabolic activity in human monocytes, primary monocytes were isolated using a Monocyte Isolation Kit II (Miltenyi Biotech) from leukapheresis packs (Amgen Washington Blood Donor Program). The negatively selected cells were 90%-95% CD14$^+$ cells as assessed by flow cytometry (data not shown). PBMC-derived nhGM-CSF or rhGM-CSF-Ile (0.05 ng/mL) was incubated for 30 minutes with 6-fold serial dilutions of the mAb starting at 20 µg/mL in 96-well flat bottom plates. CD14$^+$ cells (150,000/mL) were added in 100 µL total media (RPMI supplemented with 10% FCS, 10 mM Hepes, 2 mM L-glutamine, 50 U/mL Penicillin, 50 µg/mL Streptomycin, and 55 µM beta-mercaptoethanol) to the plates and incubated for 5 days at 37° C., 5% CO$_2$. GM-CSF-induced metabolic activity was assessed by addition of 20 µL of a 1:1 mixture of Alamar Blue (BioSource, DAL1025, Invitrogen, Carlsbad, Calif.) and media, and calculating the absorbance at 570-600 nm 4-8 hours later. The percent inhibition of human CD14$^+$ monocyte activity by recombinant mAb was calculated using the following equation:

$$([OD_{570-600} \text{ of A} - OD_{570-600} \text{ of B}]/[OD_{570-600} \text{ of A} - OD_{570-600} \text{ of C}])*100$$

Where A=cells+cytokine, B=cells+mAb+cytokine, and C=cells only

Non-linear regression analysis and 50% inhibition of proliferation (IC50) value calculations were generated using Microsoft Excel. Experiments in which the amount of cytokine used to stimulate cells was within two-fold of its EC90 value were used to calculate average IC50 values for the mAb (Table 8). The transient- and stable cell line-generated recombinant antibodies inhibited GM-CSF-induced AML-5 cell proliferation in a dose-dependent manner. The antibodies inhibited human GM-CSF with IC50$_{hm}$ values <0.13 nM and cynomolgus GM-CSF with IC50$_{hm}$ values <0.31 nM.

TABLE 8

Table of IC50 (nM) values for recombinant mAb in the TF-1 Stat5 phosphorylation assay.

| Cytokine | Antibody | n | IgG A | IgG B | IgG C | IgG E |
|---|---|---|---|---|---|---|
| rhGM-CMS-Ile | 1$^{st}$ TT | 1 | 0.117 | 0.046 | 0.072 | 0.101 |
| | 2$^{nd}$ TT | 2 | 0.016 | 0.013 | 0.012 | |
| | 1$^{st}$ SCL | 1 | 0.011 | 0.008 | 0.002 | |
| | 2$^{nd}$ SCL | 1 | 0.027 | 0.009 | 0.011 | |
| rhGM-CSF-Thr | 1$^{st}$ TT | 1 | 0.114 | 0.052 | 0.050 | 0.068 |
| nhGM-CSF (PBMC) | 2$^{nd}$ TT | 1 | 0.009 | 0.008 | 0.009 | |
| | 2$^{nd}$ SCL | 1 | 0.010 | 0.008 | 0.009 | |
| nhGM-CSF (SAEC supe) | 1$^{st}$ TT | 1 | 0.042 | 0.025 | 0.022 | 0.030 |
| rcynoGM-CSF | 1$^{st}$ TT | 2 | 0.050 | 0.021 | 0.031 | 0.052 |
| | 2$^{nd}$ TT | 1 | 0.230 | 0.183 | 0.305 | |
| | 2$^{nd}$ SCL | 1 | 0.128 | 0.149 | 0.196 | |
| ncynoGM-CSF (lung sup,) | 2$^{nd}$ TT | 1 | 0.179 | 0.079 | 0.141 | 0.191 |
| ncynoGM-CSF (PBMC sup.) | 1$^{st}$ TT | 1 | | 0.0022 | | |
| | 2$^{nd}$ SCL | 1 | | 0.0004 | | |

The transient- and stable cell line-generated recombinant antibodies inhibited GM-CSF-induced human monocyte activity in a dose-dependent manner. The lead antibodies, regardless of expression method, inhibited both native and recombinant hGM-CSF with IC50 values <0.55 nM. The results for the 1$^{st}$ TT material are shown in FIG. 13. A summary of IC50 values for all antibodies tested in the human monocyte assay are shown in Table 9.

TABLE 9

Table of IC50 (nM) values for recombinant mAb in the human monocyte assay.

| Cytokine | Antibody | n | IgG A | IgG B | IgG C | IgG E |
|---|---|---|---|---|---|---|
| rhGM-CMS-Ile | 1$^{st}$ TT | 1 | 0.076 | 0.078 | 0.034 | 0.089 |
| | 2$^{nd}$ TT | 2 | 0.136 | 0.096 | 0.083 | 0.142 |
| | 1$^{st}$ SCL | 1 | 0.028 | 0.051 | 0.046 | |
| | 2$^{nd}$ SCL | 1 | 0.130 | 0.150 | 0.089 | |

TABLE 9-continued

Table of IC50 (nM) values for recombinant mAb in the human monocyte assay.

| Cytokine | Antibody | n | IgG A | IgG B | IgG C | IgG E |
|---|---|---|---|---|---|---|
| nhGM-CSF (PBMC) | 1st TT | 1 | 0.549 | 0.253 | 0.301 | 0.490 |
| | 2nd TT | 2 | 0.210 | 0.219 | 0.161 | 0.305 |
| | 1st SCL | 2 | 0.149 | 0.151 | 0.085 | 0.210(n1) |
| | 2nd SCL | 1 | 0.171 | 0.204 | 0.114 | |

6.4 Inhibition of GM-CSF-Induced ENA-78 or MIP-1 Beta Production in Human Whole Blood by a Recombinant Anti-GM-CSF Produced from Stable CHO Cell Lines Recombinant hGM-CSF-Ile (final concentration 2 ng/mL) was prepared in RPM' supplemented with 10% normal human serum, 100 U/mL Penicillin, 100 ug/mL Streptomycin, 2 mM L-glutamine and 25 mM Hepes and added to 6-fold serial dilutions of a recombinant mAb from a stable CHO cell line starting at 100 μg/mL in 96-well flat bottom plates. Human $IgG_2$ isotype-matched monoclonal antibody (anti-KLH) was added to all wells for a final total IgG concentration of 100 μg/mL and the plates were incubated for 30 minutes at 37° C. Cytokine was titrated in 4-fold serial dilutions +/−100 μg/mL isotype-matched human $IgG_2$ to calculate the EC90 value for that experiment. Human whole blood was collected into Na-Heparin Vacutainer tubes (Becton Dickinson) by the Amgen Whole Blood Donor Program and 228 μL (285 μL total volume) blood was added to the wells and mixed with gently pipetting. After a 40 hr incubation at 37° C., 5% $CO_2$, the plates were spun for 5 minutes at 730×g, and 55 μL plasma was carefully collected and transferred to new 96 well plates and frozen. Plasma was thawed and duplicate wells were pooled prior to analysis for ENA78 and MIP-1b by ELISA using the reagents and protocols from hENA78 and hMIP-1b DuoSets from R&D Systems. Non-linear regression analysis and half-maximal inhibition of proliferation ($IC50_{hm}$) values were calculated using GraphPad Prism 4.01.

In this human whole blood assay, the recombinant human GM-CSF mAb was shown to inhibit GM-CSF-induced production of ENA78 and MIP-1b. The $IC50_{hm}$ value was determined to be 0.155 nM for ENA78 production and 0.299 nM for MIP-1b production (FIG. 14).

Example 7

Neutralization of Yeast-Derived rhGM-CSF (Leukine®), A431-Derived nhGM-CSF, *E. coli*-Derived rhGM-CSF and *E. coli*-Derived rhGM-CSF-R23L in the GM-CSF-Induced AML-5 Proliferation Assay Human Monocyte Bioassay and GM-CSF-Induced TF-1 STAT-5 Phosphorylation in TF-1 Cells Assay The AML-5 proliferation assay was carried out as described in Example 2.4.2 using 9-fold serial dilutions of the GM-CSF mAb purified from hybridoma supernatant starting at 5 μg/mL and cytokine at previously determined EC90 concentrations (*E. coli*-derived rhGM-CSF at 0.1 ng/mL, yeast-derived rhGM-CSF at 0.05 ng/mL). The cytokines used were also titrated using 2-fold serial dilutions to calculate the EC90 value for that experiment. Cytokine and antibody were incubated for 30 minutes at 37° C. prior to the addition of $2.5 \times 10^4$ AML-5 cells/mL in a total volume of 100 μL. After 72 hours at 37° C., 10% $CO_2$, 1 microCurie of tritiated thymidine was added per well. The cell cultures were harvested 6 hours later and incorporated tritiated thymidine was measured by liquid scintillation counting. As shown in FIG. 15a, four mAb were able to neutralize the activity of *E. coli*-derived rhGM-CSF, but not yeast-derived rhGM-CSF (Leukine®).

The human monocyte assay was carried out as described in Example 6.3 using 3-fold dilutions of the mAb purified from hybridoma supernatant starting at 12 μg/mL and cytokine at previously determined EC90 concentrations (A431 cell-derived nhGM-CSF and yeast-derived rhGM-CSF at 0.04 ng/mL). The cytokines used were also titrated using 2-fold serial dilutions to calculate the EC90 value for that experiment. Cytokine and antibody were incubated together for 30 minutes at 37° C. prior to the addition of $1.5 \times 10^5$ human $CD14^+$ cells/mL in a total volume of 100 μL. The plates were incubated for 5 days at 37° C. in 5% $CO_2$ and GM-CSF-induced metabolic activity was assessed by measuring the reduction of Alamar Blue. For both assays, non-linear regression analysis and 50% inhibition of proliferation (IC50) value calculations were generated using Microsoft Excel. Experiments in which the amount of cytokine used to stimulate cells was within two-fold of its EC90 value were included in analysis. As shown in FIG. 15b, four mAb were able to neutralize the activity of A431 cell-derived rhGM-CSF, but not yeast-derived rhGM-CSF (Leukine®).

The TF-1 STAT5 phosphorylation assay was carried out as described in Example 2.2.1 using recombinant anti-GM-CSF mAb. Into duplicate wells of a 96 well plate, 6-fold serial dilutions of anti-GM-CSF mAb starting at 2 μg/mL and cytokine at previously determined $EC_{90}$ concentrations (*E. coli*-derived rhGM-CSF and *E. coli*-derived rhGM-CSF-R23L at 0.5 ng/mL, yeast-derived rhGM-CSF-R23L (Leukine®) at 0.2 ng/mL). Following 30 minute incubation, $3 \times 10^5$ TF-1 cells/ml were added to total volume of 100 μL. The plates were incubated for 15 minutes at 37° C. To fix the cells, 25 μL of 10% paraformaldehyde in PBS was added for a final concentration of 2% paraformaldehyde, and the plates were incubated for 10 minutes at 37° C. 200 μL IMDM+0.5% FBS, 10 mM Hepes, 2 mM L-glutamine, 50 U/mL Penicillin, 50 μg/mL Streptomycin, 55 uM beta-mercaptoethanol, was added to the wells to halt fixation, and the plates were centrifuged at 350×g for 10 minutes. The cell supernatant was removed and 400 μL of 90% MeOH was slowly added while vigorously mixing the cells. Following overnight incubation at −20° C., the plates were spun, washed with 600 μL PBS/2% FCS and incubated with 50 μL of a 1:5 dilution (in PBS with 2% FBS) of anti-PhosphoSTAT5-Alexa488 (Becton Dickinson 612598, Franklin Lakes, N.J.) for 30 minutes at room temperature. The cells were washed, resuspended in PBS with 2% FBS and transferred to round bottom microtiter plates for flow cytometry analysis using a MultiWell FACScalibur (Becton Dickinson). The percentage of $STAT5^+$ cells was determined using FlowJo FACS analysis software. The percent inhibition of STAT5 phosphorylation by the hybridoma supernatants was calculated using the following equation:

100−{[% STAT5+of A−% STAT5+of B]/[% STAT5+ of C−% STAT5+of B]}*100)

Where A=cells+hybridoma supernatant+rhGM-CSF, B=cells only, C=cells+rhGM-CSF

In the GM-CSF-induced TF-1 cell pSTAT5 assay, *E. coli*-derived rhGM-CSF-R23L exhibited an EC90 (0.384 ng/mL) comparable to that of yeast-derived rhGM-CSF-R23L (Leukine®) (0.130 ng/mL) and *E. coli*-derived rhGM-CSF (0.298 ng/mL). As shown in FIG. 16, anti-GM-CSF mAb neutralized *E. coli*-derived rhGM-CSF but not yeast-derived (Leukine®) or unglycosylated *E. coli*-derived rhGM-CSF-R23L. This suggests that the basis for this distinction is due to the same single amino acid difference (leucine to arginine at position 23) in the primary sequence of the yeast-derived rhGM-CSF-R23L (Leukine®) and *E. coli* rhGM-CSF-R23L, compared to native GM-CSF, rather than glycosylation difference due to yeast expression.

Example 8

Epitope Binning of Lead Six Anti-GM-CSF Monoclonal Antibodies by Binding Competition Epitope binning was performed using a binding competition assay in which one labeled mAb competed with excess amounts of other unlabeled mAb for binding to rhGM-CSF-Ile. Antibodies which competed with one another were assigned to the same bin. Five of the six lead anti-GM-CSF mAb competed with each other for binding to rhGM-CSF, while one did not.

---

What is claimed is:

1. A nucleic acid molecule encoding an isolated antigen binding protein that binds granulocyte macrophage colony stimulating factor (GM-CSF) comprising:
   A) a CDRH1 of SEQ ID NO:22, a CDRH2 of SEQ ID NO:23 and a CDRH3 of SEQ ID NO:24, and
   B) a CDRL1 of SEQ ID NO:16, a CDRL2 of SEQ ID NO:17, and a CDRL3 of SEQ ID NO: 18.

2. The nucleic acid molecule according to claim 1, wherein said nucleic acid molecule is operably linked to a control sequence.

3. A vector comprising a nucleic acid molecule according to claim 1.

4. A vector comprising a nucleic acid molecule according to claim 2.

5. A host cell comprising the nucleic acid molecule according to claim 2.

6. A host cell comprising the vector according to claim 3.

7. A method of making the antigen binding protein according to claim 1, comprising the step of preparing said antigen binding protein from a host cell that secretes said antigen binding protein.

* * * * *